United States Patent
Ikeda et al.

(10) Patent No.: US 9,705,091 B2
(45) Date of Patent: Jul. 11, 2017

(54) AROMATIC HETEROCYCLE DERIVATIVE AND ORGANIC ELECTROLUMINESCENT ELEMENT USING SAME

(75) Inventors: Kiyoshi Ikeda, Sodegaura (JP); Mitsunori Ito, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 785 days.

(21) Appl. No.: 13/994,249

(22) PCT Filed: Dec. 19, 2011

(86) PCT No.: PCT/JP2011/007071
§ 371 (c)(1),
(2), (4) Date: Jul. 5, 2013

(87) PCT Pub. No.: WO2012/086170
PCT Pub. Date: Jun. 28, 2012

(65) Prior Publication Data
US 2013/0306959 A1  Nov. 21, 2013

(30) Foreign Application Priority Data
Dec. 20, 2010 (JP) ................. 2010-283490

(51) Int. Cl.
*H01L 51/50* (2006.01)
*H01L 51/00* (2006.01)
(Continued)

(52) U.S. Cl.
CPC ........ *H01L 51/0072* (2013.01); *C07D 403/14* (2013.01); *C07D 405/14* (2013.01);
(Continued)

(58) Field of Classification Search
None
See application file for complete search history.

(56) References Cited

U.S. PATENT DOCUMENTS

2002/0048687 A1  4/2002  Hosokawa et al.
2004/0100188 A1  5/2004  Hosokawa et al.
(Continued)

FOREIGN PATENT DOCUMENTS

EP  2 166 584 A1  3/2010
JP  08-003547  1/1996
(Continued)

OTHER PUBLICATIONS

Rothmann, M.M. et al, Donor-substituted 1,3,5 Triazines as Host Materials for Blue Phosphorescent Organic Light-Emitting Diodes, Chemistry of Materials, 2010, vol. 22, No. 7, p. 2403-2410, Scheme 1,2.
(Continued)

*Primary Examiner* — Gregory Clark
(74) *Attorney, Agent, or Firm* — Foley & Lardner LLP

(57) ABSTRACT

An aromatic heterocyclic derivative represented by the following formula (1)-1 or (1)-2:

$$A\!-\!\!\left[Cz\right]_n \quad (1)\text{-}1$$

$$(A\!-\!\!-B)\!\!-\!\!\left[Cz\right]_n \quad (1)\text{-}2$$

wherein in the formula (1)-1 or (1)-2,
A is a substituted or unsubstituted nitrogen-containing heterocyclic group including 2 to 30 ring carbon atoms;
B is a substituted or unsubstituted aromatic hydrocarbon group including 6 to 30 ring carbon atoms or a substituted or unsubstituted aromatic heterocyclic group including 2 to 30 ring carbon atoms;
n is an integer of 2 or more; and
(Continued)

Czs are independently an aromatic heterocyclic group including a predetermined structure.

32 Claims, 3 Drawing Sheets

(51) Int. Cl.
  *C07D 405/14* (2006.01)
  *C07D 403/14* (2006.01)
  *C09K 11/06* (2006.01)

(52) U.S. Cl.
  CPC .......... *C09K 11/06* (2013.01); H01L 51/0067 (2013.01); H01L 51/0073 (2013.01); *C09K 2211/1007* (2013.01); *C09K 2211/1011* (2013.01); *C09K 2211/1025* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0085* (2013.01); *H01L 51/5016* (2013.01)

(56) References Cited

U.S. PATENT DOCUMENTS

| | | |
|---|---|---|
| 2006/0257684 A1 | 11/2006 | Arakane et al. |
| 2007/0052346 A1 | 3/2007 | Iwakuma et al. |
| 2007/0054151 A1 | 3/2007 | Iwakuma et al. |
| 2007/0069638 A1 | 3/2007 | Matsuura et al. |
| 2007/0104976 A1 | 5/2007 | Iwakuma et al. |
| 2007/0128467 A1 | 6/2007 | Iwakuma et al. |
| 2007/0172698 A1 | 7/2007 | Iwakuma et al. |
| 2007/0190355 A1 | 8/2007 | Ikeda et al. |
| 2007/0224448 A1* | 9/2007 | Ikeda ................ C09K 11/06 428/690 |
| 2007/0257600 A1 | 11/2007 | Matsuura et al. |
| 2007/0296328 A1 | 12/2007 | Matsuura et al. |
| 2008/0145699 A1* | 6/2008 | Yabe .................. C07D 209/86 428/690 |
| 2008/0206597 A1 | 8/2008 | Iwakuma |
| 2009/0102363 A1 | 4/2009 | Haga et al. |
| 2009/0134784 A1 | 5/2009 | Lin et al. |
| 2009/0191426 A2 | 7/2009 | Yabe et al. |
| 2009/0236973 A1 | 9/2009 | Yabe et al. |
| 2009/0243473 A1 | 10/2009 | Iwakuma et al. |
| 2010/0012931 A1 | 1/2010 | Kato et al. |
| 2010/0044689 A1 | 2/2010 | Nishimura et al. |
| 2010/0219404 A1 | 9/2010 | Endo et al. |
| 2010/0270539 A1 | 10/2010 | Nishimura et al. |
| 2010/0314644 A1 | 12/2010 | Nishimura et al. |
| 2011/0049483 A1 | 3/2011 | Nishimura et al. |
| 2011/0291081 A1 | 12/2011 | Inoue et al. |
| 2011/0309337 A1 | 12/2011 | Nishimura et al. |
| 2012/0001160 A1 | 1/2012 | Iwakuma et al. |
| 2012/0126209 A1 | 5/2012 | Kawamura et al. |
| 2012/0126217 A1 | 5/2012 | Yoshida et al. |
| 2012/0126692 A1* | 5/2012 | Ise ..................... C09K 11/06 313/504 |
| 2012/0211736 A1 | 8/2012 | Kim et al. |
| 2012/0305900 A1 | 12/2012 | Kim et al. |
| 2013/0020563 A1 | 1/2013 | Kato et al. |
| 2013/0056720 A1 | 3/2013 | Kim et al. |

FOREIGN PATENT DOCUMENTS

| | | | |
|---|---|---|---|
| JP | 2003-151774 A | 5/2003 | |
| JP | 2004-171808 | * 6/2004 | ............. C09K 11/06 |
| JP | 2006-076901 A | 3/2006 | |
| JP | 2006-131796 A | 5/2006 | |
| JP | 2007-077033 A | 3/2007 | |
| JP | 2007-220721 | 8/2007 | |
| JP | 2008-135498 A | 6/2008 | |
| JP | 2008-147400 | 6/2008 | |
| JP | 2008-147424 | 6/2008 | |
| JP | 2008-147426 | 6/2008 | |
| JP | 2008-214307 A | 9/2008 | |
| JP | 2008-252094 | 10/2008 | |
| JP | 2009-021336 A | 1/2009 | |
| JP | 2009-152528 | 7/2009 | |
| JP | 2009-152529 | 7/2009 | |
| JP | 2009-155300 | 7/2009 | |
| JP | 2009-158848 | 7/2009 | |
| JP | 2009-218547 | 9/2009 | |
| JP | 2009-267255 | 11/2009 | |
| JP | 4357781 B2 | 11/2009 | |
| JP | 2010-040830 A | 2/2010 | |
| JP | 2010-114180 | 5/2010 | |
| JP | 4474493 B1 | 6/2010 | |
| JP | 2010-212676 A | 9/2010 | |
| JP | 2010-238880 A | 10/2010 | |
| JP | 2010-245061 | 10/2010 | |
| JP | 2012-062450 | 3/2012 | |
| KR | 10-2010-0077675 A | 7/2010 | |
| KR | 20100075079 A | 7/2010 | |
| WO | WO-03/080760 A1 | 10/2003 | |
| WO | WO-2005/076669 A1 | 8/2005 | |
| WO | WO-2008/123189 A1 | 10/2008 | |
| WO | WO-2009/008347 A1 | 1/2009 | |
| WO | WO-2009/008359 A1 | 1/2009 | |
| WO | WO-2009/031855 A1 | 3/2009 | |
| WO | WO-2009/060780 A1 | 5/2009 | |
| WO | WO-2009/064661 A1 | 5/2009 | |
| WO | WO-2009/104708 A1 | 8/2009 | |
| WO | WO-2010/126270 A1 | 11/2010 | |

OTHER PUBLICATIONS

International Search Report corresponding to International Application No. PCT/JP2011/007071 dated Feb. 14, 2012.

English-language translation of Written Opinion of the International Searching Authority corresponding to International Application No. PCT/JP2011/007071 dated Jul. 4, 2013.

Guo-Liang Feng et al., "Synthesis and Optical Properties of Starburst Carbazoles Based on 9-Phenylcarbazole Core," Synlett, vol. 2006, No. 17, pp. 2841-2845, Oct. 1, 2006.

Extended European Search Report dated May 23, 2014 issued in European Application No. 11851955.2.

* cited by examiner

AROMATIC HETEROCYCLE DERIVATIVE AND ORGANIC ELECTROLUMINESCENT ELEMENT USING SAME

TECHNICAL FIELD

The invention relates to a novel aromatic heterocyclic derivative, a material for an organic electroluminescence device, and an organic electroluminescence device using the same.

BACKGROUND ART

An electroluminescence device comprising organic thin film layers including an emitting layer between an anode and a cathode which emits light from exciton energy generated by recombine of holes and electrons injected into the emitting layer has been known (see Patent Documents 1 to 8, for example).

Such an organic electroluminescence device is expected as an emitting device having high luminous efficiency, better image quality, low power consumption and excellent thin-form design, utilizing the merits as a self-emitting device. For the formation of an emitting layer, the doping method in which a host is doped with an emitting material as a dopant is known.

In the emitting layer formed using the doping method, exitons can be generated from charges injected into a host efficiently. The exiton energy of generated exitons is transferred to a dopant, whereby highly efficient emission can be obtained from the dopant.

Recently, further studies have been made on the doping method and a suitable host material has been developed in order to improve the performance of an organic electroluminescence device. As an invention which describes such a host material, Patent Documents 1 to 8 can be given, for example. Patent Documents 1 to 8 describe compounds containing a carbazole skeleton and a nitrogen-containing aromatic ring in one molecule, and compounds containing a plurality of carbazole skeletons in one molecule, as shown in the following compounds I to VIII.

The compounds I and II described in Patent Document 1 each have a structure formed by bonding of a carbazole skeleton to a benzene ring and an electron deficient nitrogen-containing hetero aromatic ring structure. A carbazole skeleton has been known as a main skeleton of a hole-transporting material as represented by polyvinyl carbazole. In contrast, an electron deficient nitrogen-containing hetero-aromatic ring structure is known as a structure having a high electron-transporting ability. Therefore, compounds I and II described in Patent Document 1 is a material produced so as to balance the charge transport by combining a hole-transporting skeleton and an electron transporting skeleton.

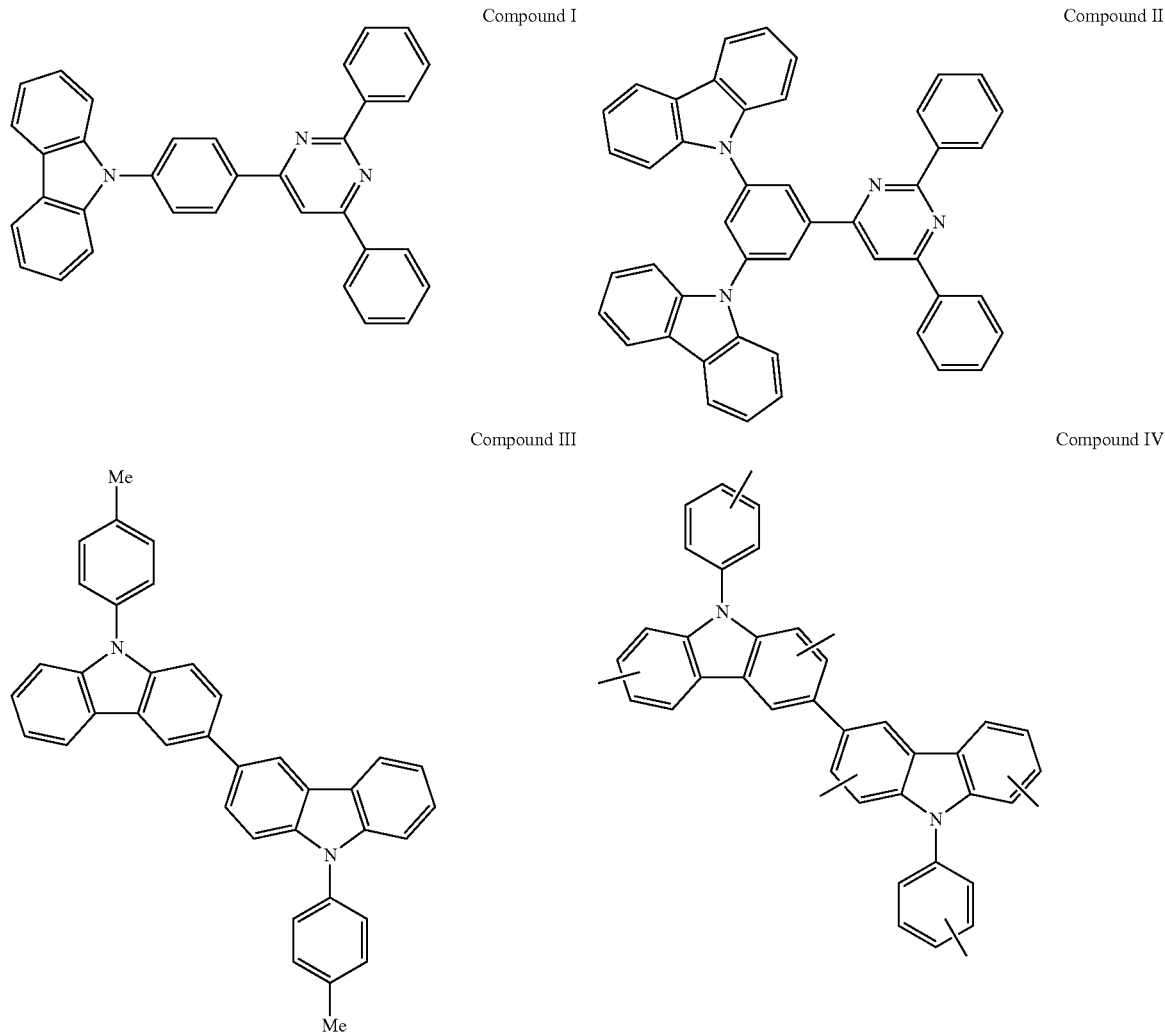

Compound I

Compound II

Compound III

Compound IV

Compound V
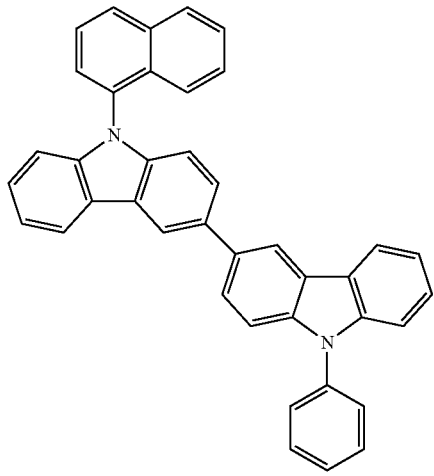
Compound VI
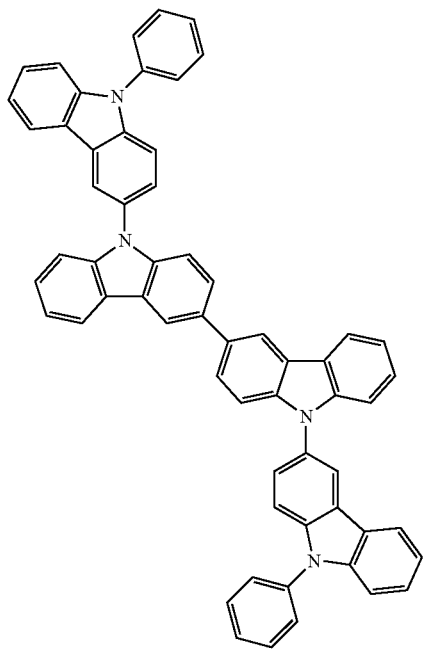
Compound VII
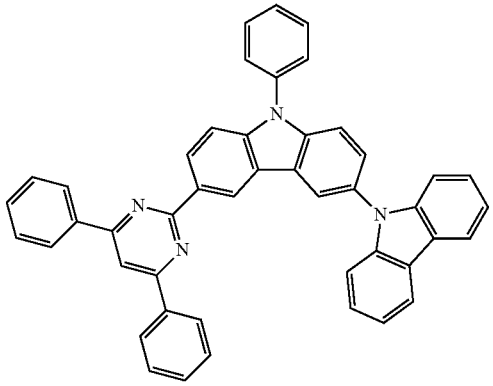
Compound VIII
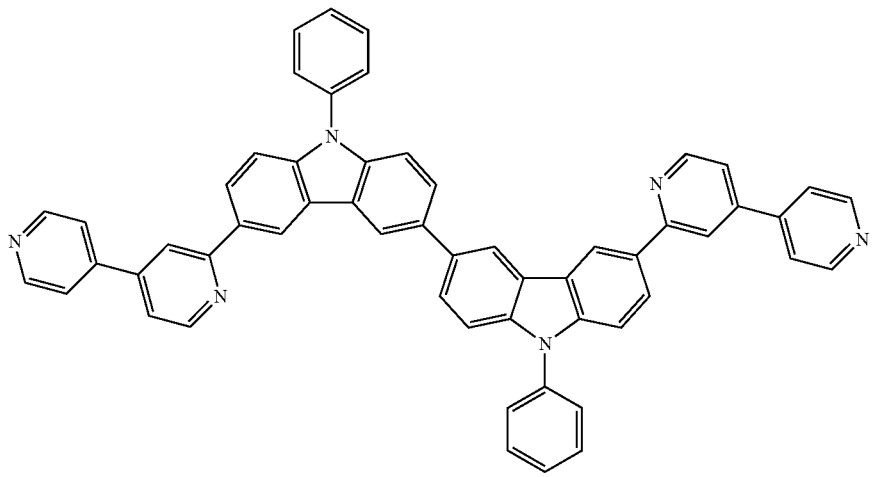

However, compound I has an insufficient hole-transporting ability due to the presence of only one carbazole skeleton, and hence, good emission properties cannot be obtained. In addition, although compound II has two carbazolyl groups, these carbazolyl groups are arranged with being separated into right and left with respect to the bond axis of a pyrimidine ring and a benzene ring (two conjugated aromatic rings). As a result, the overlapping of carbazole skeleton parts in a molecule is prevented, and hence sufficient hole-transporting ability cannot be obtained, whereby the position of charge recombination tends to locate towards to an anode. Therefore, good emission properties and life properties may not be obtained.

Under such circumstances, in order to develop sufficient hole-transporting ability by increasing the overlapping of molecules, incorporating a structure in which carbazole skeletons are linked into a molecule have been devised. For example, compounds III to VI described in Patent Documents 2 to 5 have the structure in which two carbazole skeletons are linked into a molecule. However, any of these compounds do not contain an electron deficient nitrogen-containing hetero aromatic ring structure. As a result, it is difficult to adjust carrier balance of holes and electrons, whereby good emission property cannot be obtained.

In addition, compound VII described in Patent Document 6 has an electron deficient nitrogen-containing hetero aromatic ring structure and a carbazole linking structure. However, the two carbazole structures are bonded through carbon on the third position and nitrogen. In this structure, two carbazole skeletons are twisted with each other, leading to deterioration of the planarity. As a result, the degree of overlapping between molecules becomes small, which leads to an insufficient hole-transporting ability. Therefore, no good emission property and life property may be obtained.

Compound VIII described in Patent Document 7 has a structure in which a bipyridyl group as a nitrogen-containing aromatic heterocyclic group is bonded to a benzene ring of a carbazole skeleton. Although this compound is used as a material for an electron-transporting layer, the performance of the phosphorescent host material is not disclosed. However, it is assumed that since the compound has a high electron-transporting ability, the carrier balance in the emitting layer is bad when used as a host material, whereby a good emission property cannot be obtained.

In Patent Document 8, a linking group is required to be present between a heterocyclic ring and a carbazole group, whereby compounds having desired properties may not be obtained (for example, having low solubility).

RELATED ART DOCUMENTS

Patent Documents

| | |
|---|---|
| [Patent Document 1] | WO2003-080760 |
| [Patent Document 2] | Japan Patent No. 3139321 |
| [Patent Document 3] | Japan Patent No. 4357781 |
| [Patent Document 4] | JP-A-2003-151774 |
| [Patent Document 5] | JP-A-2008-135498 |
| [Patent Document 6] | JP-A-2009-21336 |
| [Patent Document 7] | JP-A-2008-214307 |
| [Patent Document 8] | JP-A-2010-040830 |

SUMMARY OF THE INVENTION

Under the above-mentioned circumstances, an object of the invention is to provide a novel aromatic heterocyclic derivative which has a hole-transporting ability and an electron-transporting ability together and high carrier balance, a material for an organic electroluminescence device, and an organic electroluminescence device using the same. In particular, a material which has solubility and is suitable for application process is provided.

The inventors have been made intensive studies to achieve the above objects. As a result, it is found that an aromatic heterocyclic derivative comprising two or more carbazole derivative residues and a nitrogen-containing aromatic heterocyclic ring functions effectively in order to optimize a carrier balance in an emitting layer of an organic EL device, whereby the invention is achieved.

According to the invention, the following aromatic heterocyclic derivative, material for an organic electroluminescence device, material solution for an organic electroluminescence device and organic electroluminescence device using the same are provided.

1. An aromatic heterocyclic derivative represented by the following formula (1)-1 or (1)-2:

(1)-1

(1)-2 wherein
in the formula (1)-1 or (1)-2,
A is a substituted or unsubstituted nitrogen-containing heterocyclic group including 2 to 30 carbon atoms that form a ring (hereinafter referred to as "ring carbon atoms");
B is a substituted or unsubstituted aromatic hydrocarbon group including 6 to 30 ring carbon atoms or a substituted or unsubstituted aromatic heterocyclic group including 2 to 30 ring carbon atoms;
n is an integer of 2 or more; and
Czs are independently an aromatic heterocyclic group represented by the following formula (2) or (3); in the formula (1)-1, n of Czs may be independently bonded to any position of A, and when A includes a substituent, n of Czs may be bonded to any position of the substituent; and in the formula (1)-2, n of Czs may be independently bonded to any position of A or B, and when A or B includes a substituent, n of Czs may be bonded to any position of the substituent:

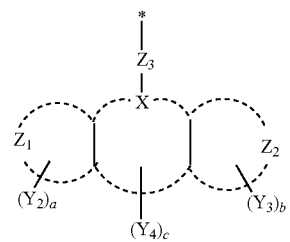

(2)

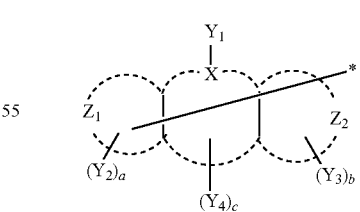

(3)

wherein
in the formula (2) or (3),
* indicates the bonding position to A or B;
$Z_1$ and $Z_2$ are independently atoms that form an aromatic hydrocarbon ring, an aromatic heterocyclic ring or an aliphatic ring, and are selected from the group consisting of carbon atoms, nitrogen atoms, oxygen atoms and sulfur atoms;

$Z_3$ is a single bond or a divalent linking group:

X is a nitrogen atom in the formula (2) and is a nitrogen atom, an oxygen atom or a sulfur atom in the formula (3):

the ring comprising X comprises atoms that form the ring and are selected from the group consisting of carbon atoms, nitrogen atoms, oxygen atoms and sulfur atoms in addition to X, the ring formed of $Z_1$ is an aromatic hydrocarbon ring, an aromatic heterocyclic ring or an aliphatic ring; the aromatic hydrocarbon ring, the aromatic heterocyclic ring or the aliphatic ring, and the ring comprising X share two carbon atoms which form each ring; and the ring formed of $Z_2$ is an aromatic hydrocarbon ring, an aromatic heterocyclic ring or an aliphatic ring; the aromatic hydrocarbon ring, the aromatic heterocyclic ring or the aliphatic ring, and the ring comprising X share two carbon atoms which form each ring;

$Y_1$, $Y_2$, $Y_3$ and $Y_4$ are independently selected from the group consisting of a hydrogen atom, a deuterium atom, a halogen atom, a cyano group, a substituted or unsubstituted linear, branched or cyclic alkyl group including 1 to 20 carbon atoms, a substituted or unsubstituted linear, branched or cyclic alkoxy group including 1 to 20 carbon atoms, a substituted or unsubstituted linear, branched or cyclic haloalkyl group including 1 to 20 carbon atoms, a substituted or unsubstituted linear, branched or cyclic haloalkoxy group including 1 to 20 carbon atoms, a substituted or unsubstituted linear, branched or cyclic alkylsilyl group including 1 to 10 carbon atoms, a substituted or unsubstituted arylsilyl group including 6 to 30 ring carbon atoms, a substituted or unsubstituted aromatic hydrocarbon group including 6 to 30 ring carbon atoms and a substituted or unsubstituted aromatic heterocyclic group including 2 to 30 ring carbon atoms, provided that in the formula (3), when X is an oxygen atom or a sulfur atom, $Y_1$ is not present:

a, b and c are independently an integer of 0, or 1 or more: and when $Y_2$, $Y_3$ and $Y_4$ are 2 or more, adjacent groups of $Y_2$s, $Y_3$s and $Y_4$s may be bonded to each other to form a substituted or unsubstituted, saturated or unsaturated ring structure:

provided that the following aromatic heterocyclic derivatives are excluded;

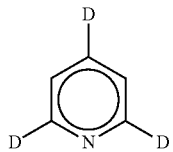

wherein Ds are independently any of the following groups (D1) to (D4):

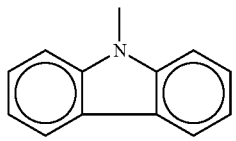
(D1)

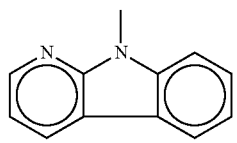
(D2)

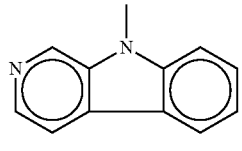
(D3)

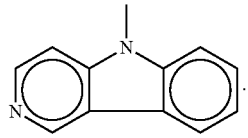
(D4)

2. The aromatic heterocyclic derivative according to 1, wherein the aromatic heterocyclic group represented by the formula (2) or (3) is selected from the group consisting of a substituted or unsubstituted carbazolyl group, a substituted or unsubstituted azacarbazolyl group, a substituted or unsubstituted benzcarbazolyl group, a substituted or unsubstituted hydrocarbazolyl group, a substituted or unsubstituted acrydinyl group, a substituted or unsubstituted indolyl group and a substituted or unsubstituted xanthenyl group.

3. The aromatic heterocyclic derivative according to 1 or 2, wherein $Y_2$ and $Y_3$ in the aromatic heterocyclic group represented by the formula (2) or (3) are independently a substituted or unsubstituted aromatic heterocyclic group including 2 to 30 ring carbon atoms.

4. The aromatic heterocyclic derivative according to 3, wherein $Y_2$ and $Y_3$ in the aromatic heterocyclic group represented by the formula (2) or (3) are independently selected from the group consisting of a substituted or unsubstituted carbazolyl group, a substituted or unsubstituted N-phenylcarbazolyl group and a substituted or unsubstituted dibenzofuranyl group.

5. The aromatic heterocyclic derivative according to any of 1 to 4, wherein n is 2 or 3.

6. The aromatic heterocyclic derivative according to any of 1 to 5, wherein A is selected from the group consisting of n-valent groups derived from a substituted or unsubstituted pyridine group, a substituted or unsubstituted pyrimidine group, a substituted or unsubstituted triazine group, a substituted or unsubstituted quinoline group, a substituted or unsubstituted isoquinoline group, a substituted or unsubstituted quinoxaline group or a substituted or unsubstituted quinazoline group.

7. A material for an organic electroluminescence device comprising the aromatic heterocyclic derivative according to any of 1 to 6.

8. A material solution for an organic electroluminescence device obtained by dissolving the aromatic heterocyclic derivative according to any of 1 to 6 in a solvent.

9. An organic electroluminescence device comprising:
an anode, a cathode, and
a plurality of organic thin film layers including an emitting layer between the anode and the cathode,
wherein at least one of the organic thin film layers comprises the aromatic heterocyclic derivative according to any of claims 1 to 6.

10. The organic electroluminescence device according to 9, wherein the emitting layer comprises the aromatic heterocyclic derivative according to any of 1 to 6 as a host material.

11. The organic electroluminescence device according to 9 or 10, wherein the emitting layer comprises a phosphorescent material.

12. The organic electroluminescence device according to 11, wherein the phosphorescent material is an ortho-metalized complex of a metal atom selected from the group consisting of iridium (Ir), osmium (Os) and platinum (Pt).

13. The organic electroluminescence device according to any of 9 to 12, comprising an electron-injecting layer between the cathode and the emitting layer, the electron-injecting layer comprising a nitrogen-containing ring derivative.

14. The organic electroluminescence device according to any of 9 to 13, comprising an electron-transporting layer between the cathode and the emitting layer, the electron-transporting layer comprising the aromatic heterocyclic derivative according to any of 1 to 6.

15. The organic electroluminescence device according to any of 9 to 14, comprising a hole-transporting layer between the anode and the emitting layer, the hole-transporting layer comprising the aromatic heterocyclic derivative according to any of 1 to 6.

16. The organic electroluminescence device according to any of 9 to 15, wherein a reducing dopant is added in the interface region between the cathode and the organic thin film layers.

According to the invention, an organic EL device having an excellent luminous efficiency and a prolonged life, an aromatic heterocyclic derivative which can realize the same, and a material for an organic EL device using the same can be provided.

If a material, for which the film-forming by deposition is impossible (for example, a compound with a large molecule weight or oligomers), is a soluble aromatic heterocyclic derivative, an organic EL device can be produced by film-forming technique using a solution obtained by dissolving a material.

MODE FOR CARRYING OUT THE INVENTION

Figure 1:
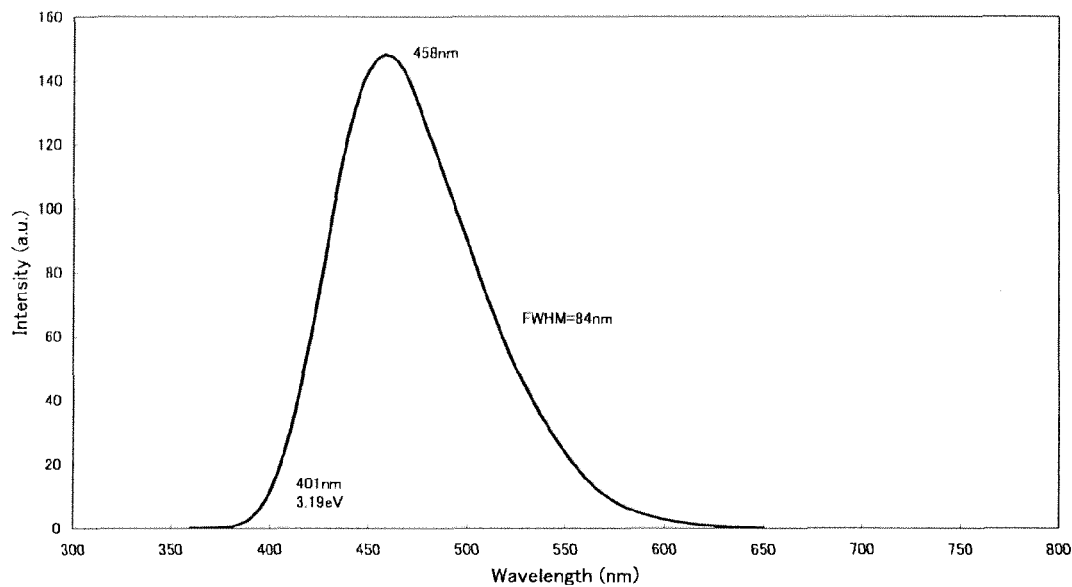
FIG. 1 is a chart showing a fluorescent spectrum of a thin film of the aromatic heterocyclic derivative H-2 of the invention.

I. An explanation will be given on an aromatic heterocyclic derivative represented by the following formula (1)-1 or (1)-2 (herein below, referred to as the "aromatic heterocyclic derivative of the invention").

 (1)-1

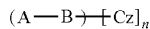 (1)-2 wherein
in the formula (1)-1 or (1)-2,
A is a substituted or unsubstituted nitrogen-containing heterocyclic group having 2 to 30 carbon atoms that form a ring (hereinafter referred to as the "ring carbon atoms");
B is a substituted or unsubstituted aromatic hydrocarbon group having 6 to 30 ring carbon atoms or a substituted or unsubstituted aromatic heterocyclic group having 2 to 30 ring carbon atoms;
n is an integer of 2 or more, preferably 2 or 3, and more preferably 2; and
Czs are independently an aromatic heterocyclic group represented by the following formula (2) or (3); in the formula (1)-1, n of Czs may be independently bonded to any position of A, and when A has a substituent, n of Czs may be bonded to any position of the substituent, and when A has a plurality of substituents, n of Czs may be independently bonded to any of the substituents, and may be bonded to any position of these substituents; and in the formula (1)-2, n of Czs may be independently bonded to A or B and may be bonded to any position of A or B, and when A or B has a substituent, n of Czs may be bonded to any position of the substituent, and when A or B has a plurality of substituents, n of Czs may be independently bonded to any of the substituents, and may be bonded to any position of these substituents.

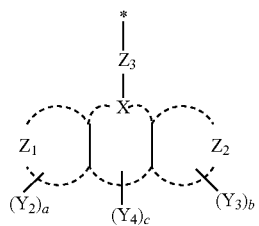 (2)

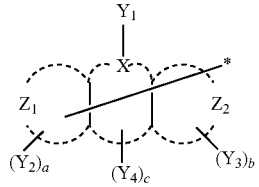 (3)

In the formula (2) or (3), "*" indicates the bonding position to A or B. The bonding position to A or B in the formula (3) may be either a ring including $Z_1$, a ring including X or a ring including $Z_2$.

The aromatic hydrocarbon group and the aromatic heterocyclic group in this specification include a fused aromatic hydrocarbon group and a fused aromatic heterocyclic group. Also, it includes one obtained by bonding of a monocycle and a fused ring by a single bond.

$Z_3$ is a single bond or a divalent linking group. Although no specific restrictions are imposed on the divalent linking group, a group derived from a substituted or unsubstituted aromatic hydrocarbon group having 6 to 25 ring carbon atoms or a group derived from a substituted or unsubstituted aromatic heterocyclic group having 2 to 25 ring carbon atoms or a group which is obtained by bonding these through a single bond is preferable. A substituted or unsubstituted phenyl group, a substituted or unsubstituted biphenyl group, a substituted or unsubstituted terphenyl group, a substituted or unsubstituted naphthyl group and a substituted or unsubstituted fluorenyl group are particularly preferable.

X is a nitrogen atom in the formula (2) and a nitrogen atom, an oxygen atom or a sulfur atom in the formula (3).

The ring containing X is formed of atoms necessary for forming an aromatic heterocyclic ring selected from a carbon atom, a nitrogen atom, an oxygen atom and a sulfur atom, in addition to X.

The aromatic hydrocarbon ring, the aromatic heterocyclic ring or the aliphatic ring formed by and the aromatic heterocyclic ring containing X share two carbon atoms forming each ring. The aromatic hydrocarbon ring, the aromatic heterocyclic ring or the aliphatic ring formed by $Z_2$ and the aromatic heterocyclic ring containing X share two carbon atoms forming each ring.

$Y_1$, $Y_2$, $Y_3$ and $Y_4$ are independently selected from the group consisting of a hydrogen atom, a deuterium atom, a halogen atom, a cyano group, a substituted or unsubstituted linear, branched or cyclic alkyl group having 1 to 20 carbon atoms, a substituted or unsubstituted linear, branched or cyclic alkoxy group having 1 to 20 carbon atoms, a substituted or unsubstituted linear, branched or cyclic haloalkyl group having 1 to 20 carbon atoms, a substituted or unsubstituted linear, branched or cyclic haloalkoxy group having 1 to 20 carbon atoms, a substituted or unsubstituted linear, branched or cyclic alkylsilyl group having 1 to 10 carbon atoms, a substituted or unsubstituted arylsilyl group having 6 to 30 ring carbon atoms, a substituted or unsubstituted aromatic hydrocarbon group having 6 to 30 ring carbon atoms and a substituted or unsubstituted aromatic heterocyclic group having 2 to 30 ring carbon atoms.

Of these, a substituted or unsubstituted aromatic hydrocarbon group having 6 to 30 ring carbon atoms or a substituted or unsubstituted aromatic heterocyclic group having 2 to 30 ring carbon atoms are preferable. A substituted or unsubstituted phenyl group, a substituted or unsubstituted biphenyl group, a substituted or unsubstituted terphenyl group, a substituted or unsubstituted naphthyl group, a substituted or unsubstituted fluorenyl group, a substituted or unsubstituted carbazolyl group, a substituted or unsubstituted dibenzofuranyl group and a substituted or unsubstituted dibenzothiophenyl group are more preferable. In particular, a substituted or unsubstituted N-phenyl-substituted carbazolyl group and a substituted or unsubstituted carbazolyl group are preferable.

In the formula (3), if X is an oxygen atom or a sulfur atom, no $Y_1$ is present.

a, b and c are independently 0 or an integer of 1 or more.

If $Y_2$, $Y_3$ and $Y_4$ are 2 or more, adjacent groups of $Y_2$, $Y_3$ and $Y_4$ may be bonded with each other to form a substituted or unsubstituted saturated or unsaturated ring structure.

However, the following aromatic heterocyclic derivative is excluded.

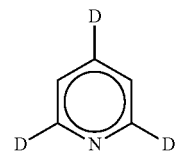

wherein Ds are independently any of the following groups (D1) to (D4).

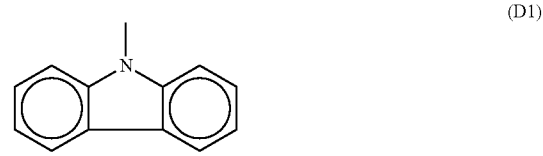

(D1)

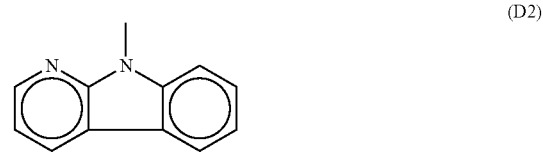

(D2)

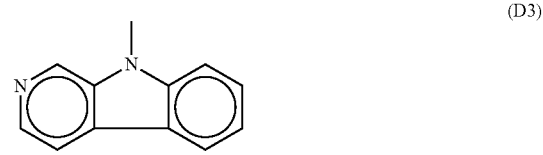

(D3)

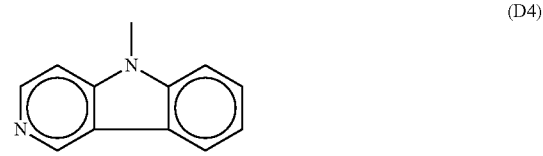

(D4)

Preferred examples of each group will be explained.

(1) A: Substituted or unsubstituted nitrogen-containing heterocyclic group having 2 to 30 ring carbon atoms An n-valent group derived from a nitrogen-containing aromatic ring selected from a pyrrole ring, a pyrazole ring, an imidazole ring, a triazole ring, a pyridine ring, a pyrimidine ring, a pyridazine ring, a pyrazine ring, a triazine ring, an indole ring, an indazole ring, a benzimidazole ring, a quinoline ring, an isoquinoline ring, a phthalazine ring, a naphthyridine ring, a cinnoline ring, a quinoxaline ring, a quinazoline ring, an imidazopyridine ring and the like, which are substituted or unsubstituted, are preferable. Further, an n-valent group derived from a pyridine ring, a pyrimidine ring, a triazine ring, a quinoline ring, an isoquinoline ring, a quinoxaline ring, a phthalazine ring or a quinazoline ring, which are substituted or unsubstituted, are preferable.

In particular, an n-valent group derived from a substituted or unsubstituted pyrimidine ring or a substituted or unsubstituted triazine ring is preferable.

It is more preferred that the n-valent group derived from a pyridine ring, a pyrimidine ring, a triazine ring, a quinoline ring, an isoquinoline ring, a quinoxaline ring, a phthalazine ring or a quinazoline ring be independently represented by the following formula.

Here, Y is a substituent. Examples of the substituent will be given later. Plural Ys may be present. If plural Ys are present, the plural Ys may be the same or different. Of the examples of the substituent given later, a substituted or unsubstituted aromatic hydrocarbon group having 6 to 30 ring carbon atoms is preferable as Y, with a substituted or unsubstituted phenyl group, a substituted or unsubstituted biphenyl group, a substituted or unsubstituted terphenyl group, a substituted or unsubstituted naphthyl group and a substituted or unsubstituted fluorenyl group being particularly preferable. A substituted or unsubstituted aromatic heterocyclic group having 2 to 30 ring carbon atoms is preferable, with a substituted or unsubstituted carbazolyl group or a substituted or unsubstituted dibenzofuranyl group being particularly preferable.

When Cz is bonded to A, although the bonding position may be any of the positions of A, the position indicated by * in the following formula is preferable.

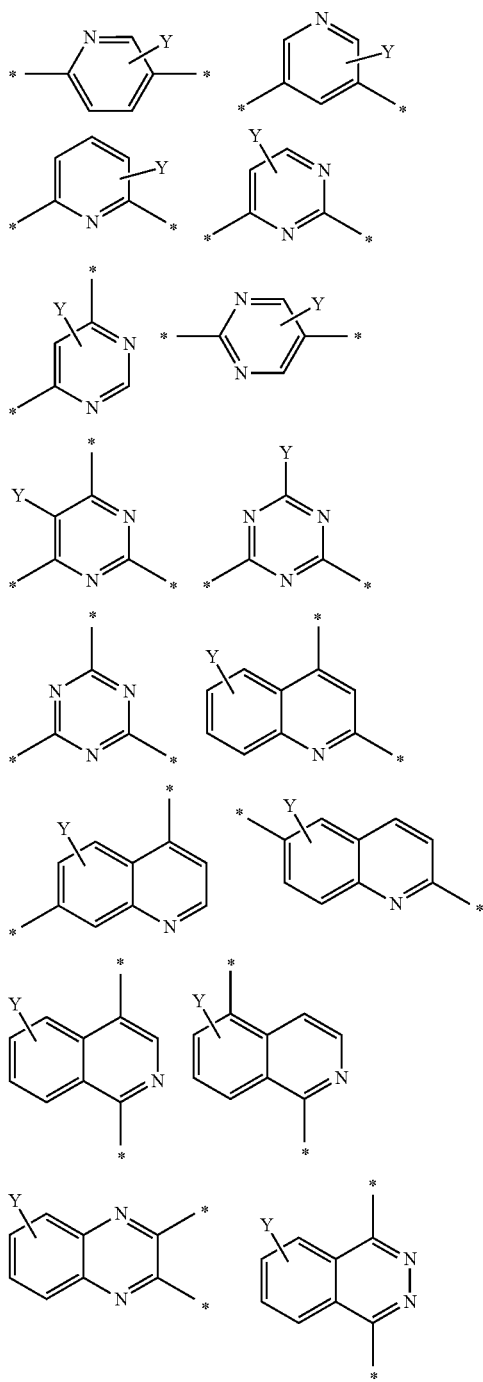

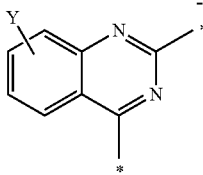

(2) B: A substituted or unsubstituted aromatic hydrocarbon group having 6 to 30 ring carbon atoms or a substituted or unsubstituted aromatic heterocyclic group having 2 to 30 ring carbon atoms As an aromatic hydrocarbon group having 6 to 30 ring carbon atoms, a group derived from an aromatic hydrocarbon group such as benzene, naphthalene, biphenyl, terphenyl, fluorene, phenanthrene, triphenylene, perylene, chrysene, fluoranthene, benzofluorene, benzotriphenylene, benzochrysene and anthracene can be given. A group derived from benzene, naphthalene, biphenyl, terphenyl, fluorene and phenanthrene is preferable.

As the aromatic heterocyclic group having 2 to 30 ring carbon atoms, a group or the like formed from a pyrrolyl group, a pyrazinyl group, a pyridinyl group, an indolyl group, an isoindolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenanthridinyl group, an acrydinyl group, a phenanthrolinyl group, a thienyl group, a pyridine ring, a pyrazine ring, a pyrimidine ring, a pyridazine ring, a triazine ring, an indole ring, a quinoline ring, an acridine ring, a pyrrolidine ring, a dioxane ring, a piperidine ring, a morpholine ring, a piperadine ring, a carbazole ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, and a dibenzofuran ring can be given. A group formed from a pyridine ring, a pyrazine ring, a pyrimidine ring, a pyridazine ring and a triazine ring is preferable.

When Cz is bonded to B, it may be bonded to any of the positions of B.

(3) Cz: Aromatic heterocyclic group represented by the formula (2) or (3)

Specifically, the following groups i) to vii) are preferably given.

i) Carbazolyl-Derived Group

A group represented by the following formulas (4) to (6) is preferable. In the following formulas, * indicates the bonding position to A or B.

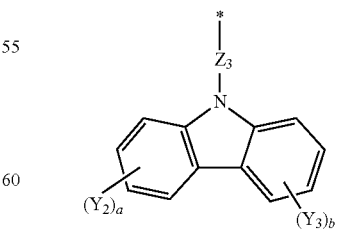

(4)

In the formula (4), $Y_2$ and $Y_3$ are independently an atom or a group selected from the group consisting of
a hydrogen atom, a deuterium atom, a fluorine atom, a cyano group, a substituted or unsubstituted linear, branched or cyclic alkyl group having 1 to 20 carbon atoms, a substituted or unsubstituted linear, branched or cyclic alkoxy group having 1 to 20 carbon atoms, a substituted or unsubstituted linear, branched or cyclic haloalkyl group having 1 to 20 carbon atoms, a substituted or unsubstituted linear, branched or cyclic haloalkoxy group having 1 to 20 carbon atoms, a substituted or unsubstituted linear, branched or cyclic alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms and a substituted or unsubstituted aromatic heterocyclic group having 2 to 10 ring carbon atoms.

Of these, it is preferred that $Y_2$ and $Y_3$ be independently a substituted or unsubstituted aromatic heterocyclic group having 2 to 30 ring carbon atoms. Specifically, a substituted or unsubstituted carbazolyl group, a substituted or unsubstituted N-phenylcarbazolyl group or a substituted or unsubstituted dibenzofuranyl group is preferable.

As for the positions at which $Y_2$ and $Y_3$ bond to the group represented by the formula (4), they may be any of the positions of $Y_2$ and $Y_3$.

$Z_3$ is a single bond or a divalent linking group. Specific examples of $Z_3$ if $Z_3$ is a divalent linking group include:

an unsubstituted linear, branched or cyclic alkylene group having 1 to 20 carbon atoms;

a substituted or unsubstituted linear, branched or cyclic alkyleneoxy group having 1 to 20 carbon atoms;

a substituted or unsubstituted linear, branched or cyclic haloalkylene group having 1 to 20 carbon atoms;

a substituted or unsubstituted linear, branched or cyclic haloalkoxylene group having 1 to 20 carbon atoms;

a substituted or unsubstituted linear, branched or cyclic alkylsilylene group having 1 to 10 carbon atoms;

a substituted or unsubstituted arylsilylene group having 6 to 30 carbon atoms;

a substituted or unsubstituted aromatic hydrocarbon group having 6 to 30 ring carbon atoms; and a substituted or unsubstituted aromatic heterocyclic group having 2 to 10 ring carbon atoms.

Of these, a substituted or unsubstituted phenylene group, a substituted or unsubstituted biphenylene group, a substituted or unsubstituted terphenylene group, a substituted or unsubstituted naphthylene group and a substituted or unsubstituted fluorenylene group are particularly preferable.

a and b are independently 0 or an integer of 1 or more. It is preferred that a and b be 0 or 1.

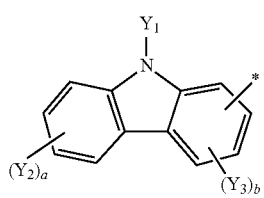

(5)

In the formula (5), $Y_2$ and $Y_3$ are independently as exemplified in the formula (4). $Y_2$ and $Y_3$ are preferably a substituted or unsubstituted aromatic heterocyclic group having 2 to 30 ring carbon atoms. Specifically, a substituted or unsubstituted carbazolyl group, a substituted or unsubstituted N-phenylcarbazolyl group or a substituted or unsubstituted dibenzofuranyl group are preferable. As for the positions at which $Y_2$ and $Y_3$ bond to the group represented by the formula (5), they may be any of the positions in $Y_2$ and $Y_3$.

$Y_1$ is the same as $Y_2$ and $Y_3$ shown in the formula (4). It is preferred that $Y_1$ be a substituted or unsubstituted aromatic hydrocarbon group having 6 to 30 ring carbon atoms or a substituted or unsubstituted aromatic heterocyclic group having 2 to 10 ring carbon atoms. As for the positions at which $Y_1$ bonds to the nitrogen atom in the formula (5), they may be any of the positions in $Y_1$.

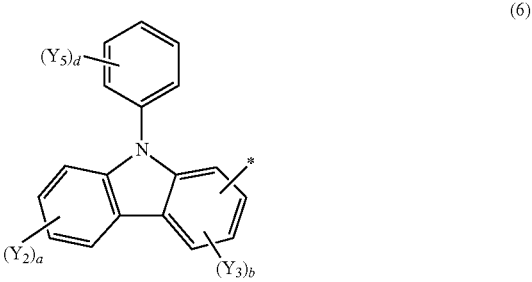

(6)

In the formula (6), $Y_2$ and $Y_3$ are independently as mentioned in the formula (4). Further, as $Y_2$ or $Y_3$, a substituted or unsubstituted aromatic heterocyclic group having 2 to 30 ring carbon atoms is preferable. Specifically, a substituted or unsubstituted carbazolyl group, a substituted or unsubstituted N-phenylcarbazolyl group or a substituted or unsubstituted dibenzofuranyl group is preferable. As for the position at which these $Y_2$ and $Y_3$ are bonded to the group in the formula (6), it may be any of the positions in $Y_2$ and $Y_3$.

$Y_5$ is the same as those in $Y_2$ and $Y_3$ represented in the formula (4). As for the position at which $Y_5$ bonds to the phenyl group in the formula (6), it may be any of the positions in $Y_5$.

In the formulas (4) to (6), a and b are independently an integer of 0 to 4 and d is an integer of 0 to 5.

ii) Azacarbazolyl Derivative Group

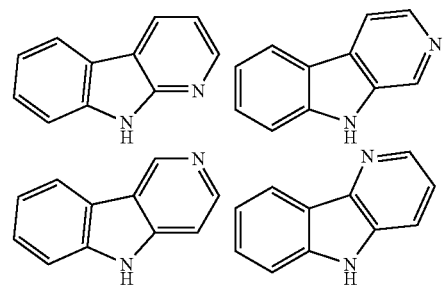

The bonding position to A may be arbitral. That is, it may be bonded to A through any of carbon atoms and may be bonded to A through any of nitrogen atoms.

The above-mentioned azacarbazolyl derivative group may have a substituent (mentioned later) on any of carbon atoms or any of nitrogen atoms.

iii) Benzcarbazolyl Derivative Group

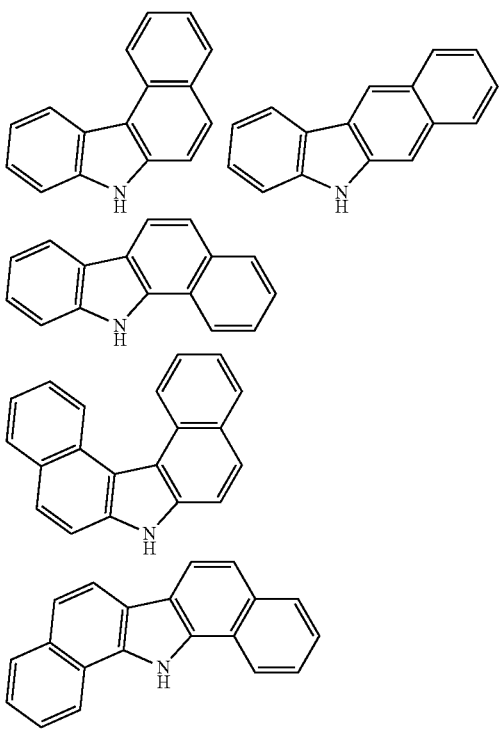

The bonding position to A may be arbitral. That is, it may be bonded to A through any of carbon atoms or may be bonded to A through any of nitrogen atoms.

The above-mentioned hydrocarbazolyl derivative group may have a substituent (mentioned later) on any of carbon atoms or any of nitrogen atoms.

iv) Hydrocarbazolyl Derivative Group

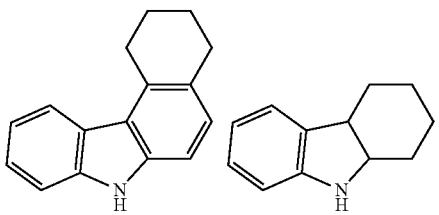

The bonding position to A may be arbitral. That is, it may be bonded to A through any of carbon atoms or may be bonded to A through any of nitrogen atoms.

The above-mentioned benzcarbazolyl derivative group may have a substituent (mentioned later) on any of carbon atoms or any of nitrogen atoms.

v) Acrydinyl Derivative Group

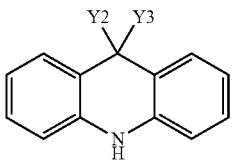

The bonding position to A is arbitral. That is, it may be bonded to A through any of carbon atoms or may be bonded to A through any of nitrogen atoms.

In the above formula, $Y_2$ and $Y_3$ are independently as mentioned in formula (4).

The above-mentioned hydrocarbazolyl derivative group may have a substituent (mentioned later) on any of carbon atoms or any of nitrogen atoms.

vi) Indolyl Group

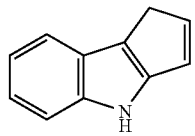 [SMILES: C1=Cc2[nH]c3ccccc3c2C1]

The bonding position to A is arbitral. That is, it may be bonded to A through any of carbon atoms or may be bonded to A through any of nitrogen atoms.

The above-mentioned hydrocarbazolyl derivative group may have a substituent (mentioned later) on any of carbon atoms or any of nitrogen atoms.

vii) Xanthenyl Group

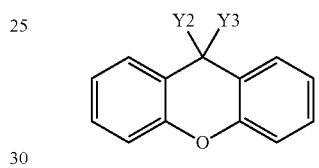

The bonding position to A is arbitral. That is, it may be bonded to A through any of carbon atoms.

In the formula, $Y_2$ and $Y_3$ are independently as mentioned in the formula (4).

The xanthenyl derivative group mentioned above may have a substituent (mentioned later) on any of carbon atoms.

(4) It is preferred that the aromatic heterocyclic group shown in i) to vii) above have an aromatic heterocyclic ring group as the substituent. In particular, it is preferred that the aromatic heterocyclic ring group have a substituted or unsubstituted carbazolyl group or a substituted or unsubstituted dibenzofuranyl group. No specific restrictions are imposed, for the substituent or the aromatic heterocyclic ring given i) to vii) above, on the position at which the substituent bonds to the aromatic heterocyclic ring group given i) to vii) above.

It is preferred that Cz represented by the formula (2) or (3) be selected from a group consisting of a substituted or unsubstituted carbazolyl group, a substituted or unsubstituted azacarbazolyl group, a substituted or unsubstituted benzcarbazolyl group, a substituted or unsubstituted hydrocarbazolyl group, a substituted or unsubstituted acrydinyl group, a substituted or unsubstituted indolyl group and a substituted or unsubstituted xantenyl group.

$Y_2$ and/or $Y_3$ in Cz represented by the formula (2) or (3) are preferably a substituted or unsubstituted aromatic heterocyclic group having 2 to 30 ring carbon atoms.

(5) Explanation on each group

As the linear, branched or cyclic alkyl group having 1 to 20 carbon atoms, a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecycl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, a 3-methylpentyl group, a cyclopentyl group, a cyclohexyl group, a cyclooctyl group, a 3,5-tetramethylcyclohexyl group or the like can be given.

As the linear, branched or cyclic alkoxy group having 1 to 20 carbon atoms, an alkoxy group having 1 to 6 carbon atoms is preferable. Specific examples thereof include a methoxy group, an ethoxy group, a propoxy group, a butoxy group, a pentyloxy group, a hexyloxy group or the like can be given.

As the linear, branched or cyclic haloalkyl group having 1 to 20 carbon atoms, one obtained by substituting the alkyl group having 1 to 20 carbon atoms with one or more halogens can be given, for example.

As the linear, branched or cyclic haloalkoxy group having 1 to 20 carbon atoms, one obtained by substituting the alkoxy group having 1 to 20 carbon atoms with one or more halogens can be given, for example.

As the linear, branched or cyclic alkylsilyl group having 1 to 10 carbon atoms, a trimethylsilyl group, a triethylsilyl group, a tributylsilyl group, a dimethylethylsilyl group, a dimethylisopropylsilyl group, a dimethylpropylsilyl group, a dimethylbutylsilyl group, a dimethyl-tert-butylsilyl group, a diethylisopropylsilyl group or the like can be given, for example.

As the arylsilyl group having 6 to 30 ring carbon atoms, a phenyldimethylsilyl group, a diphenylmethylsilyl group, a diphenyl-tert-butylsilyl group, a triphenylsilyl group or the like can be given, for example.

As the aromatic hydrocarbon group having 6 to 30 ring carbon atoms, a group derived from an aromatic hydrocarbon compound such as benzene, naphthalene, biphenyl, terphenyl, fluorene, phenanthrene, triphenylene, perylene, chrysene, fluoranthene, benzofluorene, benzotriphenylene, benzochrysene and anthracene. In particular, a group derived from benzene, naphthalene, biphenyl, terphenyl and fluorene is preferable.

As the aromatic heterocyclic ring group having 2 to 30 ring carbon atoms, a group or the like formed by a pyrrolyl group, a pyrazinyl group, a pyridinyl group, an indolyl group, an isoindolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenanthrydinyl group, an acridinyl group, a phenanthrolinyl group, a thienyl group, a pyridine ring, a pyrazine ring, a pyrimidine ring, a pyridazine ring, a triazine ring, an indole ring, a quinoline ring, an acrydine ring, a pyrrolidine ring, a dioxane ring, a piperidine ring, a morpholine ring, a piperazine ring, a carbazole ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyrane ring, a dibenzofuran ring and the like can be given. A carbazolyl group, a dibenzofuranyl group and a dibenzothiophenyl group are particularly preferable. Of these, an N-phenylcarbazolyl group is preferable.

(6) Explanation on the substituent

In the specification, as the substituent in the "substituted or unsubstituted" or the "substituent", the groups exemplified in the above-mentioned "explanation on each group" can be given. No specific restrictions are imposed on the position at which the substituent bonds to each group. That is, any of the positions in the substituent may be bonded in any of the positions of each group.

(7) Preferable examples of the aromatic heterocyclic derivative represented by the formula (1)-1 or (1)-2 are as follows:

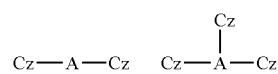

(8) The aromatic heterocyclic derivative given below is included in the above formula (1), but excluded from the aromatic heterocyclic derivative of the invention.

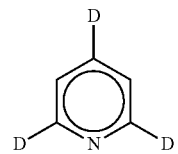

wherein Ds are independently any of the following (D1) to (D4).

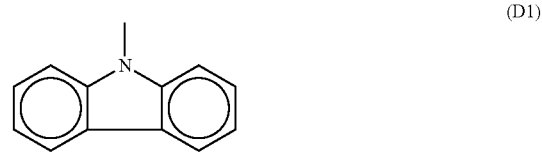

(D1)

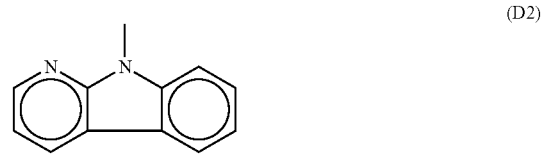

(D2)

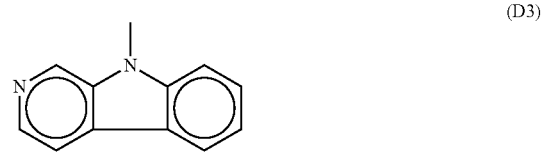

(D3)

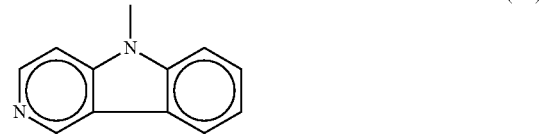

(D4)

(9) Method for producing an aromatic heterocyclic derivative of the invention

No specific restrictions are imposed on the method for producing an aromatic heterocyclic derivative of the invention. For the production, it is possible to use an Ullmann reaction or a Buchwald reaction of a halogen compound and carbazole, a method in which hydrogen of carbazole is withdrawn by a base such as sodium hydride (NaH) or potassium carbonate to form a salt, followed by a reaction with a halogen compound or the like.

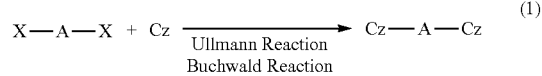

(1)

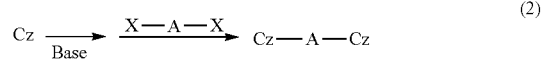

(2)

(10) Of the aromatic heterocyclic derivatives of the invention, the following compounds are not preferable.

i) Of the Aromatic Heterocyclic Derivatives Represented by the Formula (1), the Following Compounds:

wherein $Q_1$ is a substituent. In particular, $Q_1$ is a phenyl group having a substituent (a carbazolyl group, in particular), a fluorenyl group having a substituent, a pyridyl group or a carbazolyl group having a substituent (a carbazolyl group, a phenyl group and/or a pyridyl group, in particular).

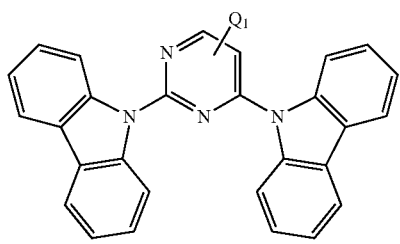

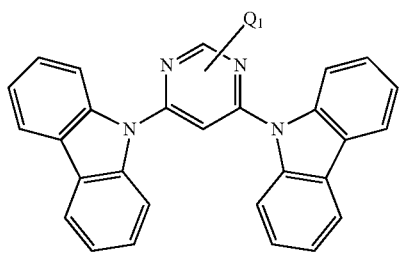

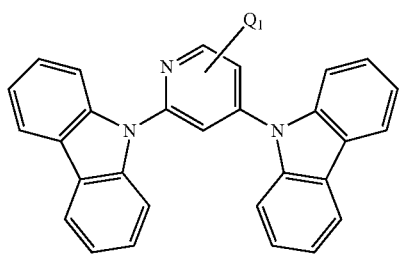

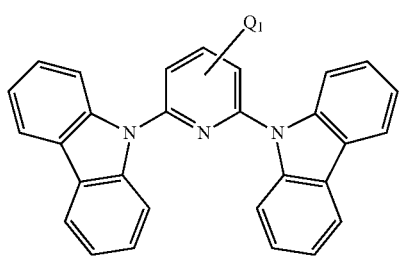

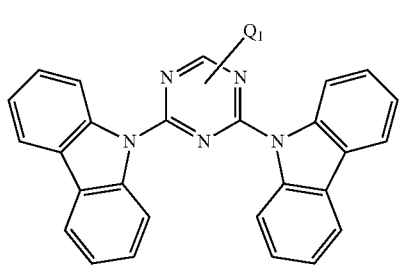

ii) Aromatic Heterocyclic Derivative Represented by the Formula (1)

$Q_2$ is a hydrogen atom or a substituent. In particular, $Q_2$ is a pyrimidyl group having a substituent (a phenyl group, in particular).

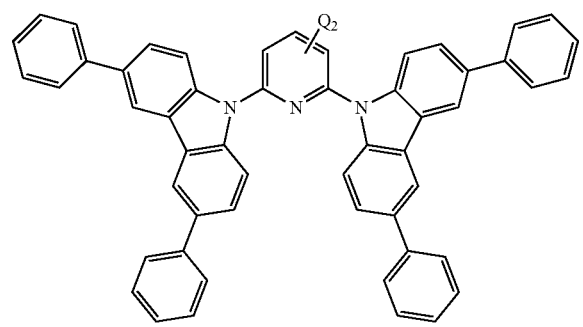

iii) Specific Compounds which are not Preferable Include the Following:

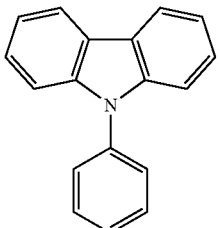

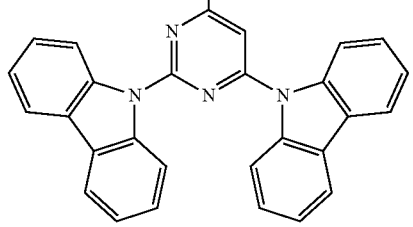

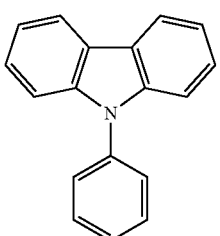

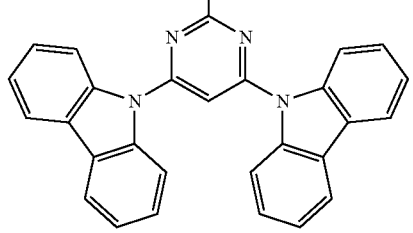

-continued
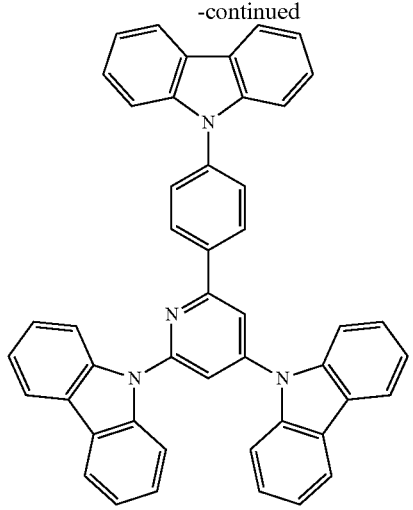
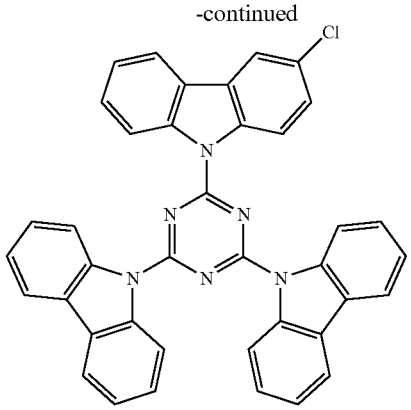
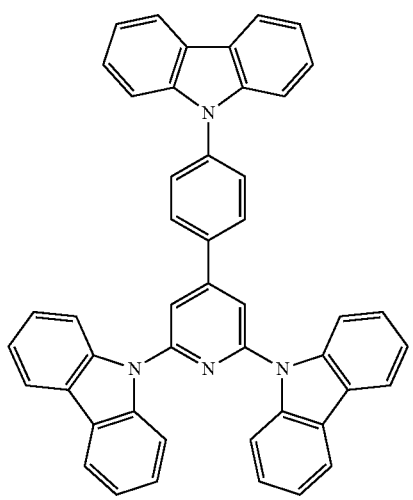
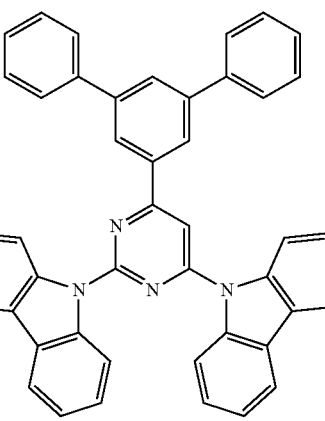
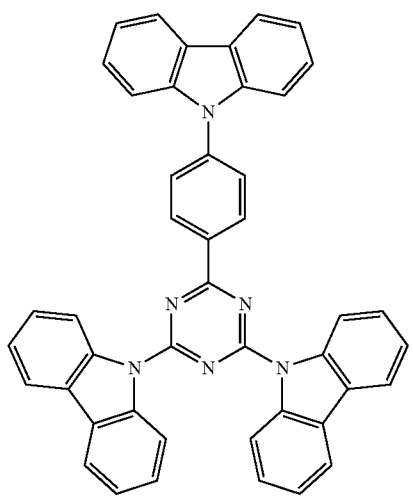
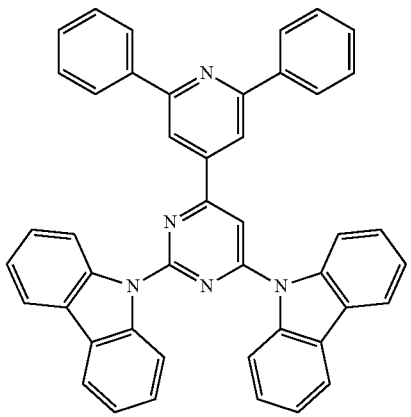

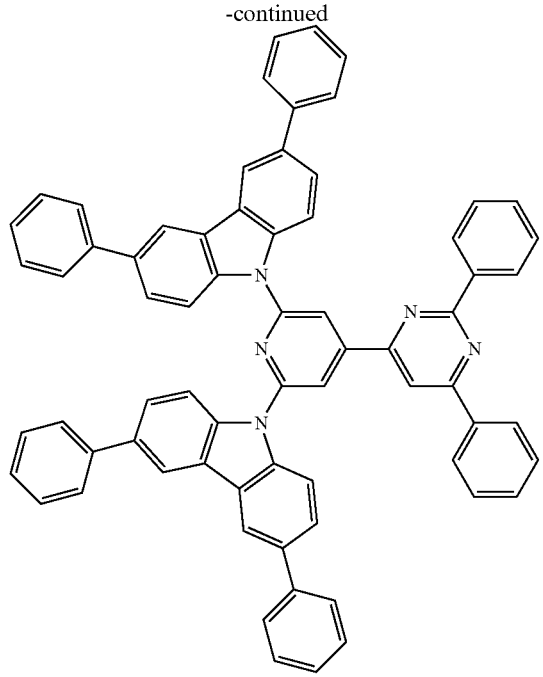
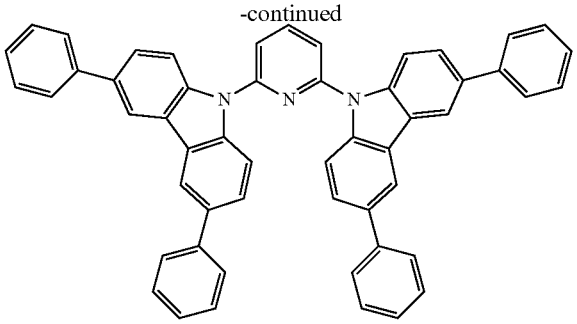
II. Examples of the Aromatic Heterocyclic Derivative of the Invention
Specific examples of the aromatic heterocyclic derivative of the invention will be given below.
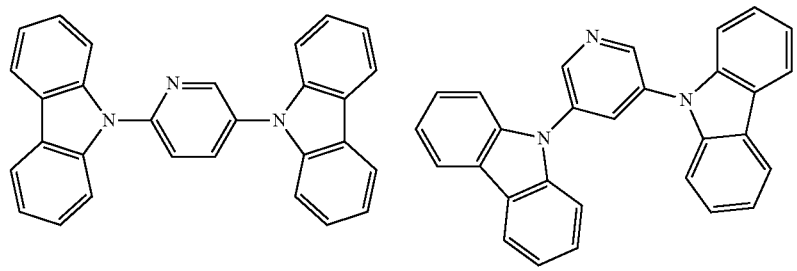
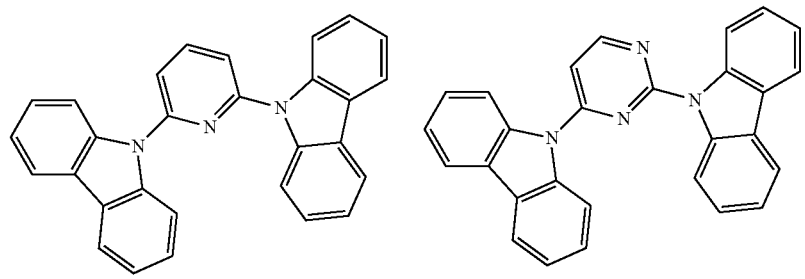
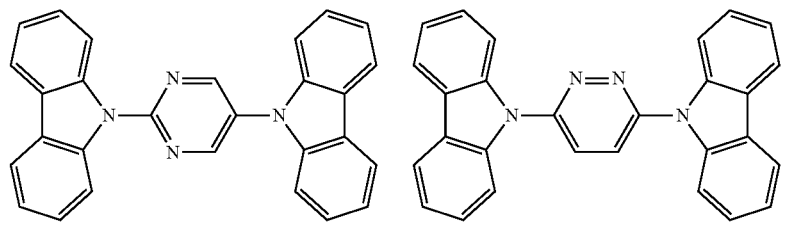
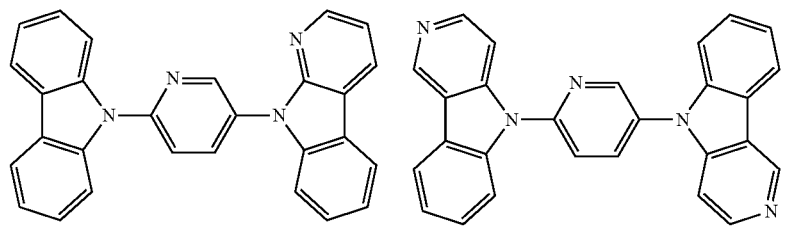

-continued
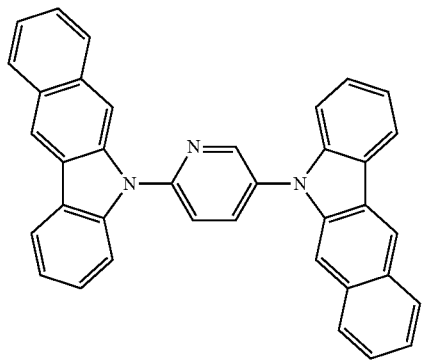
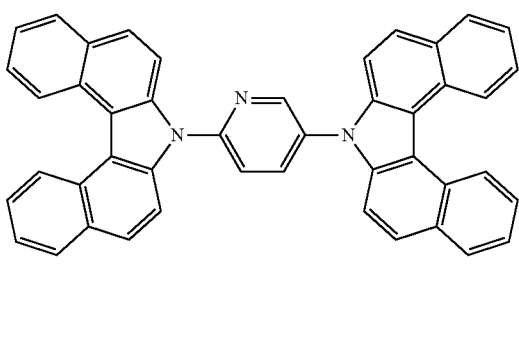
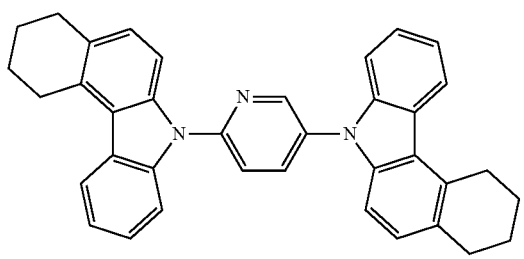
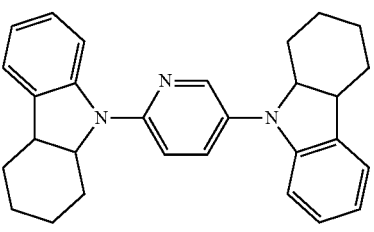
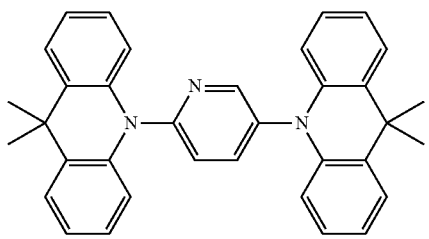
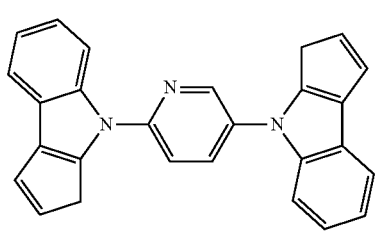
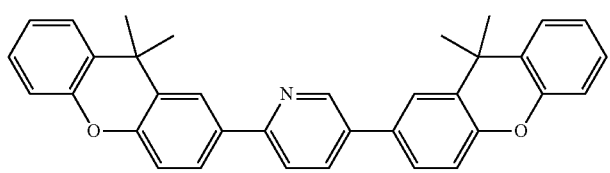
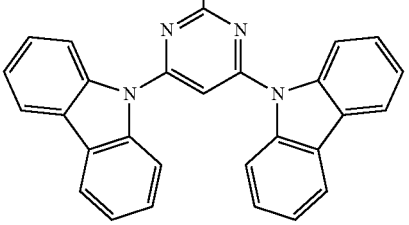
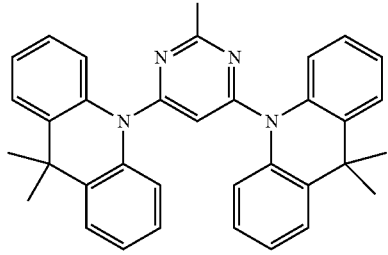
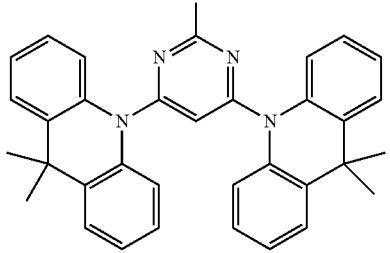

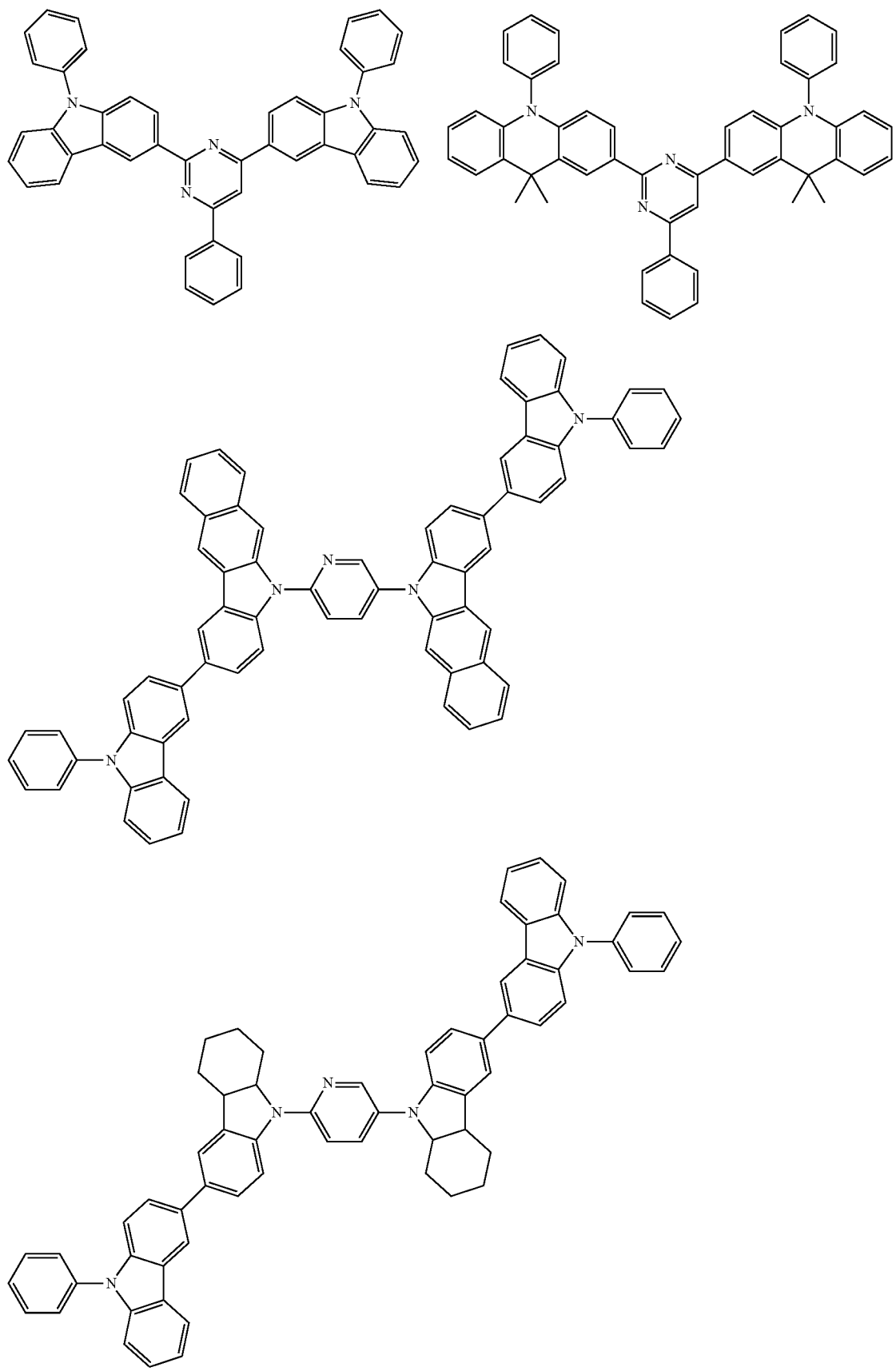

-continued
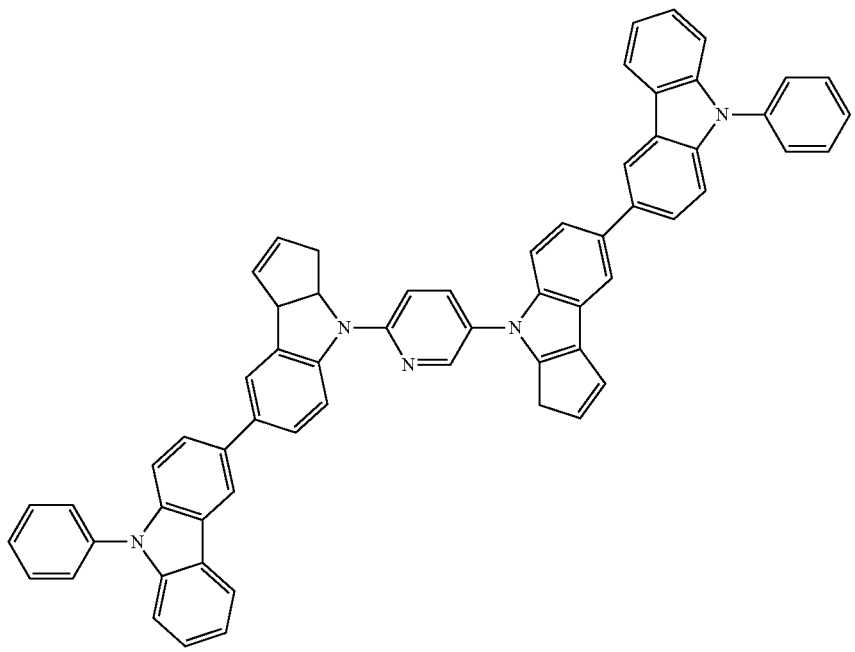
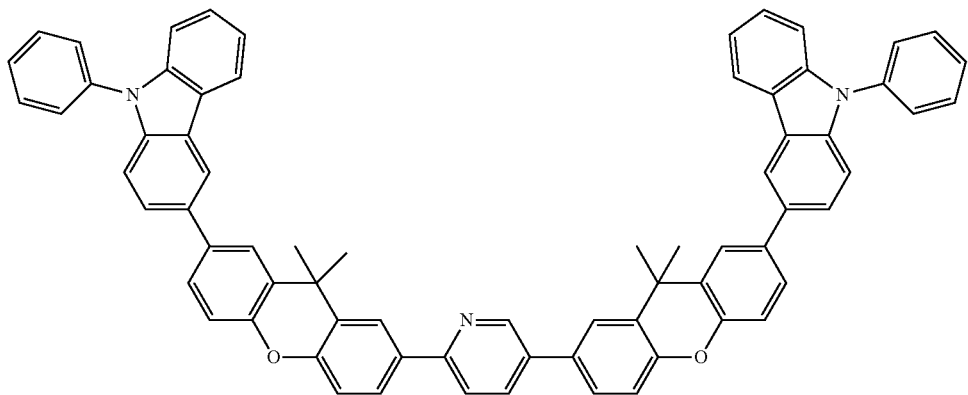
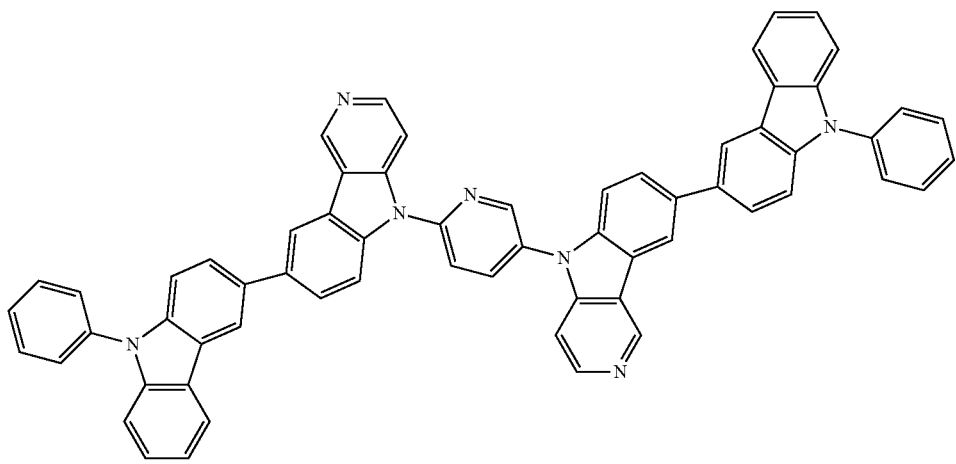

-continued
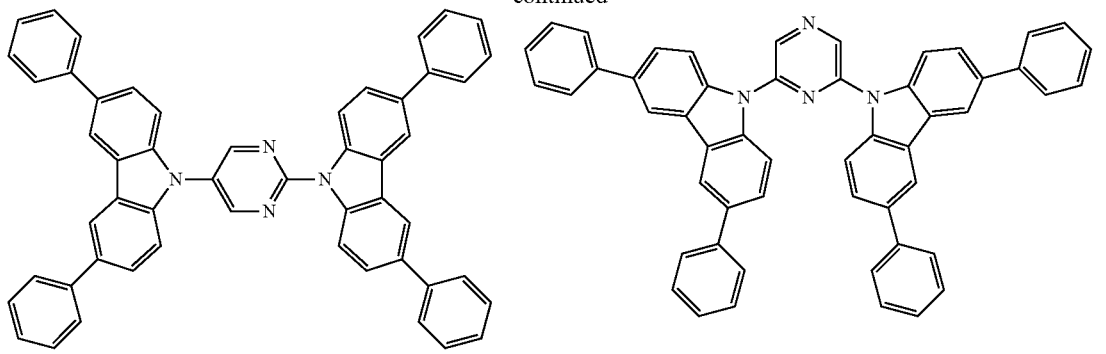
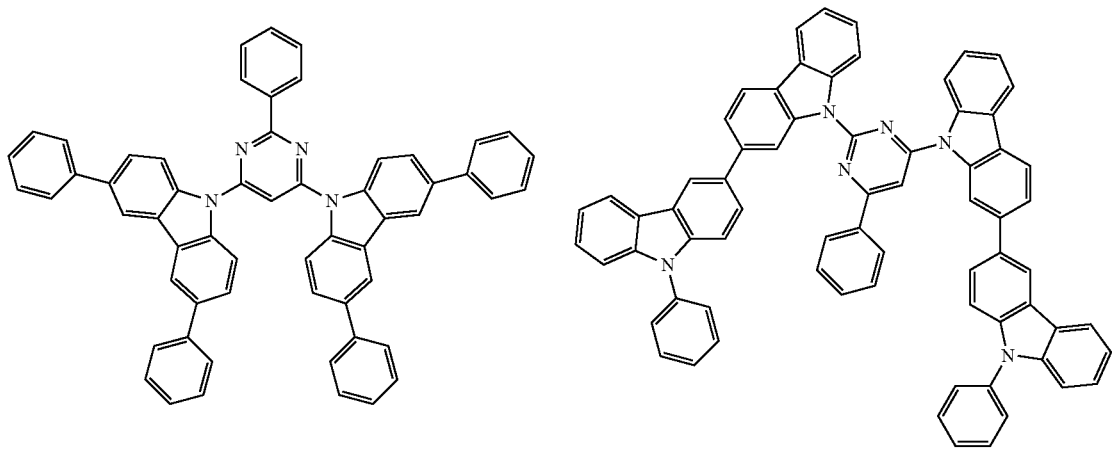
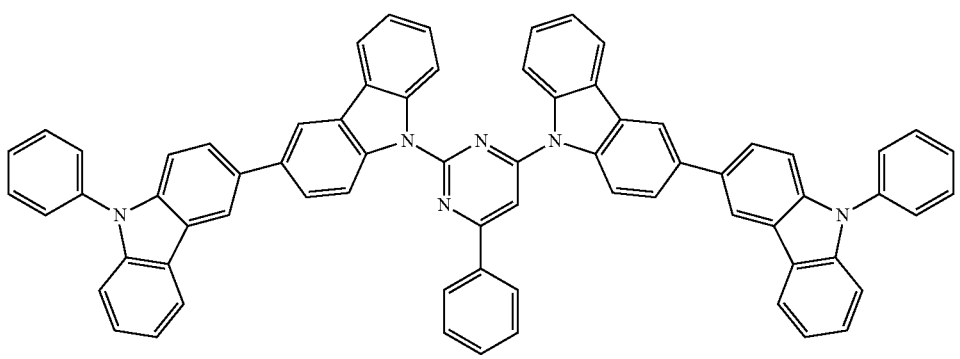
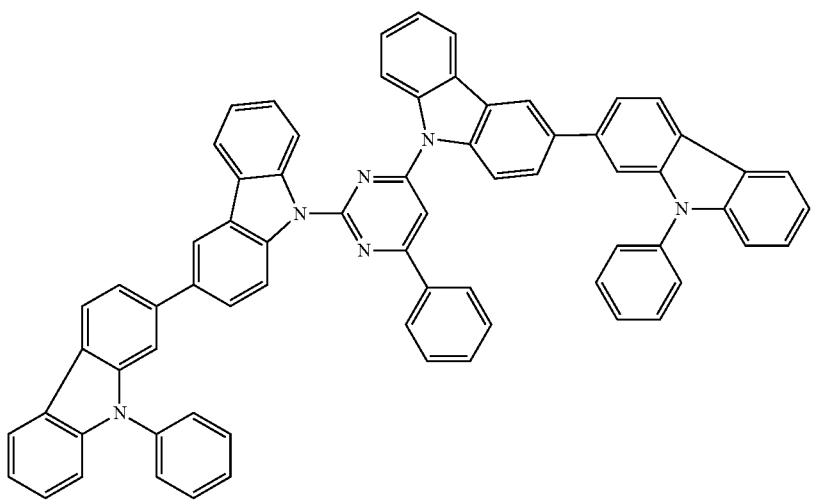

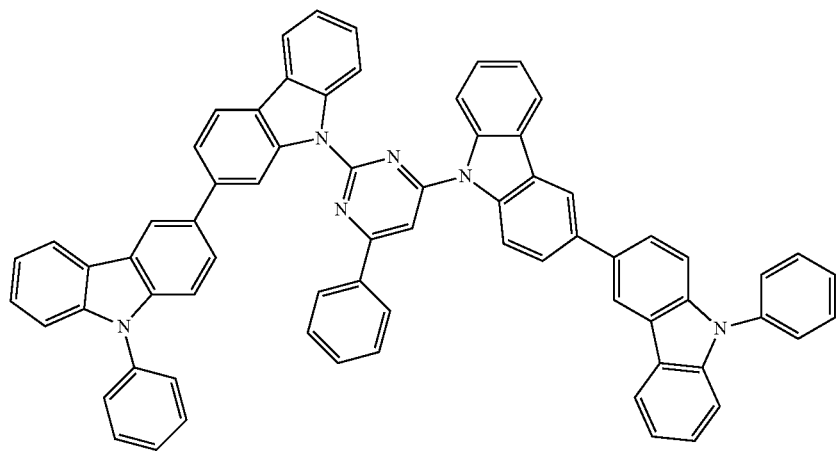
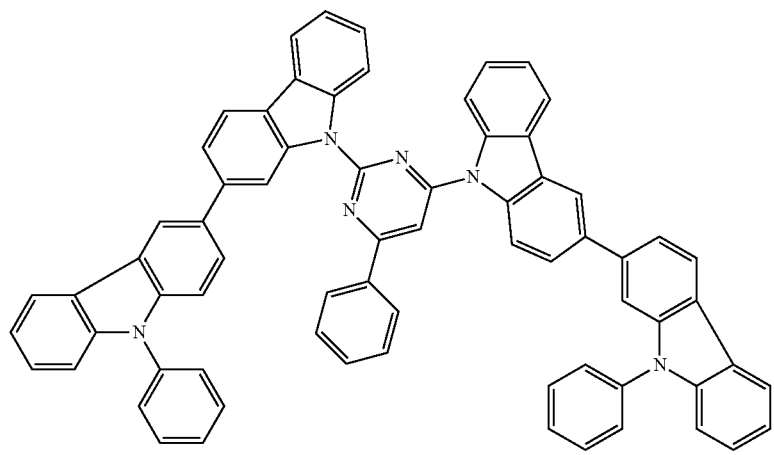
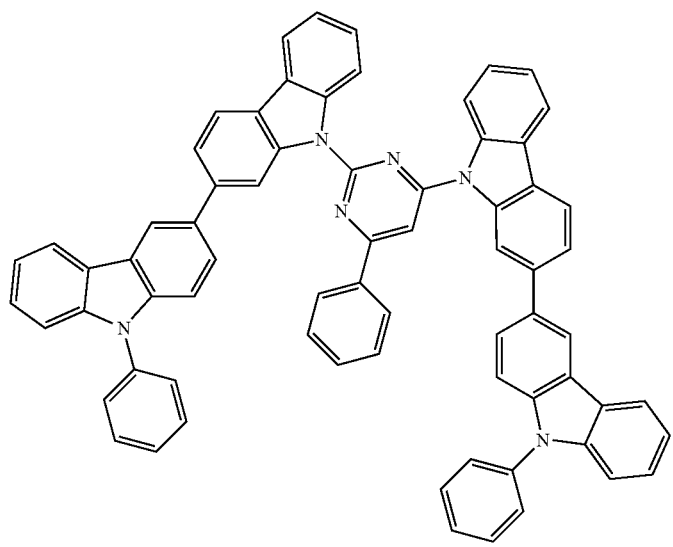

-continued
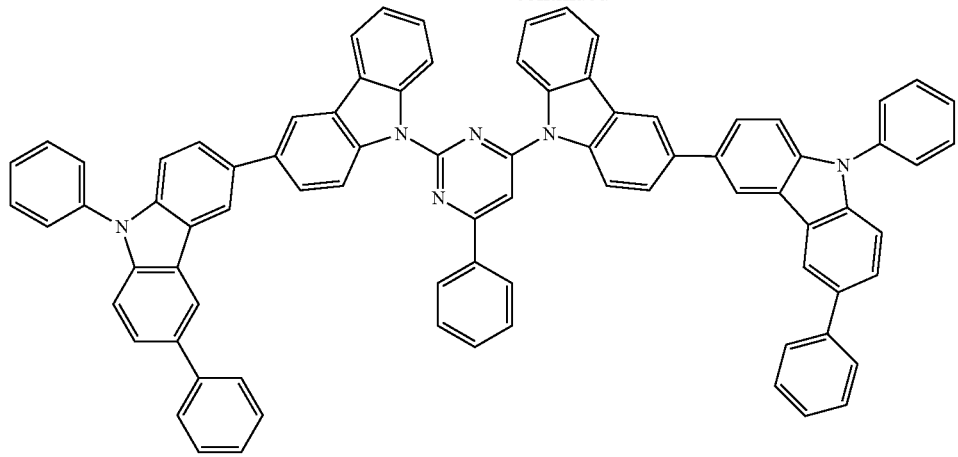
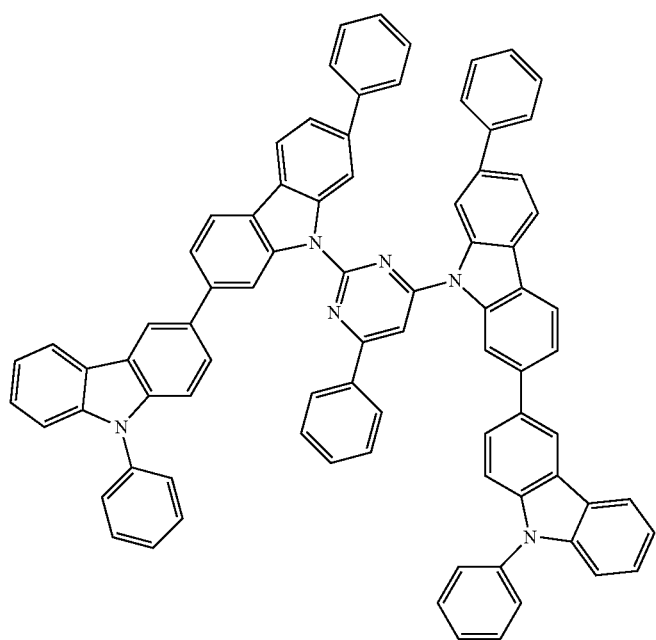
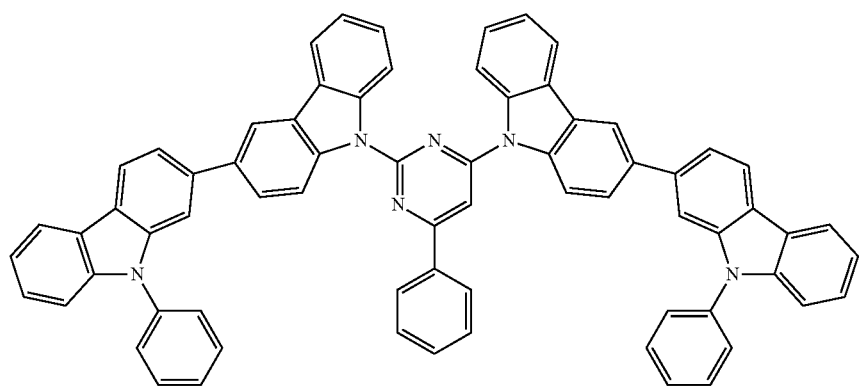

-continued
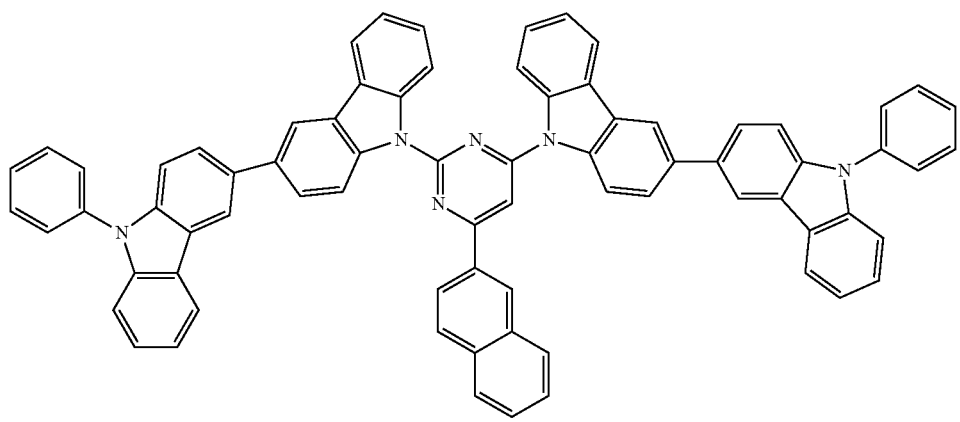
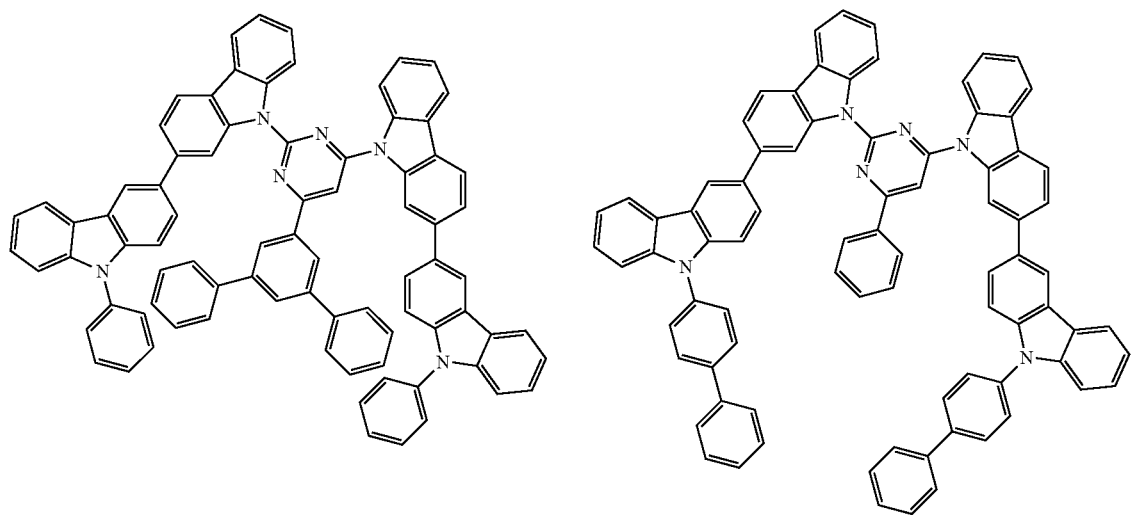
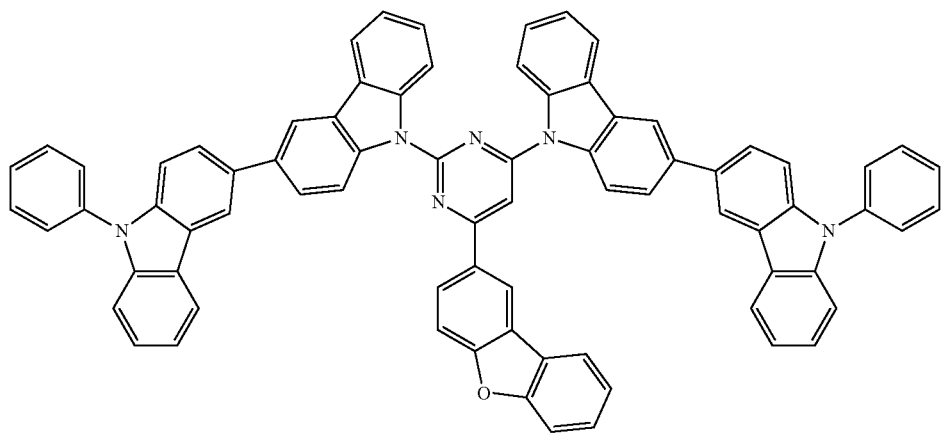

-continued
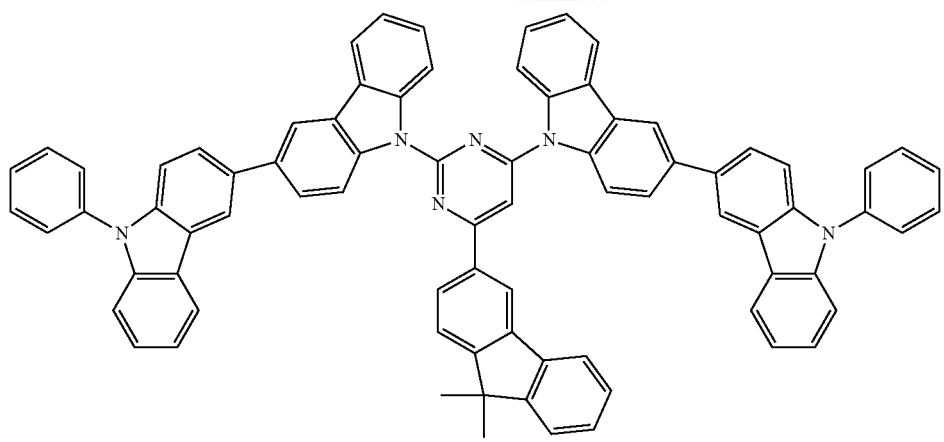
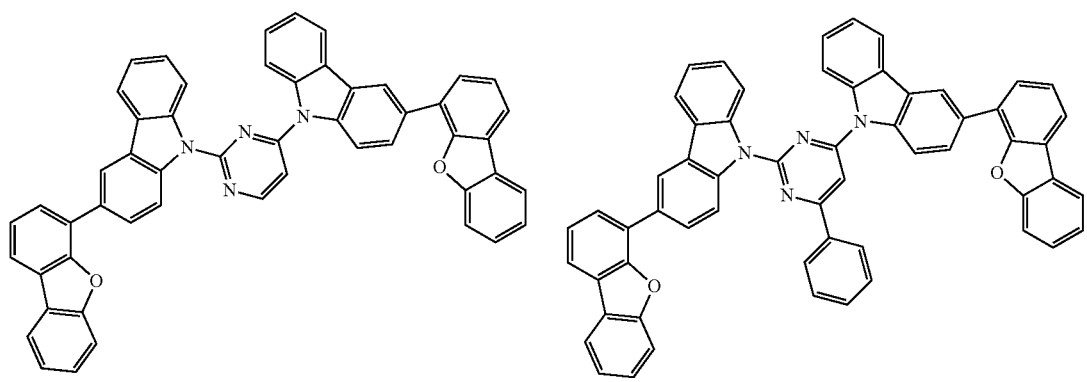
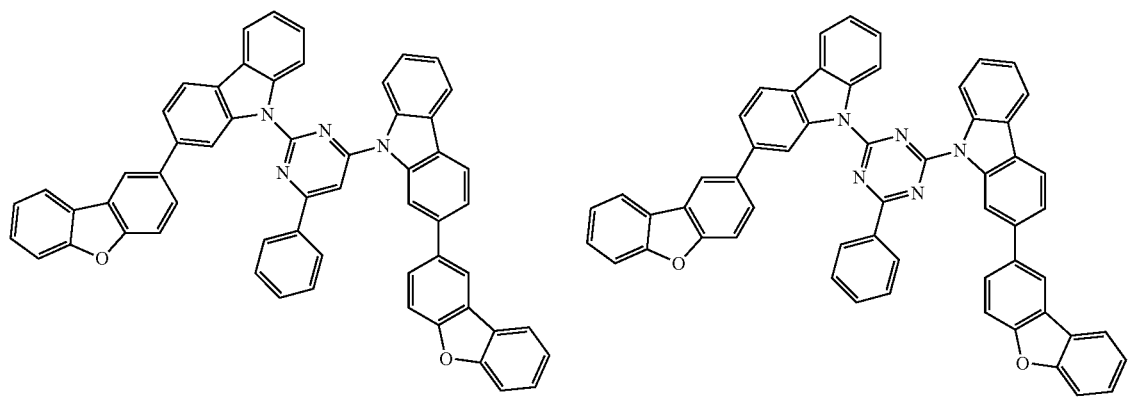
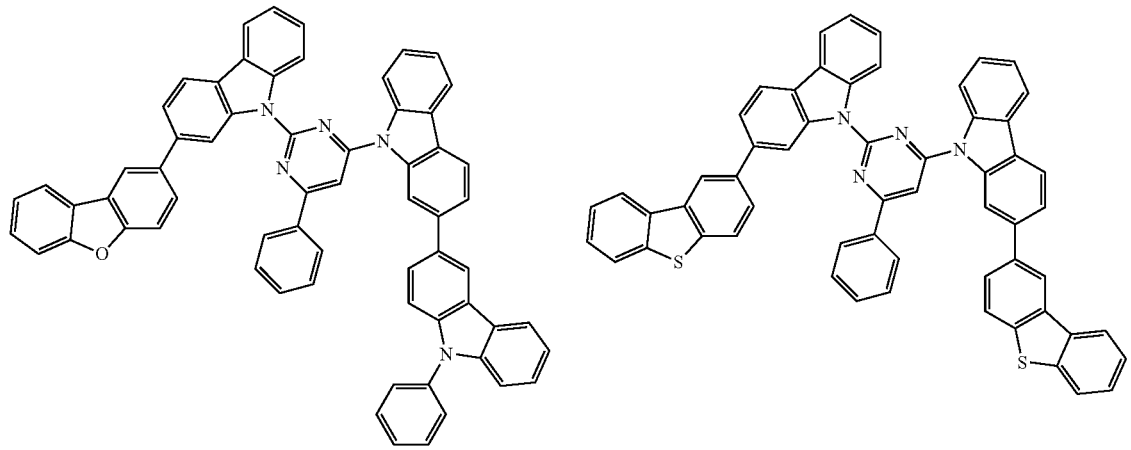

-continued
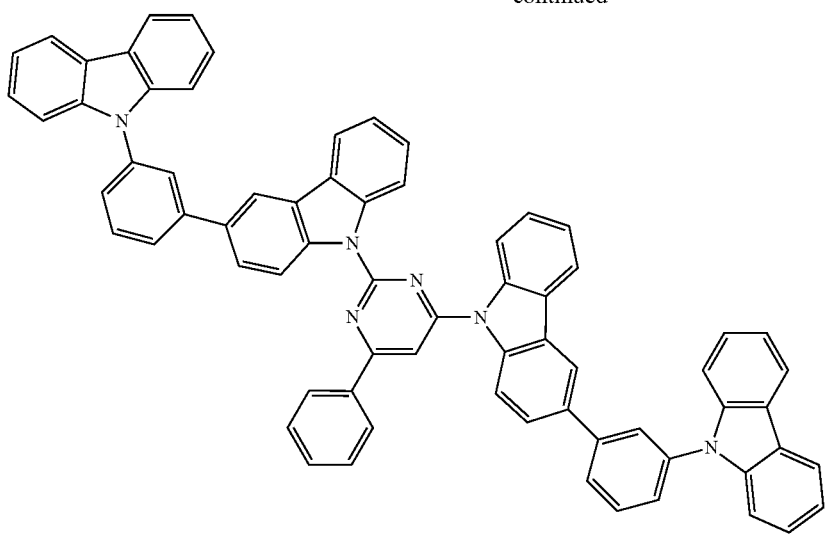
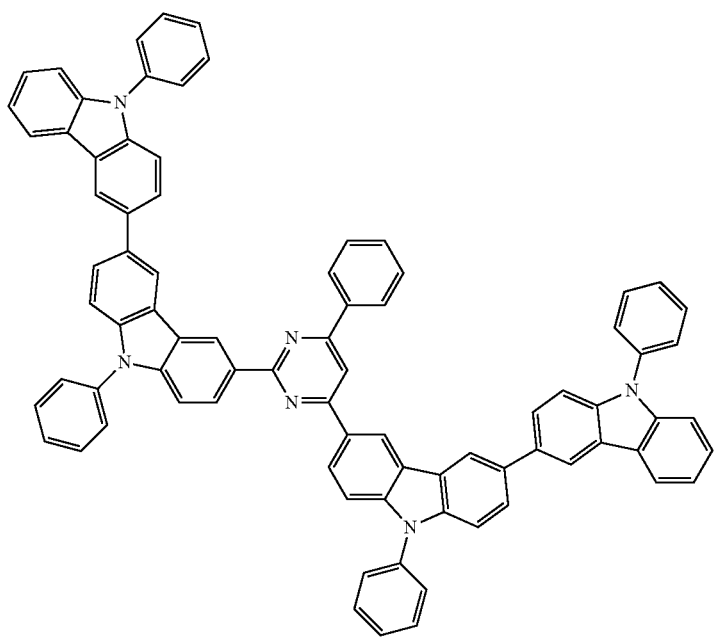
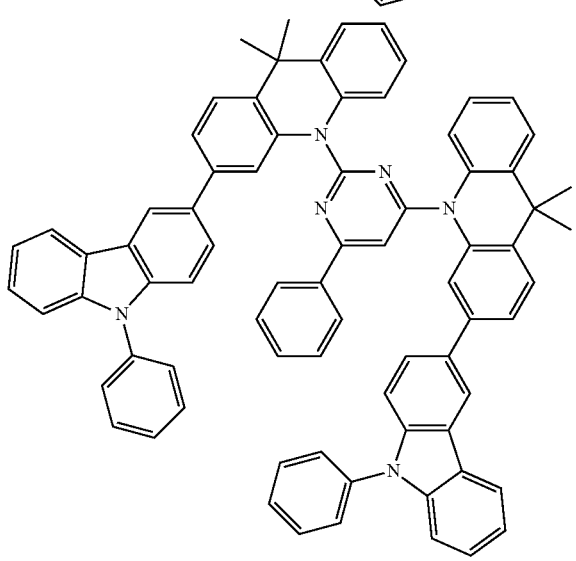

-continued
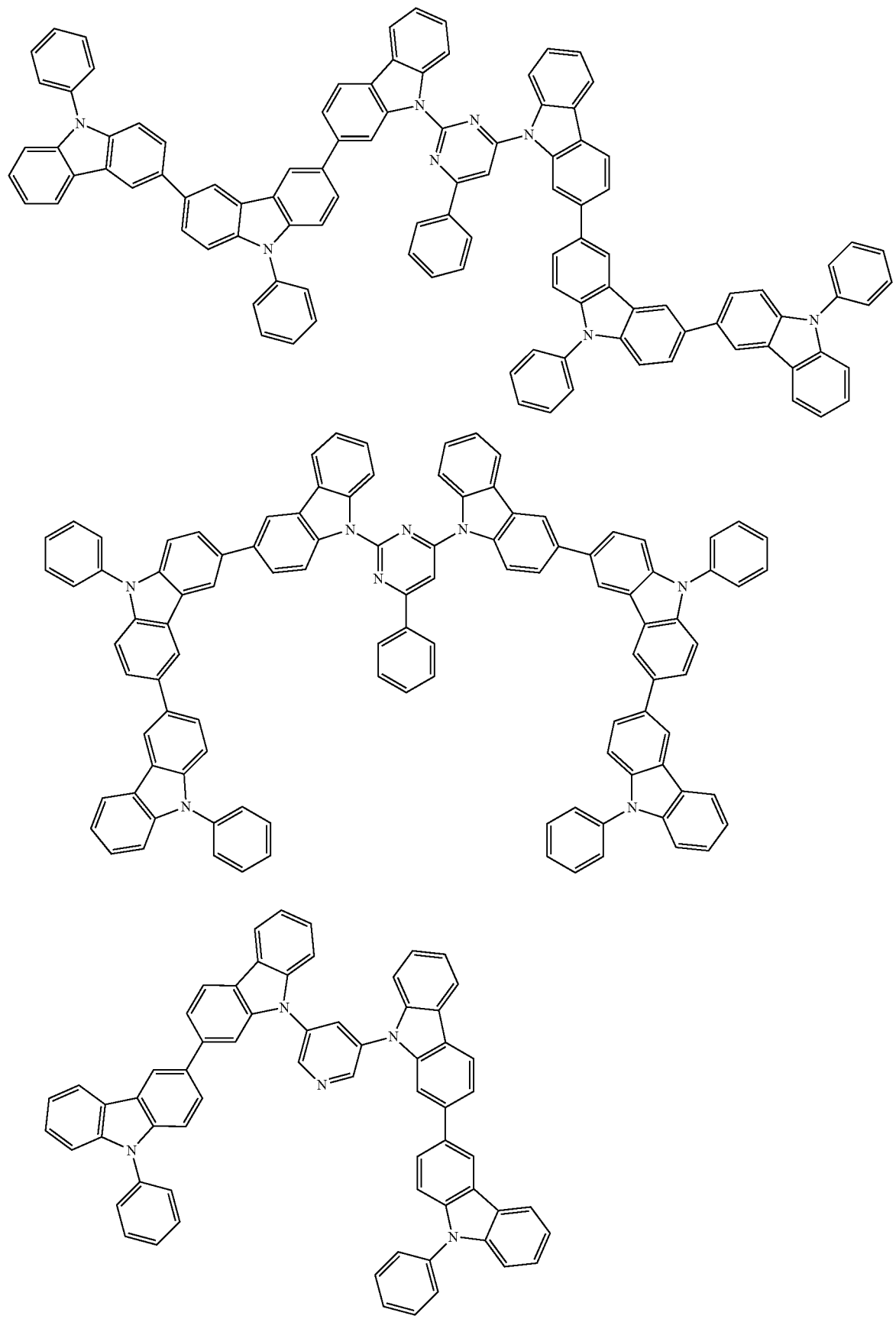

-continued
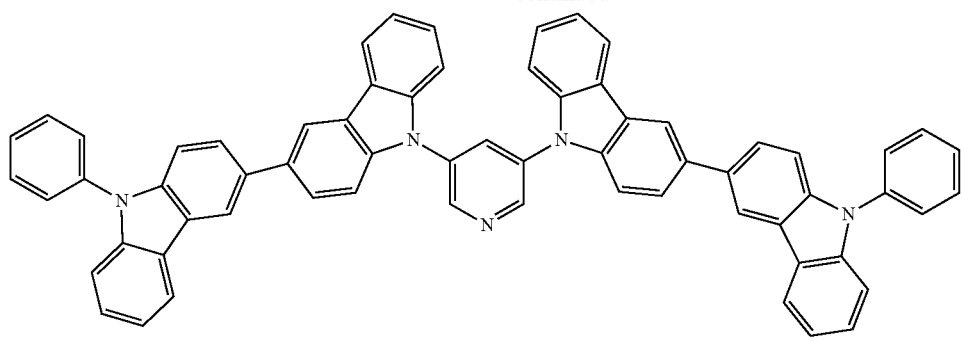
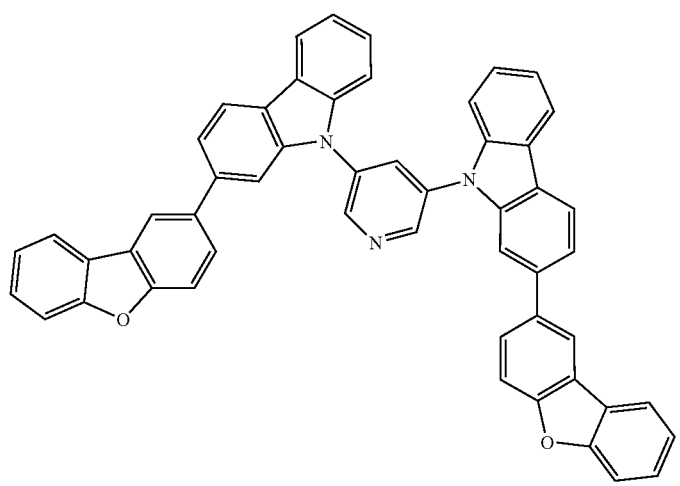
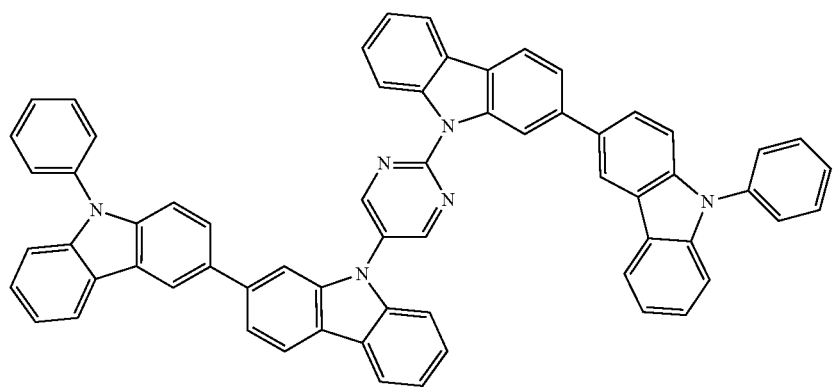
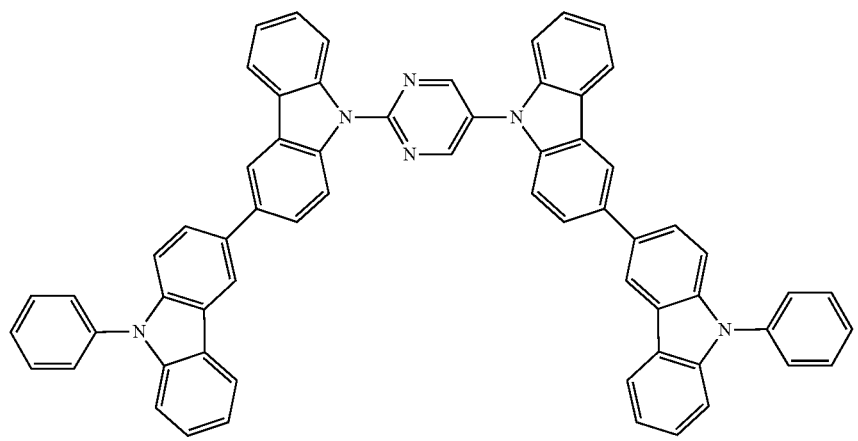

-continued
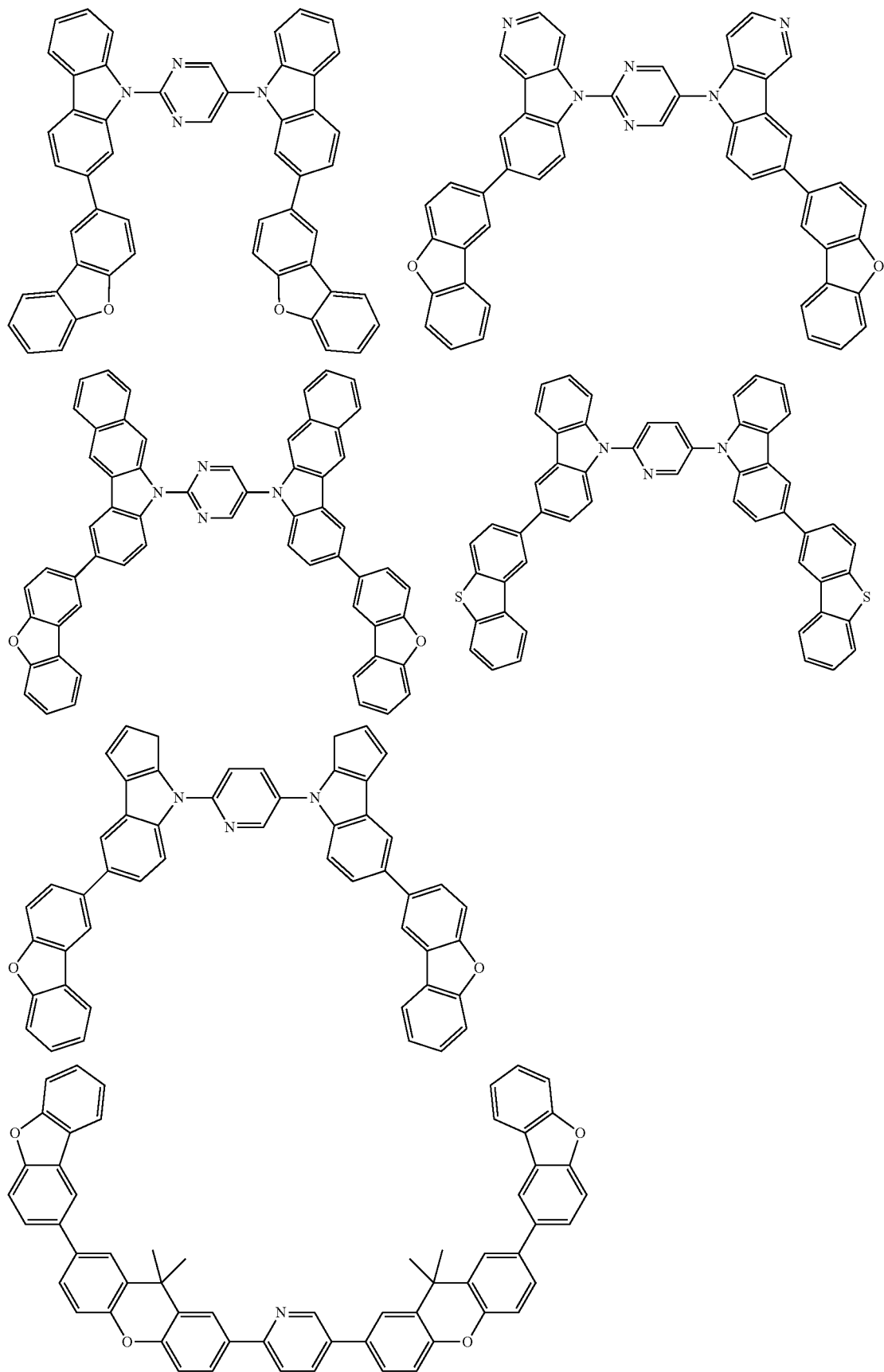

-continued
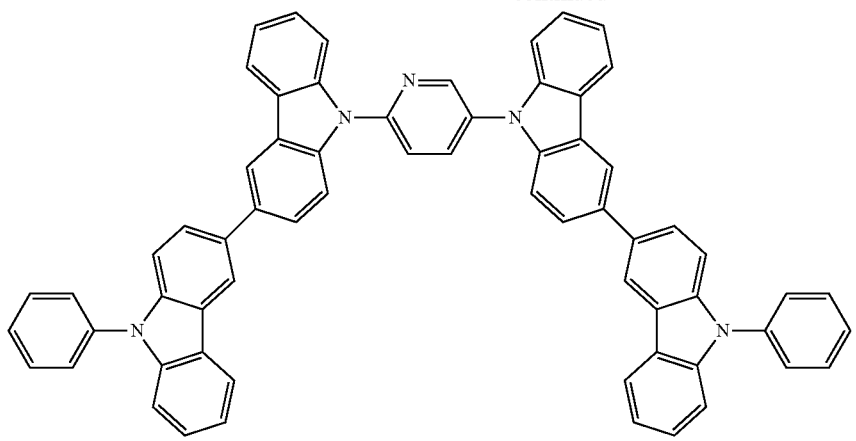
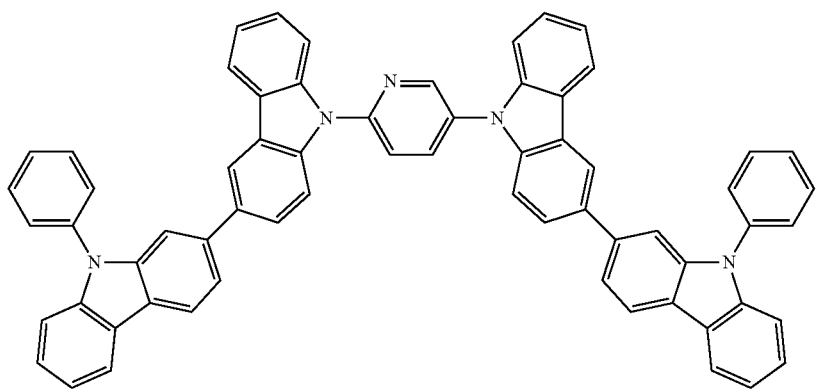
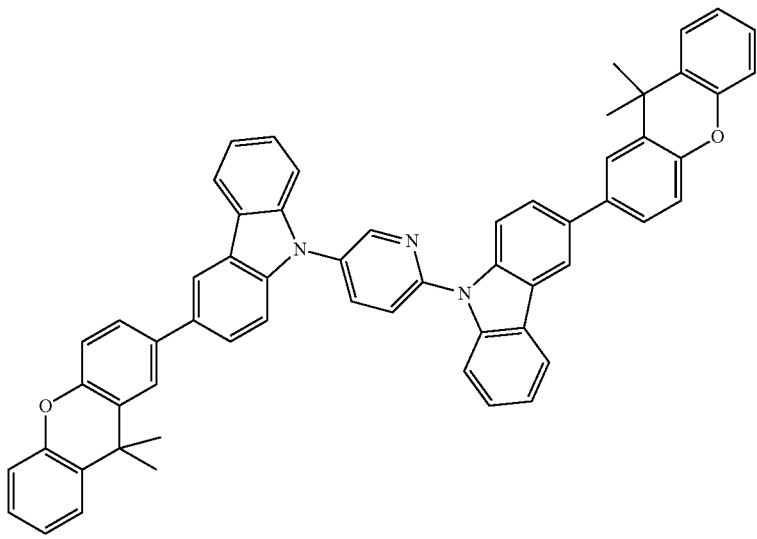

-continued
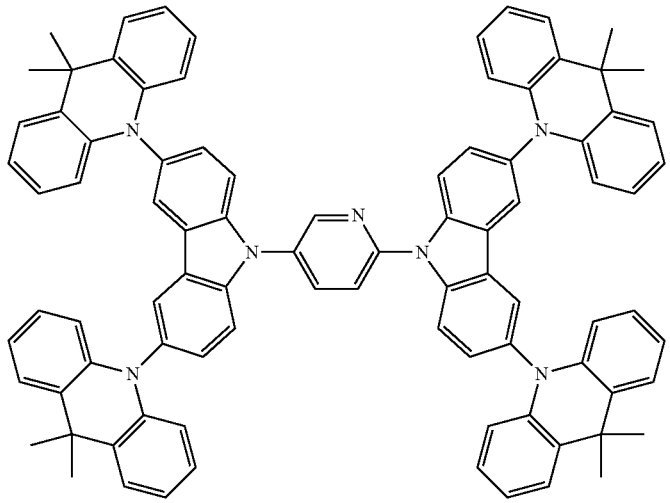
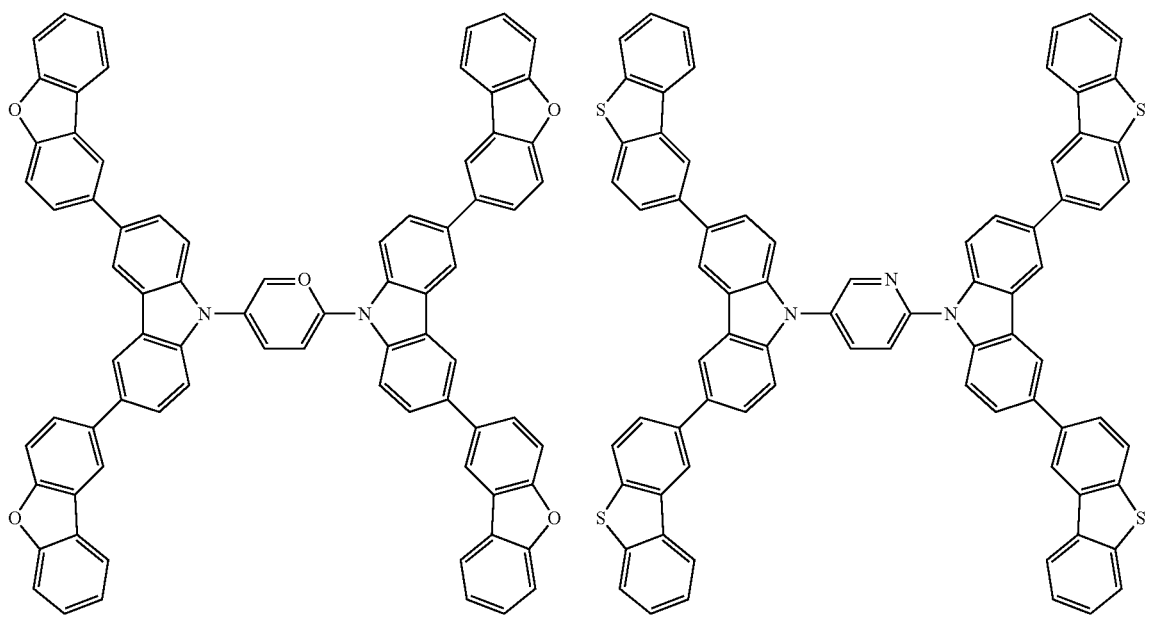
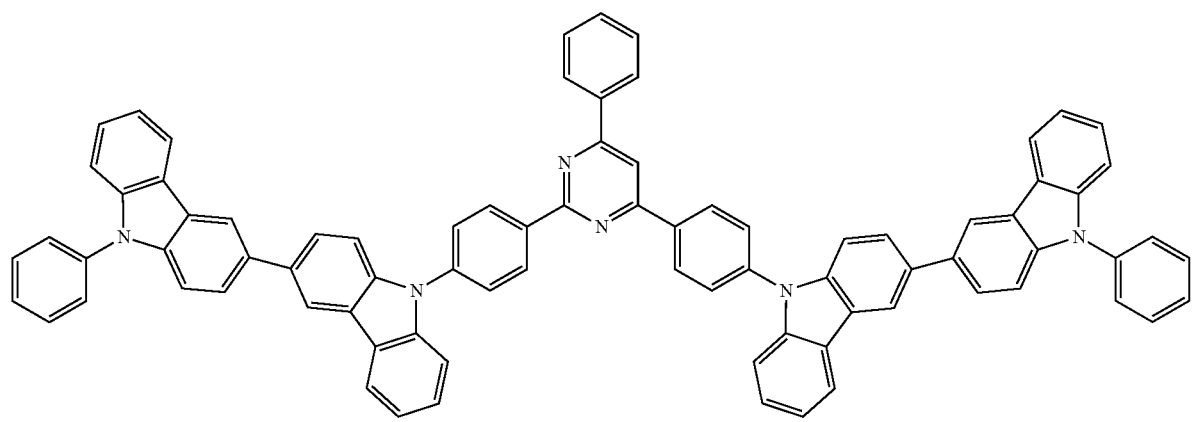

-continued
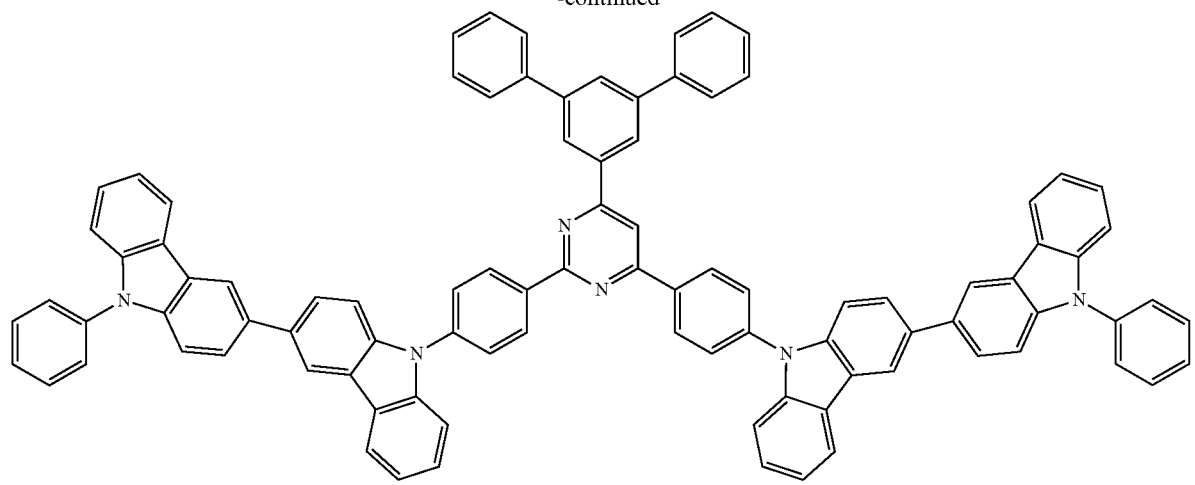
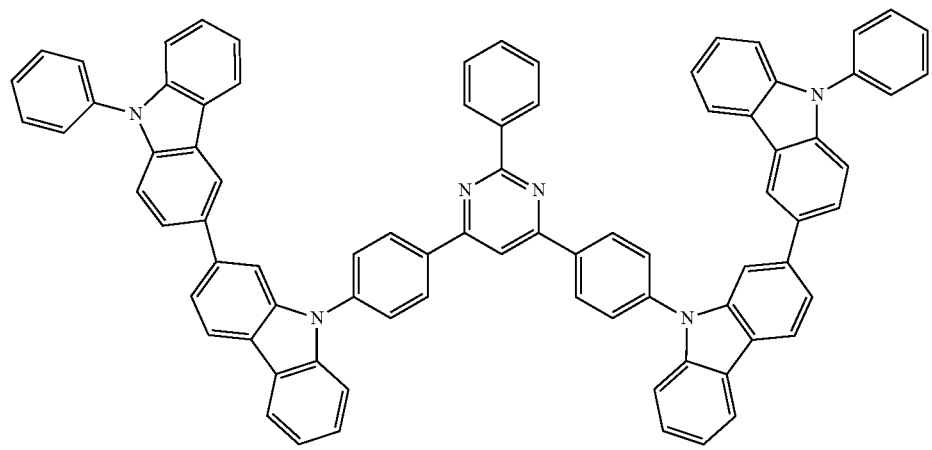
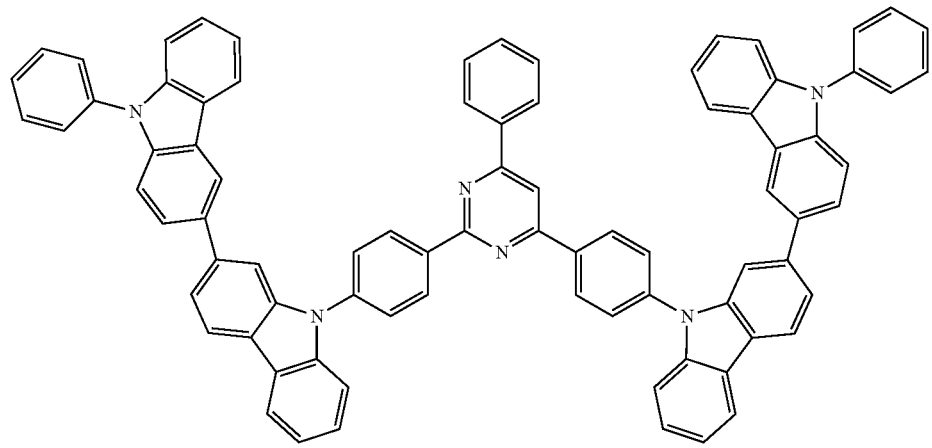

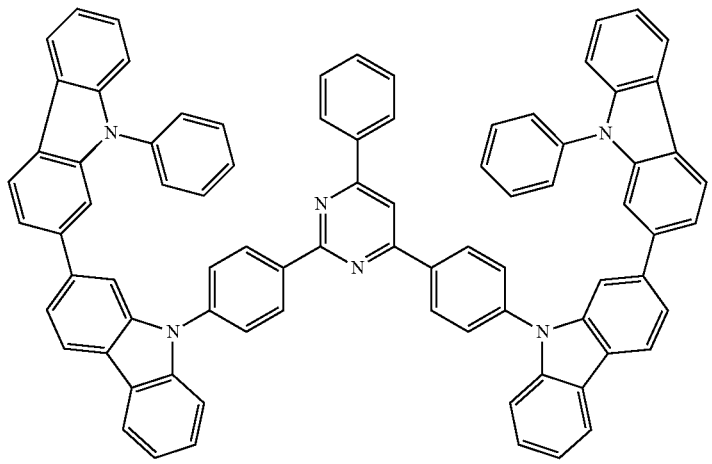
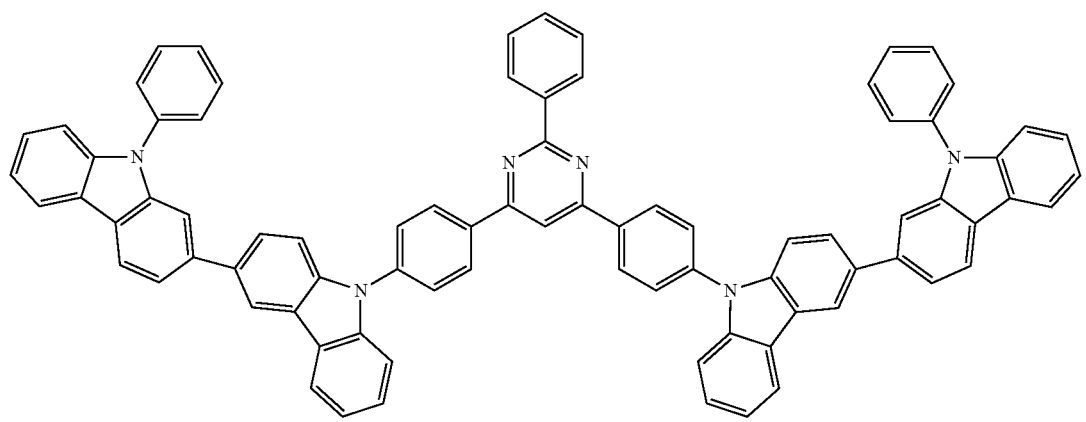
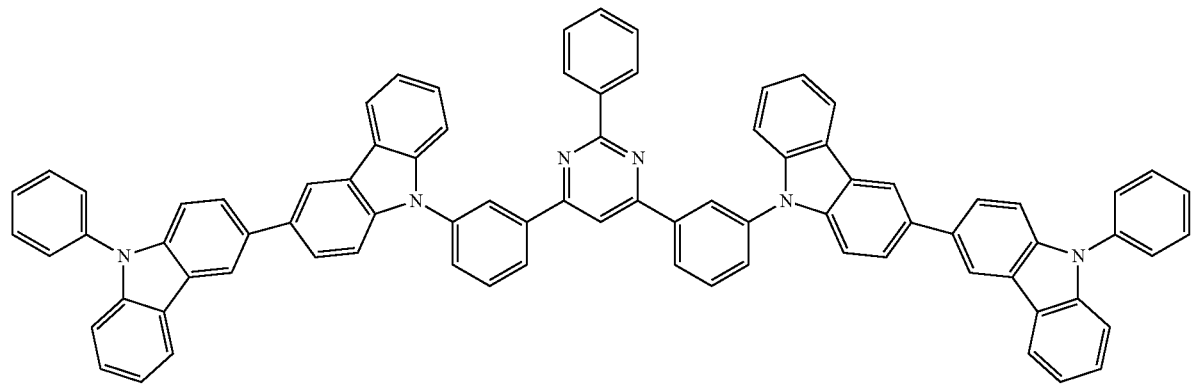

-continued
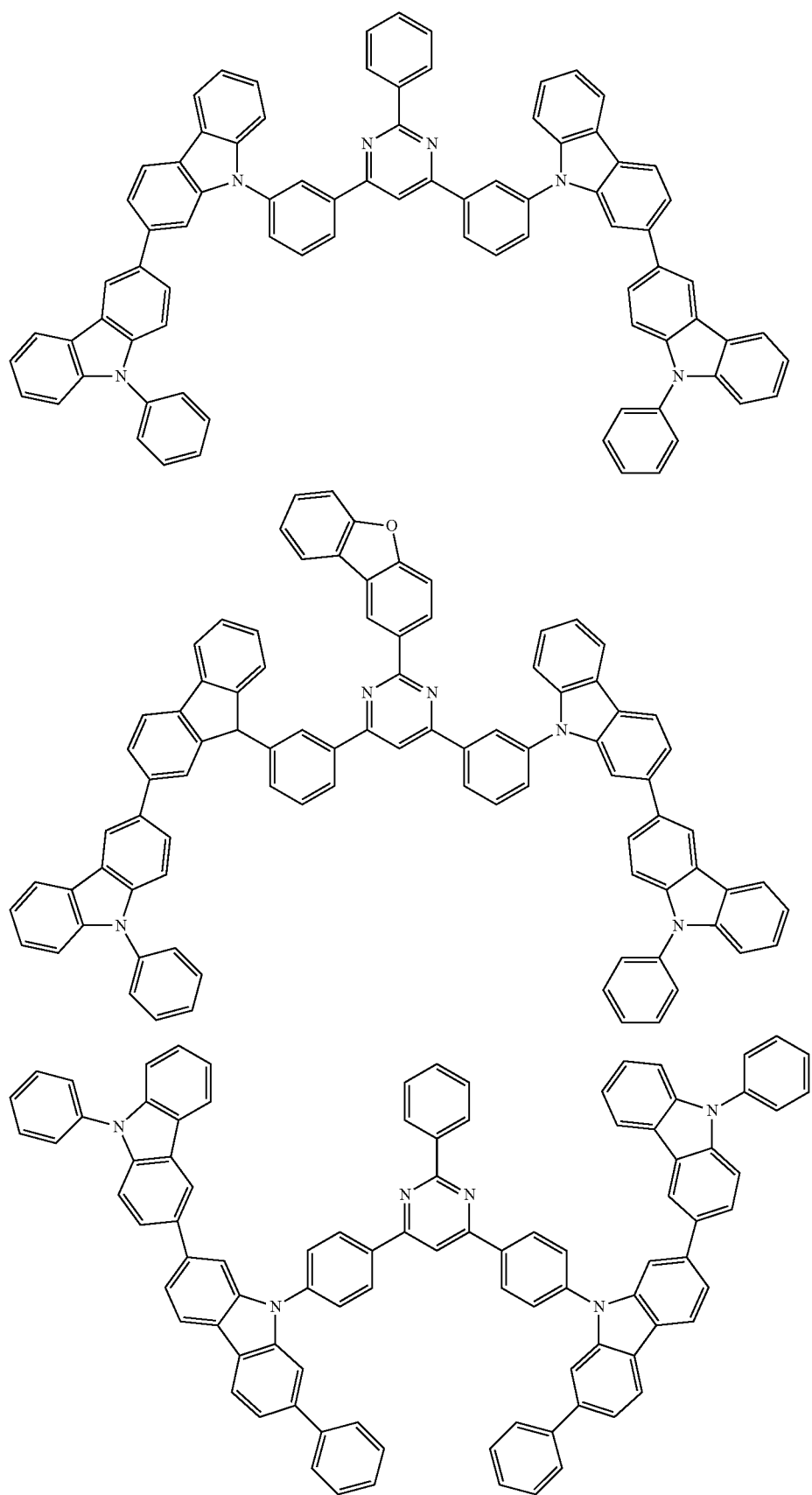

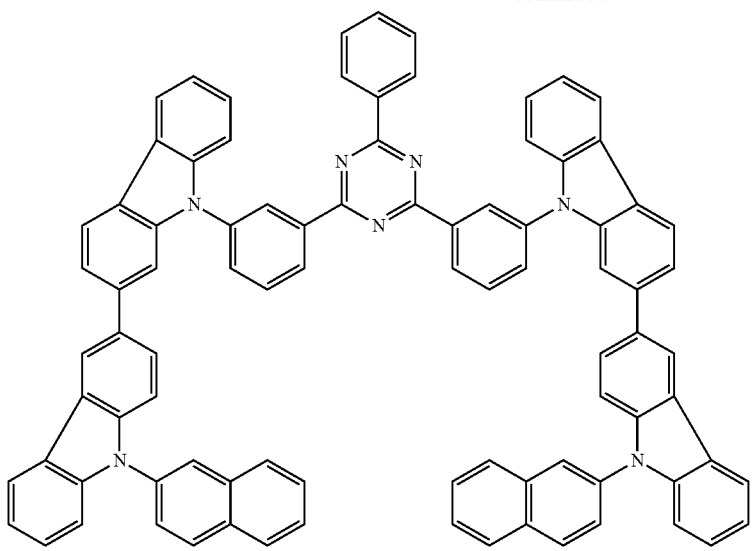
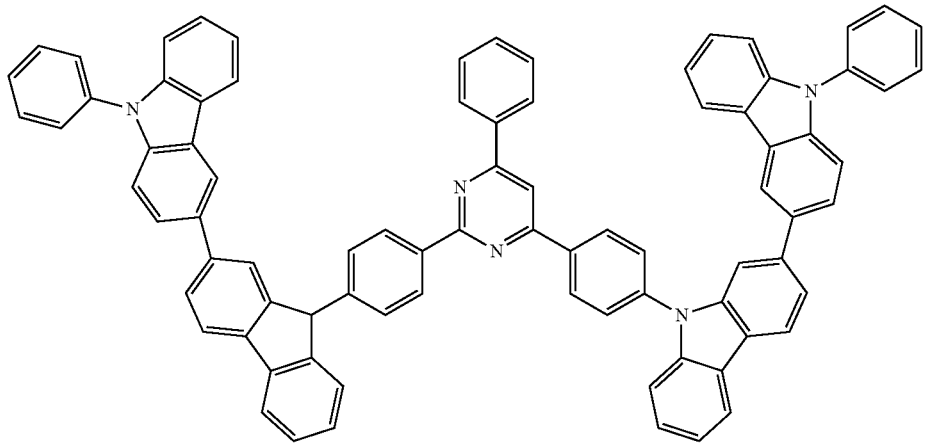
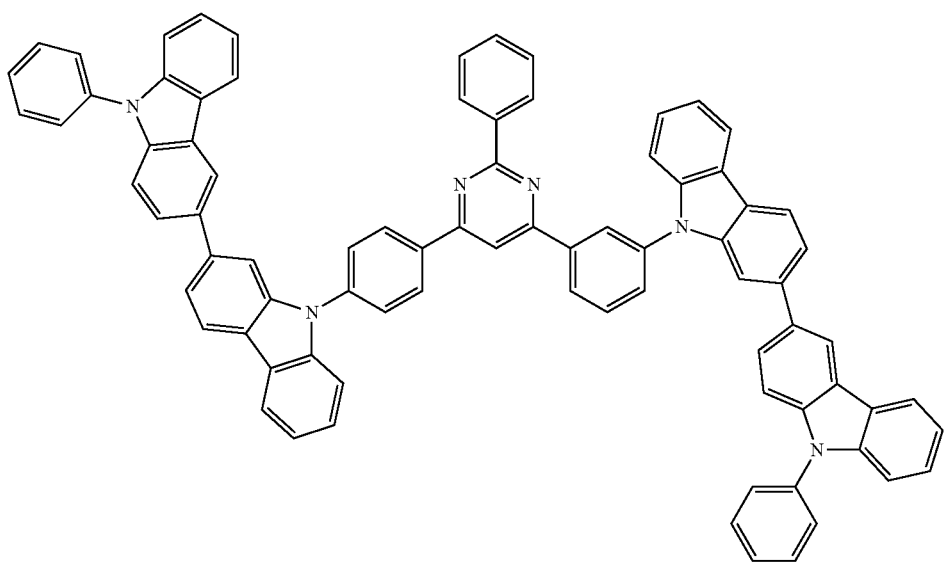

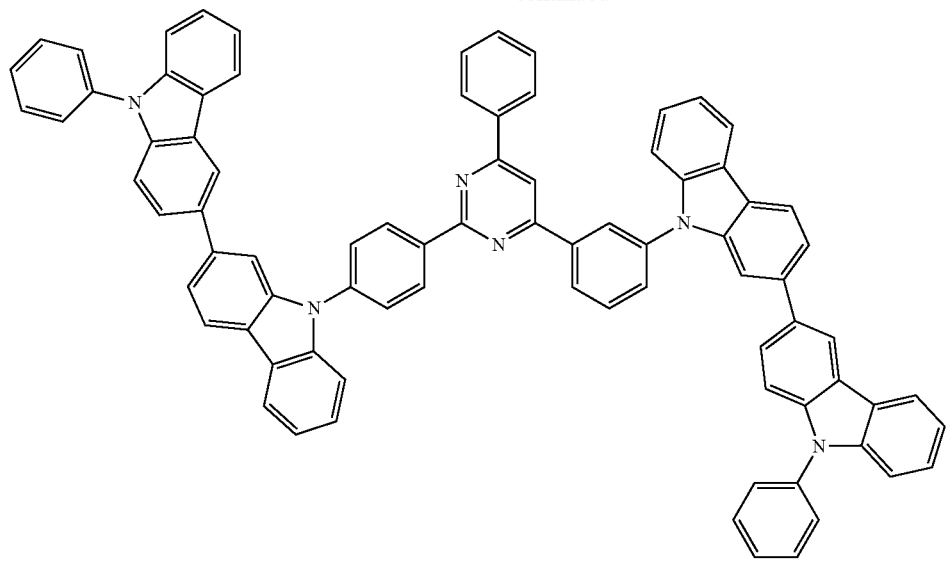
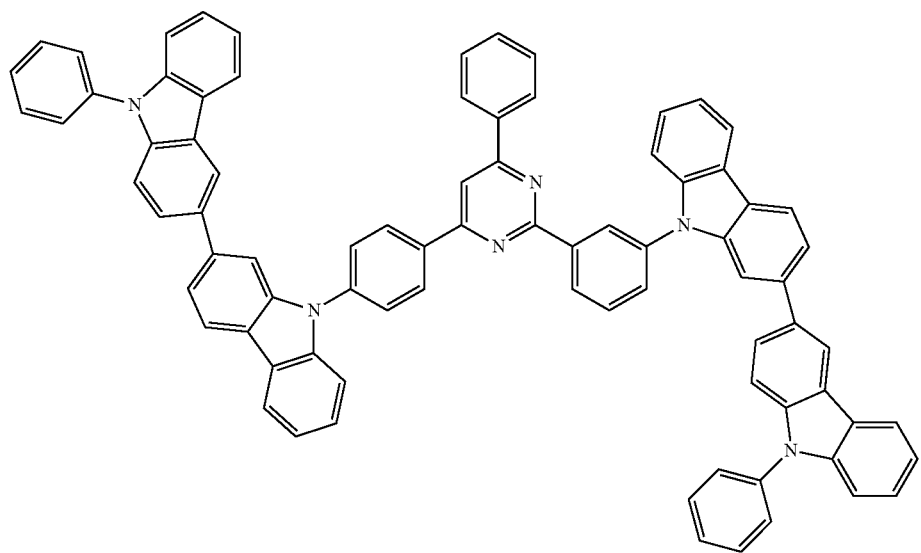
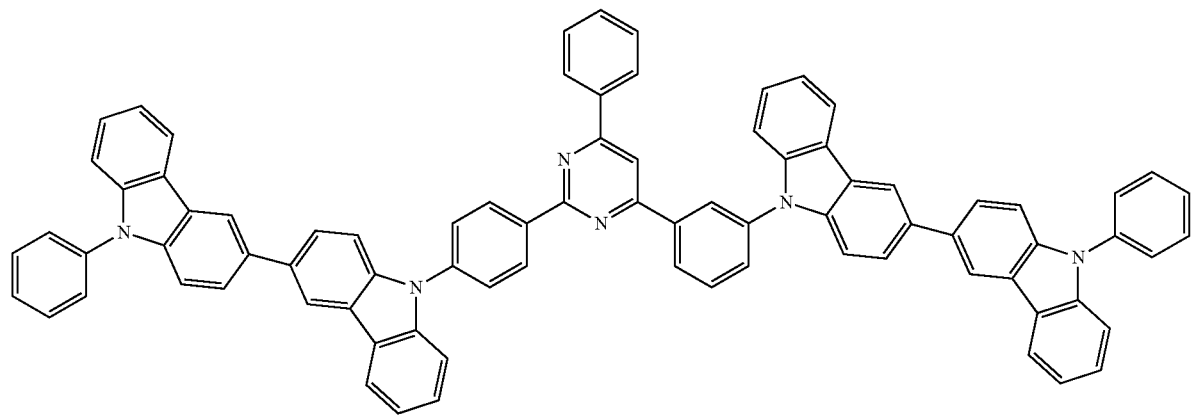

-continued
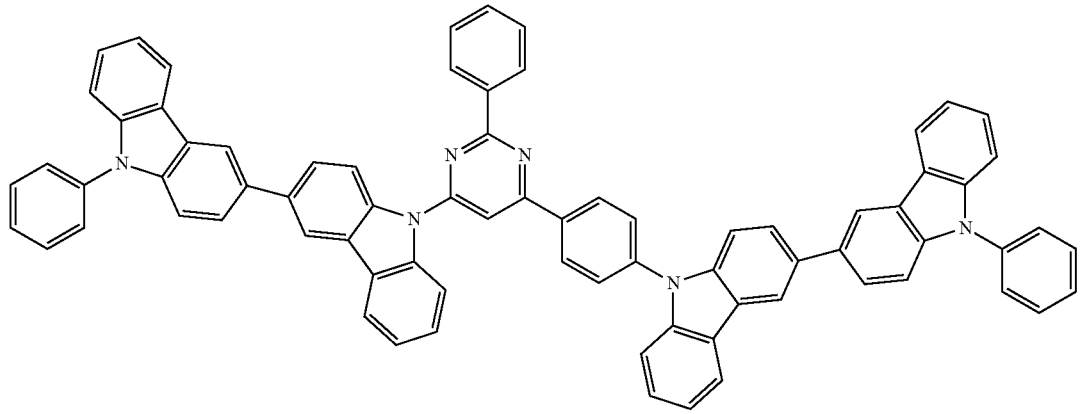
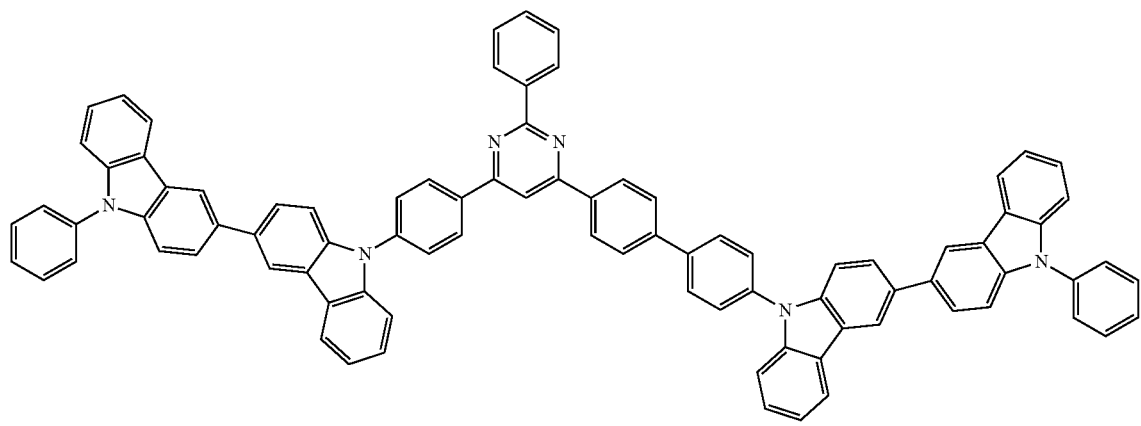
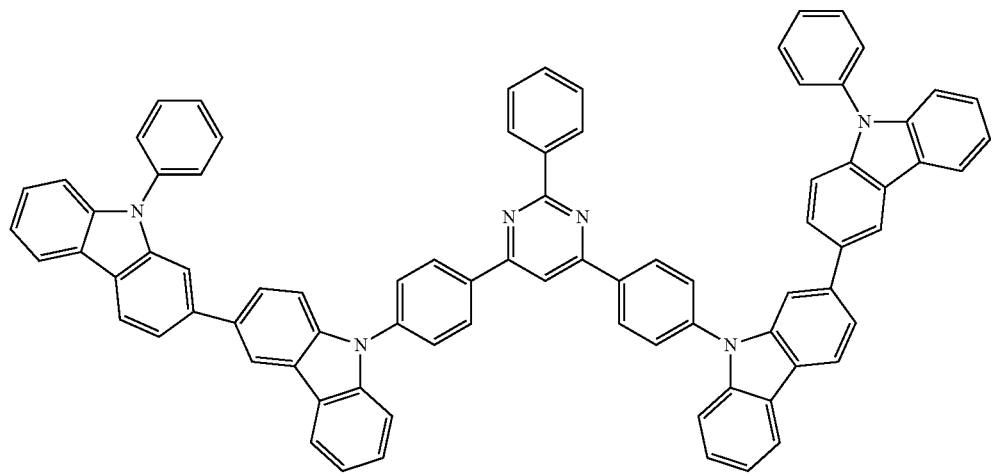

-continued
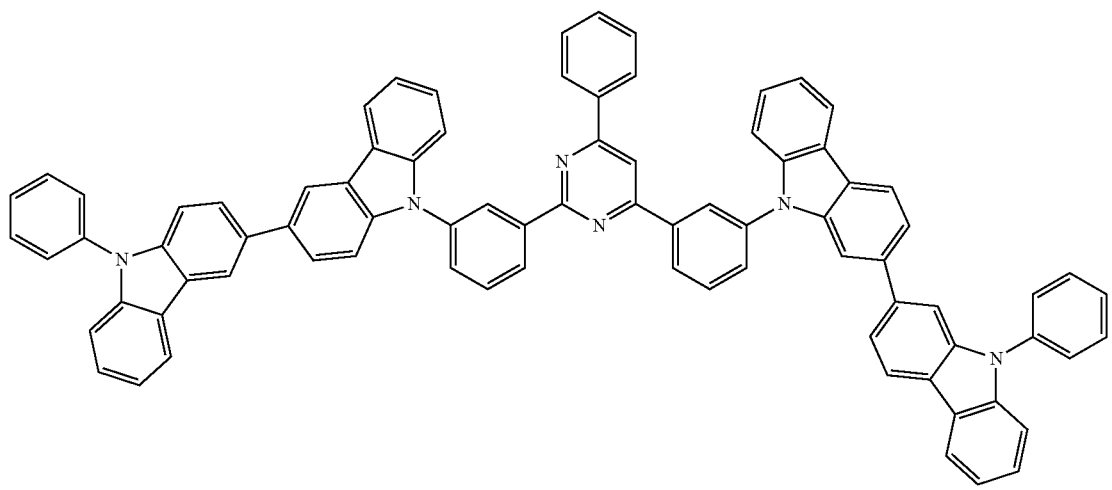
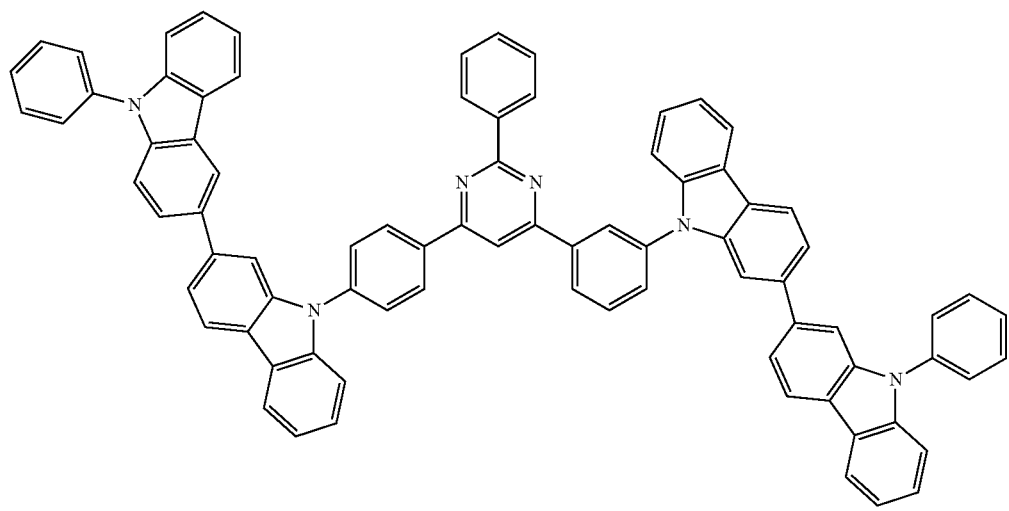
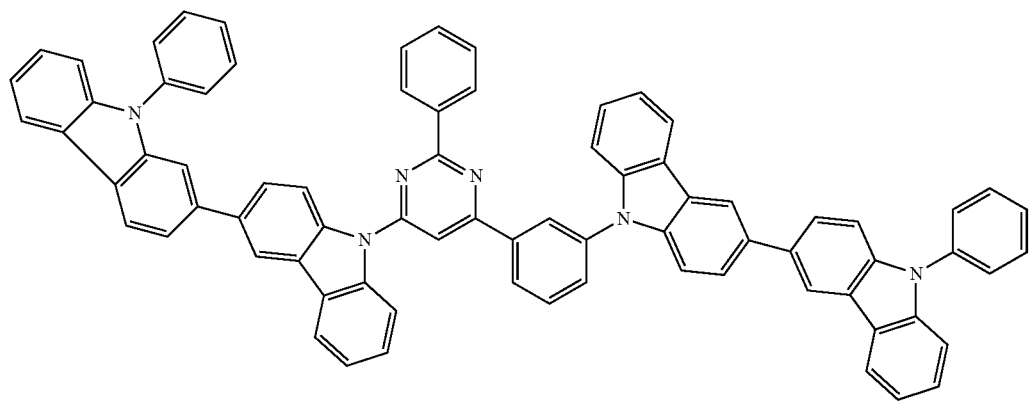

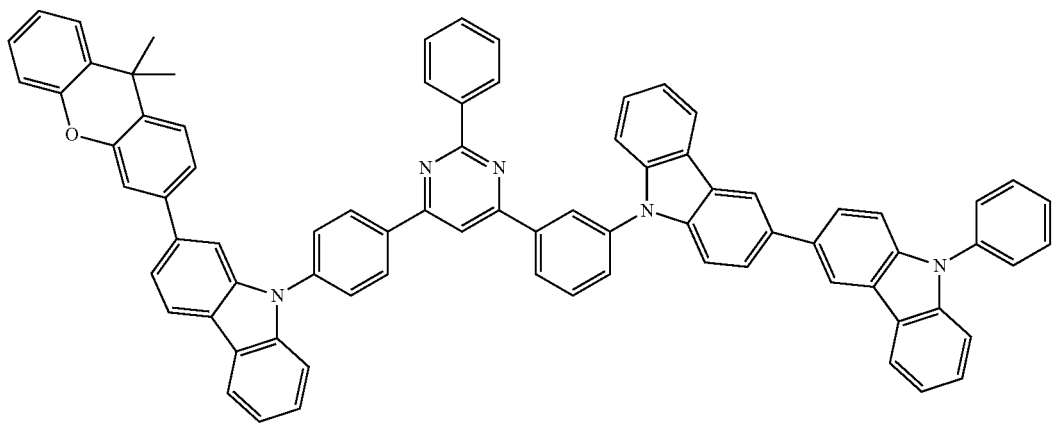
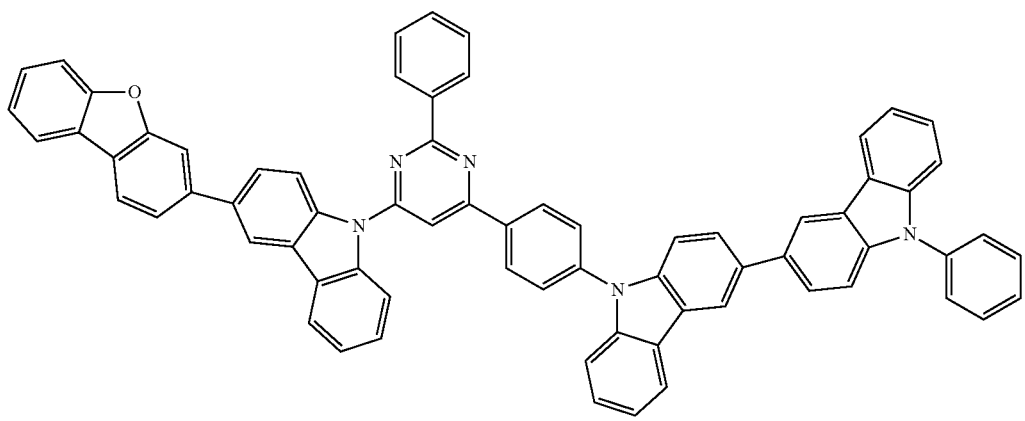
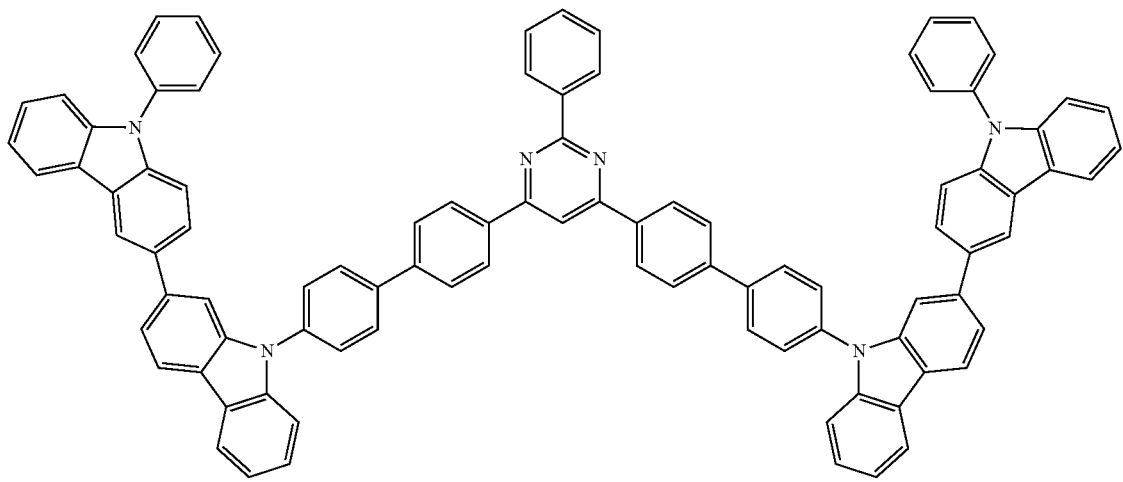

-continued
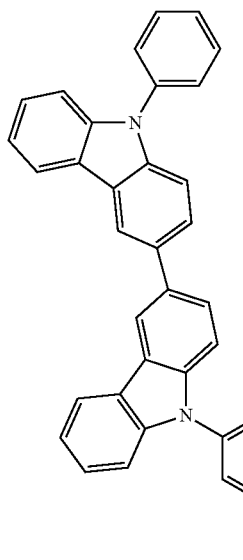
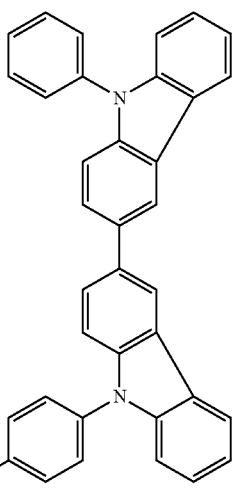
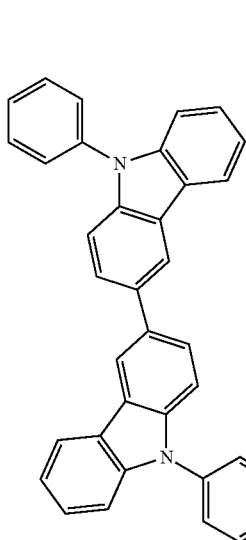
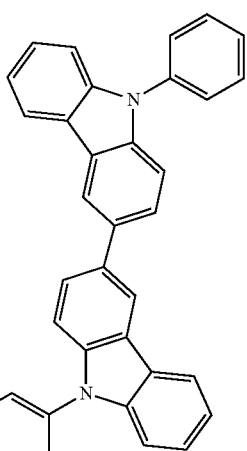
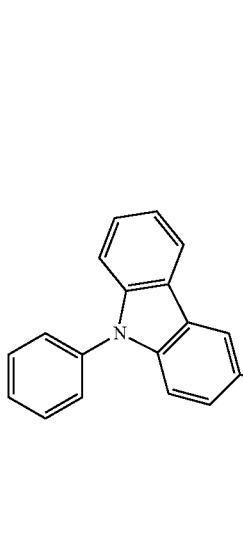
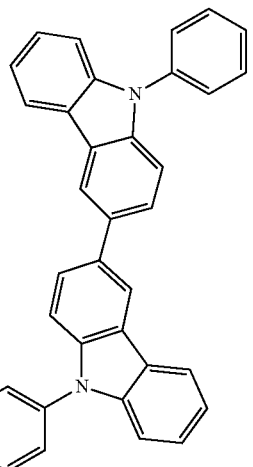

-continued
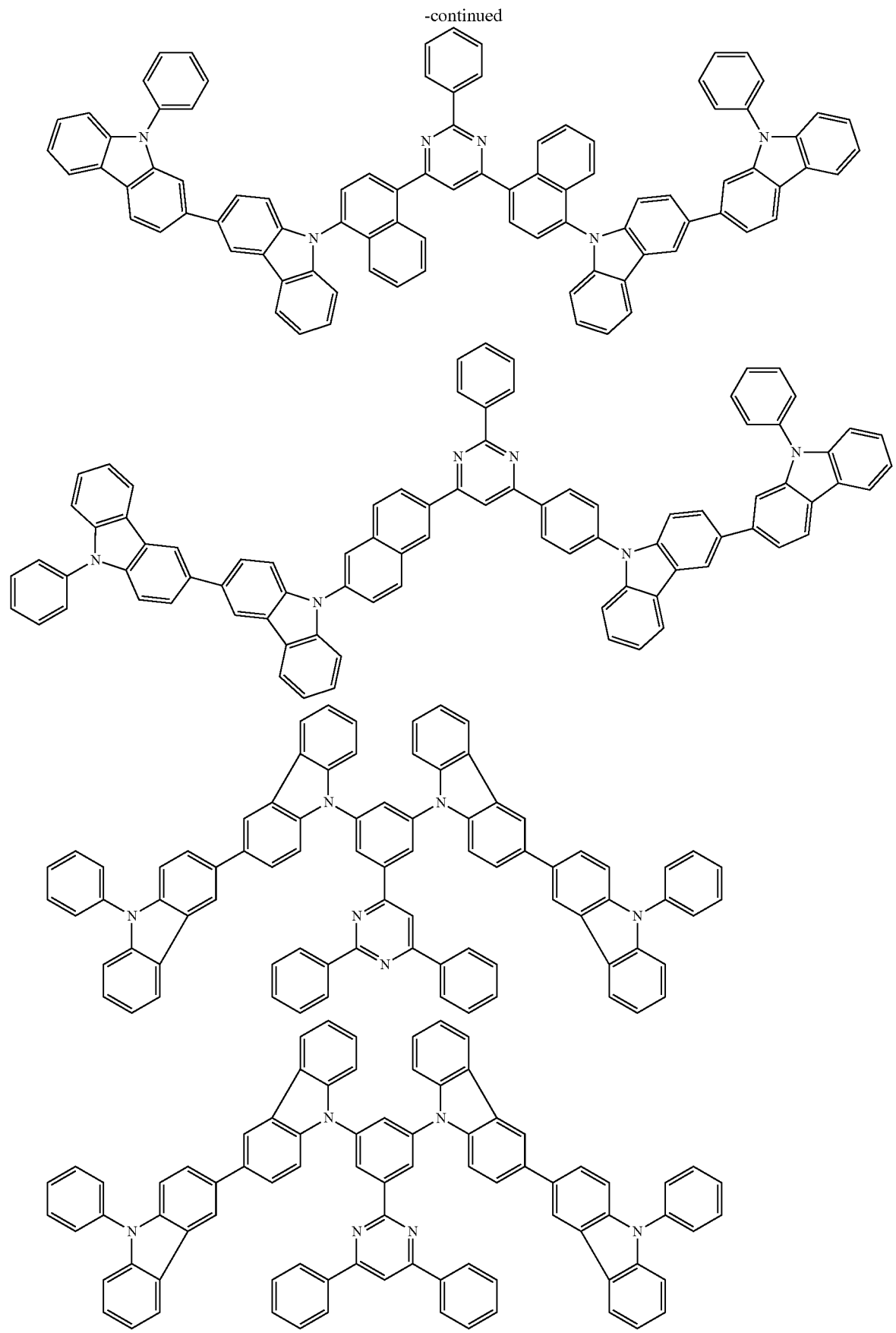

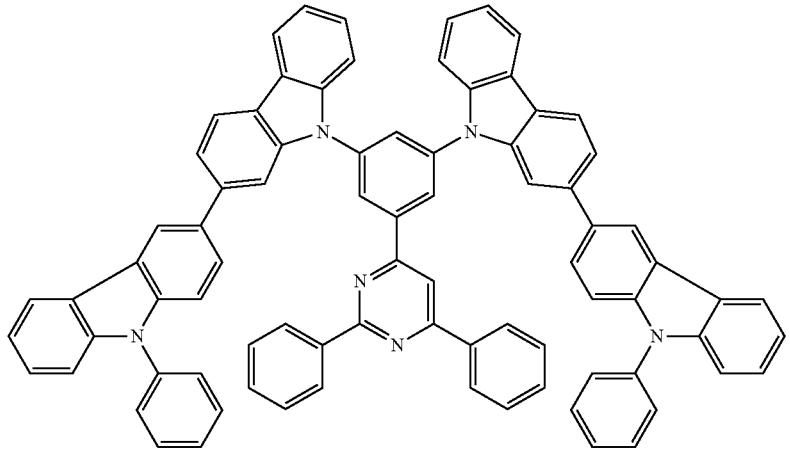
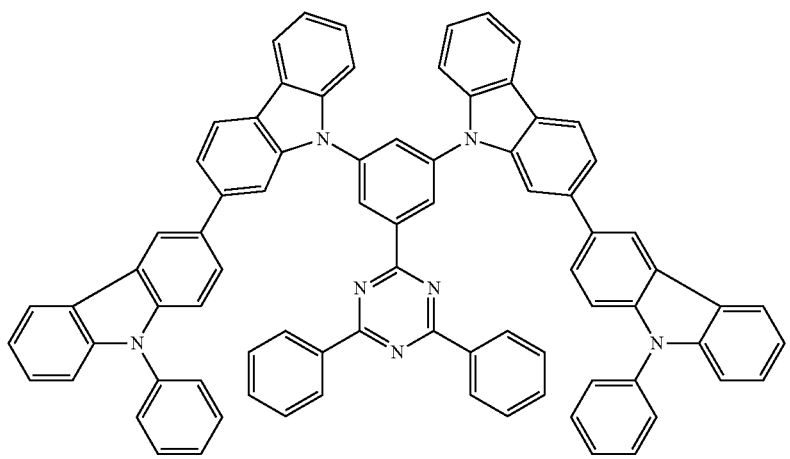
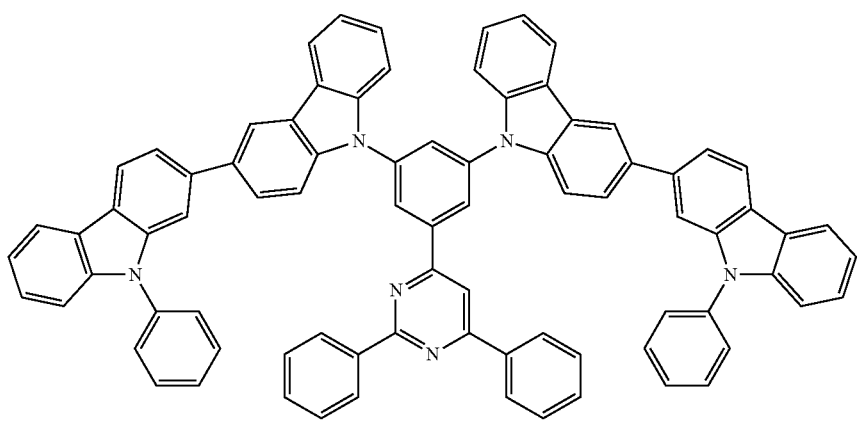

-continued
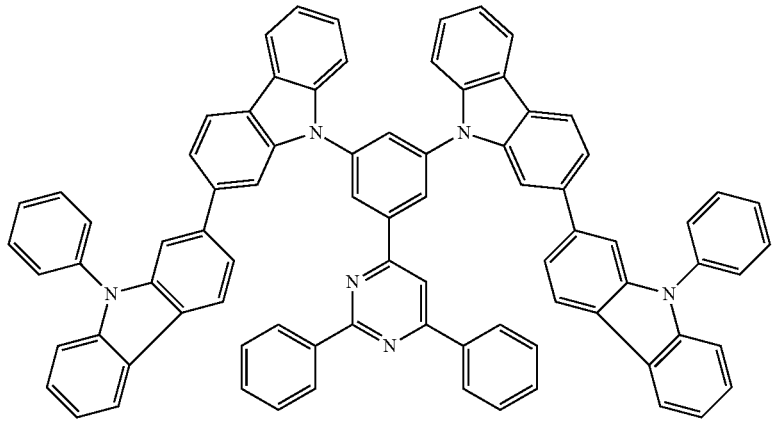
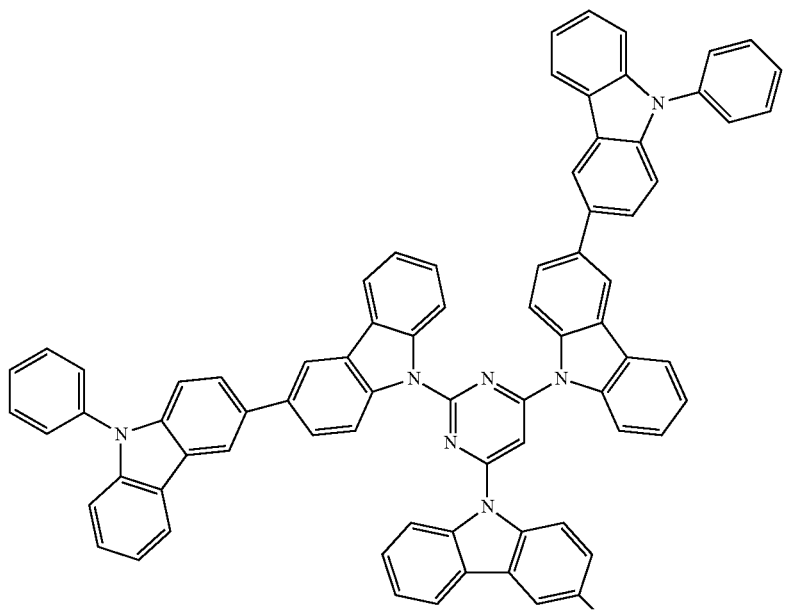
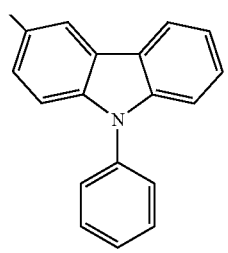

-continued
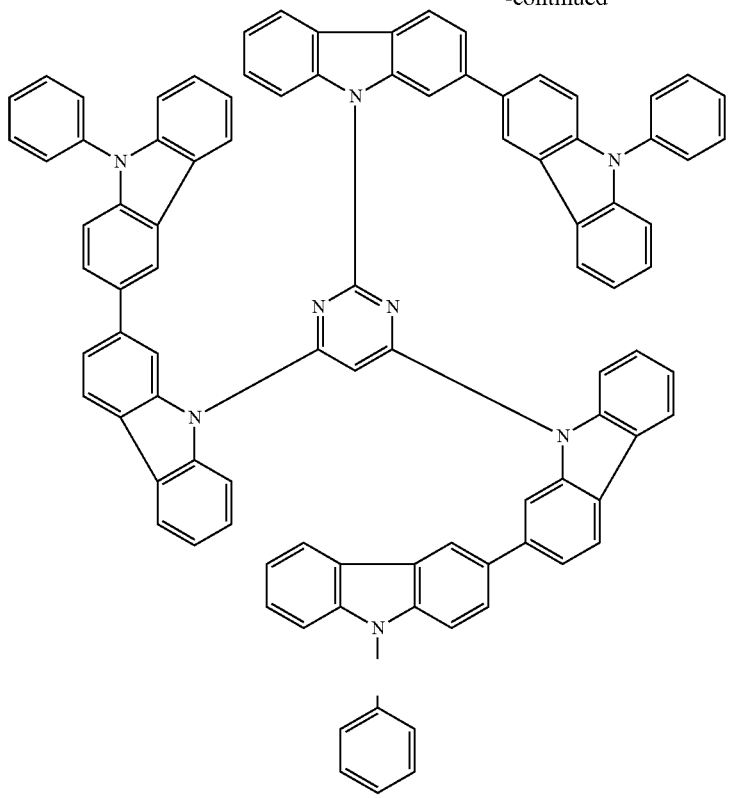
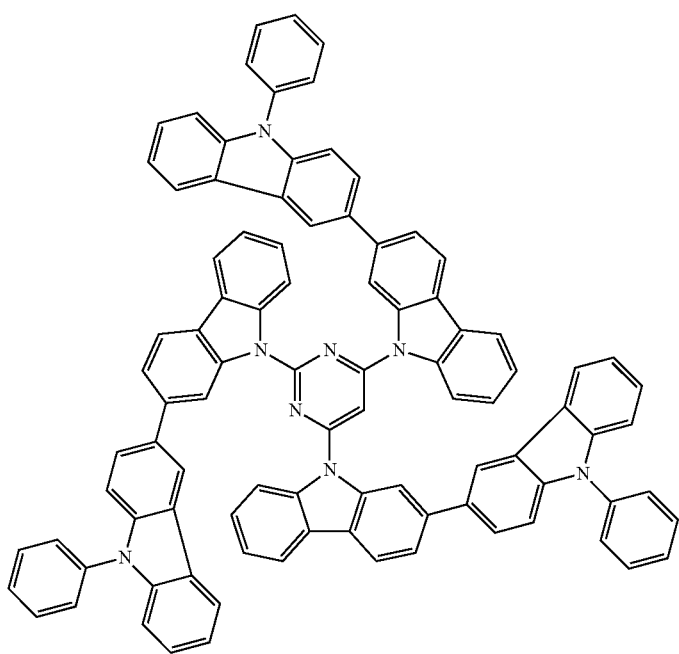

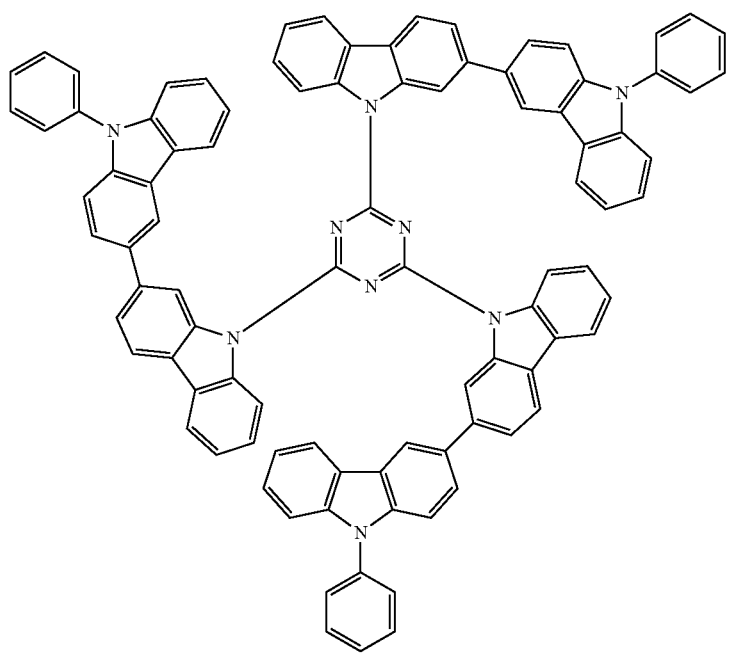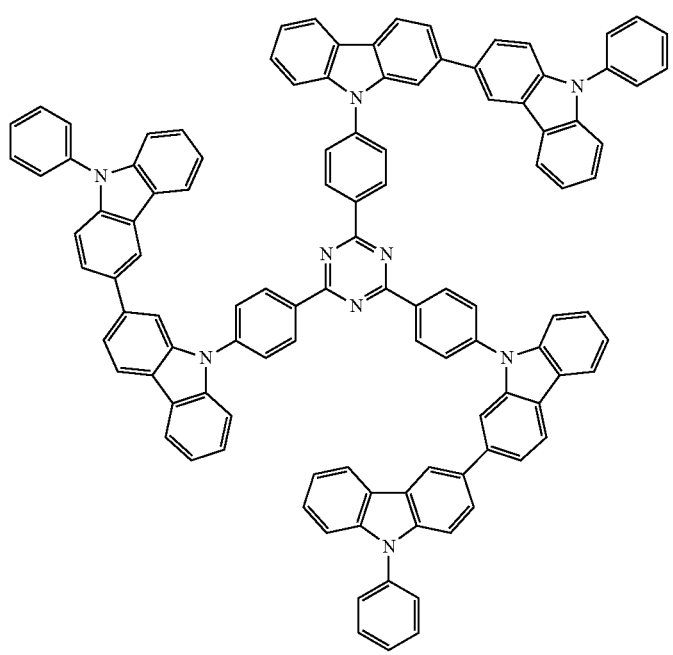

-continued
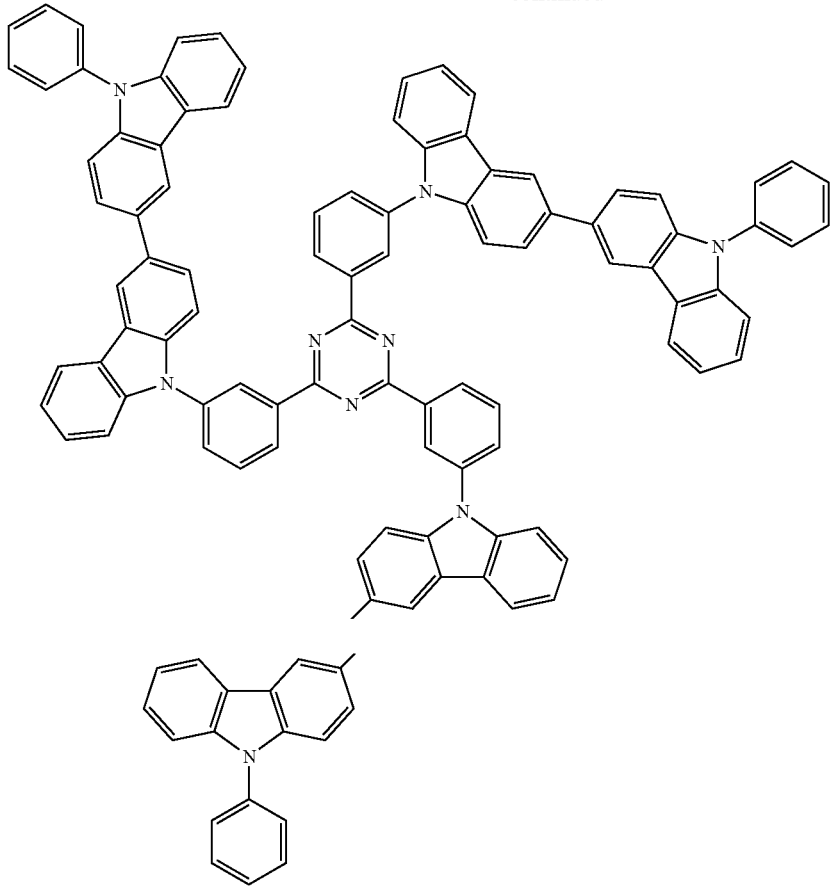
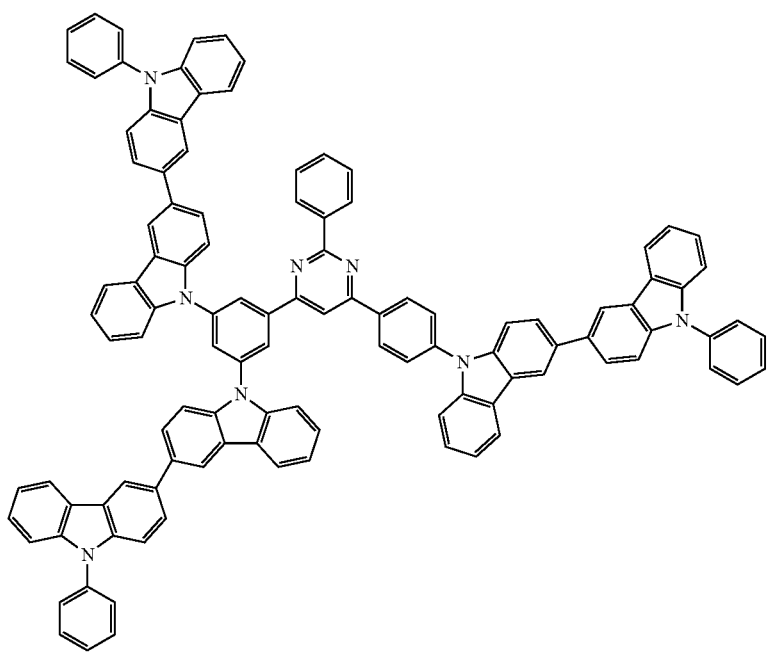

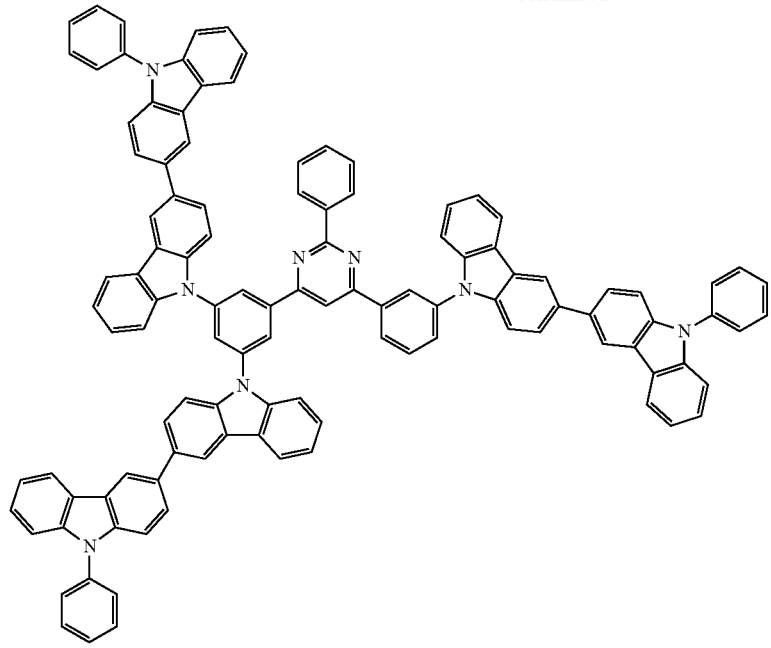
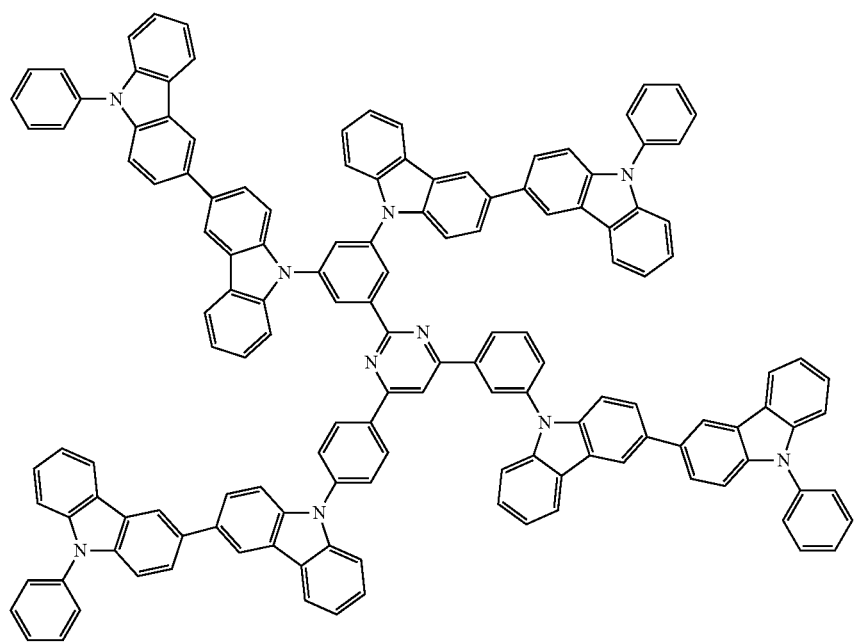

-continued
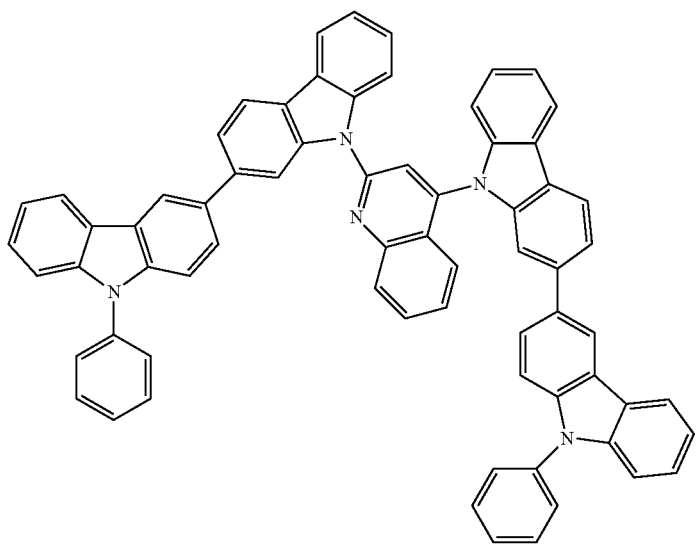
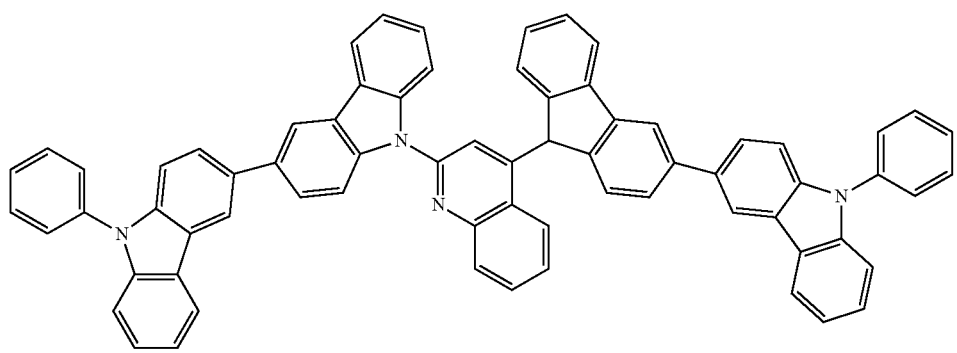
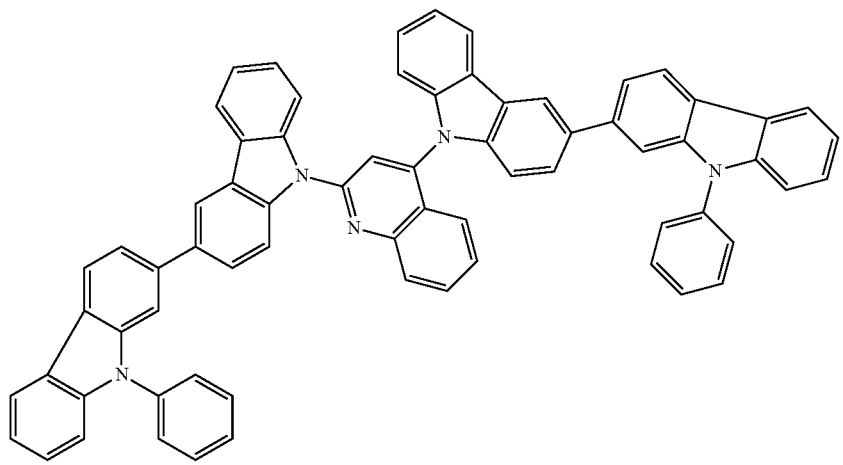

-continued
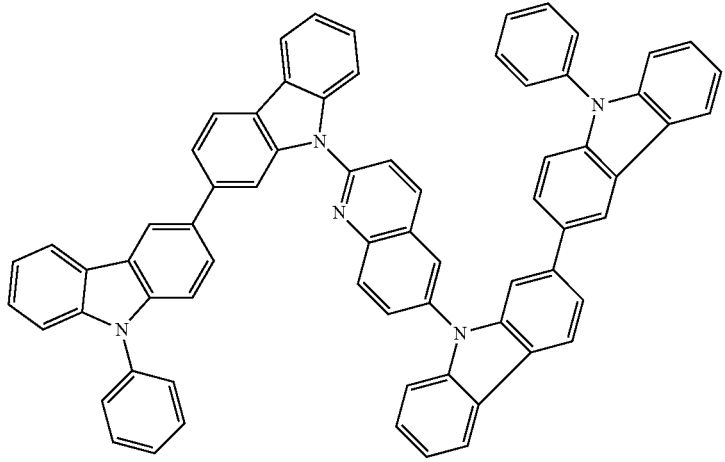
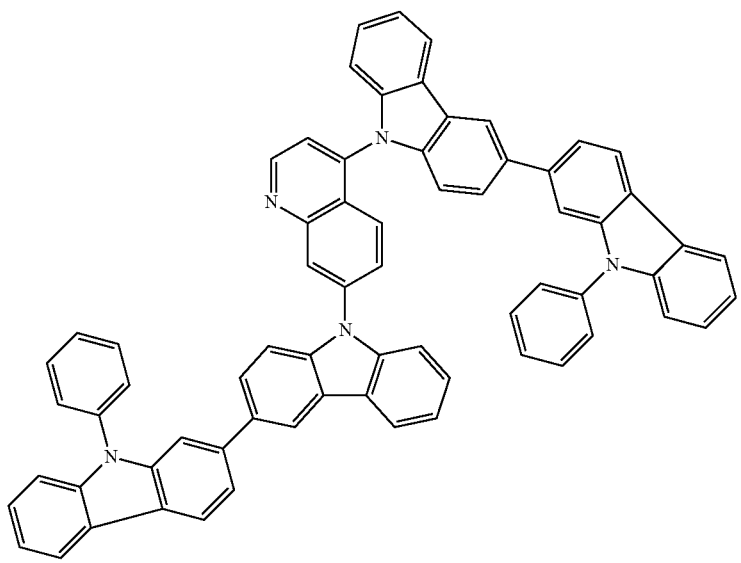
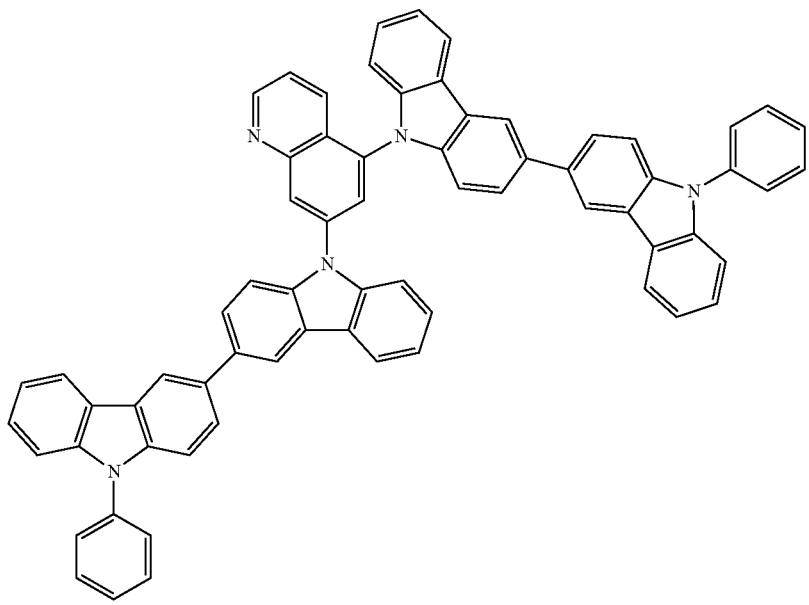

-continued
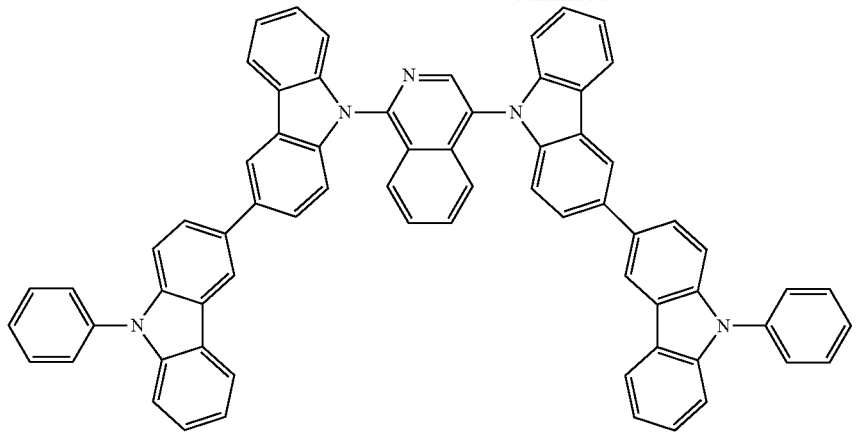
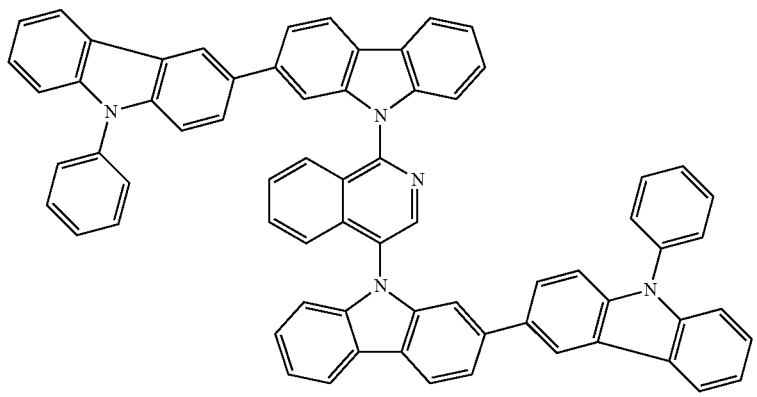
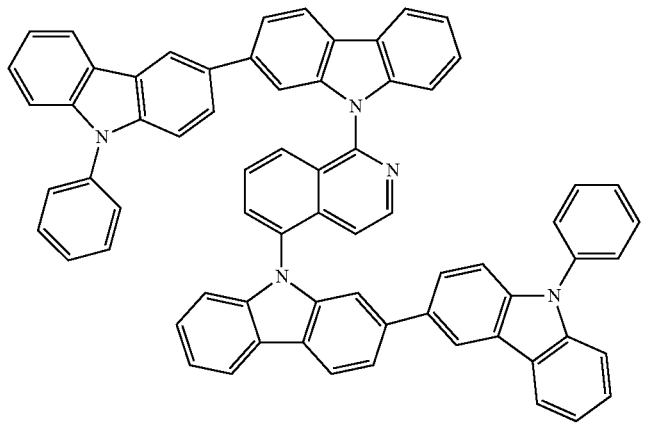
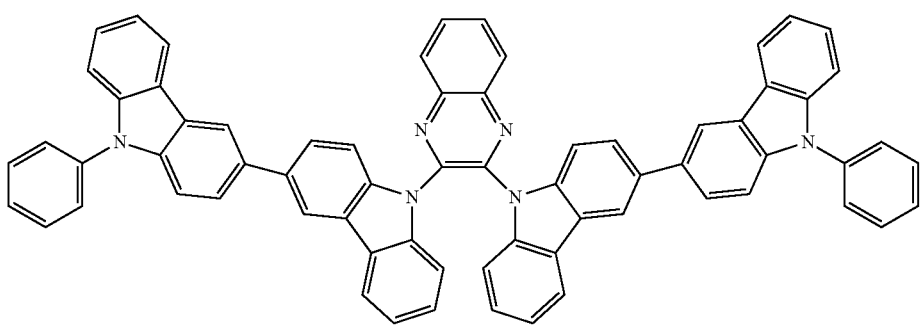

-continued
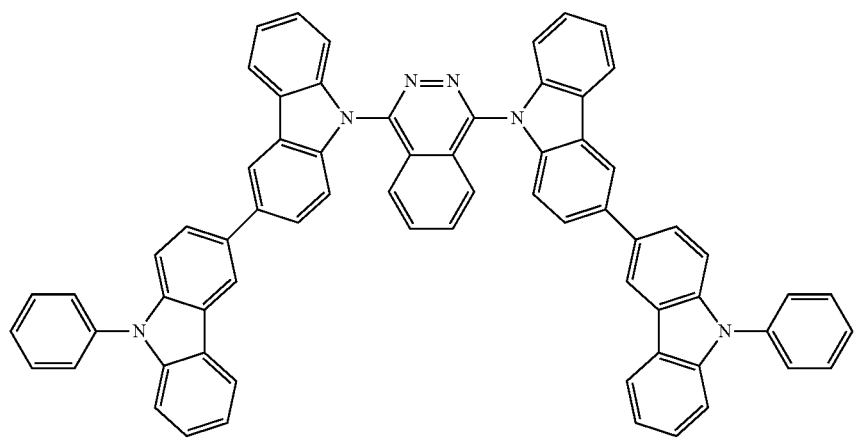
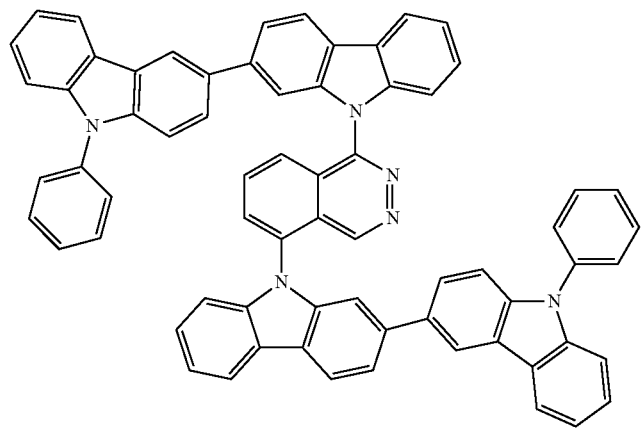
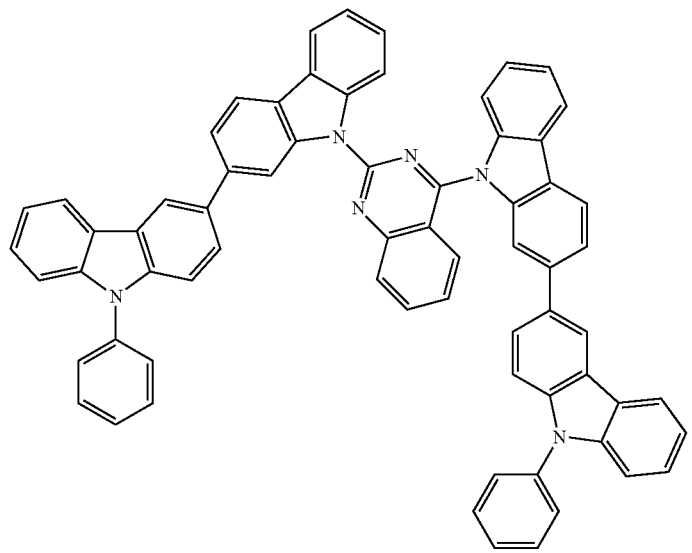

-continued
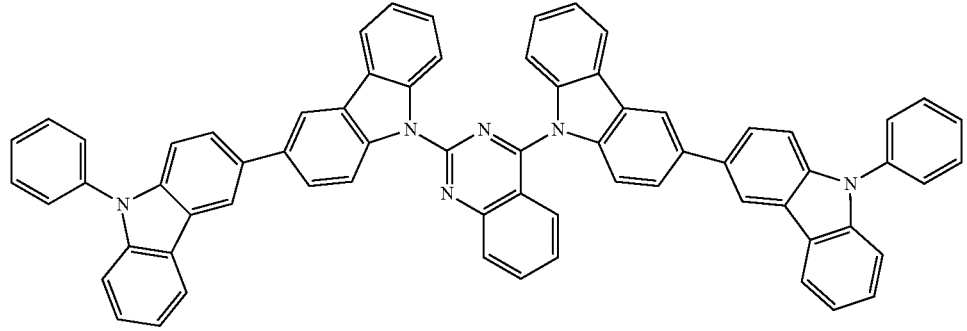
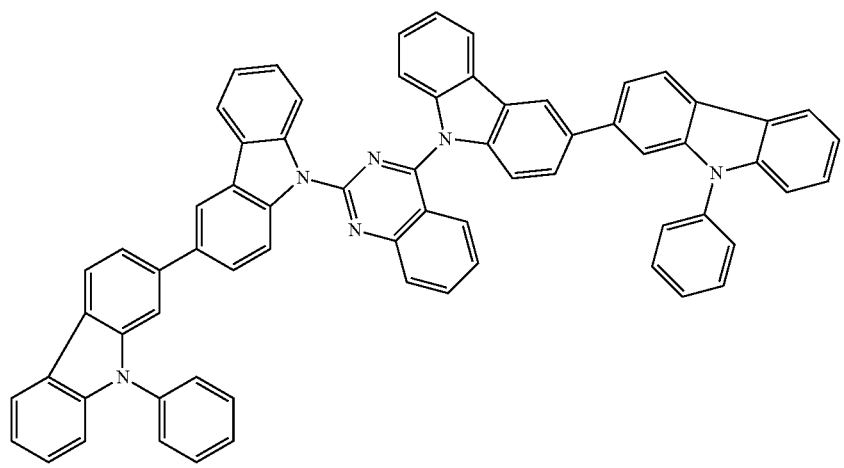
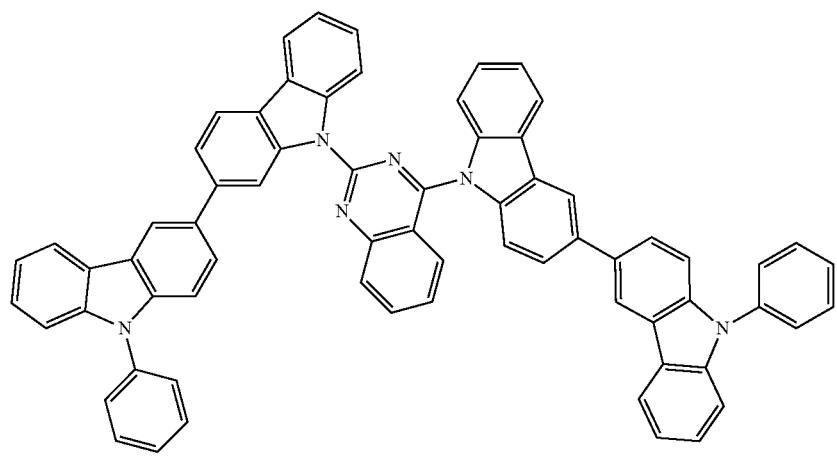
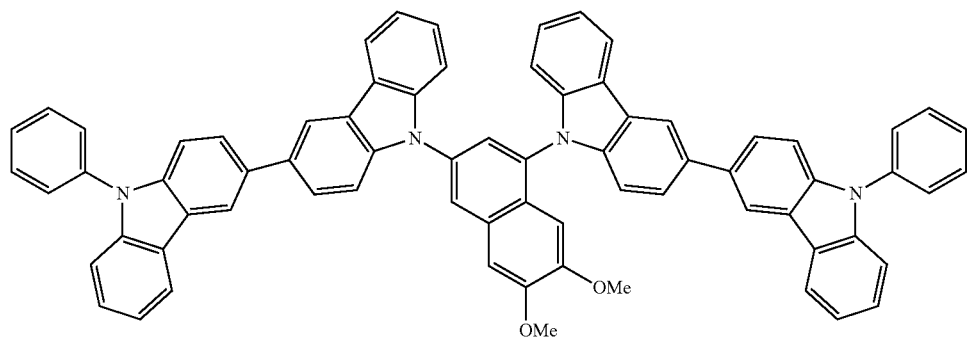

-continued
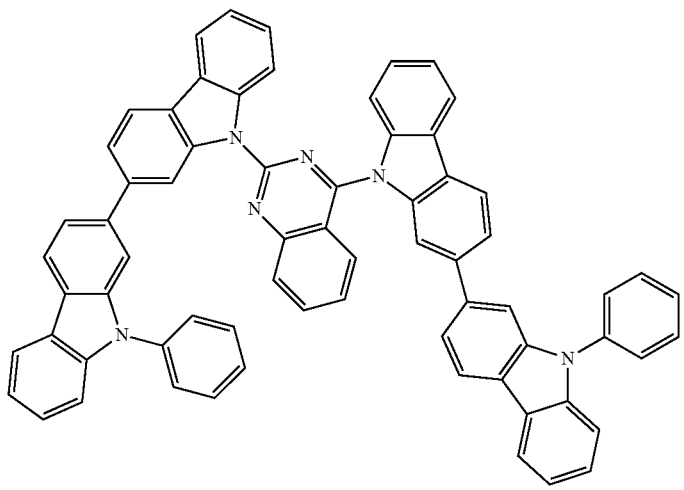
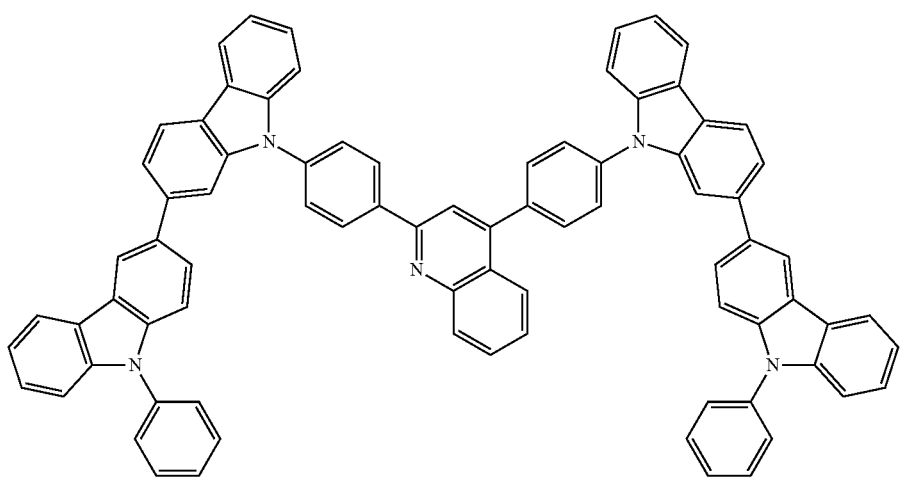
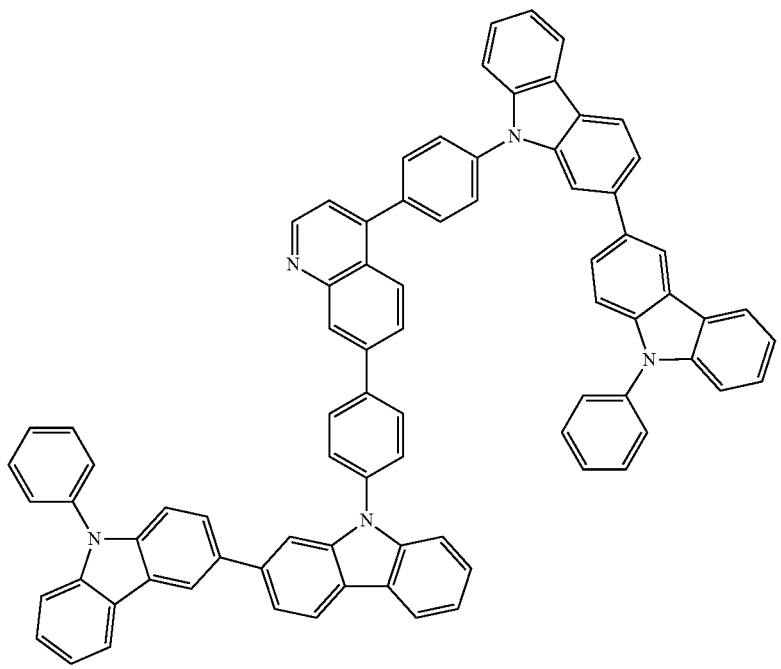

-continued
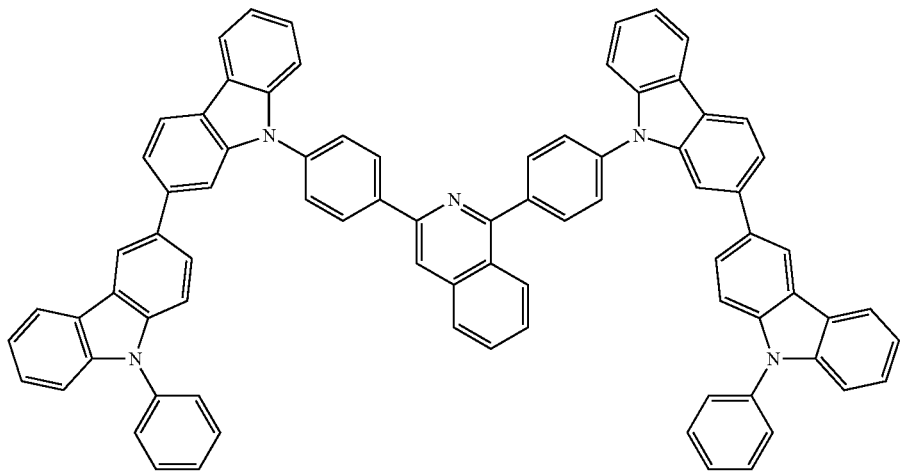
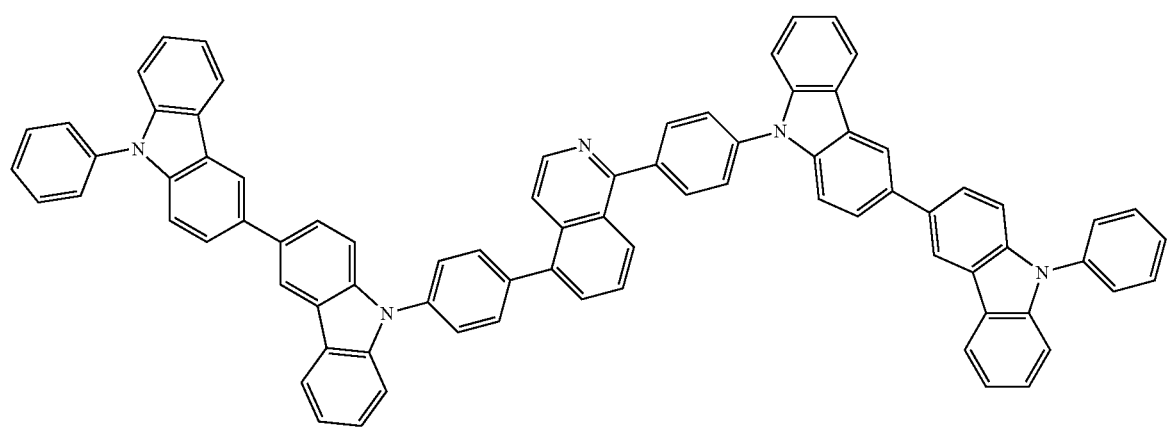
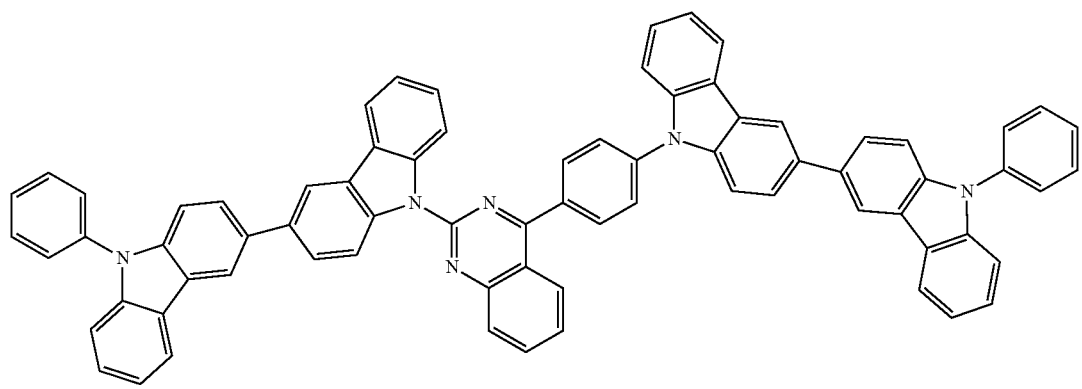
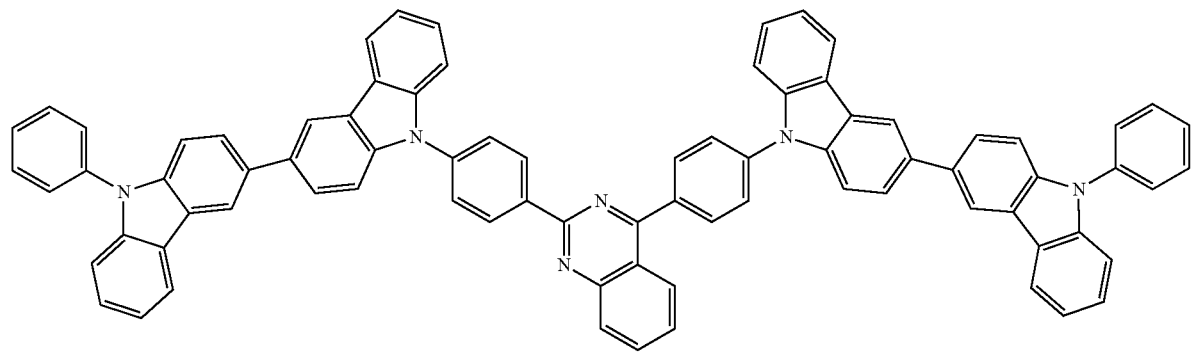

101
102
-continued
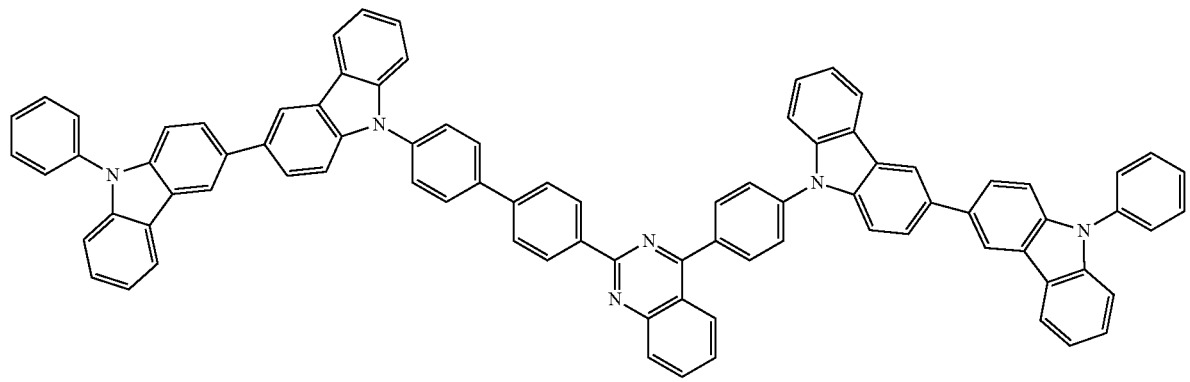
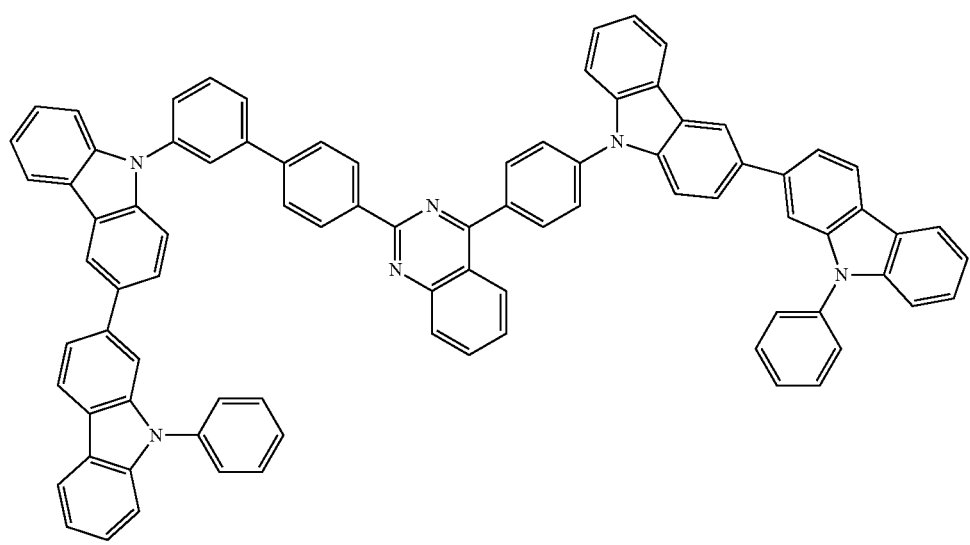
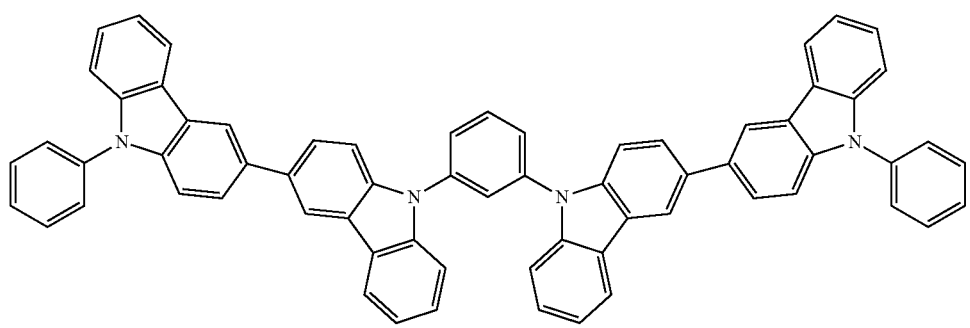

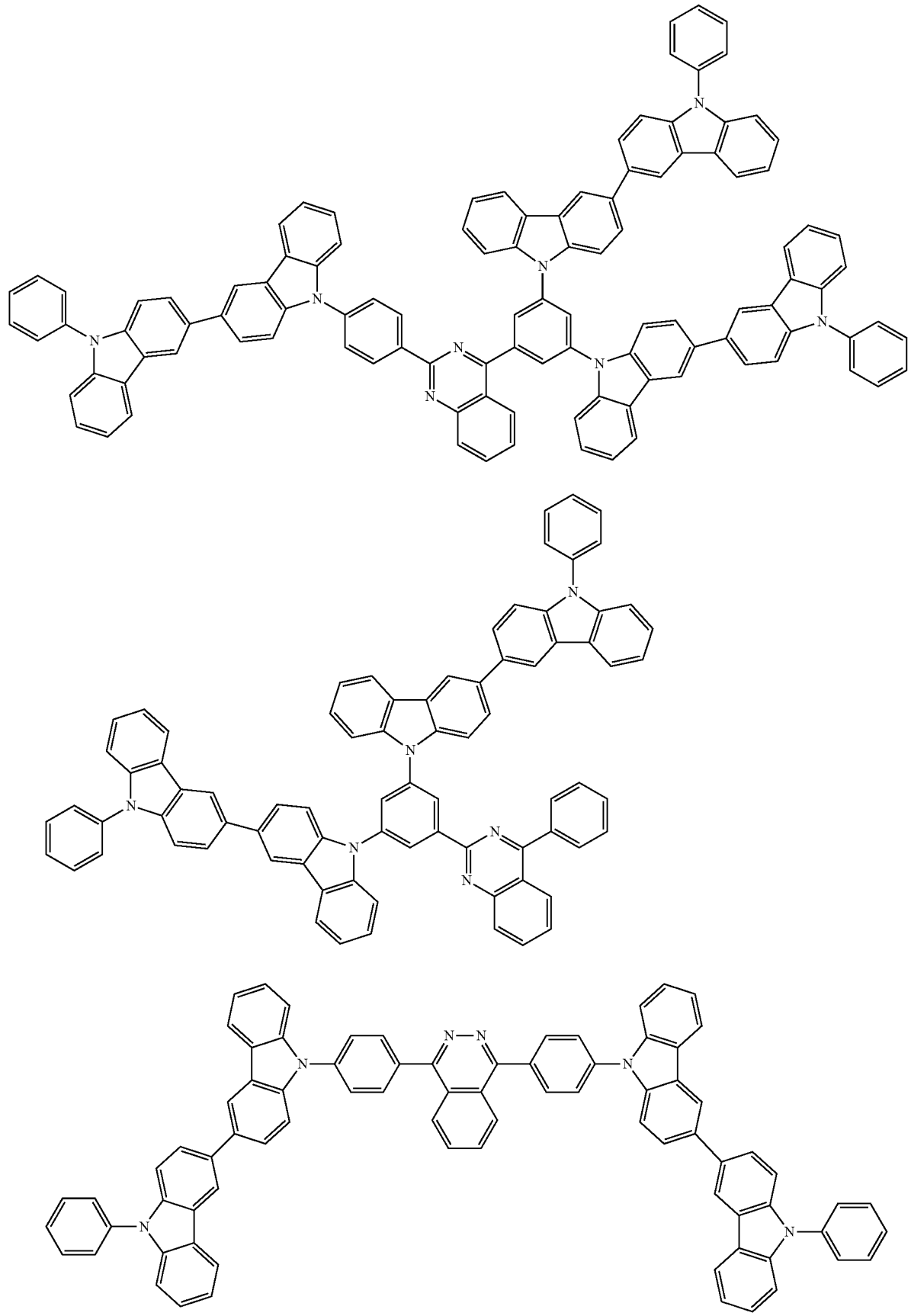

-continued
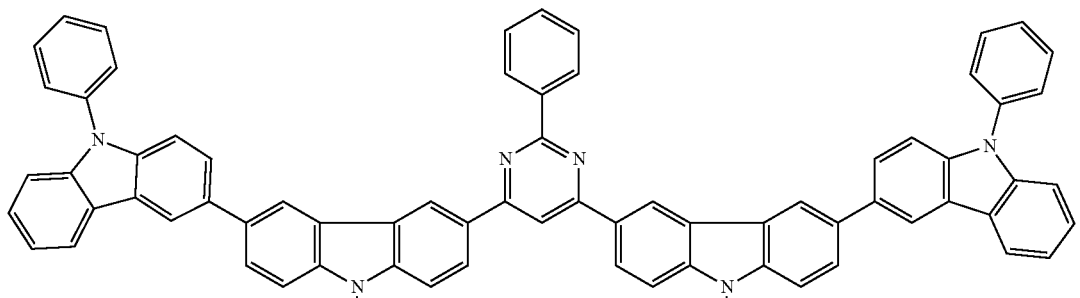
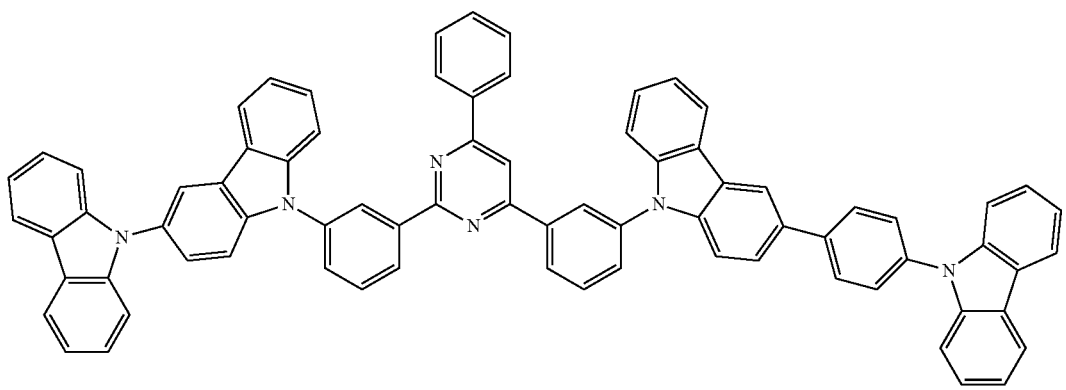
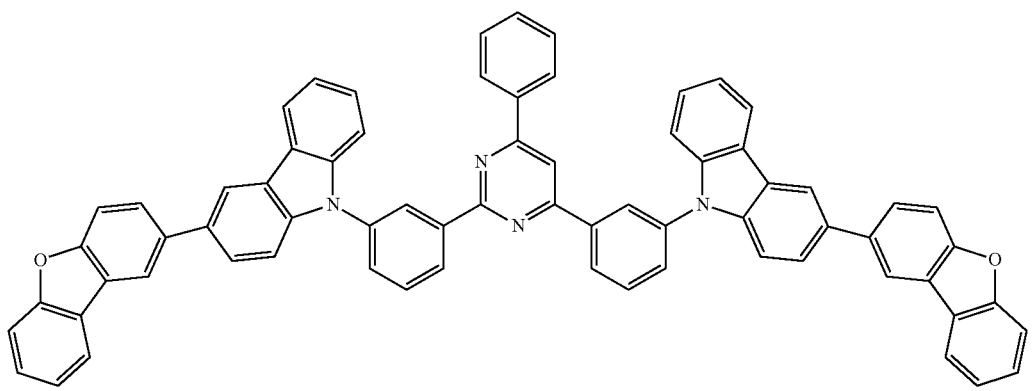
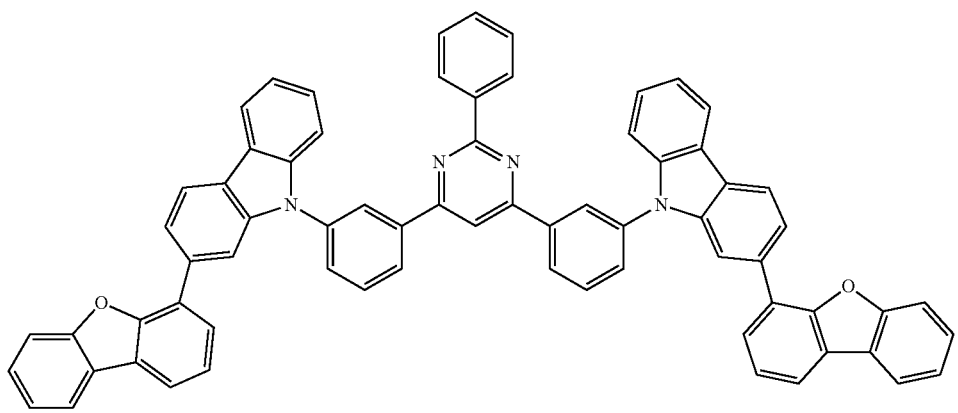

107 108
-continued
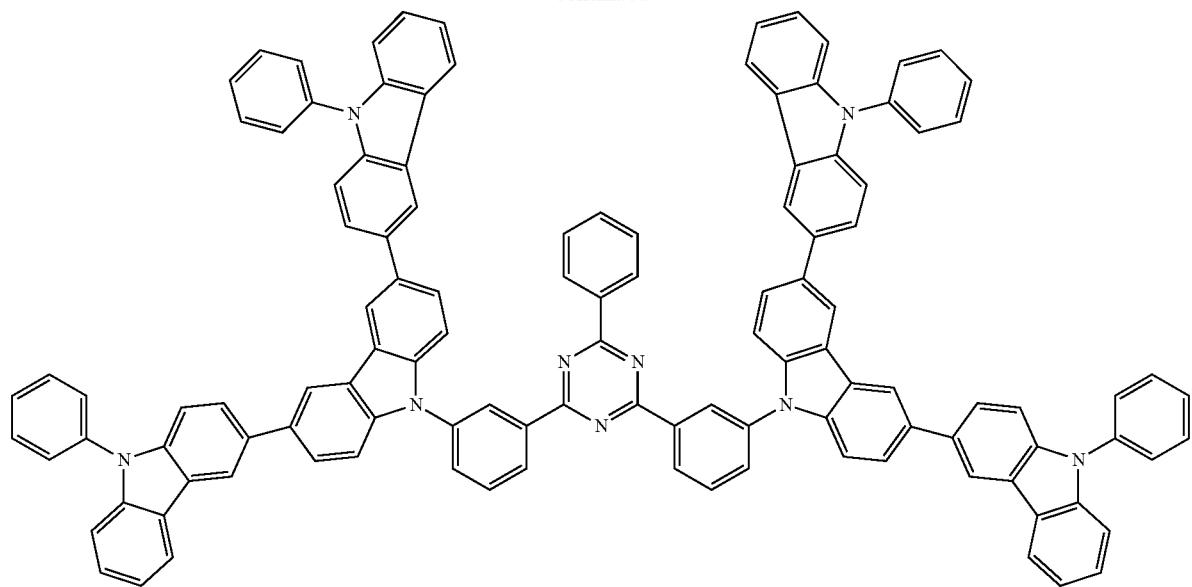
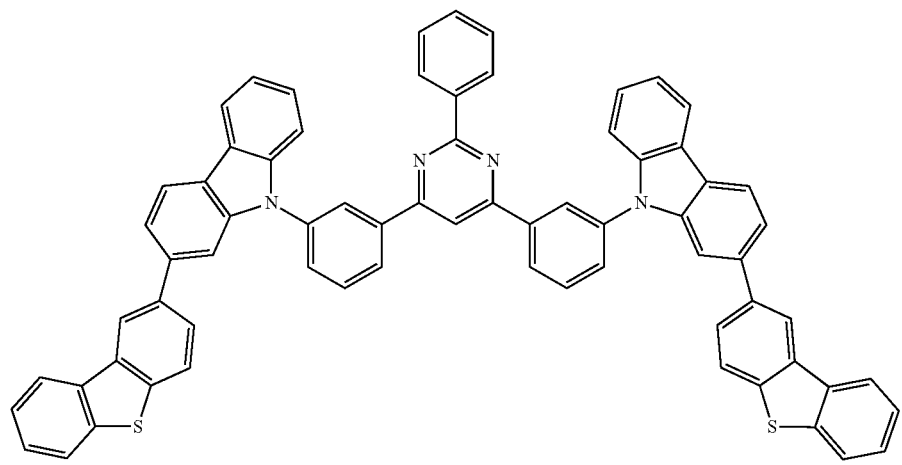
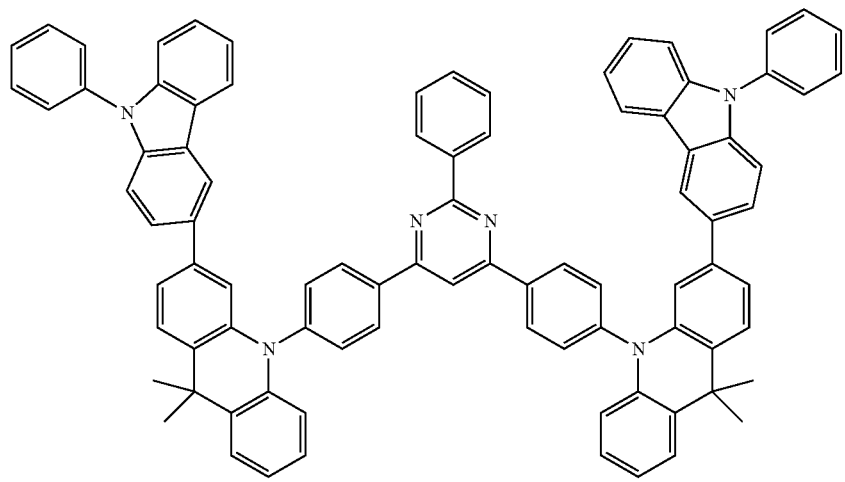

-continued
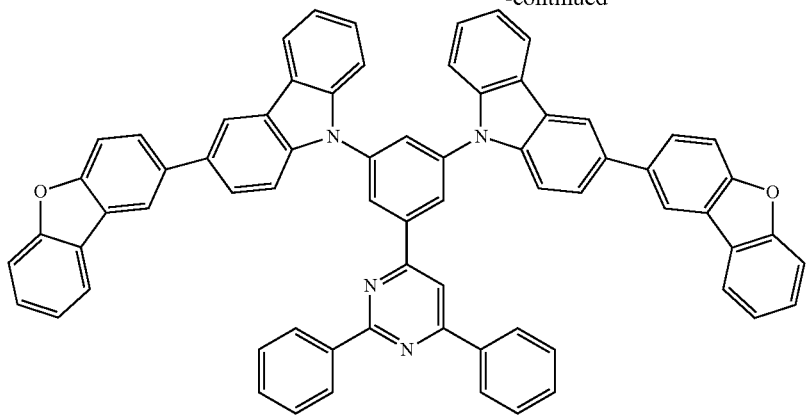
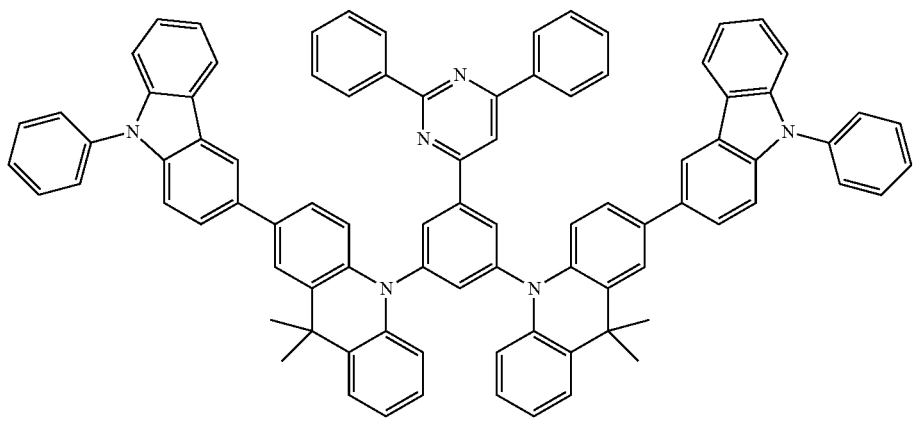
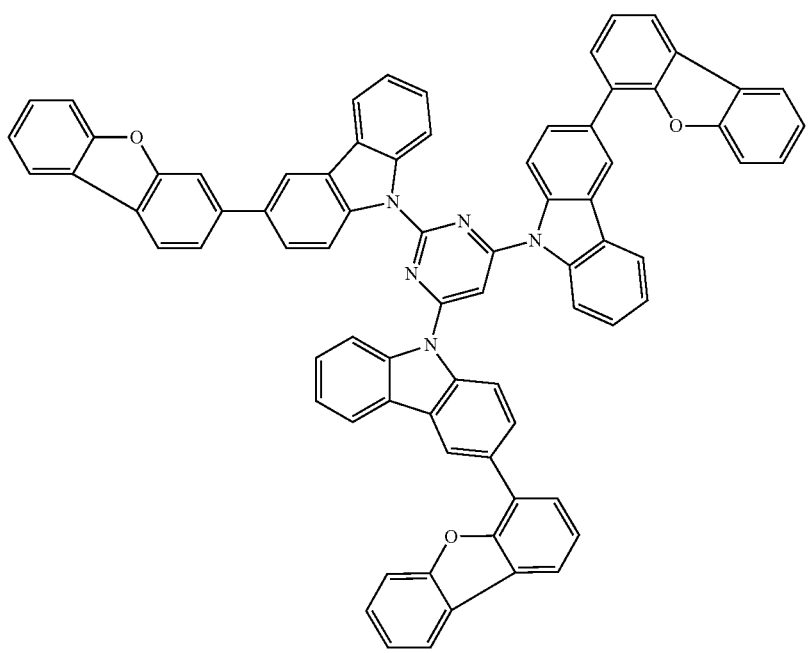

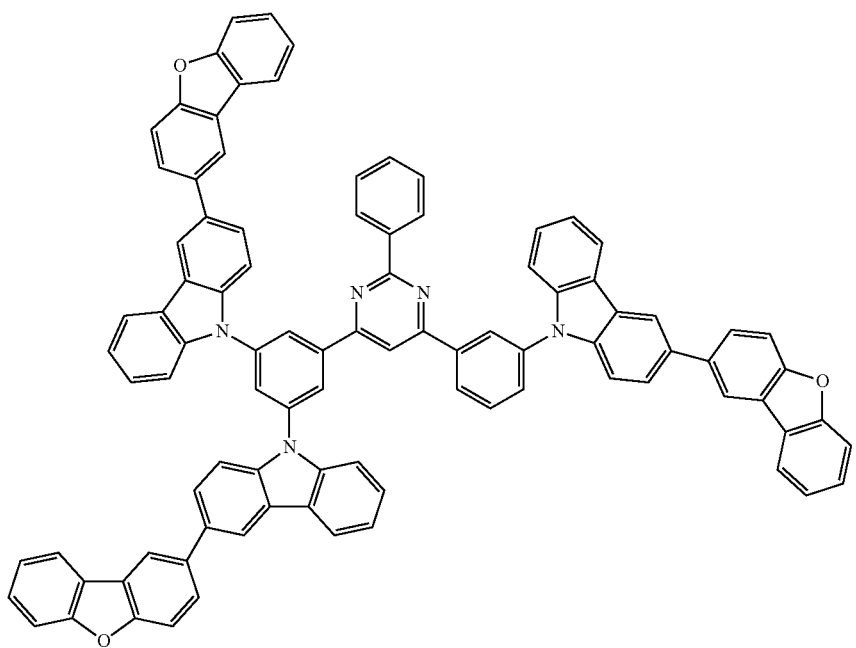
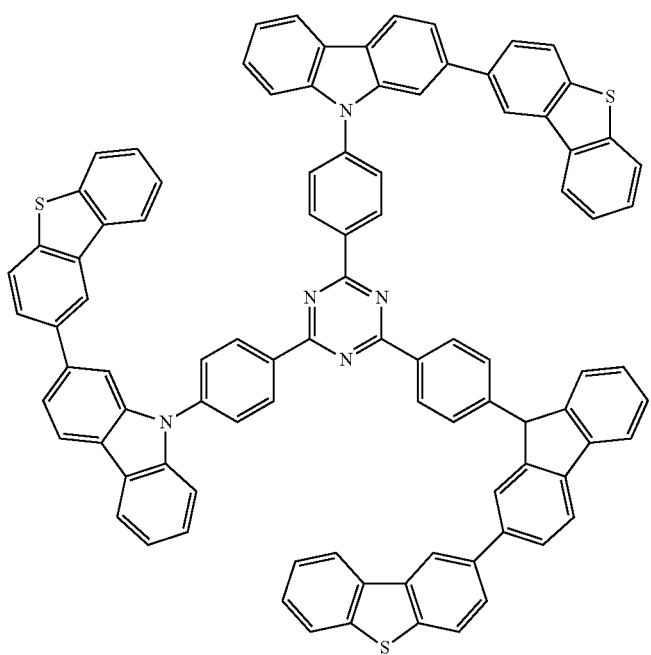

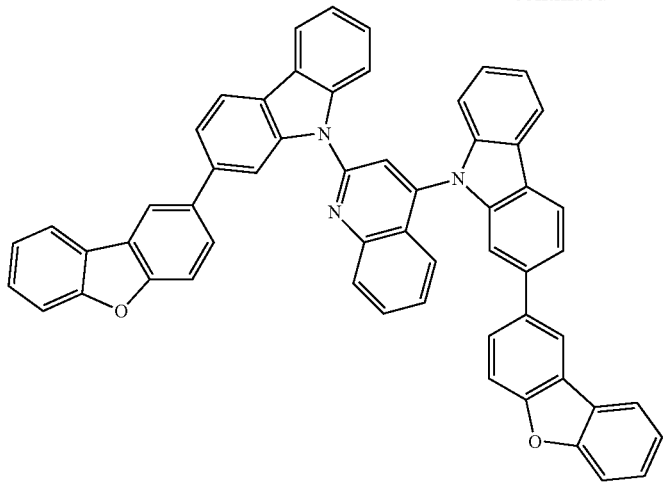
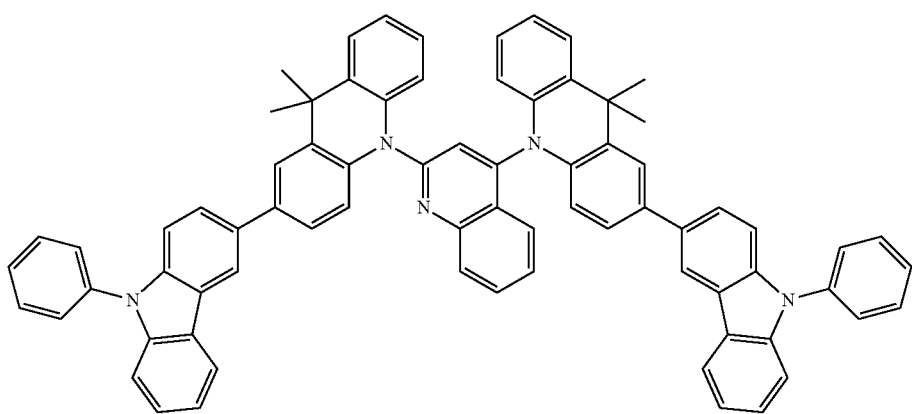
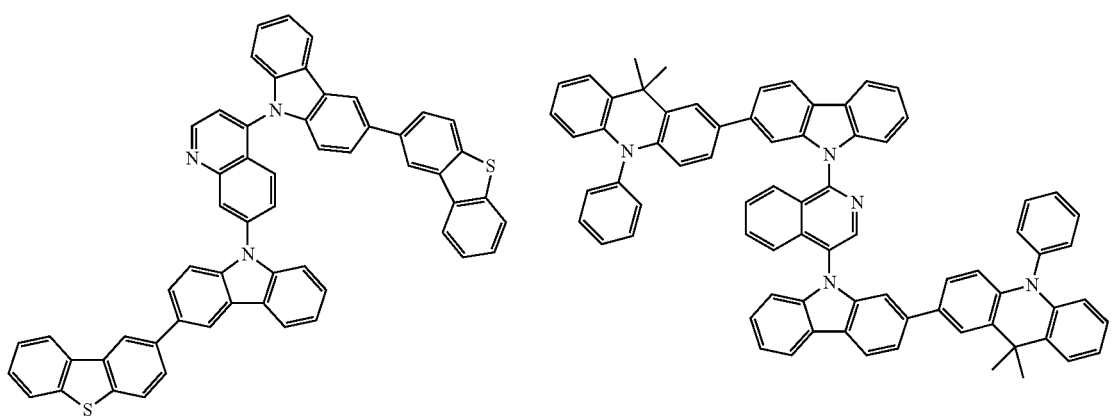
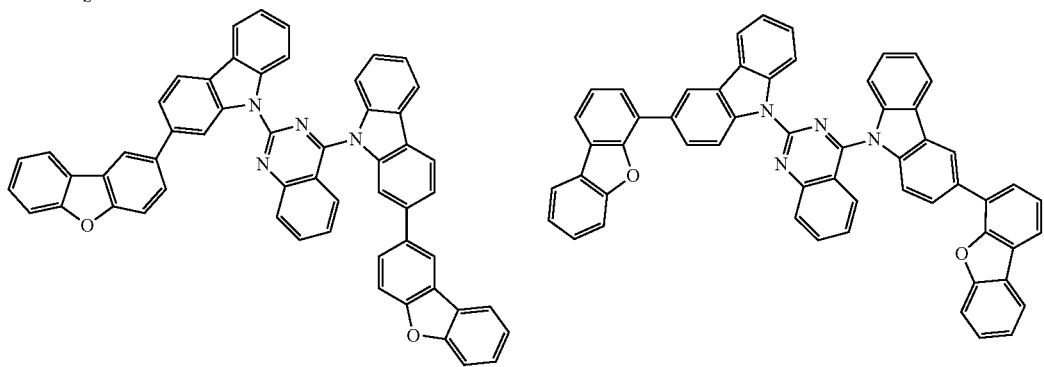

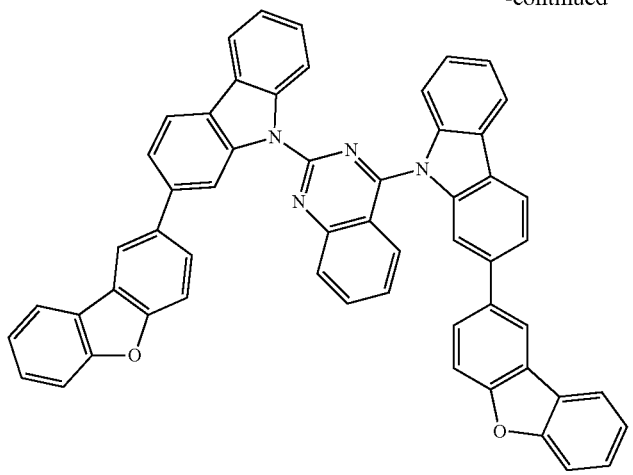
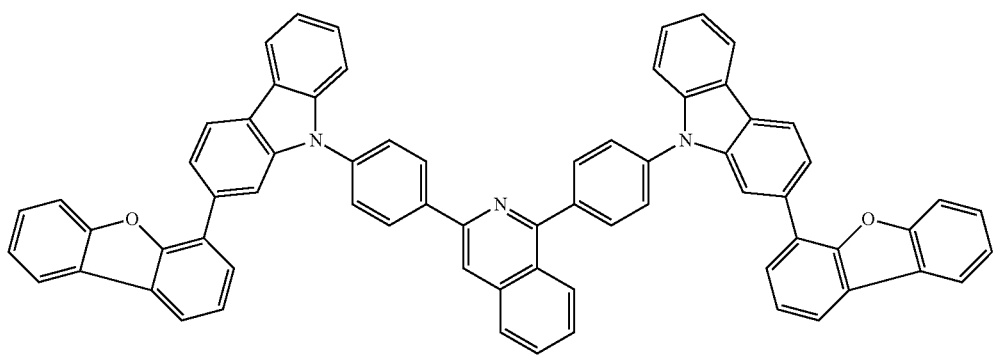
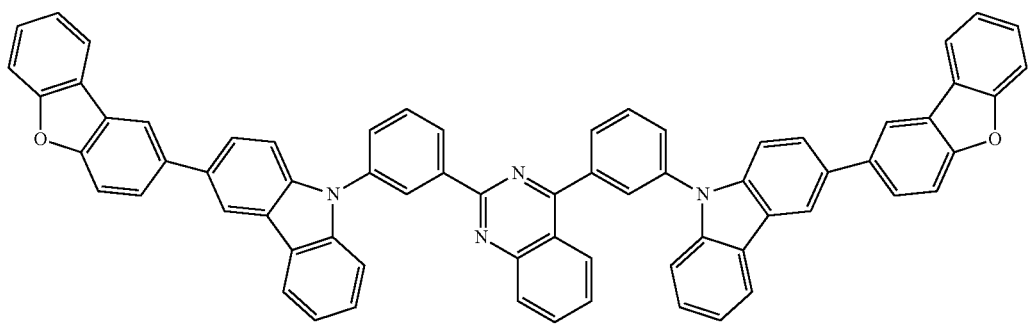
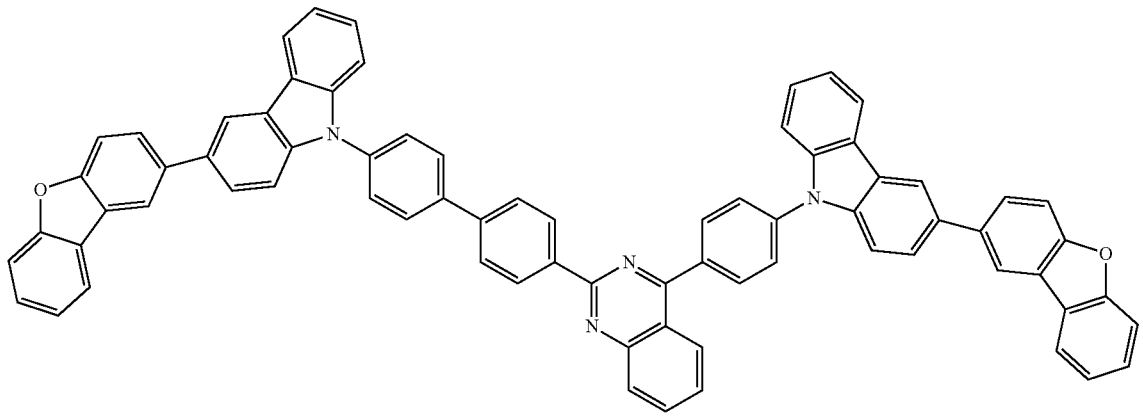

117
118
-continued
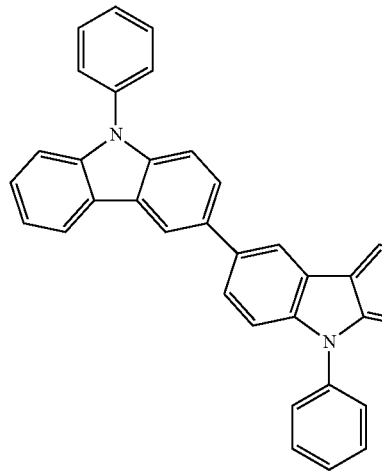
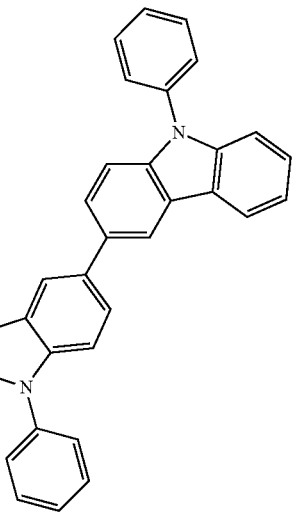
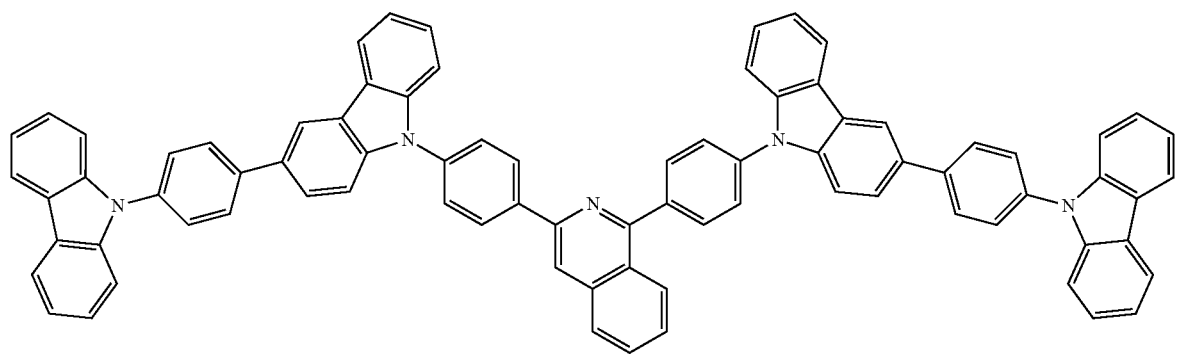
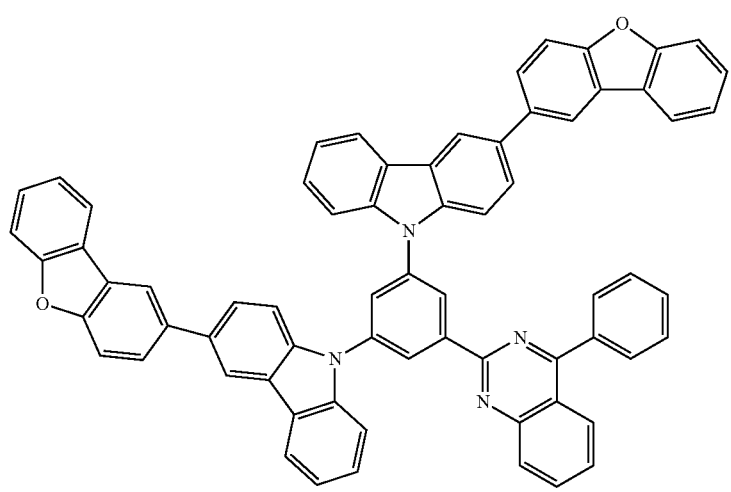

-continued
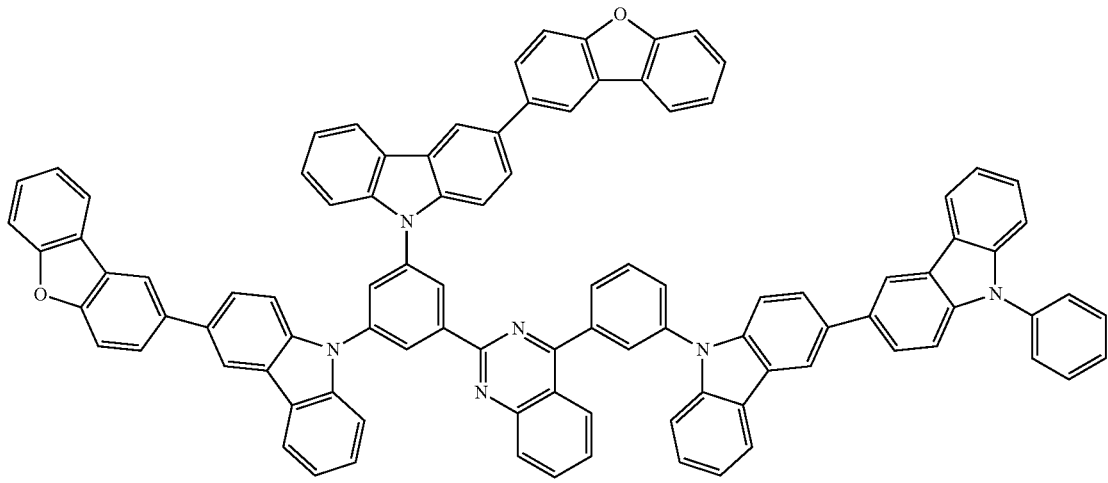
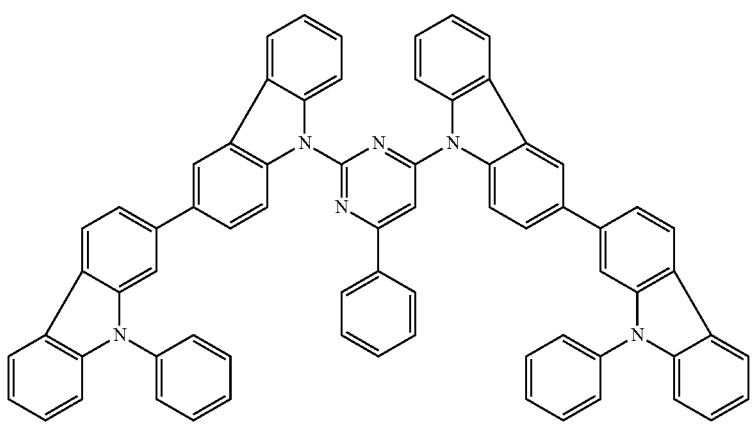
H-5
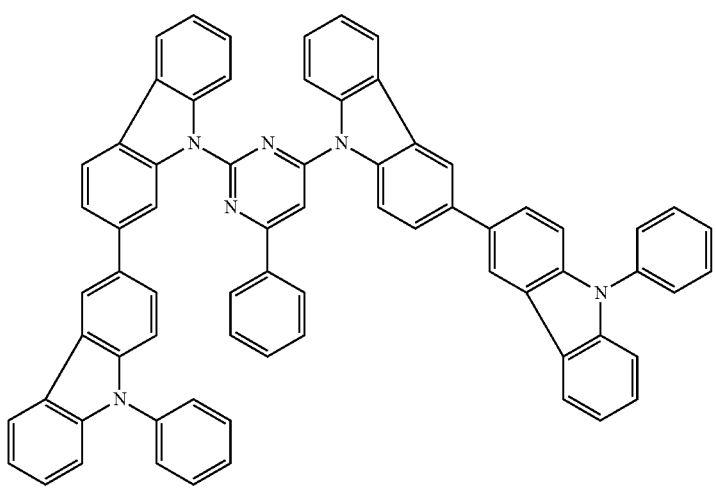
H-6

H-7
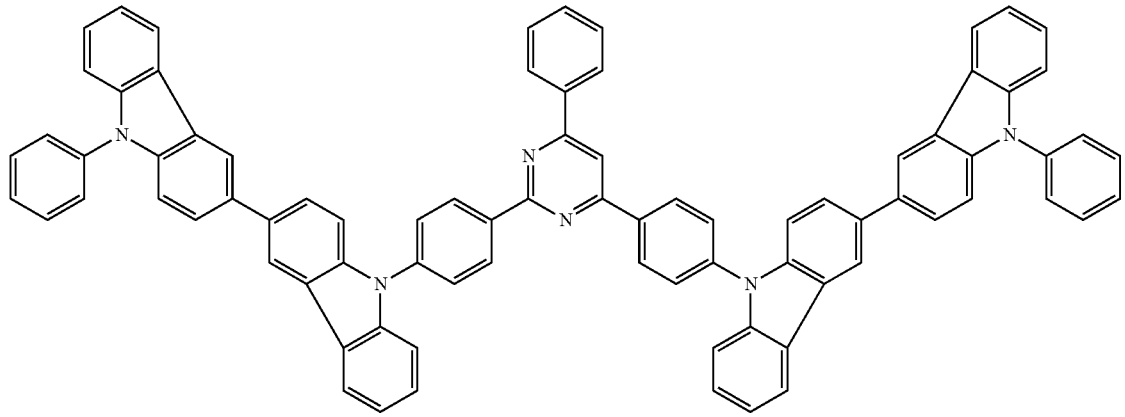
H-8
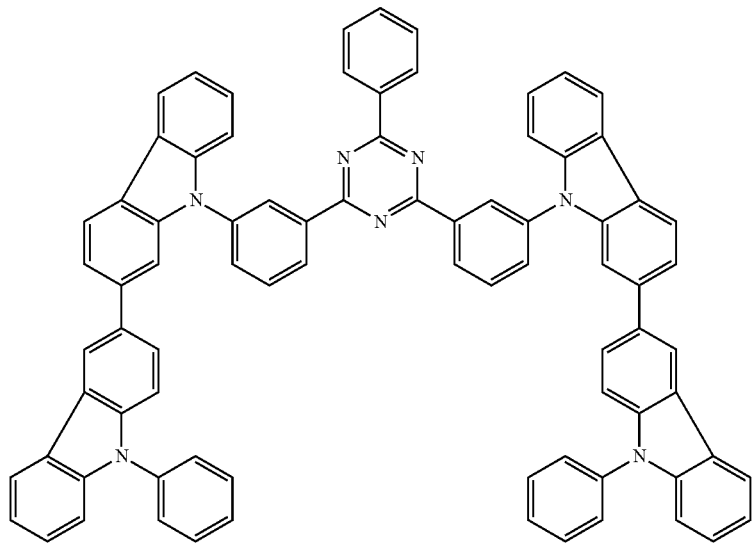
H-9
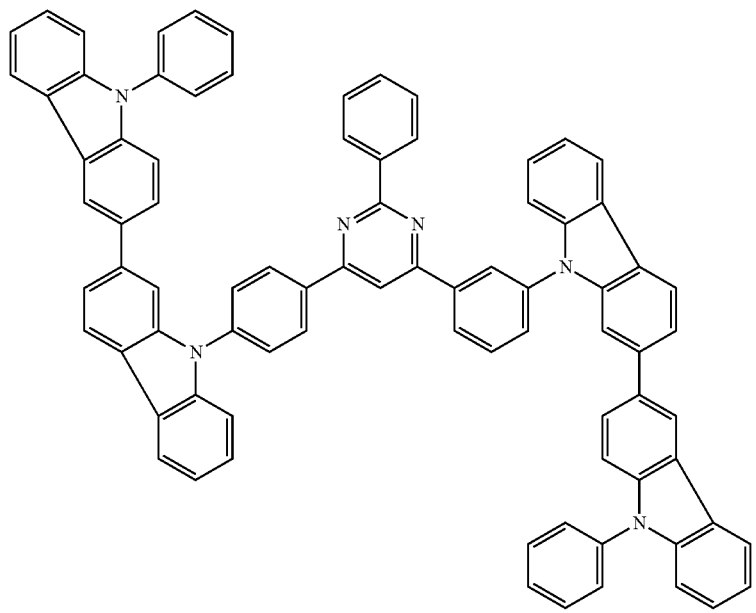

H-10
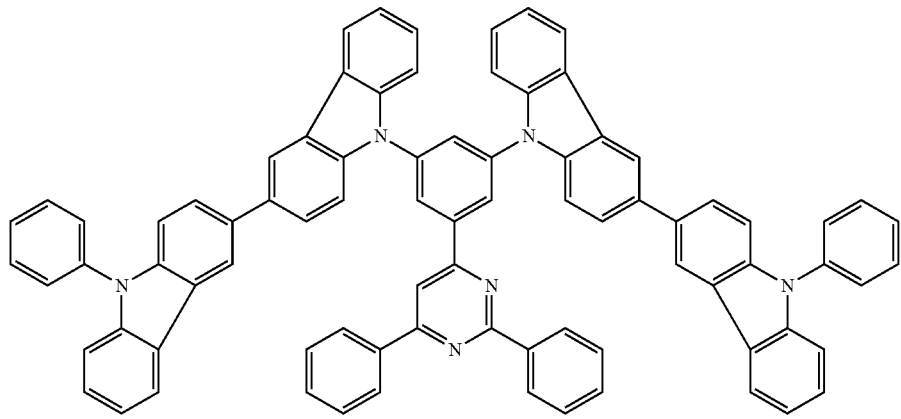
H-11
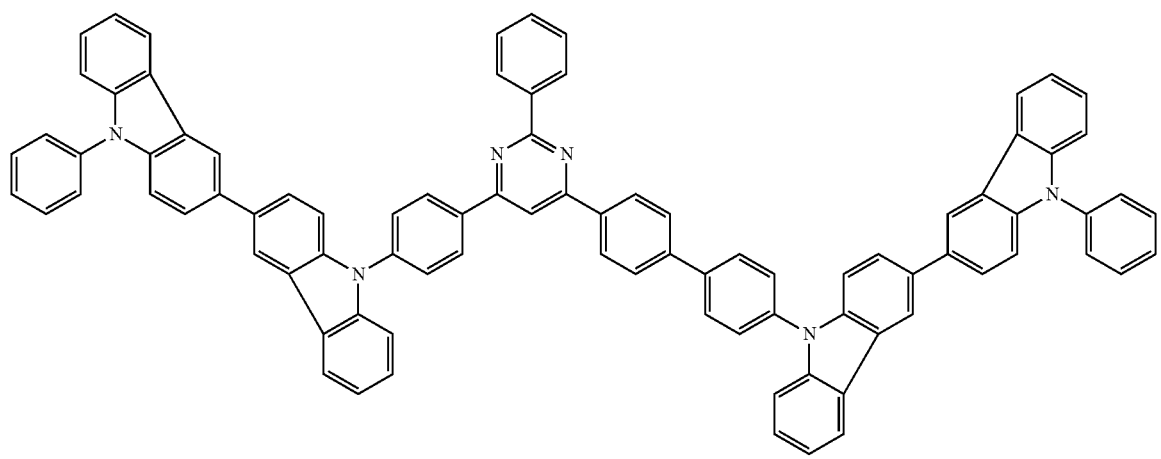
H-12
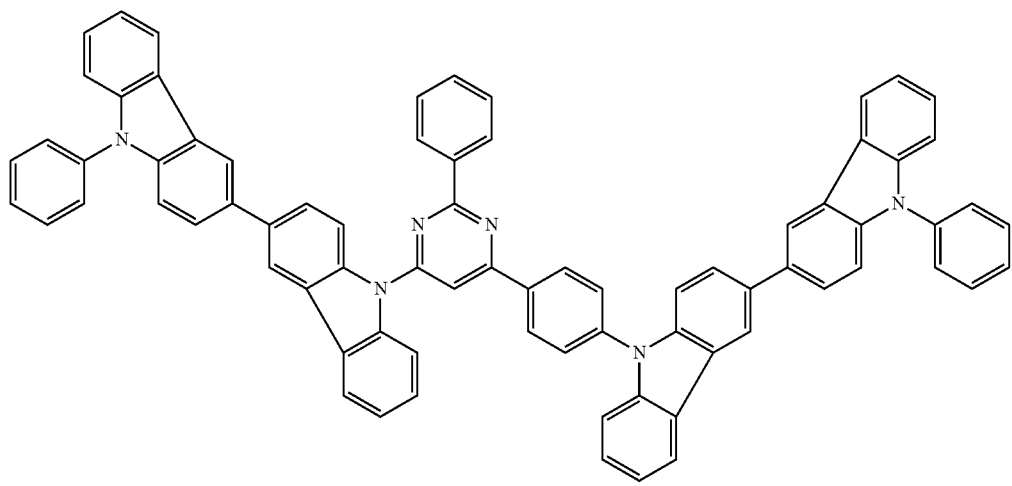

H-13

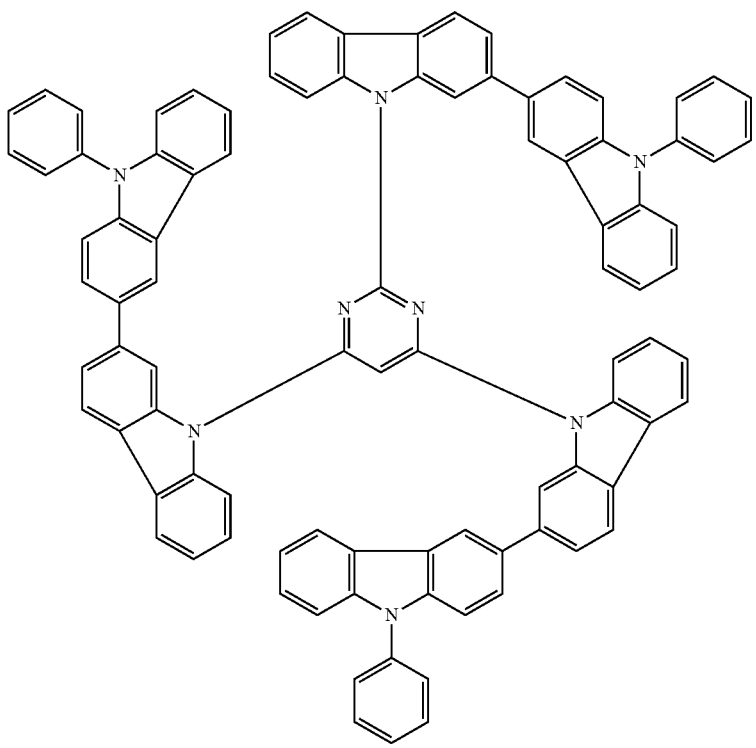

H-14

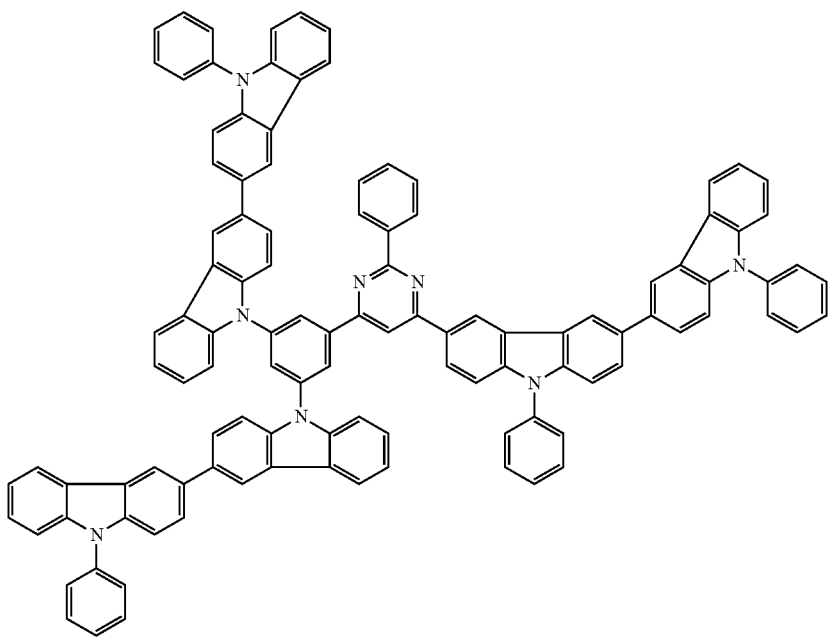

III. An Explanation Will be Given on the Material for an Organic EL Device and the Organic EL Device of the Invention.

The material for an organic EL device of the invention is characterized in that it comprises the above-mentioned aromatic heterocyclic derivative of the invention.

A solution of the material of an organic EL device of the invention is characterized in that it is obtained by dissolving the aromatic heterocyclic derivative of the invention in a solvent.

The organic EL device of the invention is characterized in that it comprises an anode, a cathode and a plurality of organic thin film layers including an emitting layer between the cathode and the anode, and at least one of the organic thin film layers comprises the aromatic heterocyclic derivative of the invention.

The aromatic heterocyclic derivative of the invention is contained in at least one layer of the organic thin film layers of the organic EL device of the invention. In particular, when the aromatic heterocyclic derivative of the invention is used as the host material or a material to be used in an electron-transporting layer and a hole-transporting layer in the emitting layer, the device is expected to have a high luminous efficiency and a long life.

First Embodiment

As specific examples of the multi-layer organic EL device, one obtained by stacking a plurality of layers to have the following multi-layer configurations can be given, for example.

(1) Anode/Hole-transporting layer (Hole-injecting layer)/Emitting layer/Cathode (2) Anode/Emitting layer/Electron-transporting layer (Electron-injecting layer)/Cathode (3) Anode/Hole-transporting layer (Hole-injecting layer)/Emitting layer/Electron-transporting layer (Electron-injecting layer)/Cathode (4) Anode/Hole-transporting layer (Hole-injecting layer)/Emitting layer/Hole-blocking layer/Electron-transporting layer (Electron-injecting layer)/Cathode In the organic EL device of the invention, it is preferred that the emitting layer contain the aromatic heterocyclic derivative of the invention as the host material. Further, it is preferred that the emitting layer be composed of a host material and a phosphorescent emitting material, and that the host material be the aromatic heterocyclic derivative of the invention.

The aromatic heterocyclic derivative of the invention may be a host material to be used together with the phosphorescent emitting material and an electron-transporting material to be used together with the phosphorescent emitting material. It is preferred that the lowest excited triplet energy be 2.2 to 3.2 eV, with 2.5 to 3.2 eV being more preferable. The "triplet energy" means a difference in energy between the lowest excited triplet state and the ground state.

As the phosphorescent emitting material, in respect of high phosphorescent quantum yield and further improvement in external quantum efficiency of an emitting device, a compound containing iridium (Ir), osmium (Os), ruthenium (Ru) or platinum (Pt) is preferable. It is further preferable that the phosphorescent emitting material be a metal complex such as an iridium complex, an osmium complex, a ruthenium complex and a platinum complex. Of these, an iridium complex and a platinum complex are more preferable. An orthometalated complex of a metal atom selected from iridium, osmium (Os) and platinum (Pt) is most preferable. Specific examples of a metal complex such as an iridium complex, an osmium complex, a ruthenium complex and a platinum complex are shown below.

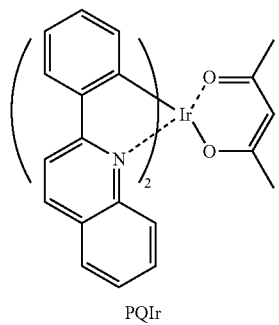

PQIr

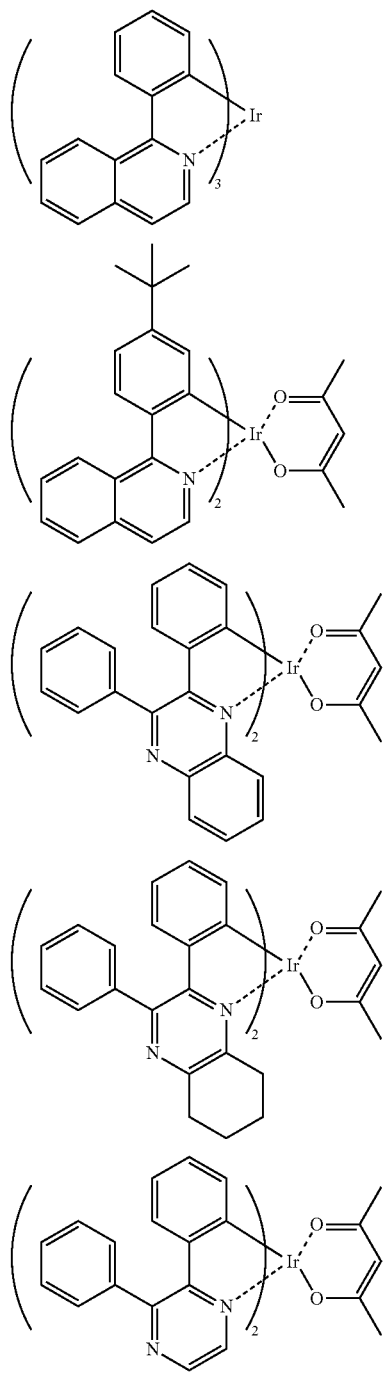

-continued

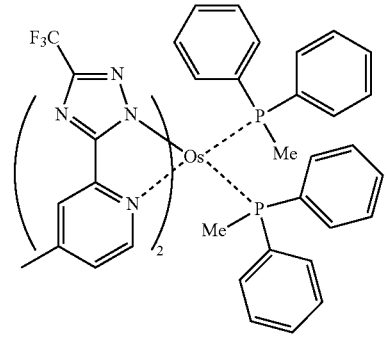

129
-continued
130
-continued
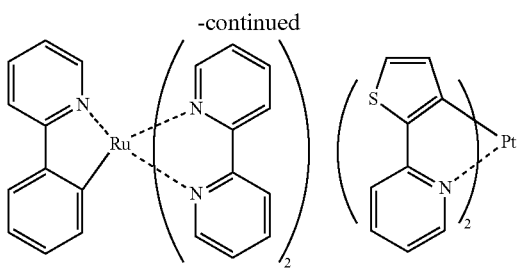
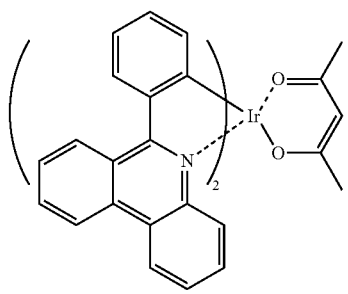
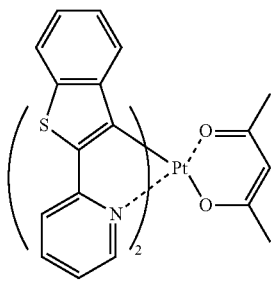
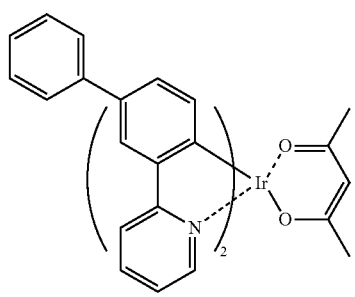
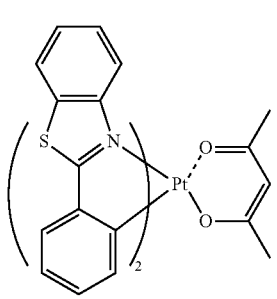
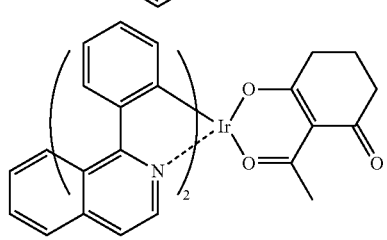
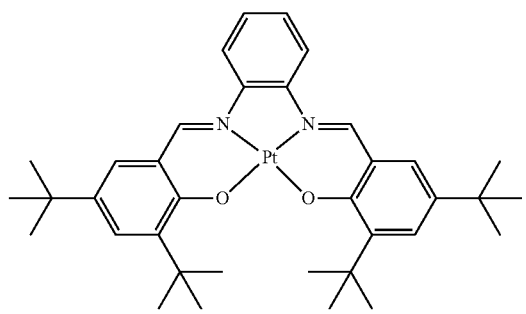
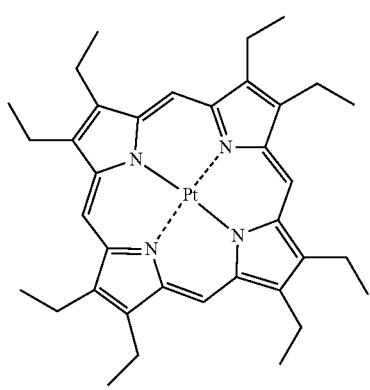
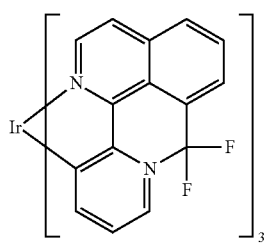
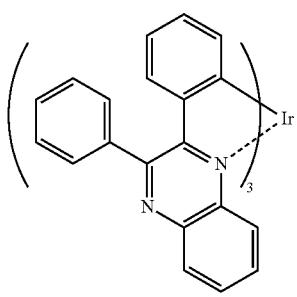
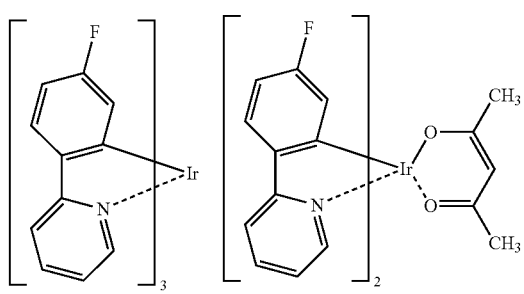

-continued
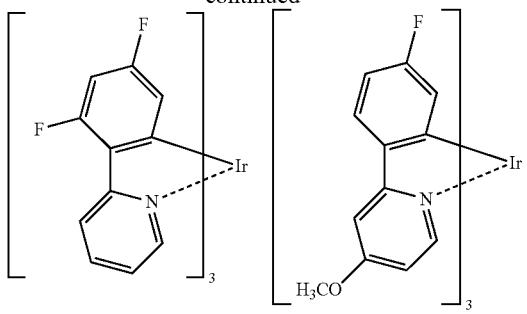
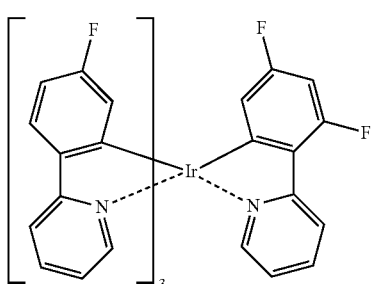
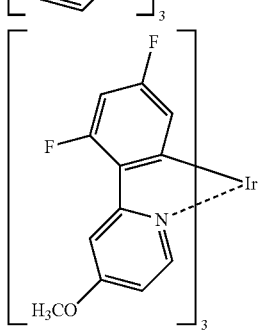
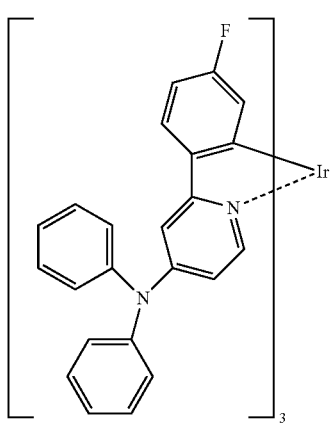
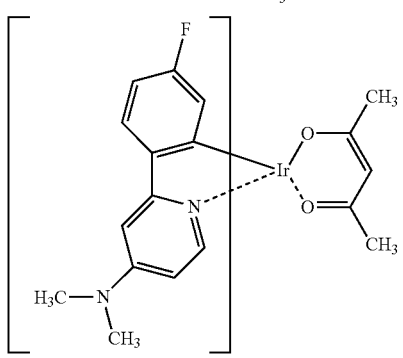
-continued
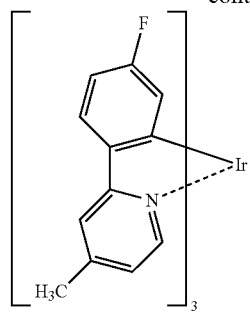
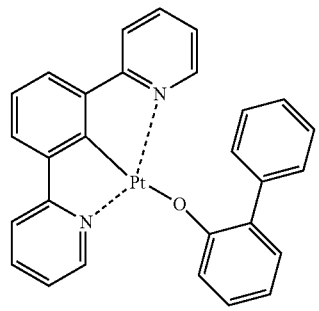
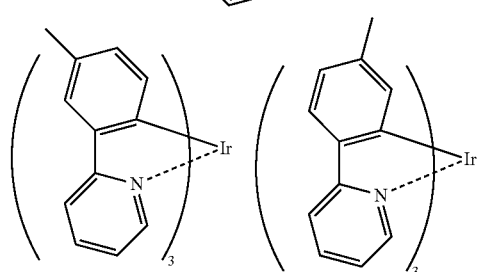
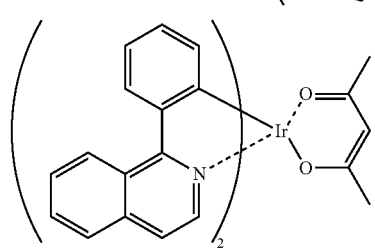
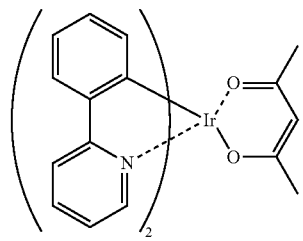
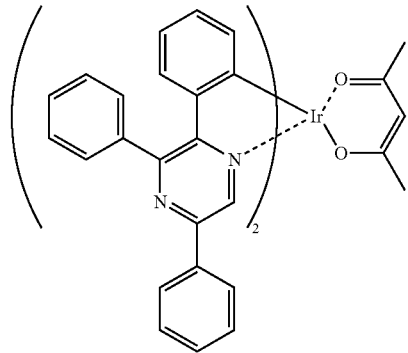

-continued
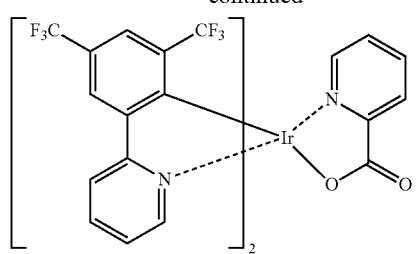
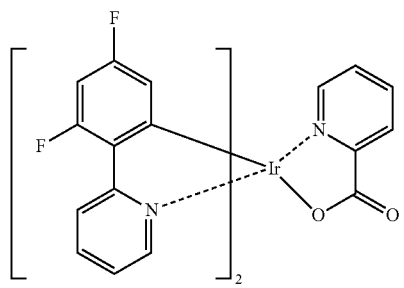
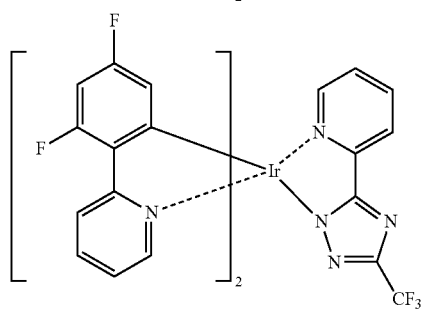
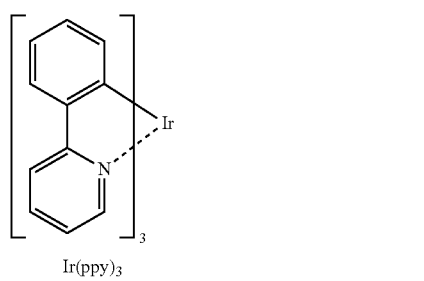
Ir(ppy)₃
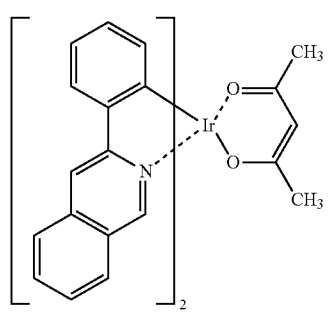
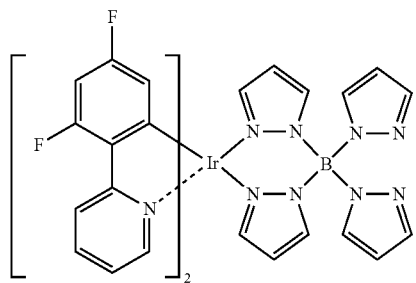
-continued
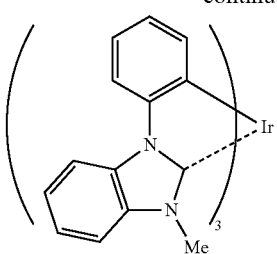
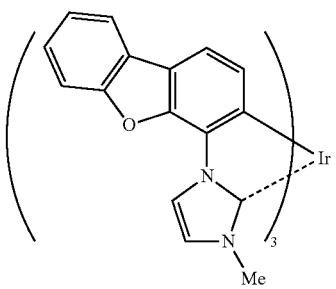
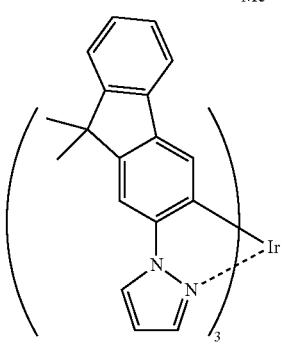
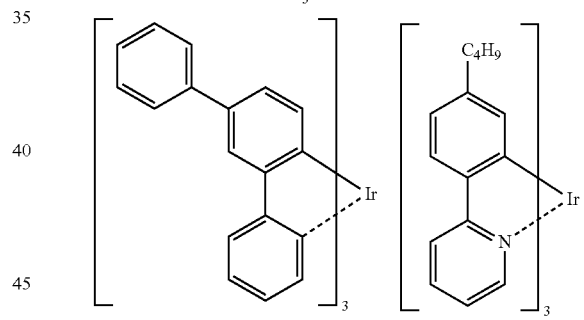
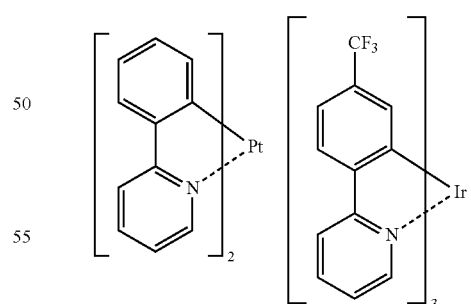
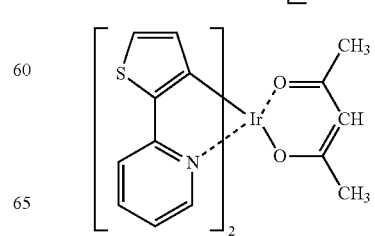

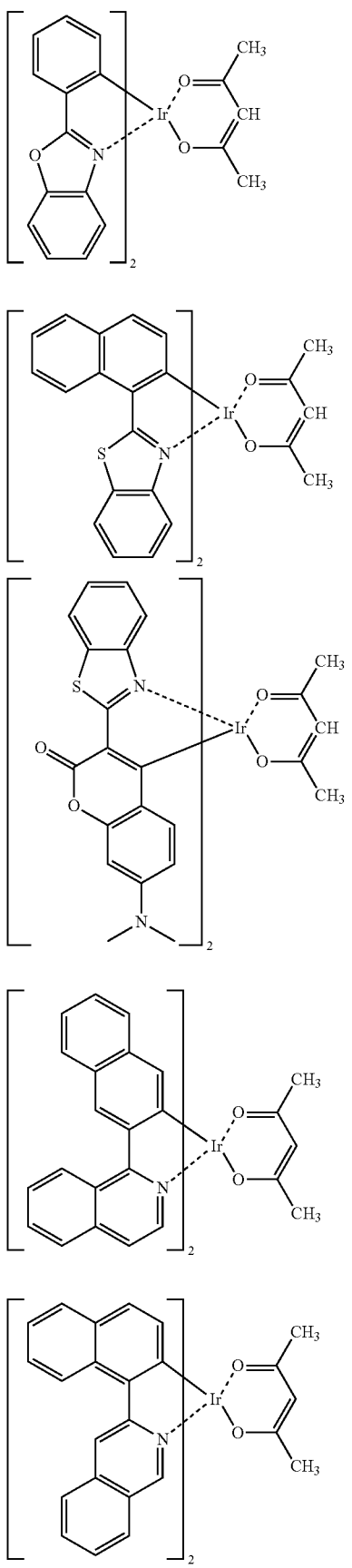

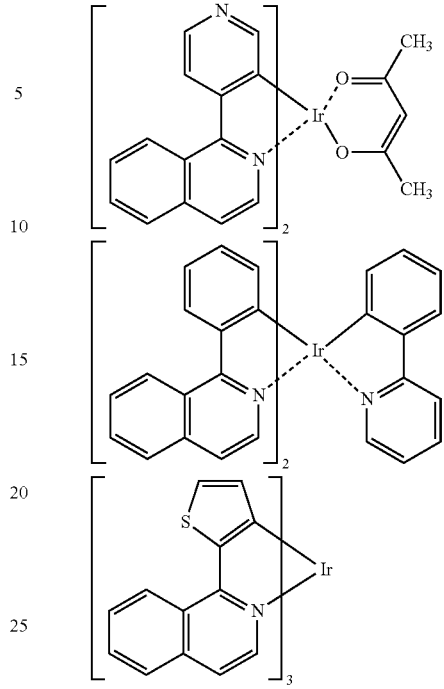

As for the organic EL device of the invention, it is preferred that the emitting layer comprise a host material and a phosphorescent emitting material, and contain a metal complex of which the maximum value of the emission wavelength is 450 nm or more and 720 nm or less.

It is preferred that the organic EL device of the invention have a reductive dopant in the interfacial region between the cathode and the organic thin film layer (for example, an electron-injecting layer, an emitting layer, or the like). As examples of the reductive dopant, at least one selected from an alkali metal, an alkali metal complex, an alkali metal compound, an alkaline earth metal, an alkaline earth metal complex, an alkaline earth metal compound, a rare earth metal, a rare earth metal complex, a rare earth metal compound and the like can be given.

As the alkali metal, one having a work function of 2.9 eV or less can be given. Specifically, Na (work function: 2.36 eV), K (work function: 2.28 eV), Rb (work function: 2.16 eV), Cs (work function: 1.95 eV) or the like can be preferably given. Of these, K, Rb and Cs are more preferable, and Rb or Cs are further preferable, with Cs being most preferable.

As the alkaline earth metal, one having a work function of 2.9 eV or less can be preferably given. Specifically, Ca (work function: 2.9 eV), Sr (work function: 2.0 to 2.5 eV), Ba (work function: 2.52 eV) or the like can preferably be given.

As the rare earth metal, one having a work function of 2.9 eV or less can be preferably given. Specifically, Sc, Y, Ce, Tb, Yb or the like can preferably be given.

Of the above-mentioned metals, one which has high reduction power and is capable of improving the luminance or prolonging the lifetime of the organic EL device by adding a relatively small amount to the electron-injecting region is preferable.

As the alkali metal compound, an alkali oxide such as $Li_2O$, $Cs_2O$ and $K_2O$ and an alkali halide such as LiF, NaF, CsF and KF can be given. Of these, LiF, $Li_2O$ and NaF are preferable.

As the alkaline earth metal compound, BaO, SrO, CaO, a mixture of these, e.g. $Ba_mSr_{1-m}O$ (0<m<1), $Ba_mCa_{1-m}O$ (0<m<1), or the like can be given. Of these, BaO, SrO and CaO are preferable.

As the rare earth metal compound, $YbF_3$, $ScF_3$, $ScO_3$, $Y_2O_3$, $Ce_2O_3$, $GdF_3$, $TbF_3$ or the like can be given. Of these, $YbF_3$, $ScF_3$ and $TbF_3$ are preferable.

As for the alkali metal complex, the alkaline earth metal complex and the rare earth metal complex, no specific restrictions are imposed as long as they contain at least one of an alkali metal ion, an alkaline earth metal ion and a rare earth metal ion as the metal ion. As the ligand, quinolinol, benzoquinolinol, acrydinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzimidazole, hydroxybenzo triazole, hyroxyfluborane, bipyridyl, phenanthroline, phthalocyanine, porphyrin, cyclopentadiene, β-diketone, azomethine, and derivatives thereof are preferable, but not limited thereto.

The reductive dopant is preferably added in the form of a layer or an island in the interfacial region. As the method for forming a layer or an island of the dopant in the interfacial region, a method is preferable in which, while depositing a reductive dopant by the resistance heating evaporation method, an organic substance, which is an emitting material or an electron-injecting material that forms an interfacial region, is simultaneously deposited, whereby a reductive dopant is dispersed in the organic substance. The dispersion concentration is preferably organic substance:reductive dopant=100:1 to 1:100 in terms of molar ratio, with 5:1 to 1:5 being more preferable.

When forming a reductive dopant in the form of a layer, after forming into a layer the emitting material or the electron-injecting material which is the organic layer of the interface, the reductive dopant is singly deposited by the resistance heating evaporation method, preferably in a layer thickness of 0.1 to 15 nm.

When forming a reductive dopant in the form of an island, after forming into an island the emitting material or the electron-injecting material which is the organic layer of the interface, the reductive dopant is singly deposited by the resistance heating evaporation method, preferably in an island thickness of 0.05 to 1 nm.

In the organic EL device of the invention, when an electron-injecting layer is present between the emitting layer and the cathode, as the electron-transporting material used in the electron-injecting layer, an aromatic heterocyclic compound having one or more hetero atoms in its molecule is preferable. A nitrogen-containing ring derivative is particularly preferable.

As this nitrogen-containing ring derivative, a nitrogen-containing ring metal chelate complex represented by the following formula (A) is preferable.

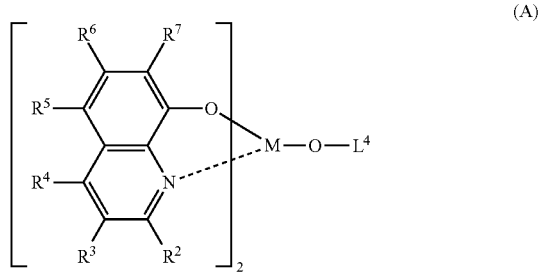

(A)

$R^2$ to $R^7$ are independently a hydrogen atom, a halogen atom, an amino group, a hydrocarbon group having 1 to 40 carbon atoms, an alkoxy group, an aryloxy group, an alkoxy-carbonyl group or a heterocyclic group, which may be substituted.

M is aluminum (Al), gallium (Ga) or indium (In). M is preferably indium.

$L^4$ in the formula (A) is a group represented by the following formula (A') or (A").

(A')

(A")

wherein $R^8$ to $R^{12}$ are independently a hydrogen atom or a substituted or unsubstituted hydrocarbon group having 1 to 40 carbon atoms, and adjacent groups may form a ring structure. $R^{13}$ to $R^{27}$ are independently a hydrogen atom or a substituted or unsubstituted hydrocarbon group having 1 to 40 carbon atoms, and adjacent groups may form a ring structure.

As the nitrogen-containing ring derivative, a nitrogen-containing compound other than a metal complex can be given. For example, a five-membered or six-membered ring having a skeleton shown in (a) or a structure shown in (b) can be given, for example.

(a)

(b)

in the formula (b), X is a carbon atom or a nitrogen atom. $Z^1$ and $Z^2$ are independently a group of atoms which can form a nitrogen-containing heterocycle.

(c)

An organic compound having a nitrogen-containing aromatic polycyclic group composed of a five-membered ring or a six-membered ring is preferable. Further, in the case of a nitrogen-containing aromatic polycyclic group having such a plurality of nitrogen atoms, a nitrogen-containing aromatic polycyclic organic compound having a skeleton combining (a) and (b) or (a) and (c) is preferable.

The nitrogen-containing group of the nitrogen-containing heterocyclic derivative can be selected from the nitrogen-containing heterocyclic groups represented by the following formula.

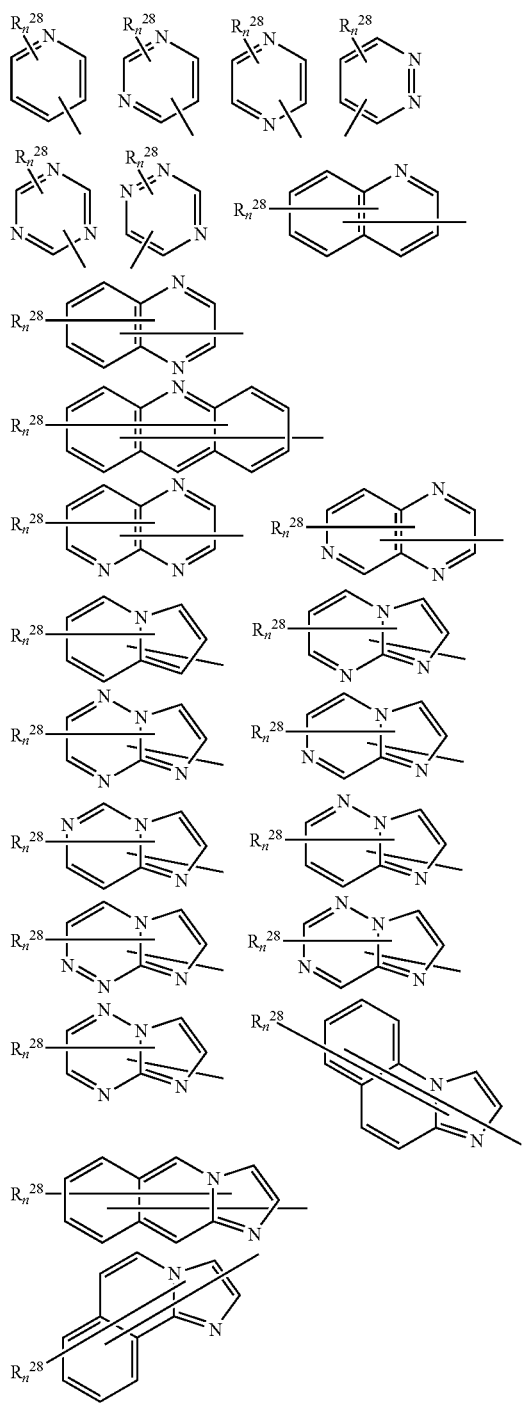

wherein $R^{28}$ is an aryl group having 6 to 40 carbon atoms, a heteroaryl group having 3 to 40 carbon atoms, an alkyl group having 1 to 20 carbon atoms or an alkoxy group having 1 to 20 carbon atoms; and n is an integer of 0 to 5, and when n is an integer of 2 or more, plural $R^{28}$s may be the same or different.

As specific examples of the preferable compound, a nitrogen-containing heterocyclic derivative represented by the following formula can be given.

$$HAr^a\text{-}L^6\text{-}Ar^b\text{—}Ar^c$$

wherein $HAr^a$ is a nitrogen-containing heterocyclic group having 3 to 40 carbon atoms which may have a substituent; $L^6$ is a single bond; an arylene group having 6 to 40 carbon atoms that may have a substituent or a heteroarylene group having 3 to 40 carbon atoms that may have a substituent; $Ar^b$ is a divalent aromatic hydrocarbon group having 6 to 40 carbon atoms that may have a substituent; and $Ar^c$ is an aryl group having 6 to 40 carbon atoms that may have a substituent and a heteroaryl group having 3 to 40 carbon atoms that may have as a substituent.

$HAr^a$ is selected from the following group, for example.

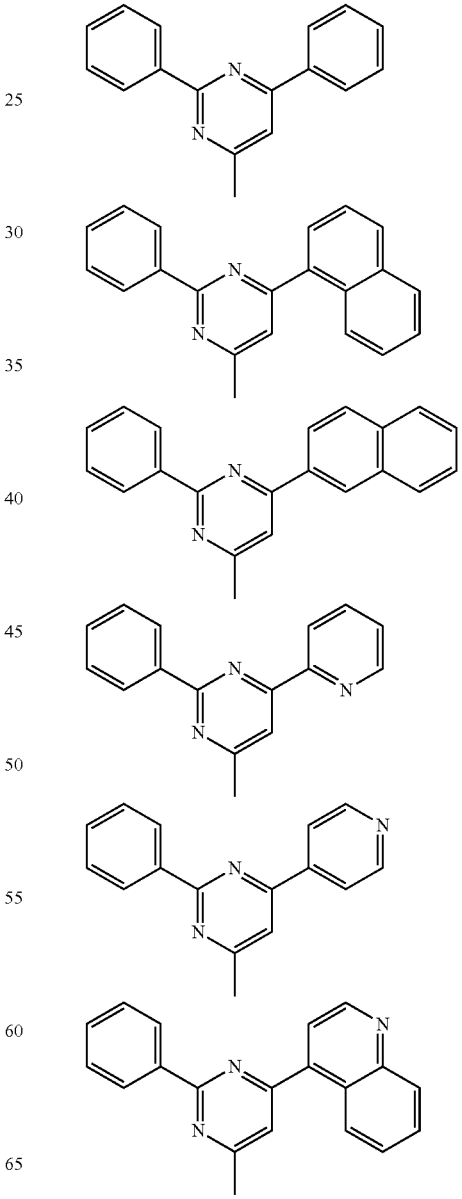

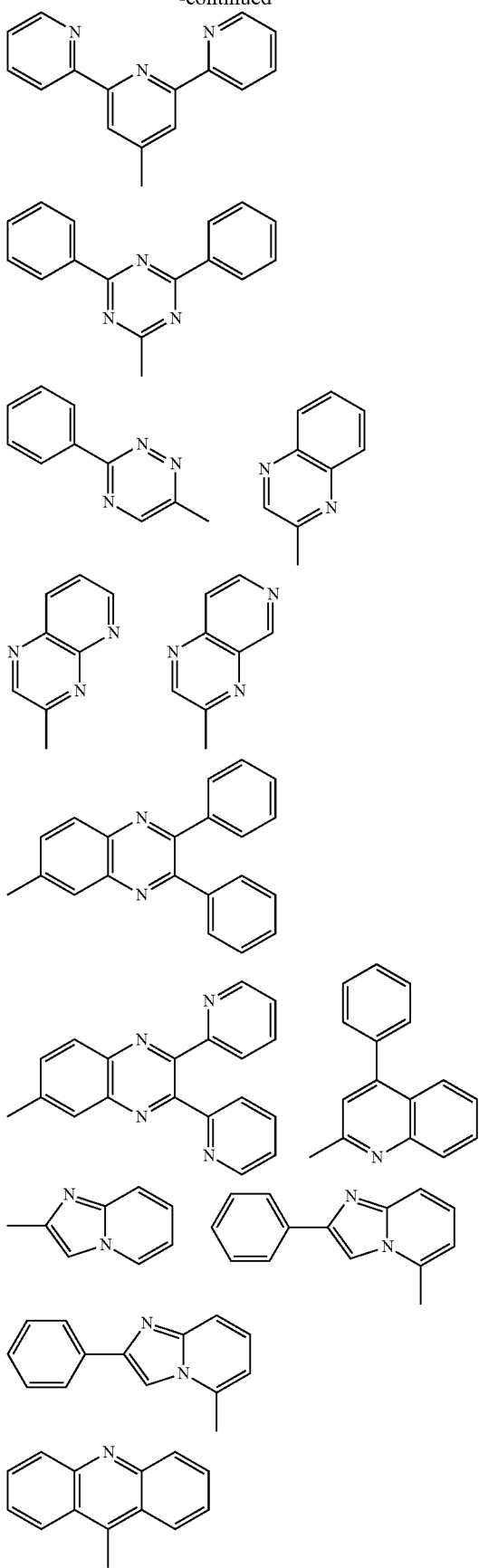
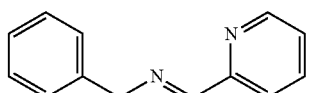
$L^6$ is selected from the following group, for example.
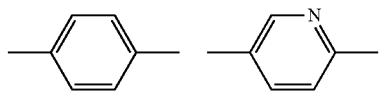
$Ar^c$ is selected from the following group, for example.
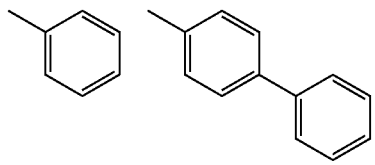
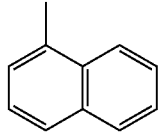 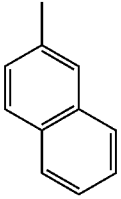
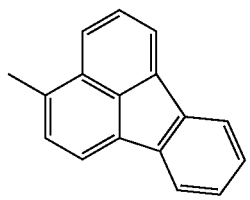 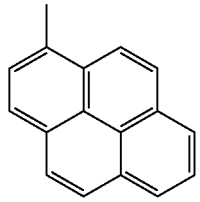
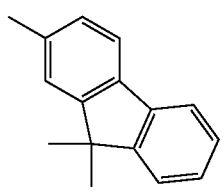
$Ar^b$ is selected from the following arylanthranyl group, for example.
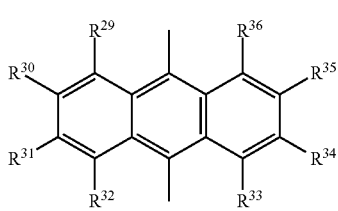

-continued

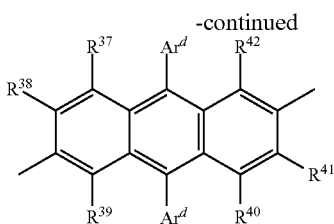

wherein $R^{29}$ to $R^{42}$ are independently a hydrogen atom, a halogen atom, an alkyl group having 1 to 20 carbon atoms, an alkoxy group having 1 to 20 carbon atoms, an aryloxy group having 6 to 40 carbon atoms, an aryl group having 6 to 40 carbon atoms which may have a substituent or a heteroaryl group having 3 to 40 carbon atoms which may have a substituent; and $Ar^d$ is an aryl group having 6 to 40 carbon atoms which may have a substituent or a heteroaryl group having 3 to 40 carbon atoms which may have a substituent.

It is preferred that the $Ar^b$ represented by the above formula be a nitrogen-containing heterocyclic derivative in which any of $R^{29}$ to $R^{36}$ is a hydrogen atom.

Other than these, the following compounds (see JP-A-H09-3448) can preferably be used.

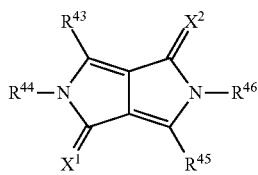

wherein $R^{43}$ to $R^{46}$ are independently a hydrogen atom, a substituted or unsubstituted aliphatic group, a substituted or unsubstituted alicyclic group, a substituted or unsubstituted carbocyclic aromatic ring group or a substituted or unsubstituted heterocyclic group; and $X^1$ and $X^2$ are independently an oxygen atom, a sulfur atom or a dicyanomethylene group.

The following compound (JP-A-2000-173774) can be preferably used.

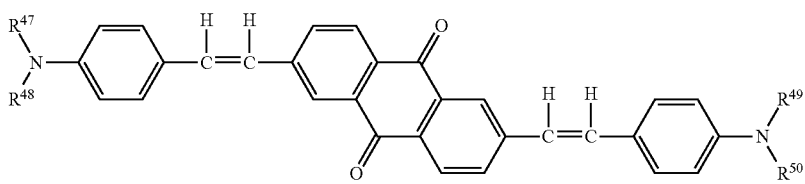

wherein $R^{47}$, $R^{48}$, $R^{49}$ and $R^{50}$ are the same or different groups, and is an aryl group represented by the following formula.

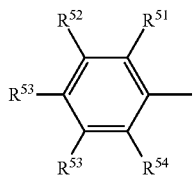

wherein $R^{51}$, $R^{52}$, $R^{53}$, $R^{54}$ and $R^{55}$ are the same or different groups, and is a hydrogen atom or at least one of them is a saturated or unsaturated alkoxyl group, a saturated or unsaturated alkyl group, a saturated or unsaturated amino group or a saturated or unsaturated alkylamino group.

Further, it may be a polymer compound containing a nitrogen-containing heterocyclic group or a nitrogen-containing heterocyclic derivative.

It is preferred that the electron-transporting layer contain a nitrogen-containing heterocyclic derivative, in particular, a nitrogen-containing five-membered ring derivative. Examples of the nitrogen-containing five-membered ring include an imidazole ring, a triazole ring, a tetrazole ring, an oxadiazole ring, a thiadiazole ring, an oxatriazole ring and a thiatriazole ring. As examples of the nitrogen-containing five-membered ring derivative, a benzimidazole ring, a benzotriazole ring, a pyridinoimidazole ring, a pyrimidinoimidazole ring and a pyridazinoimidazole ring can be given.

Specifically, it is preferred that at least one of the nitrogen-containing heterocyclic derivatives represented by the following formulas (201) to (203) be contained.

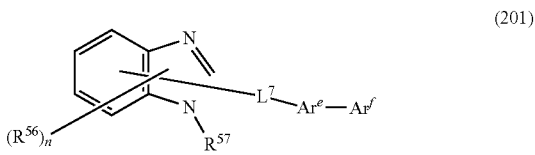
(201)

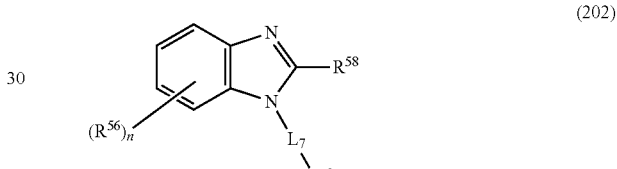
(202)

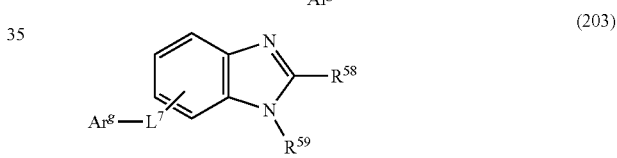
(203)

In the formulas (201) to (203), $R^{56}$ is a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent; n is an integer of 0 to 4; $R^{57}$ is an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent; $R^{58}$ and $R^{59}$ are independently a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent; $L^7$ is a single bond, an arylene group having 6 to 60 carbon atoms which may have a substituent, a pyridinylene group which may have a substituent, a quinolinylene group which may have a substituent or a fluorenylene group which may have a substituent; $Ar^e$ is an arylene group having 6 to 60 carbon atoms which may have a substituent, a pyridinylene group which may have a substituent or a quinolinylene group which may have a substituent; and $Ar^f$ is a hydrogen atom, an aryl group having 6 to 60 carbon atoms which may have a substituent, a pyridyl group which may have a substituent, a quinolyl group which may have a substituent, an alkyl group having 1 to 20 carbon atoms which may have a substituent or an alkoxy group having 1 to 20 carbon atoms which may have a substituent.

$Ar^g$ is an aryl group having 6 to 60 carbon atoms which may have a substituent, a pyridyl group which may have a substituent, a quinolyl group which may have a substituent; an alkyl group having 1 to 20 carbon atoms which may have a substituent, an alkoxy group having 1 to 20 carbon atoms which may have a substituent, or a group represented by —$Ar^e$—$Ar^f$ ($Ar^e$ and $Ar^f$ are respectively the same as mentioned above).

As the compound constituting the electron-injecting layer and the electron-transporting layer, in addition to the aromatic heterocyclic derivative of the invention, a compound having a structure in which an electron-deficient nitrogen-containing five-membered ring structure or an electron-deficient nitrogen-containing six-membered ring structure and a substituted or unsubstituted indole skeleton, a substituted or unsubstituted carbazole skeleton or a substituted or unsubstituted azacarbazole skeleton are combined or the like can be given. Further, as the electron-deficient nitrogen-containing five-membered ring or the electron-deficient nitrogen-containing six-membered ring structure, pyridine, pyrimidine, pyrazine, triazine, triazole, oxadiazole, pyrazole, imidazole, quinoxaline, pyrrole skeletons, and a molecular skeleton such as benzimidazole and imidazopyridine in which the above-mentioned skeletons are fused with each other. Of these combinations, combinations of pyridine, pyrimidine, pyrazine or triazine skeletons with carbazole, indole, azacarbazole or quinoxaline skeletons can be preferably given. These skeletons may be either substituted or unsubstituted.

The electron-injecting layer and the electron-transporting layer may be a single-layer structure composed of one or two or more of the above-mentioned materials or may be a multi-layer structure formed of a plurality of layers having the same composition or the different compositions. It is preferred that the materials of these layers have a π-electron-deficient nitrogen-containing heterocyclic group.

As the constituent components of the electron-injecting layer, it is preferable to use an insulator or a semiconductor as an inorganic compound in addition to the nitrogen-containing ring derivative. If the electron-injecting layer is composed of an insulator or a semiconductor, leakage of electric current can be effectively prevented, whereby electron-injection property can be improved.

As such an insulator, it is preferable to use at least one metal compound selected from the group consisting of an alkali metal chalcogenide, an alkaline earth metal chalcogenide, a halide of an alkali metal and a halide of an alkaline earth metal. It is preferable if the electron-injecting layer is formed of these alkali metal chalcogenides or the like, since the electron-injecting property can be further improved. Specifically, as preferable alkali metal chalcogenides, $Li_2O$, $K_2O$, $Na_2S$, $Na_2Se$ and $Na_2O$ can be given. As preferable alkaline earth metal chalcogenides, CaO, BaO, SrO, BeO, BaS and CaSe can be given, for example. As preferable halides of an alkali metal, LiF, NaF, KF, LiCl, KCl and NaCl can be given, for example. As preferable halides of an alkaline earth metal, a fluoride such as $CaF_2$, $BaF_2$, $SrF_2$, $MgF_2$ and $BeF_2$ and a halide other than a fluoride can be given, for example.

As the semiconductor, an oxide, a nitride or a nitric oxide containing at least one element selected from Ba, Ca, Sr, Yb, Al, Ga, In, Li, Na, Cd, Mg, Si, Ta, Sb and Zn, or the like can be given, for example. They can be used singly or in combination of two or more. Further, it is preferred that an inorganic compound constituting the electron-injecting layer be a finely-crystallized or amorphous insulating thin film. If the electron-injecting layer is formed of these insulating thin films, generation of pixel defects such as dark spots can be reduced since more homogeneous thin film is formed. As such an inorganic compound, an alkali metal chalcogenide, an alkaline earth metal chalcogenide, a halide of an alkali metal and a halide of an alkaline earth metal or the like can be given, for example.

In the electron-injecting layer of the invention, the above-mentioned reductive dopant can preferably be contained.

Although no specific restrictions are imposed on the film thickness of the electron-injecting layer or the electron-transporting layer, the thickness is preferably 1 to 100 nm.

In the hole-injecting layer or the hole-transporting layer (including the hole-injecting/transporting layer), an aromatic amine compound, for example, an aromatic amine derivative represented by the formula (I) can preferably be used.

(I)

In the formula (I), $Ar^1$ to $Ar^4$ are a substituted or unsubstituted aryl group having 6 to 50 ring carbon atoms or a substituted or unsubstituted heteroaryl group having 5 to 50 atoms that form a ring (hereinafter referred to as the "ring atoms").

L is a linking group. Specifically, it is a substituted or unsubstituted arylene group having 6 to 50 ring carbon atoms, a substituted or unsubstituted heteroarylene group having 5 to 50 ring atoms, or a divalent group obtained by bonding two or more arylene groups or two or more heteroarylene groups by a single bond, an ether bond, a thioether bond, an alkylene group having 1 to 20 carbon atoms, an alkenylene group having 2 to 20 carbon atoms or an amino group.

The aromatic amine represented by the following formula (II) can preferably be used in the hole-injecting layer or the hole-transporting layer.

(II)

In the formula (II), $Ar^1$ to $Ar^3$ are defined as $Ar^1$ to $Ar^4$ in the formula (I).

Since the aromatic heterocyclic derivative of the invention is a compound transporting holes or electrons, it can also be used in the hole-injecting layer or the hole-transporting layer, the electron-injecting layer or the electron-transporting layer.

In the invention, the anode of an organic EL device serves to inject holes to the hole-transporting layer or the emitting layer. It is effective that the anode has a work function of 4.5 eV or more. As specific examples of the anode materials used in the invention, an indium tin oxide alloy (ITO), tin oxide (NESA), gold, silver, platinum, copper or the like can be given. As the cathode, a material having a small work function is preferable in order to inject electrons to the electron-injecting layer or the emitting layer. Although no specific restrictions are imposed on the cathode material, specific examples thereof include indium, aluminum, magnesium, a magnesium-indium alloy, a magnesium-aluminum alloy, an aluminum-lithium alloy, an aluminum-scandium-lithium alloy and a magnesium-silver alloy.

The method for forming each layer of the organic EL device of the invention is not particularly restricted. A conventionally known film-forming method such as the vacuum deposition method and the spin coating method can be used. The organic thin film layers containing the aromatic heterocyclic derivative of the invention used in the organic EL device of the invention can be formed by known methods such as the vacuum deposition method, the molecular beam epitaxy method (MBE method), a dipping method in which a solution obtained by dissolving the aromatic heterocyclic derivative of the invention in a solvent is dipped, or a coating method such as spin coating, casting, bar-coating, roll coating or the like.

No specific restrictions are imposed on the film thickness of each organic layer of the organic EL device of the invention. In general, if the film thickness is too small, generation of defects such as pin holes are likely to occur. If the film thickness is too large, a high voltage is required to be applied, leading to a lowering in efficiency. The film thickness is normally several nm to 1 μm.

As the method for forming a layer (an emitting layer, in particular) containing the aromatic heterocyclic derivative of the invention, it is preferable to use a film-forming method in which a solution containing the aromatic heterocyclic derivative of the invention and, if necessary, a dopant or other materials is formed into a film.

As the film-forming method, a known coating method can effectively be used. For example, a spin coating method, a casting method, a micro gravure coating method, a gravure coating method, a bar coating method, a roll coating method, a slit coating method, a wire bar coating method, a dip coating method, a spray coating method, a screen printing method, a flexo printing method, an offset printing method, an inkjet method, and a nozzle printing method or the like can be given. When a pattern is formed, a screen printing method, a flexo printing method, an offset printing method, an inkjet method or the like are preferable. Film formation by these methods can be conducted under conditions which known by a person skilled in the art.

After film formation, the film is dried by heating (upper limit: 250° C.) under vacuum to remove the solvent. No polymerization reaction by light or heating at high temperatures exceeding 250° C. is necessary. Therefore, deterioration of device performance by light or heating at a temperature exceeding 250° C. can be suppressed.

It suffices that the solution for film formation contains at least one aromatic heterocyclic derivative of the invention. Other hole-transporting materials, electron-transporting materials, emitting materials, and acceptor materials, a solvent, additives such as a stabilizer or the like may also be contained.

The solution for film formation may contain an additive for controlling the viscosity and/or the surface tension, i.e. a thickener (a high molecular compound, a poor solvent of the polymer compound of the invention or the like), a viscosity depressant (a low molecular compound, or the like), a surfactant or the like. In order to improve storage stability, it may contain an anti-oxidant such as a phenol-based anti-oxidant and a phosphor-based anti-oxidant which may not affect the performance of the organic EL device.

The content of the aromatic heterocyclic derivative in the film formation solution is preferably 0.1 to 15 mass % relative to the entire film formation solution, with 0.5 to 10 mass % being more preferable.

As the high molecular compound which can be used as the thickener, insulating resins such as polystyrene, polycarbonate, polyarylate, polyester, polyamide, polyurethane, polysulfone, polymethyl methacrylate, polymethyl acrylate and cellulose and a copolymer thereof, a photoconductive resin such as poly-N-vinyl carbazole and polysilane, and a conductive resin such as polythiophene and polypyrrole can be given.

As the solvent for the film formation solution, a chlorine-based solvent such as chloroform, methylene chloride, 1,2-dichloroethane, 1,1,2-trichloroethane, chlorobenzene, and o-dichlorobenzene, an ether-based solvent such as tetrahydrofuran, dioxane, dioxolane and anisole, aromatic hydrocarbon-based solvent such as toluene and xylene, an aliphatic hydrocarbon-based solvent such as cyclohexane, methylcyclohexane, n-pentane, n-hexane, n-heptane, n-octane, n-nonane and n-decane, a ketone-based solvent such as acetone, methyl ethyl ketone, cyclohexanone, benzophenone and acetophenone, an ester-based solvent such as ethyl acetate, butyl acetate, ethyl cellosolve acetate, methyl benzoate and phenyl acetate, a polyvalent alcohol such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerine and 1,2-hexanediol and its derivatives, an alcohol-based solvent such as methanol, ethanol, propanol, isopropanol and cyclohexanol, a sulfoxide-based solvent such as dimethylsulfoxide, an amide-based solvent such as N-methyl-2-pyrrolidone and N,N-dimethylformamide can be given. These solvents can be used singly or in combination of two or more.

Of these solvents, in respect of solubility, uniform film formation, viscosity properties or the like, an aromatic hydrocarbon-based solvent, an ether-based solvent, an aliphatic hydrocarbon-based solvent, an ester-based solvent and a ketone-based solvent are preferable. Toluene, xylene, ethylbenzene, diethylbenzene, trimethylbenzene, n-propylbenzene, isopropylbenzene, n-butylbenzene, isobutylbenzene, 5-butylbenzene, n-hexylbenzene, cyclohexylbenzene, 1-methylnaphthalene, tetraline, 1,3-dioxane, 1,4-dioxane, 1,3-dioxolane, anisole, ethoxybenzene, cyclohexane, bicyclohexyl, cyclohexenylcyclohexanone, n-hepthylcyclohexane, n-hexylcyclohexane, decalin, methyl benzoate, cyclohexanone, 2-propylcyclohexanone, 2-heptanone, 3-heptanone, 4-heptanone, 2-octanone, 2-nonanone, 2-decanone, dicyclohexylketone, acetophenone and benzophenone are more preferable.

Second Embodiment

The organic EL device of this embodiment has a tandem device configuration in which at least two emitting layers or at least two units containing an emitting layer are provided.

In such an organic EL device, a charge-generating layer (CGL) may be interposed between the two units, whereby an electron-transporting region may be provided according to the unit.

Specific examples of the tandem device configuration are given below.

(11) Anode/hole-injecting/transporting layer/phosphorescent emitting layer/charge-generating layer/fluorescent emitting layer/electron-injecting/transporting layer/cathode
(12) Anode/hole-injecting/transporting layer/fluorescent emitting layer/electron-injecting/transporting layer/charge-generating layer/phosphorescent emitting layer/cathode In these organic EL devices, in the phosphorescent emitting layer, the aromatic heterocyclic derivative of the invention and the phosphorescent emitting material explained in the first embodiment can be used. By this, the luminous efficiency and the life time of the organic EL device can be further improved. Further, in the anode, the hole-injecting/transporting layer, the electron-injecting/transporting layer and the cathode, the materials explained in the first embodiment can be use used. As the material of the fluorescent emitting layer, a known material can be used. As the material for the charge-generating layer, a known material can be used.

Third Embodiment

The organic EL device of the embodiment has a plurality of emitting layers, and has a charge-blocking layer between any two of a plurality of emitting layers. As the constitution of the preferable organic EL device according to this embodiment, configurations disclosed in U.S. Pat. No. 4,134,280, US2007/0273270A1 and WO2008/023623A1 can be given.

Specifically, in a configuration in which an anode, a first electrode, a charge-blocking layer, a second emitting layer and a cathode are stacked in this order, an electron-transporting region having a charge-blocking layer to prevent diffusion of triplet excitons is provided between the second emitting layer and the cathode. Here, the "charge-blocking layer" is a layer having a function of controlling carrier injection to the emitting layer and of adjusting the carrier balance of electrons and holes injected to the emitting layer by providing an energy barrier in the HOMO level and the LUMO level between the layer and the adjacent emitting layer.

Specific examples of such a configuration are given below.
(21) Anode/hole-injecting/transporting layer/first emitting layer/charge-blocking layer/second emitting layer/electron-injecting/transporting layer/cathode
(22) Anode/hole-injecting/transporting layer/first emitting layer/charge-blocking layer/second emitting layer/third emitting layer/electron-injecting/transporting layer/cathode In at least any of the first emitting layer, the second emitting layer and the third emitting layer, the aromatic heterocyclic derivative of the invention and the phosphorescent emitting material explained in the first embodiment can be used. By this, the luminous efficiency and the life of the organic EL device can be improved.

Further, by allowing the first emitting layer to emit red color, by allowing the second emitting layer to emit green color and by allowing the third emitting layer to emit blue color, it is possible to allow the entire device to emit white color. Such an organic EL device can be preferably used as a surface light source such as illumination and back light.

In the anode, the hole-injecting/transporting layer, the electron-injecting/transporting layer and the cathode, materials explained in the first embodiment can be used.

As the material of the charge-blocking layer, a known material can be used.

EXAMPLES

The invention will be explained in more detail with reference to the following Examples and Comparative Examples, which should not be construed as limiting the scope of the invention.
<Examples of an Organic EL Device Prepared by Deposition>

Example 1

(1) Synthesis of Compound H-1

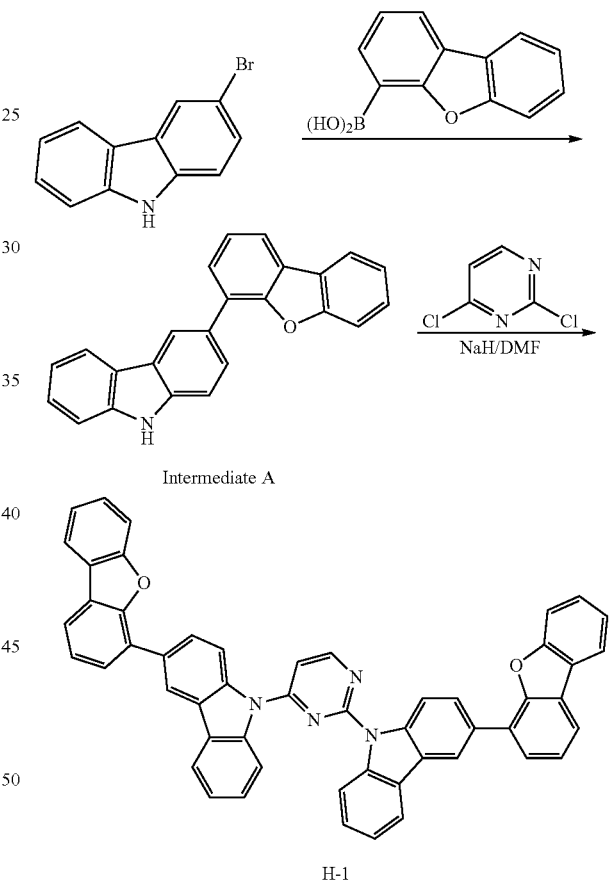

In argon atmosphere, a mixture of 4.66 g (22.0 mmol) of dibenzofuran-4-boronic acid, 4.92 g (20.0 mmol) of 3-bromo-9H-carbazole, 0.035 g (0.6 mmol) of tetrakis(triphenylphosphine)palladium(0), 120 mL of 1,2-dimethoxyethane and 60 mL of a 2M aqueous solution of sodium hydrogen carbonate was stirred while heating under reflux for 8 hours. The reaction mixture was cooled to room temperature, and extracted with toluene/ion-exchange water. The toluene phase was condensed, and the solids obtained were purified by means of silica-gel chromatography, whereby 6.00 g of a pale yellow solid intermediate A was obtained (yield: 90%).

Next, in argon atmosphere, 4.40 g (13.2 mmol) of the intermediate A and 0.691 g (about 15.8 mmol) of 55 wt % NaH (in oil) were dissolved in 30 mL of dehydrated dimethylformamide (DMF). Subsequently, to the resulting solution, a solution obtained by dissolving 0.596 g (4.00 mmol) of 2,4-dichloropyrimidine in 30 mL of dehydrated DMF was added dropwise slowly. The mixture solution was stirred for 3 hours, and a reaction was conducted. After completion of the reaction, ion-exchange water was added to the reaction solution. The precipitated matter was filtered off, heated with ethyl acetate and washed, whereby 2.22 g of white powder H-1 was obtained (yield: 75%).

For the compound obtained, results of analysis by HPLC (High Performance Liquid Chromatography) and FD-MS (Field Desorption ionization-Mass Spectrometry) are shown below.

HPLC: Purity 99.9%

FD-MS: calcd for C52h30N4O2=743.

found m/z=743 (M+, 100).

(2) Preparation of an Organic EL Device

A glass substrate of 25 mm by 75 mm by 1.1 mm thick with an ITO transparent electrode (GEOMATEC CO., LTD.) was subjected to ultrasonic cleaning with isopropyl alcohol for 5 minutes, and cleaned with ultraviolet rays and ozone for 30 minutes.

The thus cleaned glass substrate with a transparent electrode was mounted in a substrate holder of a vacuum vapor deposition apparatus. First, a 40 nm-thick film of compound A was formed on the glass surface where transparent electrode lines were formed so as to cover the transparent electrode, thereby to obtain a hole-injecting layer. Subsequently, on this film, a 20 nm-thick film of compound B was formed to obtain a hole-transporting layer.

Next, on the hole-transporting layer, compound H-1 as a phosphorescent host material and Ir(Ph-ppy)$_3$ as a phosphorescent dopant were co-deposited to obtain a phosphorescent emitting layer. The concentration of Ir(Ph-ppy)$_3$ was 10 mass %.

Subsequently, on the phosphorescent emitting layer, a 30 nm-thick film of compound C, a 1 nm-thick film of LiF and a 80 nm-thick of metal Al were stacked in this order to obtain a cathode. Meanwhile, LiF as an electron-injecting electrode was formed at a speed of 1 Å/min.

Compound A

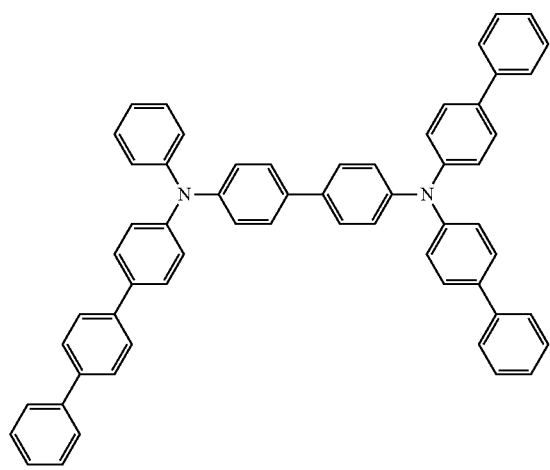

Compound B

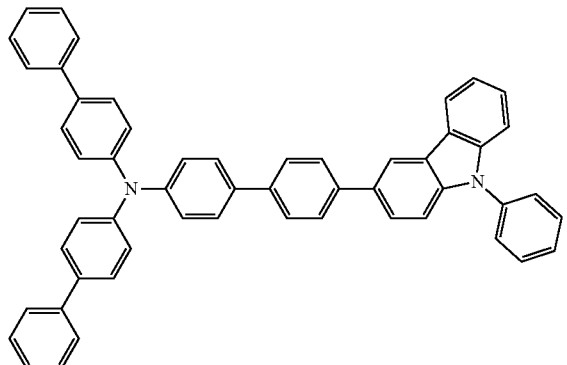

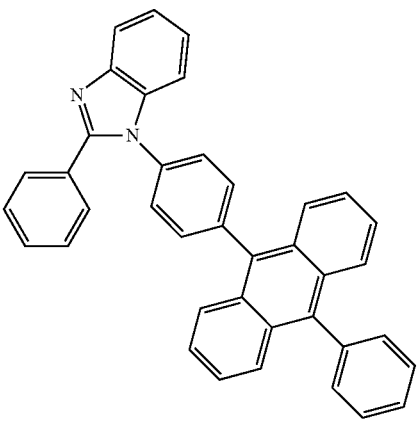

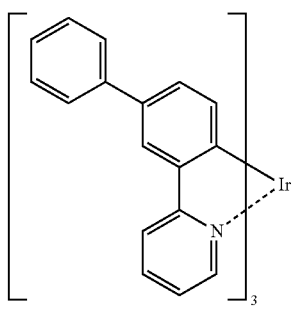

(3) Method for Evaluating an Organic EL Device

The organic EL device prepared was driven by applying direct current to emit light. The voltage (V) at a current density of 1 mA/cm$^2$ and luminous efficiency (cd/A), as well as lifetime until the luminescence decreases to 90% (LT90, initial luminescence 5200 cd/m$^2$) were measured. Results are shown in Table 1.

Examples 2 to 6 and Comparative Examples 1 to 4

Organic EL devices were prepared and evaluated in the same manner as in Example 1, except that the phosphorescent host materials were changed from H-1 to the following compounds H-2 to H-6 and compounds D to G. Results are shown in Table 1.

(Synthesis of Compound H-2)

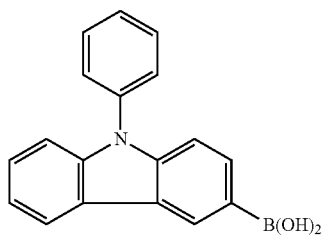

Intermediate B

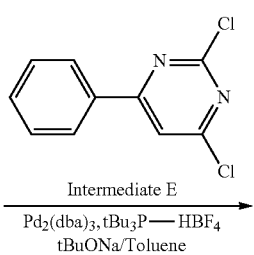

Intermediate C

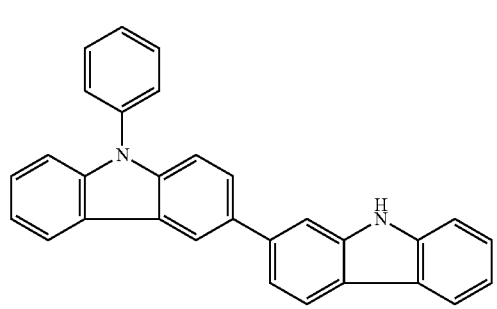

Intermediate D

Intermediate E

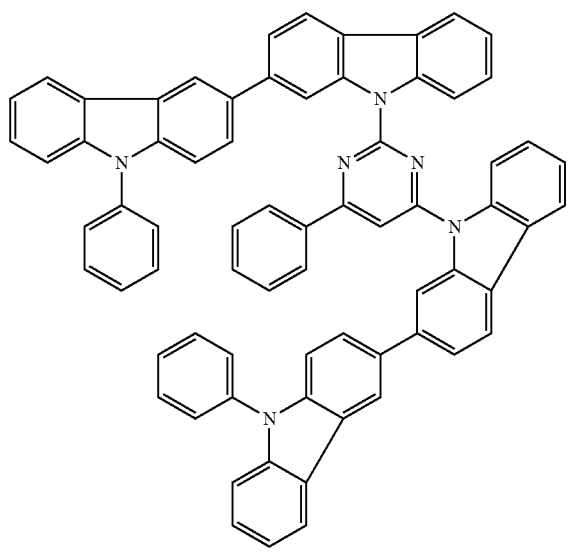

H-2

In argon atmosphere, intermediate B (2.41 g, 8.4 mmol), intermediate C (1.71 g, 7.0 mmol), dichloro(diphenylphosphinoferrocene)palladium-methylene chloride complex (0.057 g, 0.07 mmol), 1,4-dioxane (21 mL) and an aqueous solution of 2M sodium carbonate (10.5 mL) were sequentially added. The resulting mixture was heated under reflux for 4 hours.

The reaction mixture was cooled to room temperature, and the precipitated solids were filtered off and washed with 1,4-dioxane and water, followed by drying under reduced pressure. The residue obtained was purified by means of silica-gel chromatography to obtain intermediate D (2.29 g, yield: 81%).

In argon atmosphere, intermediate D (2.04 g, 5.0 mmol), intermediate E (0.56 g, 2.5 mmol), tris(dibenzilideneacetone)dipalladium (0.092 g, 0.10 mmol), tri-t-butylphosphonium tetrafluoro borate (0.116 g, 0.40 mmol), t-butoxy sodium (0.67 g, 7.0 mmol) and dehydrated toluene (25 mL) were sequentially added. The resulting mixture was heated under reflux for 8 hours.

After the reaction mixture was cooled to room temperature, the organic phase was separated, and the organic solvent was distilled off under reduced pressure. The residue obtained was purified by means of silica-gel chromatography to obtain H-2 (2.18 g, yield: 88%).

HPLC: Purity 99.9%

FD-MS: calcd for $C_{70}H_{44}N_6$=969, found m/z=969 (M+, 100).

(Synthesis of Compound H-3)

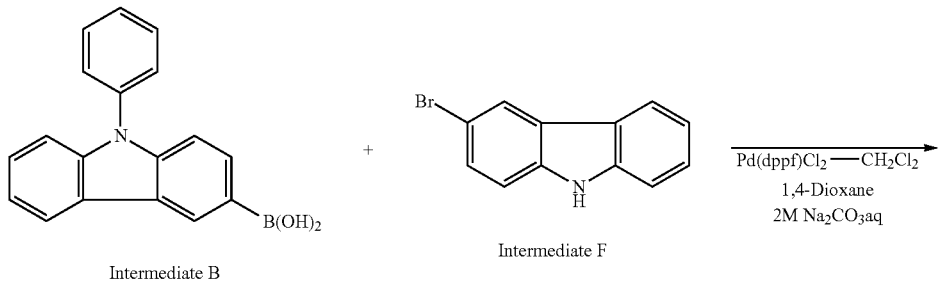

Intermediate B + Intermediate F

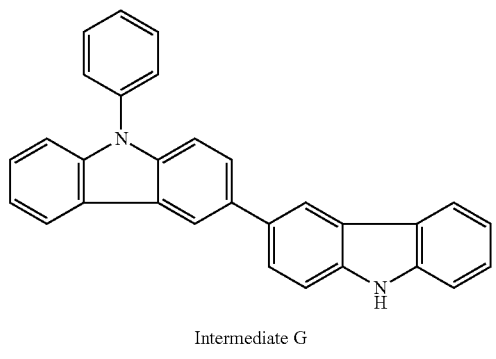

Intermediate G

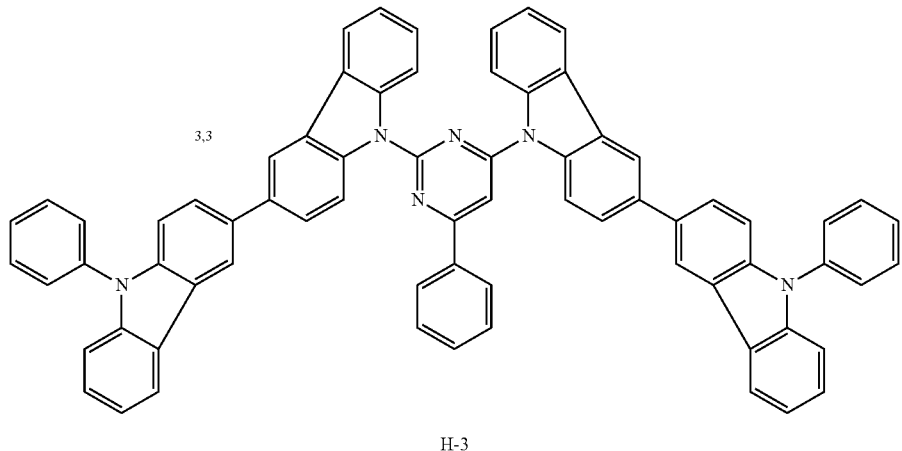

H-3

In argon atmosphere, intermediate B (2.41 g, 8.4 mmol), intermediate F (1.71 g, 7.0 mmol), dichloro(diphenylphosphinoferrocene)palladium-methylene chloride complex (0.057 g, 0.07 mmol), 1,4-dioxane (21 mL) and an aqueous solution of 2M sodium carbonate (10.5 mL) were sequentially added. The resulting mixture was heated under reflux for 4 hours.

The reaction mixture was cooled to room temperature, and the precipitated solids were filtered off and washed with 1,4-dioxane and water, followed by drying under reduced pressure. The residue obtained was purified by means of silica-gel chromatography to obtain intermediate G (2.49 g, yield: 86%).

In argon atmosphere, intermediate G (2.04 g, 5.0 mmol), intermediate E (0.56 g, 2.5 mmol), tris(dibenzilideneacetone)dipalladium (0.092 g, 0.10 mmol), tri-t-butylphosphonium tetrafluoro borate (0.116 g, 0.40 mmol), t-butoxy sodium (0.67 g, 7.0 mmol) and dehydrated toluene (25 mL) were sequentially added. The resulting mixture was heated under reflux for 8 hours.

After the reaction mixture was cooled to room temperature, the organic phase was separated, and the organic solvent was distilled off under reduced pressure. The residue obtained was purified by means of silica-gel chromatography to obtain H-3 (1.95 g, yield: 81%).

HPLC: Purity 99.9%

FD-MS: calcd for $C_{70}H_{44}N_6$=969, found m/z=969 (M+, 100).

(Synthesis of Compound H-4)

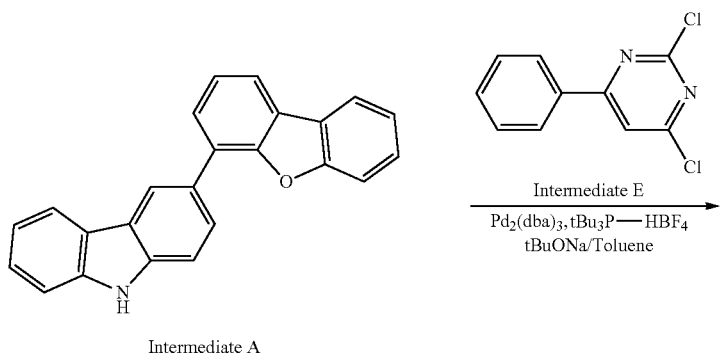

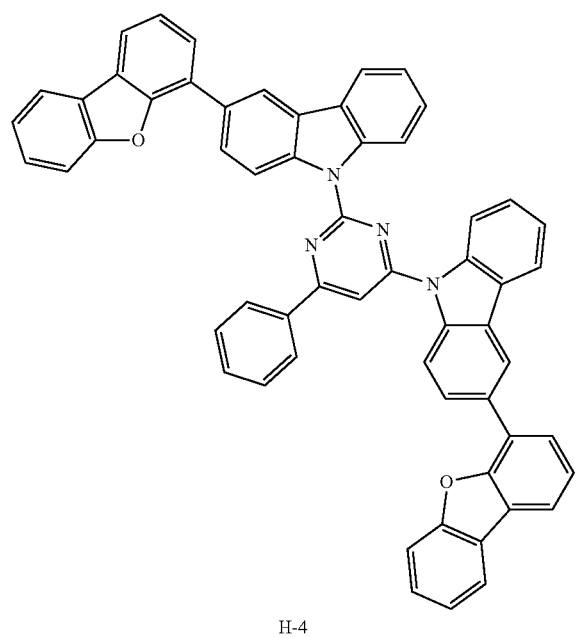

H-4

In argon atmosphere, intermediate A (1.67 g, 5.0 mmol), intermediate E (0.56 g, 2.5 mmol), tris(dibenzilideneacetone)dipalladium (0.092 g, 0.10 mmol), tri-t-butylphosphonium tetrafluoro borate (0.116 g, 0.40 mmol), t-butoxy sodium (0.67 g, 7.0 mmol) and dehydrated toluene (25 mL) were sequentially added. The resulting mixture was heated under reflux for 8 hours.

After the reaction mixture was cooled to room temperature, the organic phase was separated, and the organic solvent was distilled away under reduced pressure. The residue obtained was purified by means of silica-gel chromatography to obtain H-4 (1.72 g, yield: 84%).

HPLC: Purity 99.9%

FD-MS: calcd for C70H44N6=819, found m/z=819 (M+, 100).

(Synthesis of Compound H-5)

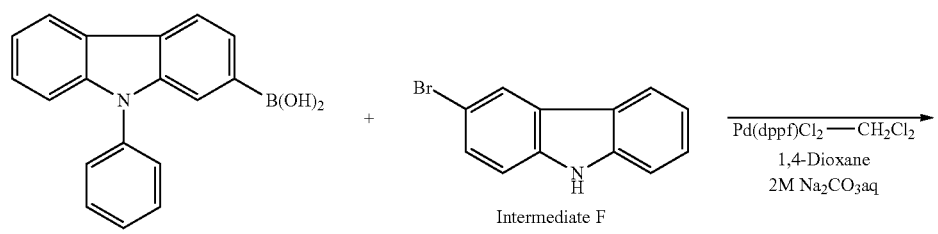

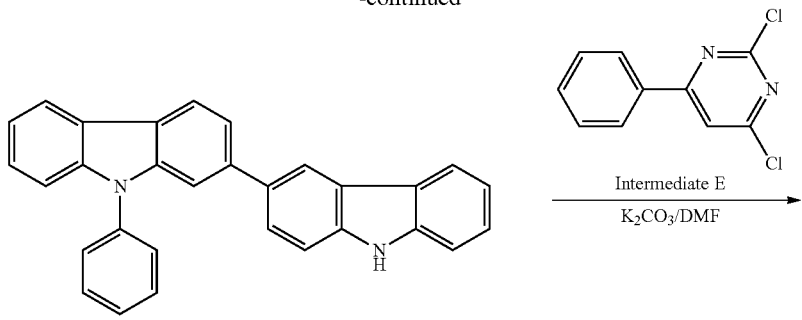

Intermediate I

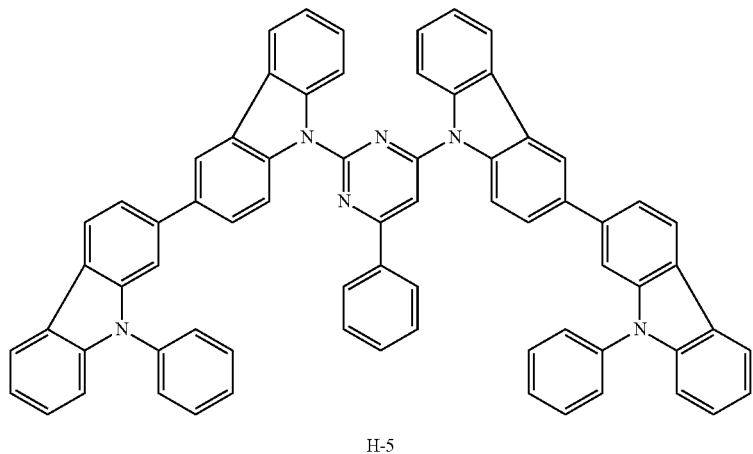

H-5

In argon atmosphere, intermediate H (3.16 g, 11 mmol), intermediate F (2.46 g, 10 mmol), dichloro(diphenylphosphinoferrocene)palladium-methylene chloride complex (0.081 g, 0.1 mmol), 1,4-dioxane (30 mL) and an aqueous solution of 2M sodium carbonate (15 mL) were sequentially added. The resulting mixture was heated under reflux for 4 hours.

The reaction mixture was cooled to room temperature, and the precipitated solids were filtered off and washed with 1,4-dioxane and water, followed by drying under reduced pressure. The residue obtained was purified by means of silica-gel chromatography to obtain intermediate I (3.27 g, yield: 80%).

In argon atmosphere, intermediate I (3.27 g, 8.2 mmol), intermediate E (0.90 g, 4.0 mmol) and potassium carbonate (1.16 g, 8.4 mmol) were added to dehydrated dimethylformamide (60 mL).

The resulting mixture was heated to 120° C. and stirred for 16 hours.

After the reaction mixture was cooled to room temperature, the mixture was diluted by adding toluene, and washed with a saturated solution of ammonium chloride. Then, the organic phase was separated, and the organic solvent was distilled off under reduced pressure. The residue obtained was purified by means of silica-gel chromatography to obtain H-5 (2.10 g, yield: 54%).

HPLC: Purity 991%

FD-MS: calcd for C70H44N6=969, found m/z=969 (M+, 100).

(Synthesis of Compound H-6)

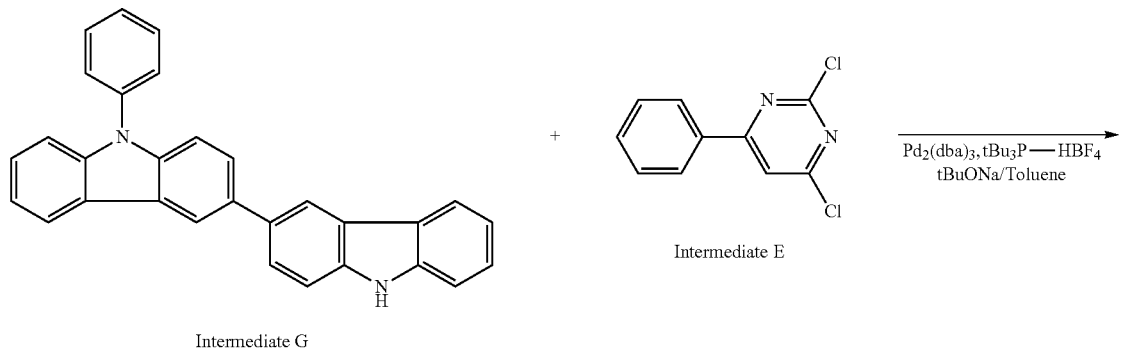

Intermediate G    Intermediate E

-continued

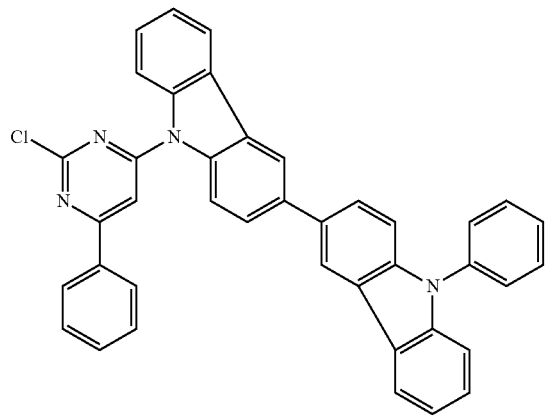

Intermediate J

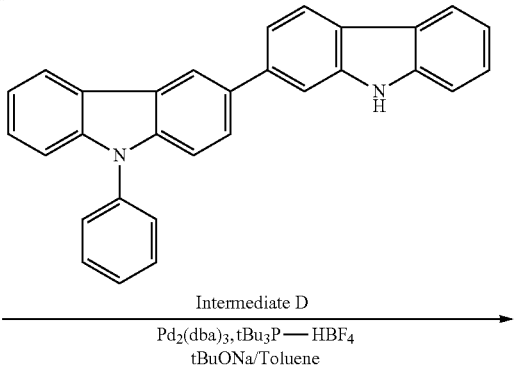

$$\xrightarrow[\text{tBuONa/Toluene}]{\text{Intermediate D} \atop \text{Pd}_2(\text{dba})_3, \text{tBu}_3\text{P}\text{---HBF}_4}$$

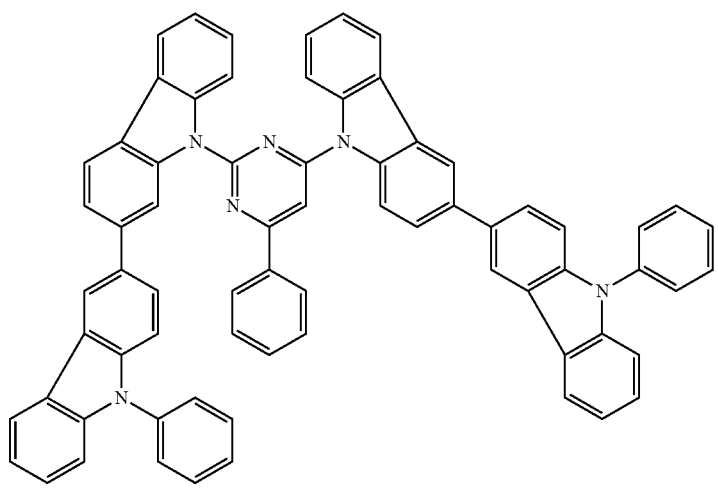

H-6

In argon atmosphere, intermediate G (12.25 g, 30 mmol), intermediate E (6.75 g, 30 mmol), tris(dibenzilideneacetone)dipalladium (0.275 g, 0.30 mmol), tri-t-butylphosphonium tetrafluoro borate (0.348 g, 1.20 mmol), t-butoxy sodium (4.04 g, 42 mmol) and dehydrated toluene (150 mL) were sequentially added. The resulting mixture was heated under reflux for 8 hours. The reaction mixture was cooled to room temperature, the organic phase was separated, and the organic solvent was distilled off under reduced pressure. The residue obtained was purified by means of silica-gel chromatography, washed with methylene chloride and then dried under reduced pressure, thereby to obtain J (8.46 g, yield: 47%).

In argon atmosphere, intermediate J (1.79 g, 3.0 mmol), intermediate D (1.29 g, 3.15 mmol), tris(dibenzilideneacetone)dipalladium (0.027 g, 0.03 mmol), tri-t-butylphosphonium tetrafluoro borate (0.035 g, 0.12 mmol), t-butoxy sodium (0.43 g, 4.5 mmol) and dehydrated toluene (60 mL) were sequentially added. The resulting mixture was heated under reflux for 16 hours.

After the reaction mixture was cooled to room temperature, insoluble matters were removed by filtration, and the organic solvent was distilled off under reduced pressure. The residue obtained was purified by means of silica-gel chromatography to obtain H-6 (2.41 g, yield: 83%).

HPLC: Purity 99.3%

FD-MS: calcd for $C_{70}H_{44}N_6=969$, found m/z=969 (M+, 100).

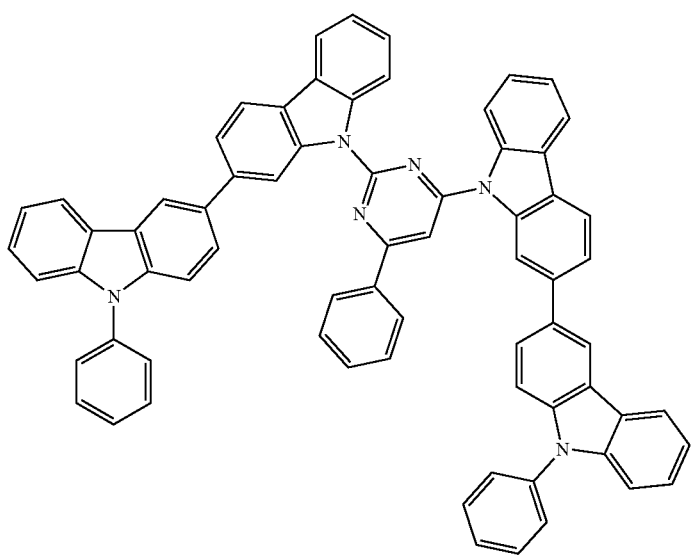
H-2
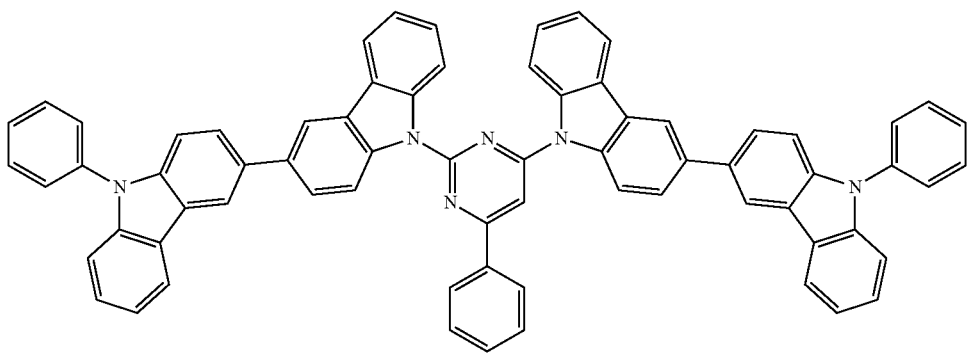
H-3
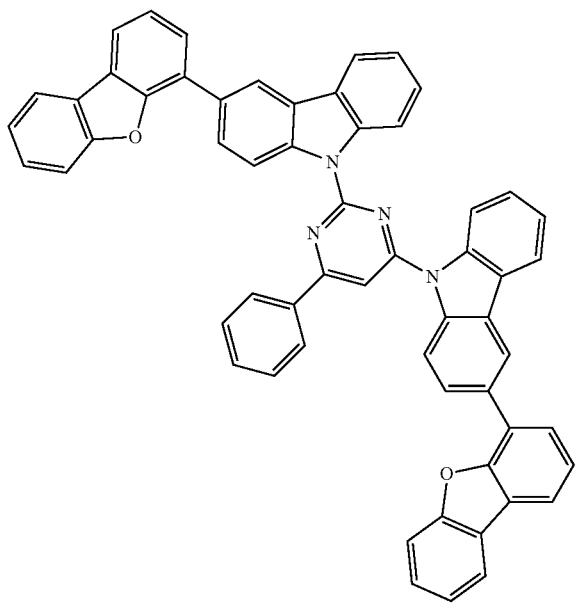
H-4

H-5
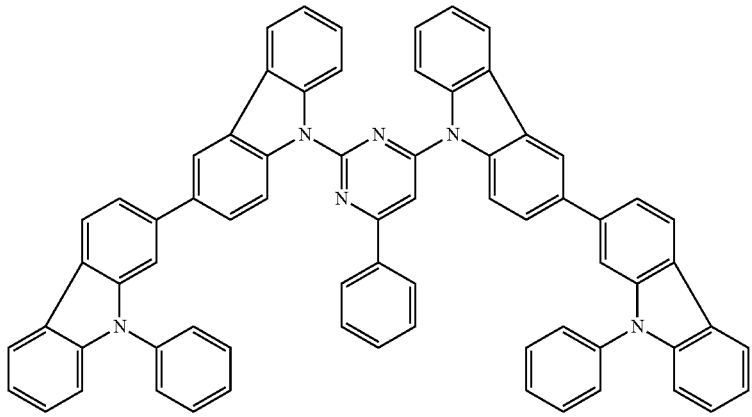
H-6
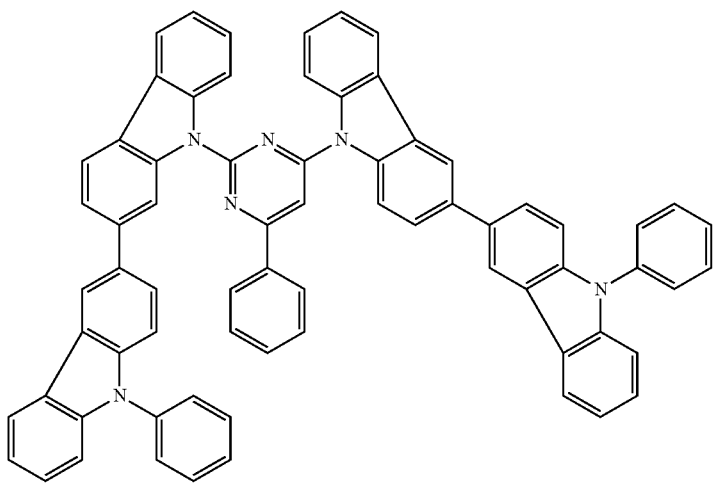
Compound D
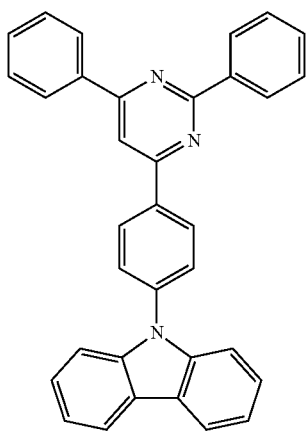

-continued
Compound E
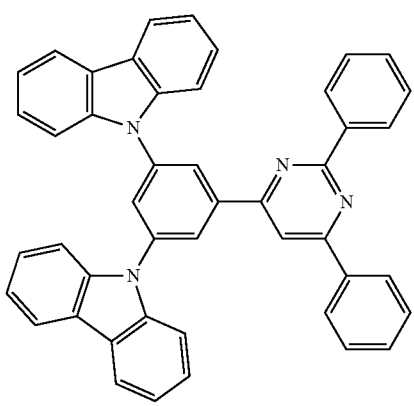
Compound F
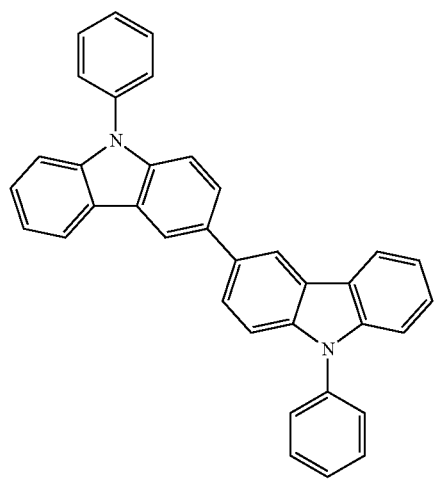
Compound G
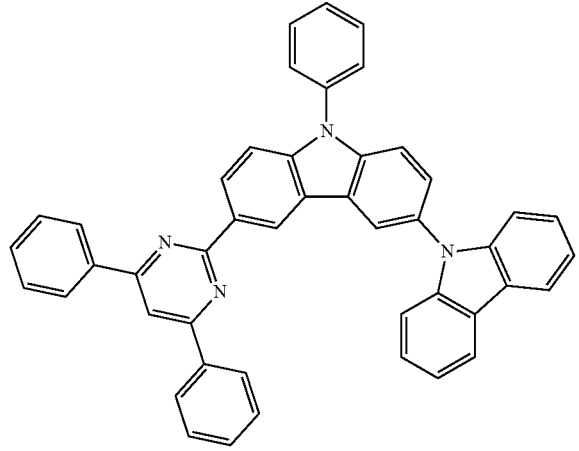
TABLE 1
| | Host material | Voltage (V) @1 mA/cm² | Luminous efficiency (cd/A) @1 mA/cm² | Life time LT90 (hrs) |
|---|---|---|---|---|
| Example 1 | Compound H-1 | 3.0 | 72 | 220 |
| Example 2 | Compound H-2 | 3.1 | 68 | 190 |
| Example 3 | Compound H-3 | 3.3 | 62 | 170 |
| Example 4 | Compound H-4 | 3.2 | 68 | 180 |
| Example 5 | Compound H-5 | 3.1 | 65 | 170 |
| Example 6 | Compound H-6 | 3.0 | 63 | 165 |
| Com. Ex. 1 | Compound D | 3.3 | 49 | 60 |
| Com. Ex. 2 | Compound E | 3.4 | 47 | 85 |

TABLE 1-continued

| Host material | Voltage (V) @1 mA/cm$^2$ | Luminous efficiency (cd/A) @1 mA/cm$^2$ | Life time LT90 (hrs) |
|---|---|---|---|
| Com. Ex. 3  Compound F | 4.9 | 38 | 20 |
| Com. Ex. 4  Compound G | 3.9 | 42 | 67 |

Examples of Organic EL Devices Prepared Using a Material Solution for an Organic EL Device Example 7

(Synthesis of Compound H-7)

4-bromobenzaldehyde (7.40 g, 40 mmol) and acetophenone (4.81, 40 mmol) were dissolved in ethanol (80 mL), and sodium hydroxide (0.16 g, 4 mmol) was added. The resulting solution was stirred at room temperature for 8 hours. Then, 4-bromobenzamidine hydrochloride (7.07 g, 30 mmol), sodium hydroxide (1.60 g, 40 mmol) and ethanol (40 mL) were added, and the resulting solution was reacted while heating under reflux for 8 hours. White powder generated was filtered off and washed with ethanol until the liquid became colorless. The powder was further washed with water and ethanol and then dried in a vacuum to obtain intermediate K (8.85 g, yield: 95%).

In argon atmosphere, intermediate G (2.57 g, 6.3 mmol), intermediate K (1.40 g, 3.0 mmol), tris(dibenzylideneacetone)dipalladium (0.055 g, 0.06 mmol), tri-t-butylphosphonium tetrafluoro borate (0.070 g, 0.24 mmol), t-butoxyso-

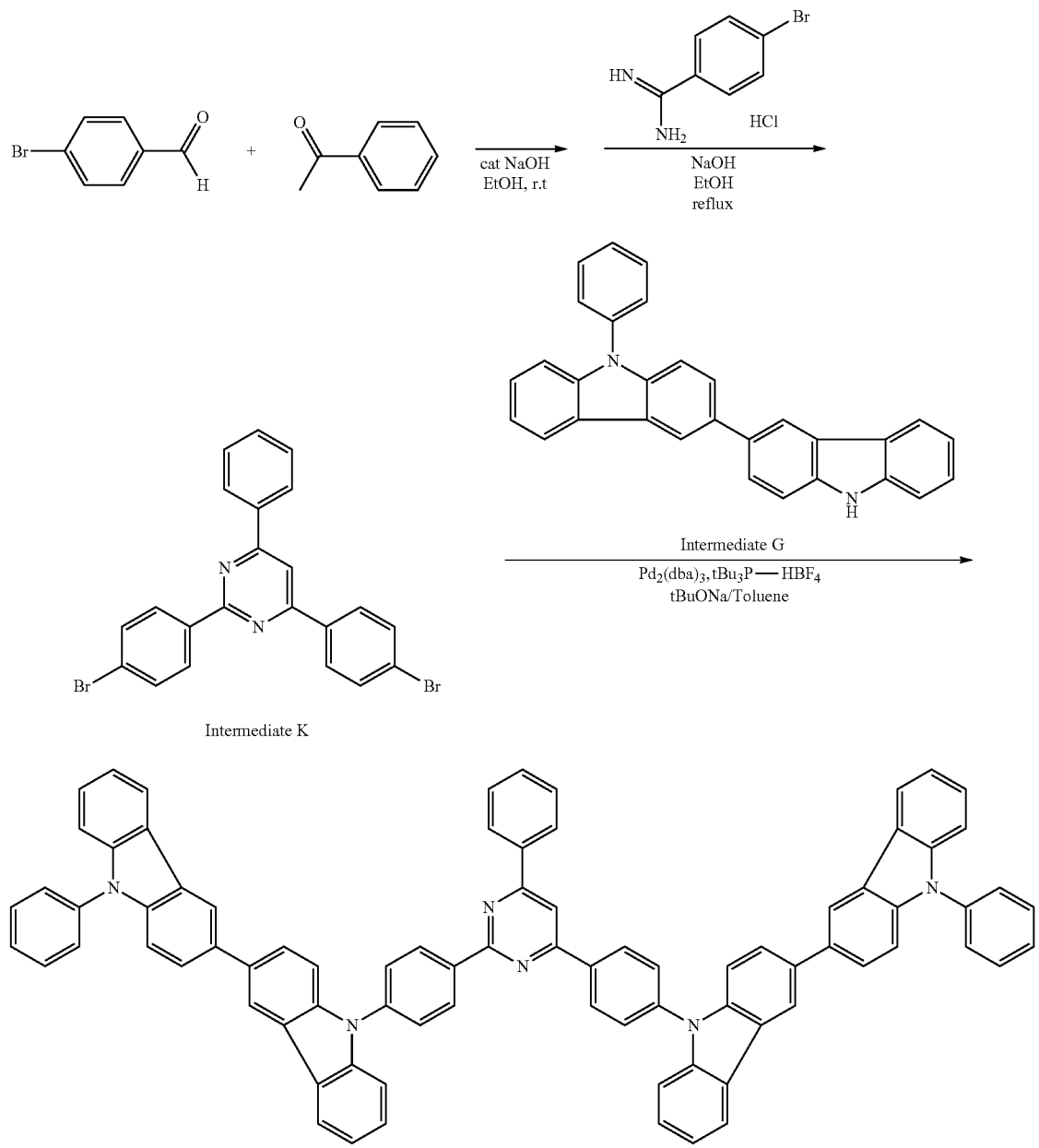

H-7 dium (0.87 g, 9.0 mmol) and anhydrous toluene (60 mL) were added sequentially, and the mixture was heated under reflux for 12 hours.

After the reaction solution was cooled to room temperature, insoluble matters were removed by filtration, and the organic solvent was distilled off under reduced pressure. The residue obtained was purified by means of silica-gel chromatography to obtain H-7 (2.76 g, yield: 82%).

HPLC: Purity 99.4%
FD-MS: calcd for C82H52N6=1121,
found m/z=1121 (M+, 100).

(PEDOT: Preparation of PSS-Coated Substrate)

A PEDO:PSS aqueous dispersion (CleviousAI4083, manufactured by H. C. Starck GmbH), water and isopropyl alcohol were mixed at the ratio of 5:3:2 to prepare a PEDO:PSS dispersion. An ITO substrate (GEOMATEC CO., LTD.) of 25 mm by 25 mm by 0.7 mm on which an electrode wiring patterns were formed was subjected to ultrasonic cleaning with isopropyl alcohol for 5 minutes, and cleaned with ultraviolet rays and ozone for 30 minutes. Subsequently, the PEDO:PSS dispersion was applied by spin coating to form a 40 nm-thick film. After film forming, an extraction electrode part was cleaned off with water. Thereafter, the resulting substrate was fired in air at 200° C. for 30 minutes to produce a PEDOT:PSS-coated substrate.

(Preparation of a Material Solution for an Organic EL Device and Film Formation of an Organic EL Emitting Layer)

As a solvent, dehydrated toluene after rectification was used, as a host, H-1 was used, and as a dopant, Ir(nBuPPy)$_3$ was added such that the concentration thereof became 20 wt % relative to a host. The resulting solution was stirred while heating at 90° C. to prepare a solution having a total solid part ratio of 2.5 wt %. Subsequently, by using the solution thus obtained, an organic EL emitting layer was formed on the PEDOT:PSS-coated substrate by spin coating (500 rpm×3 seconds, then 3000 rpm×60 seconds). After formation of the organic EL emitting layer, an extraction electrode part was cleaned off with toluene, followed by heating and drying on a hot plate at 100° C. for 30 minutes. Preparation of a solution and film formation of an organic EL emitting layer were conducted in a glove box under a nitrogen atmosphere, throughout the process.

(Fabrication of an Organic EL Device)

The substrate on which an organic EL emitting layer was formed was mounted in a substrate holder of a vacuum vapor deposition apparatus. As an electron-transporting material, compound C was formed into a 20 nm thick-film at a deposition speed of 1 Å/second. After that, lithium fluoride (LiF) was formed into a 1 nm-thick film at a deposition speed of 0.1 Å/second, and aluminum (Al) was formed into a 150 nm-thick film at a deposition speed of 3 Å/second.

(Method for Evaluating an Organic EL Device)

The organic EL devices fabricated as above were driven by applying direct current to emit light. The voltage and the luminous efficiency (cd/A) at a current density (V) of 1 mA/cm$^2$, as well as the life time until the luminance decreases to 90% (LT90, at an initial luminance of 5200 cd/m$^2$) were measured. The results were shown in Table 2.

Examples 8 to 20

Organic EL devices were fabricated and evaluated in the same manner as in Example 7, except that the phosphorescent host materials were changed from compounds H-1 to compounds H-2 to H-14. The synthesis methods of compound H-8 to H-14 are shown below. The results are shown in Table 2.

Comparative Examples 5 to 8

For compounds D to G, an attempt was made to prepare a material solution for an organic EL device and an organic EL emitting layer in the same manner as in Example 7. As a result, white turbidity was found with a compound remaining un-dissolved, or after being temporarily dissolved, material precipitation was occurred immediately, or an uniform film could not be obtained due to formation of microcrystalline at the time of film formation, etc. Thus, an organic EL emitting layer capable of emitting uniformly could not be obtained.

(Synthesis of Compound H-8)

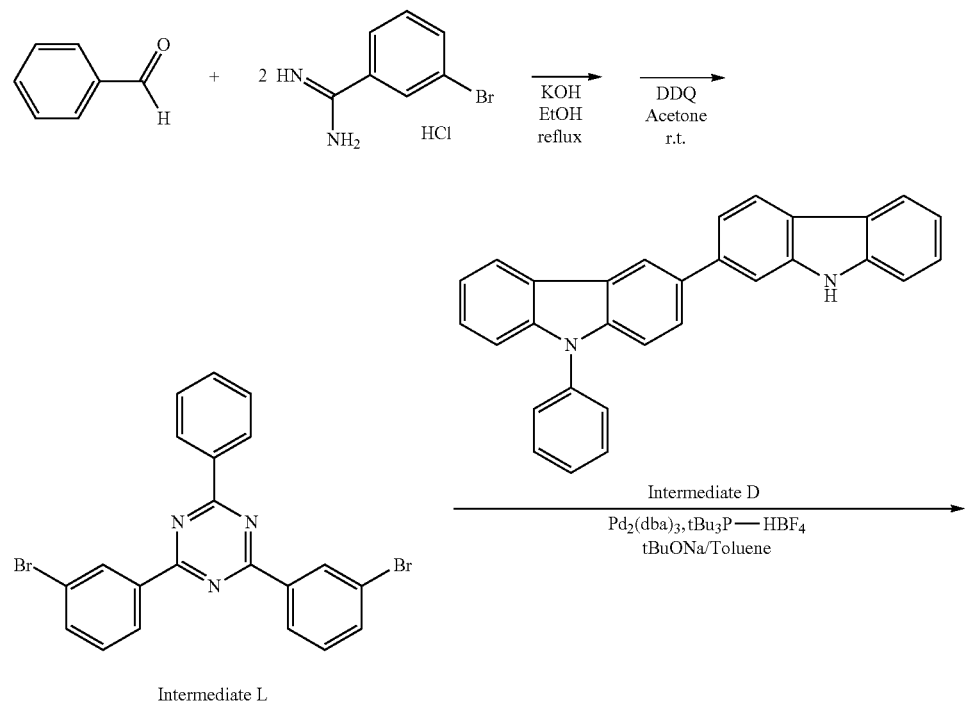

Intermediate L

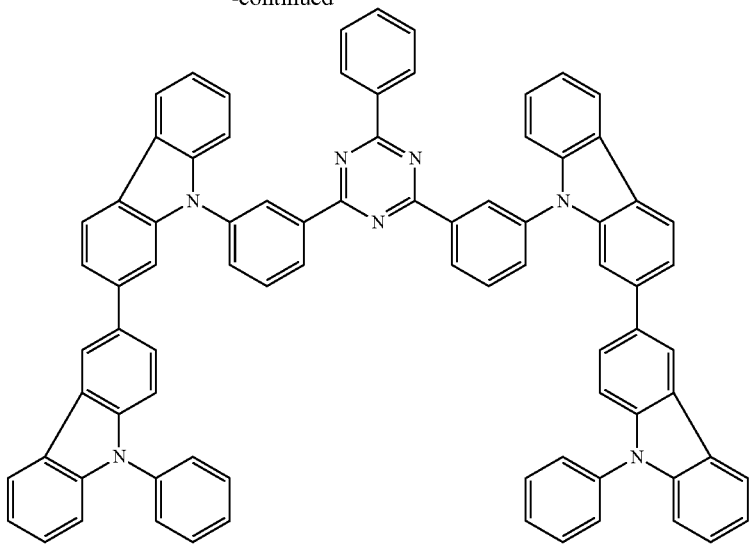

H-8

Benzaldehyde (2.12 g, 20 mmol) and 3-bromobenzamidine hydrochloride (9.42 g, 40 mmol) were dissolved in ethanol (120 mL), and potassium hydroxide (4.48 g, 80 mmol) was added, followed by reaction while heating under reflux for 8 hours. Ethanol was distilled off under reduced pressure, and the residue was dissolved in methylene chloride. After washing with a saturated ammonium chloride solution, the organic phase was separated, whereby the organic solvent was distilled off under reduced pressure.

The residue was dissolved in 100 mL of acetone. To this, DDQ (2,3-dichloro-5,6-dicyano-p-benzoquinone) (4.54 g, 20 mmol) was added in driblets and stirred further for an hour. Insoluble matters were removed by filtration, and the organic solvent was distilled off under reduced pressure. The residue obtained was purified by means of silica-gel chromatography to obtain an intended intermediate L (5.79 g, yield: 62%).

In argon atmosphere, intermediate D (2.57 g, 6.3 mmol), intermediate L (1.40 g, 3.0 mmol), tris(dibenzylideneacetone)dipalladium (0.055 g, 0.06 mmol), tri-t-butylphosphonium tetrafluoroborate (0.070 g, 0.24 mmol), t-butoxysodium (0.87 g, 9.0 mmol) and anhydrous toluene (60 mL) were added sequentially, and the mixture was heated under reflux for 16 hours.

After the reaction solution was cooled to room temperature, insoluble matters were removed by filtration, and the organic solvent was distilled off under reduced pressure. The residue obtained was purified by means of silica-gel chromatography to obtain H-8 (3.00 g, yield: 89%).

HPLC: Purity 99.2%

FD-MS: calcd for C82H51N7=1122,
found m/z=1122 (M+, 100).

(Synthesis of Compound H-9)

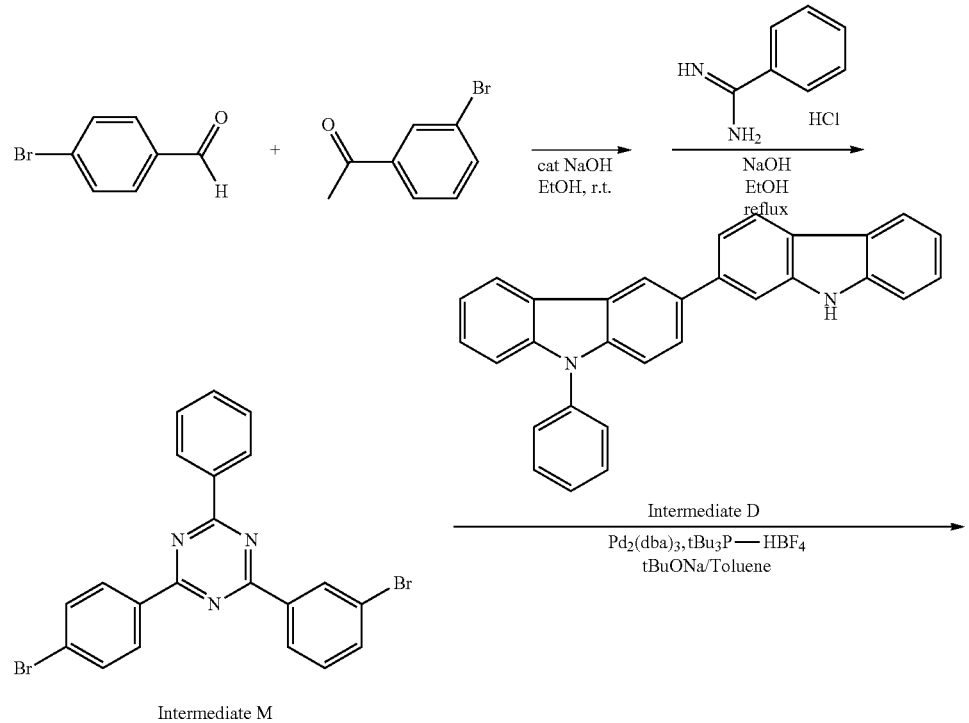

Intermediate M

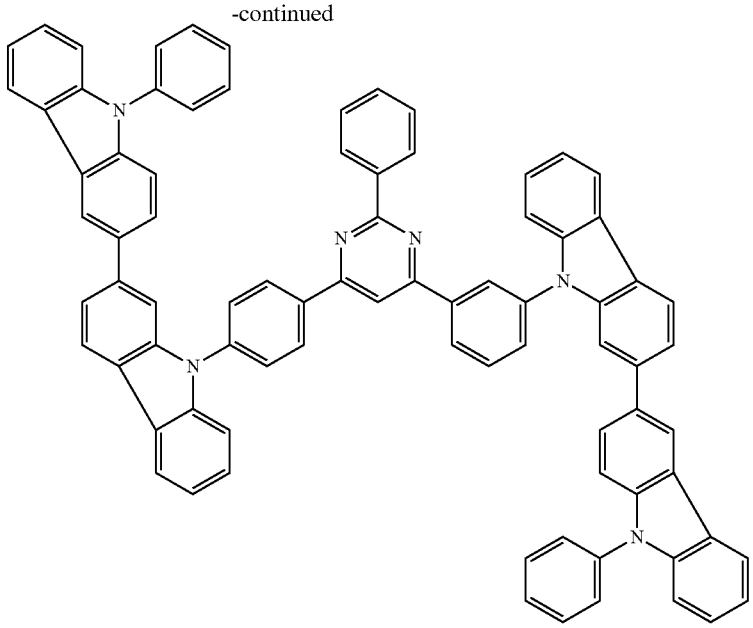

H-9

4-bromobenzaldehyde (7.40 g, 40 mmol) and 3'-bromoacetophenone (7.96, 40 mmol) were dissolved in ethanol (80 mL), and sodium hydroxide (0.16 g, 4 mmol) was added. The resulting solution was stirred at room temperature for 8 hours. Then, benzamidine hydrochloride (4.70 g, 30 mmol), sodium hydroxide (1.60 g, 40 mmol) and ethanol (40 mL) were added, and the resulting solution was reacted while heating under reflux for 8 hours. White powder generated was filtered off and washed with ethanol until the liquid become colorless. The powder was further washed with water and ethanol and then dried in a vacuum to obtain intermediate M (6.75 g, yield: 72%).

In argon atmosphere, intermediate D (2.57 g, 6.3 mmol), intermediate M (1.40 g, 3.0 mmol), tris(dibenzylideneacetone)dipalladium (0.055 g, 0.06 mmol), tri-t-butylphosphonium tetrafluoro borate (0.070 g, 0.24 mmol), t-butoxy sodium (0.87 g, 9.0 mmol) and anhydrous toluene (60 mL) were added sequentially, and the mixture was heated under reflux for 16 hours.

After the reaction solution was cooled to room temperature, insoluble matters were removed by filtration, and the organic solvent was distilled off under reduced pressure. The residue obtained was purified by means of silica-gel chromatography to obtain H-9 (2.90 g, yield: 86%).

HPLC: Purity 99.6%

FD-MS: calcd for C82H52N6=1121, found m/z=1121 (M+, 100).

(Synthesis of Compound H-10)

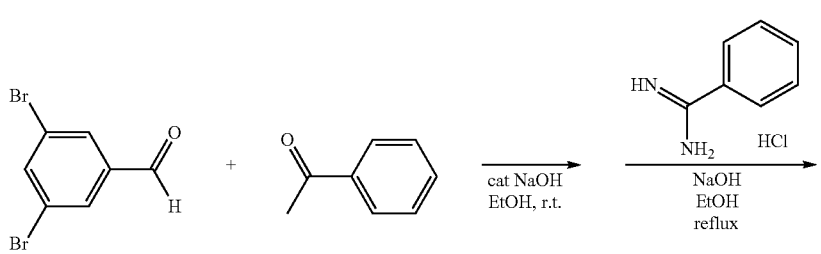

-continued

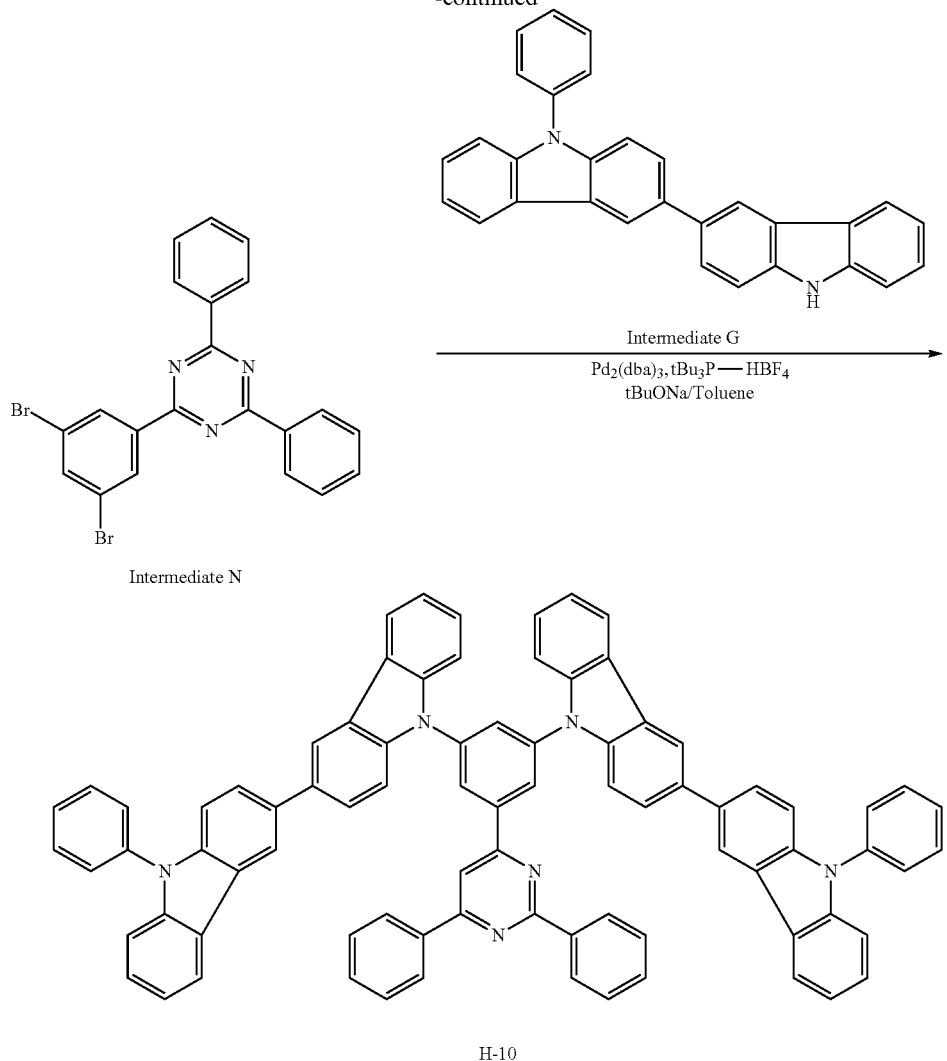

Intermediate N

H-10

3,5-dibromobenzaldehyde (10.56 g, 40 mmol) and acetophenone (4.81, 40 mmol) were dissolved in ethanol (80 mL), and sodium hydroxide (0.16 g, 4 mmol) was added. The resulting solution was stirred at room temperature for 8 hours. Then, benzamidine hydrochloride (4.70 g, 30 mmol), sodium hydroxide (1.60 g, 40 mmol) and ethanol (40 mL) were added, and the resulting solution was reacted while heating under reflux for 8 hours. White powder generated was filtered off and washed with ethanol until the liquid became colorless. The powder was further washed with water and ethanol and then dried in vacuum to obtain intermediate N (5.20 g, yield: 56%).

Under an argon atmosphere, intermediate G (2.57 g, 6.3 mmol), intermediate N (1.40 g, 3.0 mmol), tris(dibenzylideneacetone)dipalladium (0.055 g, 0.06 mmol), tri-t-butylphosphonium tetrafluoroborate (0.070 g, 0.24 mmol), t-butoxysodium (0.87 g, 9.0 mmol) and anhydrous toluene (60 mL) were added sequentially, and the mixture was heated under reflux for 16 hours.

After the reaction solution was cooled to room temperature, insoluble matters were removed by filtration, and the organic solvent was distilled off under reduced pressure. The residue obtained was purified by means of silica-gel chromatography to obtain H-10 (2.70 g, yield: 80%).

HPLC: Purity 99.2%
FD-MS: calcd for $C_{82}H_{52}N_6$=1121,
found m/z=1121 (M+, 100).

(Synthesis of Compound H-11)

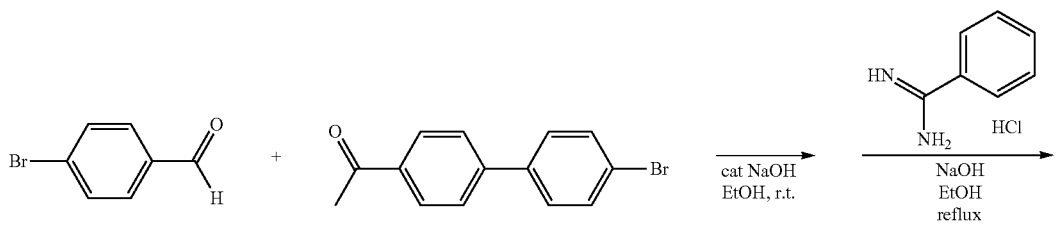

-continued

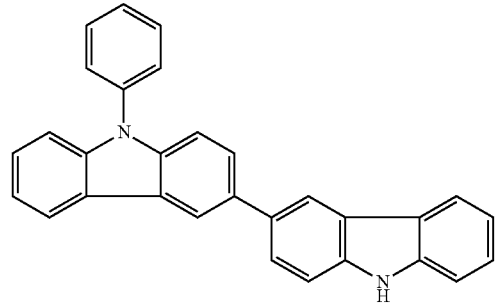

Intermediate G

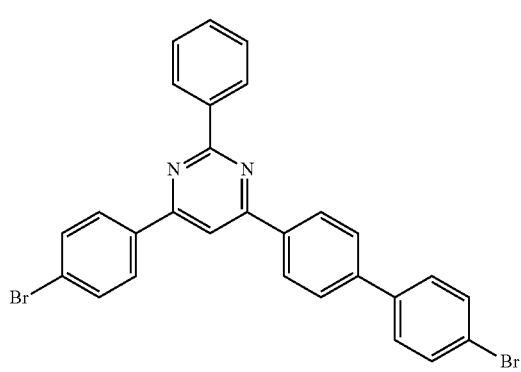

Intermediate O

→ Pd₂(dba)₃, tBu₃P—HBF₄
tBuONa/Toluene

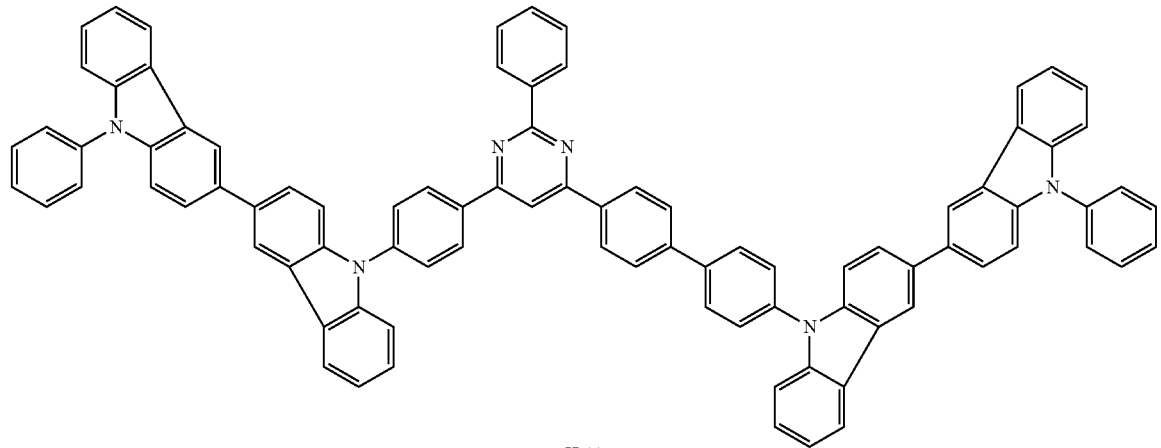

H-11

4-bromobenzaldehyde (7.40 g, 40 mmol) and 4-acetyl-4'-bromobiphenyl (11.01, 40 mmol) were dissolved in ethanol (80 mL), and sodium hydroxide (0.16 g, 4 mmol) was added. The resulting solution was stirred at room temperature for 8 hours. Then, benzamidine hydrochloride (4.70 g, 30 mmol), sodium hydroxide (1.60 g, 40 mmol) and ethanol (40 mL) were added, and the resulting solution was reacted while heating under reflux for 8 hours. White powder generated was filtered off and washed with ethanol until the liquid became colorless. The powder was further washed with water and ethanol. 200 mL of ethanol was added again, and then heated under reflux for an hour, followed by filtering. The filtered matter was dried in vacuum to obtain an intended intermediate O (9.32 g, yield: 86%).

In an argon atmosphere, intermediate G (2.40 g, 5.88 mmol), intermediate O (1.52 g, 2.80 mmol), tris(dibenzylideneacetone)dipalladium (0.055 g, 0.06 mmol), tri-t-butylphosphonium tetrafluoro borate (0.070 g, 0.24 mmol), t-butoxy sodium (0.87 g, 9.0 mmol) and anhydrous toluene (60 mL) were added sequentially, and the mixture was heated under reflux for 16 hours.

After the reaction solution was cooled to room temperature, insoluble matters were removed by filtration, and the organic solvent was distilled off under reduced pressure. The residue obtained was purified by means of silica-gel chromatography to obtain H-11 (2.75 g, yield: 82%).

HPLC: Purity 99.7%

FD-MS: calcd for C88H56N6=1197,
found m/z=1197 (M+, 100).

(Synthesis of Compound H-12)

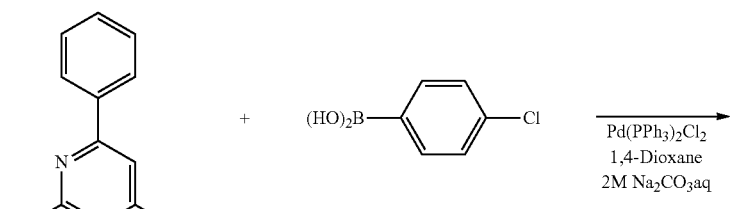

Intermediate E

→ Pd(PPh₃)₂Cl₂
1,4-Dioxane
2M Na₂CO₃aq

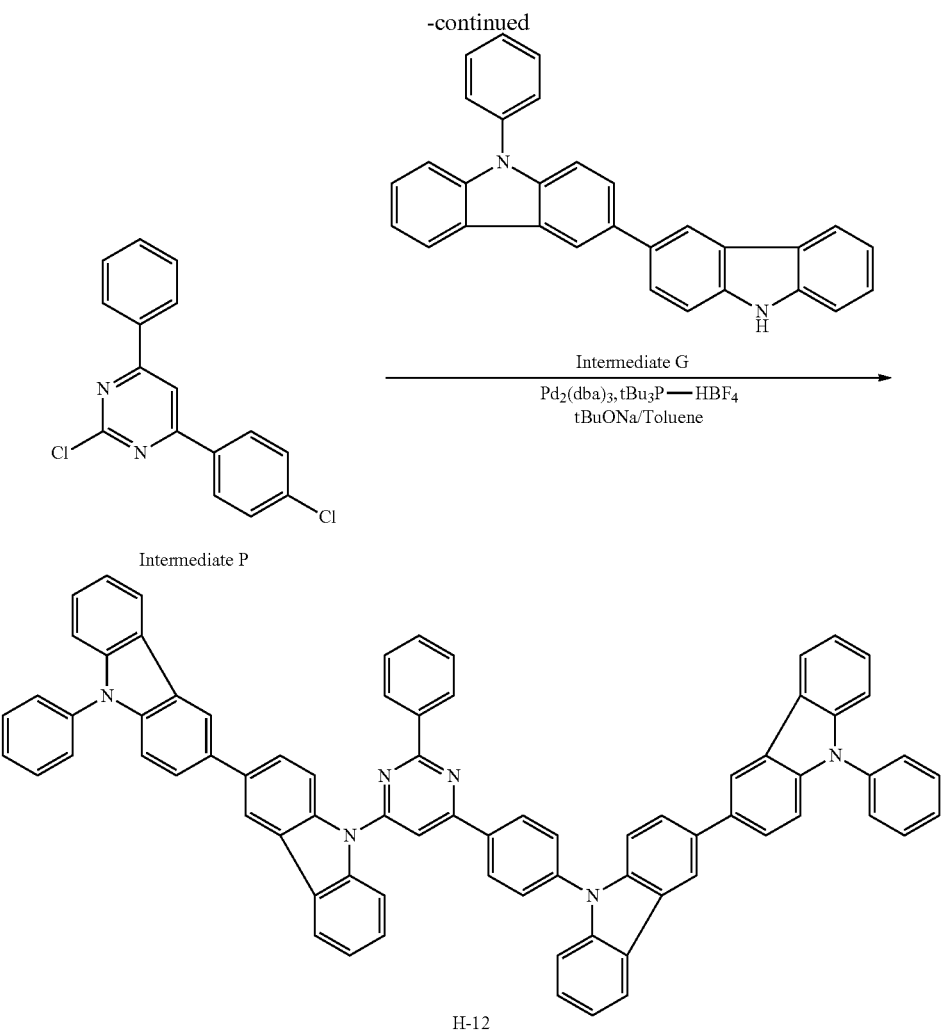

Intermediate P

H-12

In argon atmosphere, intermediate E (4.50 g, 20 mmol), 4-chlorophenylborate (3.13 g, 20 mmol), dichloro(bistriphenylphosphine)palladium complex (0.351 g, 0.5 mmol), 1,4-dioxane (80 mL) and a 2M aqueous potassium carbonate solution (40 mL) were sequentially added. The resulting mixture was heated under reflux for 8 hours.

After the reaction mixture was cooled to room temperature, the mixture was diluted by adding toluene and washed with water, followed by drying under reduced pressure. The residue obtained was purified by means of silica-gel chromatography to obtain intermediate P (4.03 g, yield: 67%).

In argon atmosphere, intermediate G (2.57 g, 6.3 mmol), intermediate P (0.90 g, 3.00 mmol), tris(dibenzilideneacetone)dipalladium (0.055 g, 0.06 mmol), tri-t-butylphosphonium tetrafluoro borate (0.070 g, 0.24 mmol), t-butoxy sodium (0.87 g, 9.0 mmol) and dehydrated toluene (60 mL) were sequentially added. The resulting mixture was heated under reflux for 10 hours.

After the reaction mixture was cooled to room temperature, insoluble matters were removed by filtration, and the organic solvent was distilled away under reduced pressure. The residue obtained was purified by means of silica-gel chromatography to obtain H-12 (2.67 g, yield: 85%).

HPLC: Purity 99.3%
FD-MS: calcd for C76H48N6=1045,
found m/z=1045 (M+, 100).

(Synthesis of Compound H-13)

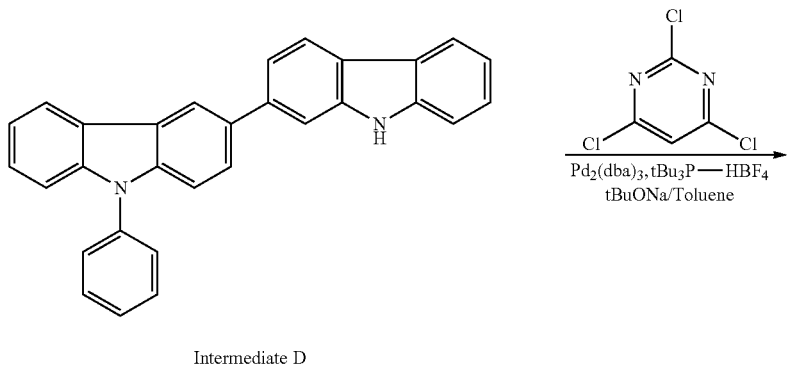

Intermediate D

-continued

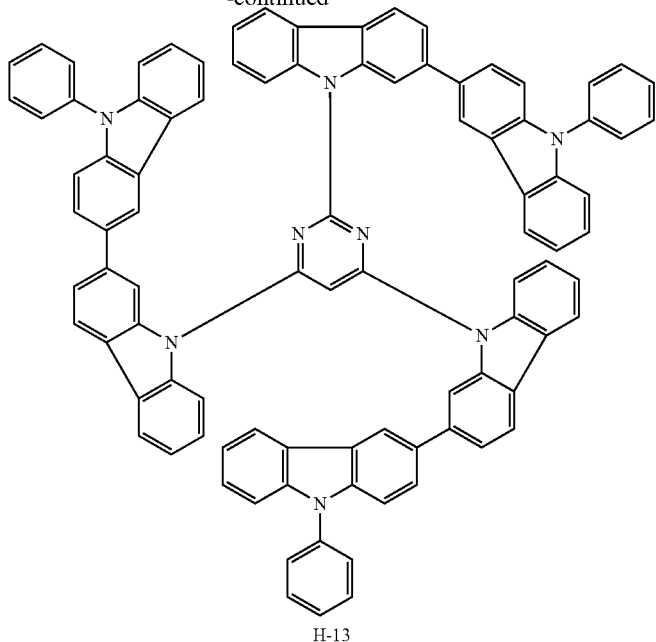

H-13

In argon atmosphere, intermediate D (2.57 g, 6.3 mmol), 2,4,6-trichloropyrimidine (0.367 g, 2.0 mmol), tris(dibenzilideneacetone)dipalladium (0.055 g, 0.06 mmol), tri-t-butylphosphonium tetrafluoro borate (0.070 g, 0.24 mmol), t-butoxy sodium (0.87 g, 9.0 mmol) and dehydrated toluene (60 mL) were sequentially added. The resulting mixture was heated under reflux for 16 hours.

After the reaction mixture was cooled to room temperature, insoluble matters were removed by filtration, and the organic solvent was distilled off under reduced pressure. The residue obtained was purified by means of silica-gel chromatography to obtain H-13 (1.95 g, yield: 75%).

HPLC: Purity 99.0%

FD-MS: calcd for C94H58N8=1299, found m/z=1299 (M+, 100).

(Synthesis of Compound H-14)

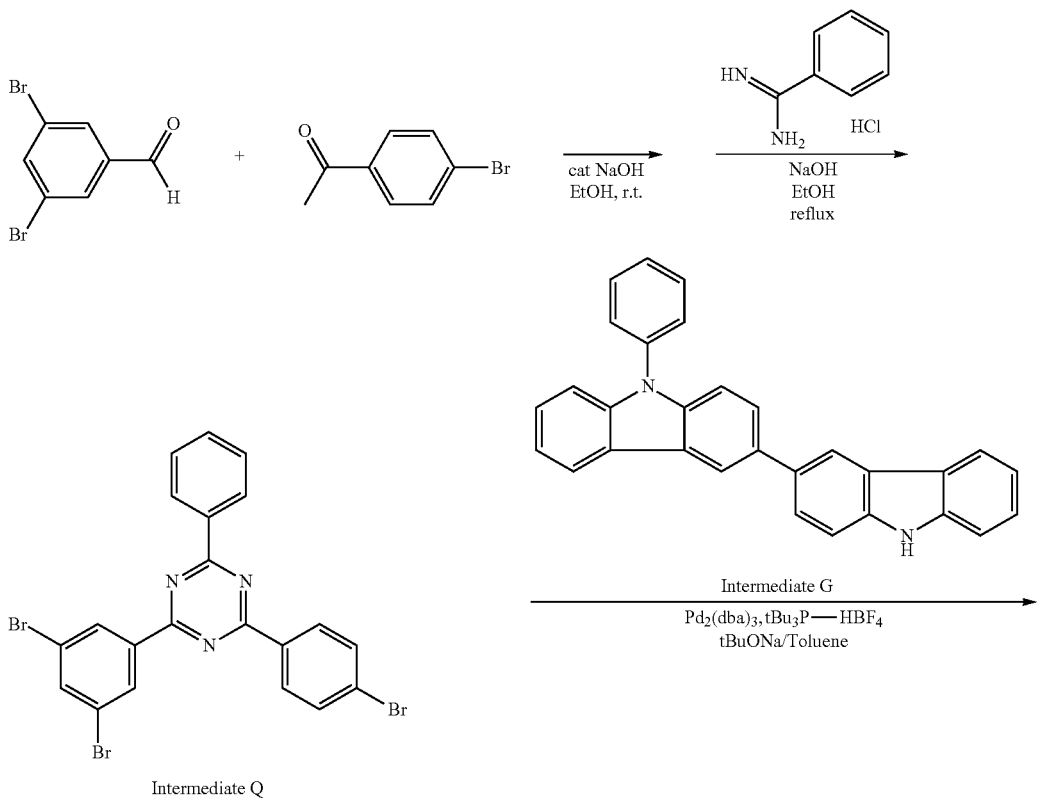

-continued

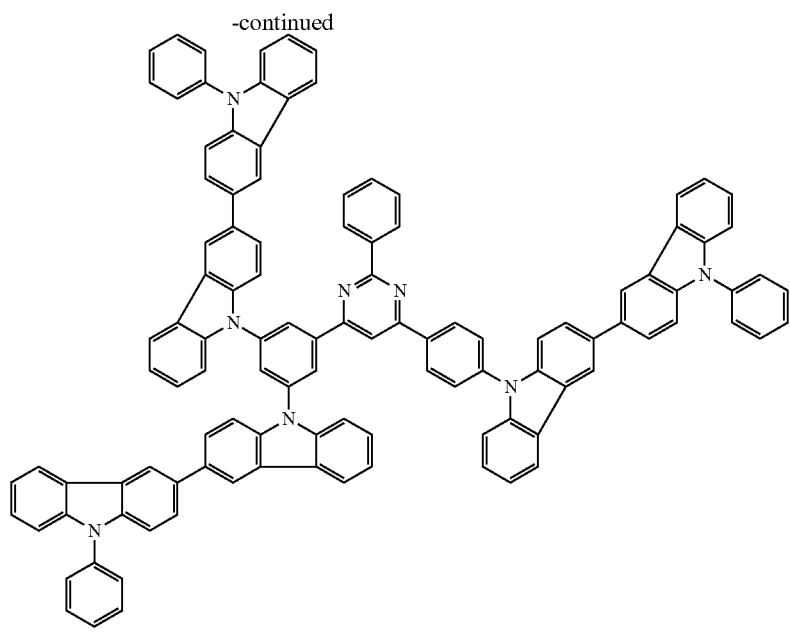

H-14

3,5-dibromobenzaldehyde (10.56 g, 40 mmol) and 4'-bromoacetophenone (7.96, 40 mmol) were dissolved in ethanol (160 mL), and sodium hydroxide (0.16 g, 4 mmol) was added. The resulting solution was stirred at room temperature for 8 hours. Then, benzamidine hydrochloride (4.70 g, 30 mmol), sodium hydroxide (1.60 g, 40 mmol) and ethanol (80 mL) were added, and the resulting solution was reacted while heating under reflux for 8 hours. White powder generated was filtered off and washed with ethanol until the liquid became colorless. The powder was further washed with water and ethanol to obtain an intended intermediate Q (9.38 g, yield: 86%).

In argon atmosphere, intermediate G (2.57 g, 6.3 mmol), intermediate Q (1.09 g, 2.0 mmol), tris(dibenzylideneacetone)dipalladium (0.055 g, 0.06 mmol), tri-t-butylphosphonium tetrafluoro borate (0.070 g, 0.24 mmol), t-butoxy sodium (0.87 g, 9.0 mmol) and anhydrous toluene (60 mL) were added sequentially, and the mixture was heated under reflux for 16 hours.

After the reaction solution was cooled to room temperature, insoluble matters were removed by filtration, and the organic solvent was distilled off under reduced pressure. The residue obtained was purified by means of silica-gel chromatography to obtain H-14 (1.95 g, yield: 75%).

HPLC: Purity 99.4%

FD-MS: calcd for C112H70N8=1528, found m/z=1528 (M+, 100).

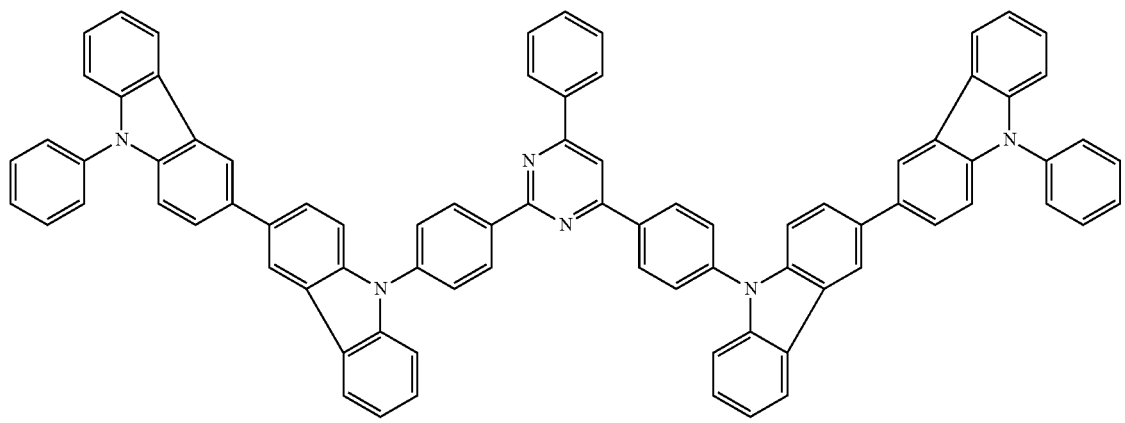

H-7

H-8
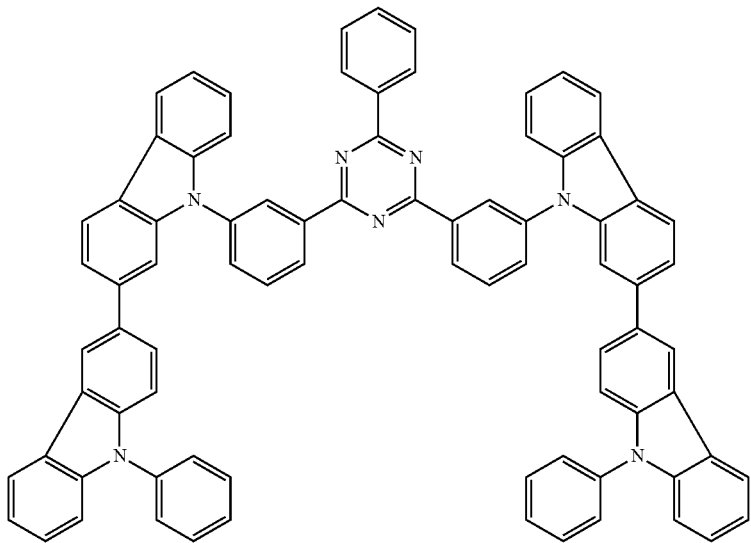
H-9
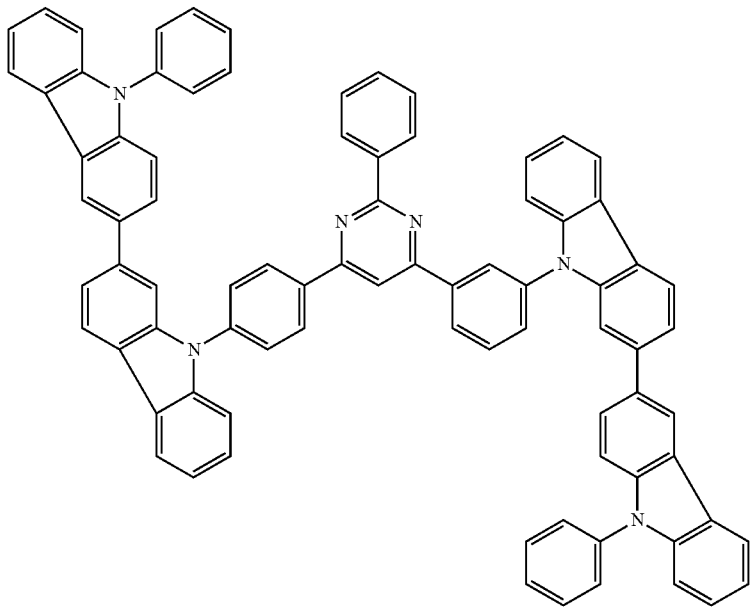
H-10
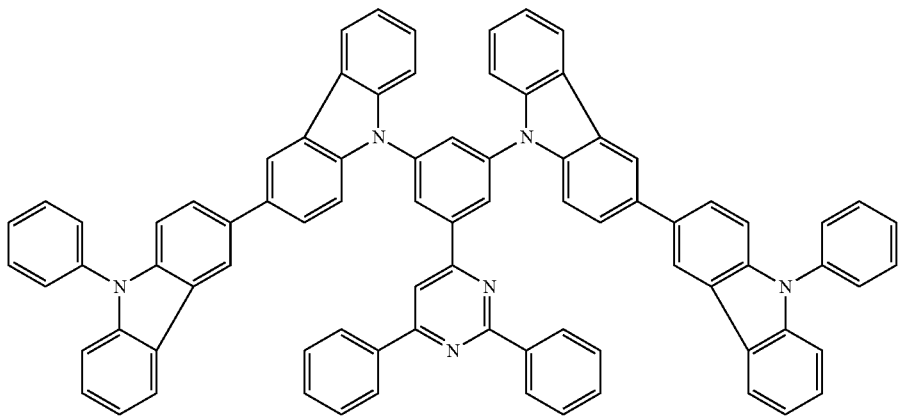

H-11
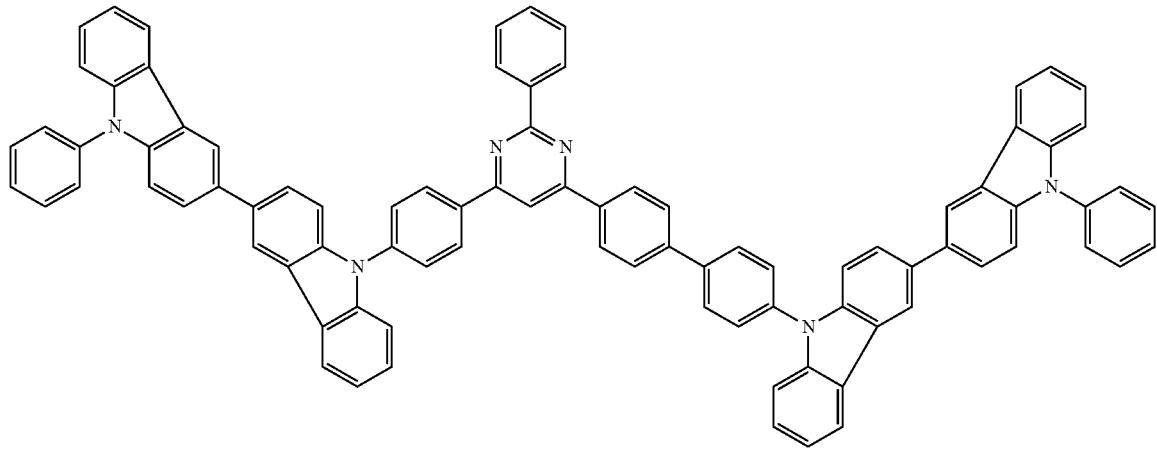
H-12
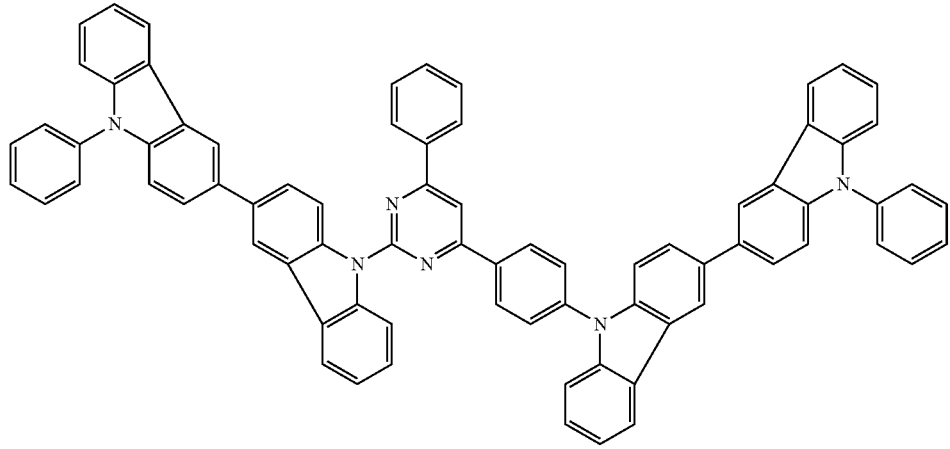
H-13
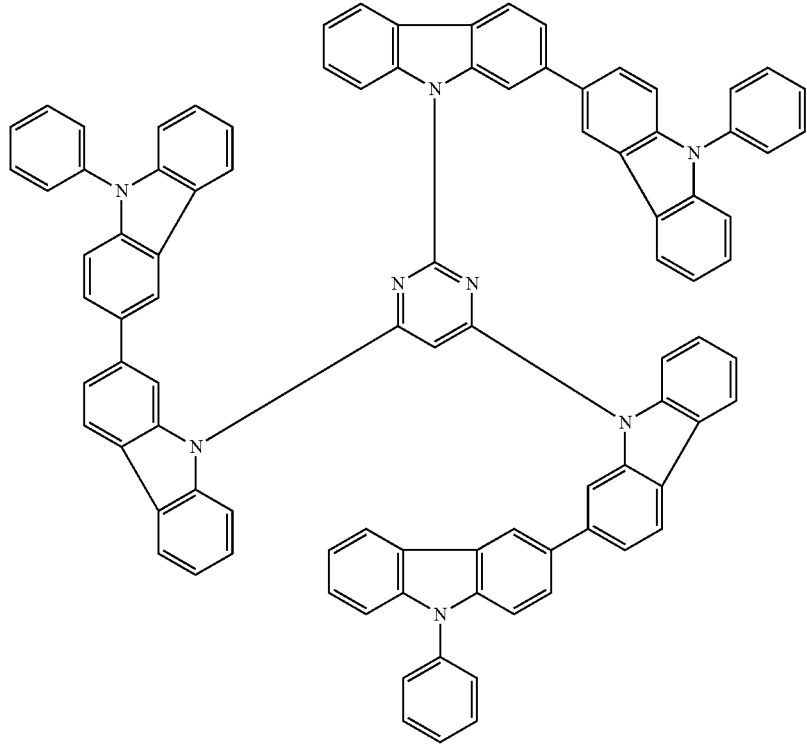

-continued

H-14

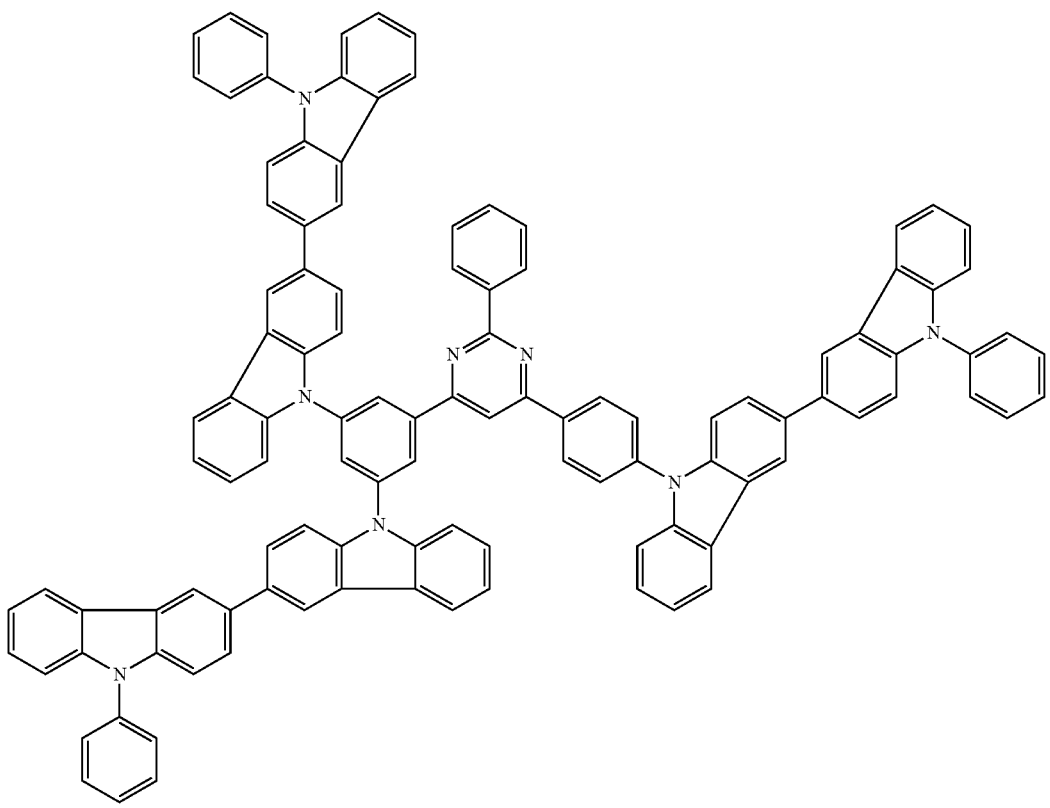

TABLE 2

| | Host material | Voltage (V) @1 mA/cm² | Luminous efficiency (cd/A) @1 mA/cm² | Life time LT90 (hrs) |
|---|---|---|---|---|
| Example 7 | Compound H-1 | 5.0 | 45 | 105 |
| Example 8 | Compound H-2 | 5.1 | 40 | 95 |
| Example 9 | Compound H-3 | 5.2 | 45 | 120 |
| Example 10 | Compound H-4 | 5.7 | 42 | 132 |
| Example 11 | Compound H-5 | 5.3 | 46 | 106 |
| Example 12 | Compound H-6 | 5.3 | 42 | 112 |
| Example 13 | Compound H-7 | 5.0 | 47 | 155 |
| Example 14 | Compound H-8 | 5.3 | 39 | 98 |
| Example 15 | Compound H-9 | 5.3 | 40 | 107 |
| Example 16 | Compound H-10 | 5.1 | 49 | 170 |
| Example 17 | Compound H-11 | 5.0 | 38 | 122 |
| Example 18 | Compound H-12 | 5.1 | 42 | 133 |
| Example 19 | Compound H-13 | 4.8 | 42 | 100 |
| Example 20 | Compound H-14 | 4.7 | 43 | 98 |

<Fluorescence Spectrum Measurement of a Thin Film Fabricated Using a Material Solution for an Organic EL Device>

Example 21

As a solvent, dehydrated 1,4-dioxane, and as a host, 1 wt % of H-2 were used. As a dopant, Ir(nBuPPy)$_3$ was added such that the concentration thereof became 5, 10 or 20 wt % relative to the host. Subsequently, the solution thus obtained was applied on a quartz substrate (25×25×1 mm) by spin coating (500 rpm×3 seconds, then 3000 rpm×60 seconds). After air drying, the substrate was dried on a hot plate at 100° C. for 30 minutes. The entire operation was conducted in a glove box under a nitrogen atmosphere.

Figure 3:
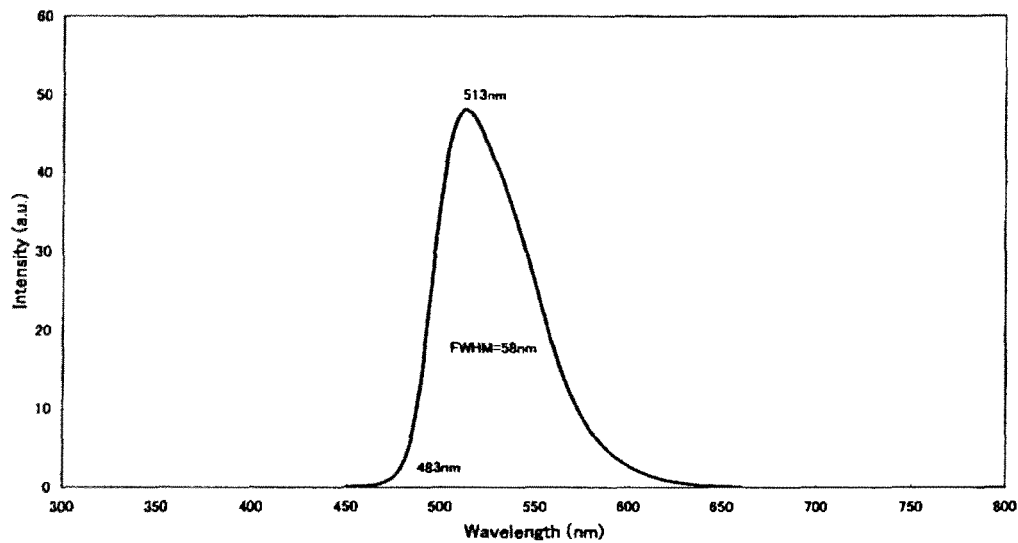
FIG. 3 is a chart showing a fluorescent spectrum (in a methylene chloride solution) of the dopant $(Ir(nBuPPy)_3)$ used in Examples 5 and 6.
Figure 4:
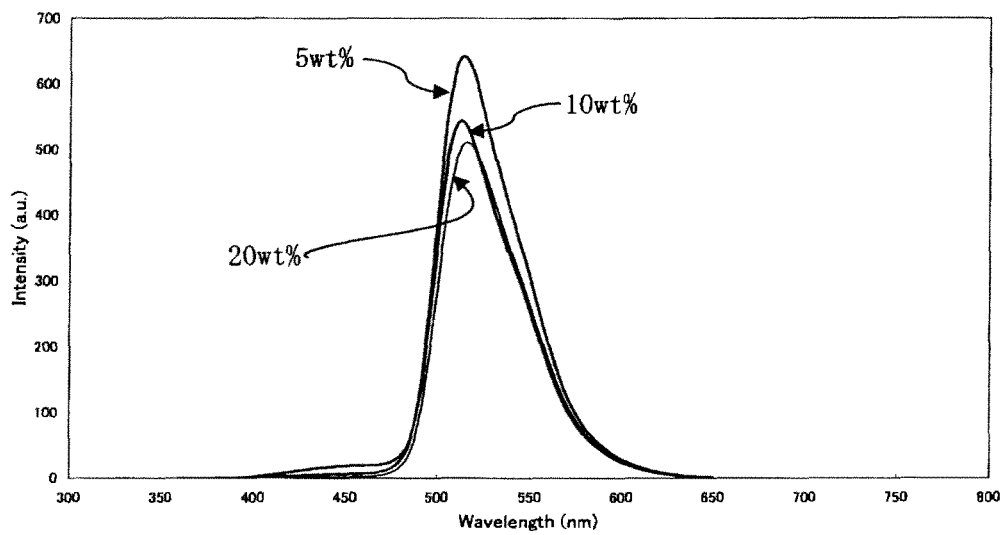
FIG. 4 is a chart showing a fluorescent spectrum of a thin film having dopant concentrations of 5, 10 and 20 wt % produced in Example 5.

Next, for the thin film obtained, the fluorescence spectrum and quantum yield were measured using exciting light of 350 nm. The results are shown in Table 3. FIG. 1 shows the fluorescence spectrum of the thin film fabricated using only H-2 as a host. FIG. 3 shows the fluorescence spectrum of the thin film fabricated using only Ir(nBuPPy)$_3$ as a dopant (peak wavelength of fluorescence spectrum: 513 nm, half width: 58 nm, fluorescence quantum yield: 0.21). FIG. 4 shows the fluorescence spectrum of the thin film fabricated by using H-2 as a host and adding as a dopant Ir(nBuPPy)$_3$ having each of the above-mentioned concentrations.

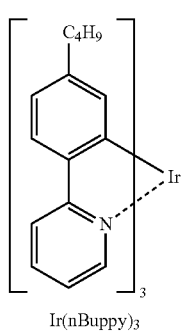

Ir(nBuppy)$_3$

Example 22

Figure 2:
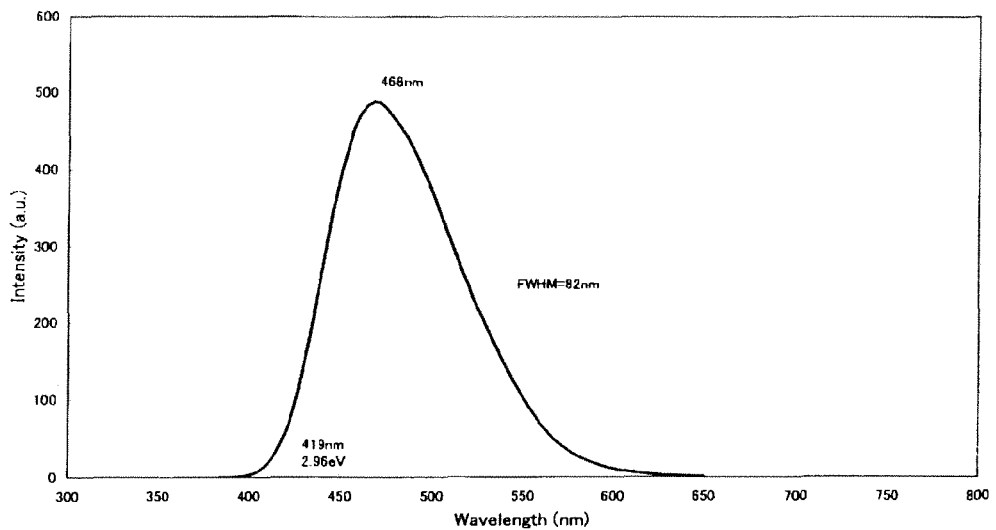
FIG. 2 is a chart showing a fluorescent spectrum of a thin film of the aromatic heterocyclic derivative H-3 of the invention.
Figure 5:
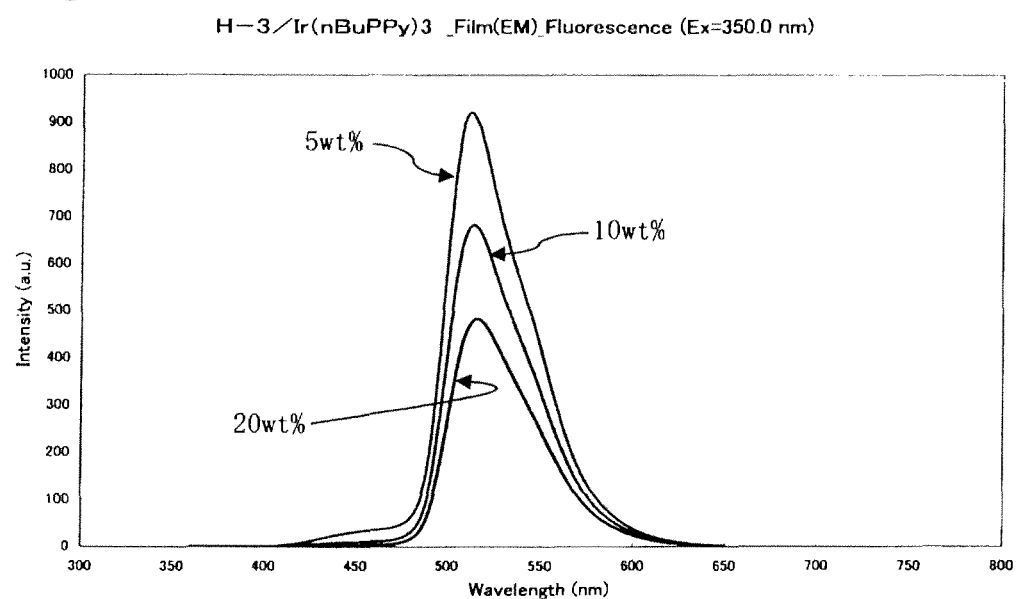
FIG. 5 is a chart showing a fluorescent spectrum of a thin film having dopant concentrations of 5, 10 and 20 wt % produced in Example 6.

A thin film was fabricated by preparing a solution in the same manner as in Example 5, except that a host was change to H-3, and the fluorescence spectrum and the quantum yield of the thin film were measured. The results are shown in Table 3. FIG. 2 shows the fluorescence spectrum of the thin film fabricated using only H-3 as a host. FIG. 5 shows the fluorescence spectrum of the thin film fabricated by using H-3 as a host and adding Ir(nBuPPy)$_3$ having each the above-mentioned concentration as a dopant.

TABLE 3

| | Host | Dopant concentration (wt %) | Peak of fluorescence spectrum (half width) (nm) | Fluorescence quantum yield |
|---|---|---|---|---|
| Ex. 21 | H-2 | 5 | 513(51) | 0.52 |
| | | 10 | 514(50) | 0.50 |
| | | 20 | 516(52) | 0.38 |
| Ex. 22 | H-3 | 5 | 512(50) | 0.60 |
| | | 10 | 514(50) | 0.52 |
| | | 20 | 516(52) | 0.36 |

It is clear from the comparison between the fluorescence spectrum of thin films that the spectrum of a thin film formed by mixing a host and a dopant was derived from the dopant. This fact demonstrates that the energy transfer from a host to a dopant occurred properly. Therefore, the host material developed by the present invention was found to be useful for a material used in coating or the like using a solution.

INDUSTRIAL APPLICABILITY

The aromatic heterocyclic derivative is useful for a material for an organic electroluminescence device.

In addition, the aromatic heterocyclic derivative of the invention having solubility and suitable for coating process is useful for a material solution for an organic electroluminescence device.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. An aromatic heterocyclic derivative represented by the following formula (1)-1 or (1)-2:

(1)-1

(1)-2 wherein
in the formula (1)-1 or (1)-2,
A is an n-valent group derived from
a substituted or unsubstituted pyrrole ring,
a substituted or unsubstituted pyrazole ring,
a substituted or unsubstituted imidazole ring,
a substituted or unsubstituted triazole ring,
a substituted or unsubstituted pyridine ring,
a substituted or unsubstituted pyrimidine ring,
a substituted or unsubstituted pyridazine ring,
a substituted or unsubstituted pyrazine ring,
a substituted or unsubstituted triazine ring,
a substituted or unsubstituted indole ring,
a substituted or unsubstituted indazole ring,
a substituted or unsubstituted benzimidazole ring,
a substituted or unsubstituted quinoline ring,
a substituted or unsubstituted isoquinoline ring,
a substituted or unsubstituted phthalazine ring,
a substituted or unsubstituted naphthyridine ring,
a substituted or unsubstituted cinnoline ring,
a substituted or unsubstituted quinoxaline ring,
a substituted or unsubstituted quinazoline ring, or
a substituted or unsubstituted imidazopyridine ring;
B is a substituted or unsubstituted aromatic hydrocarbon group including 6 to 30 ring carbon atoms or a substituted or unsubstituted aromatic heterocyclic group including 2 to 30 ring carbon atoms;
n is an integer of 2 or more; and
Czs are independently an aromatic heterocyclic group represented by the following formula (2) or (3); in the formula (1)-1, n of Czs may be independently bonded to any position of A, and when A includes a substituent, n of Czs may be bonded to any position of the substituent; and in the formula (1)-2, n of Czs may be independently bonded to any position of A or B, and when A or B includes a substituent, n of Czs may be bonded to any position of the substituent:

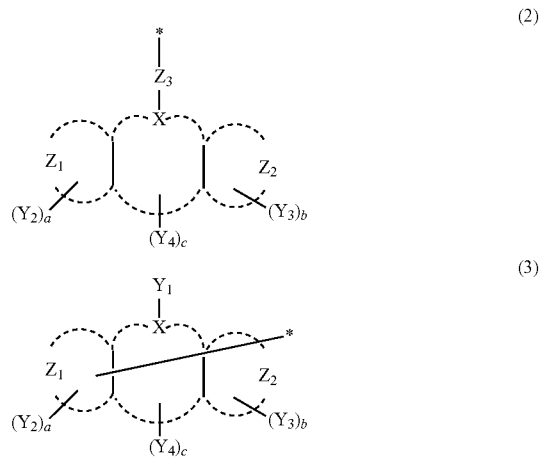

wherein
in the formula (2) or (3),
* indicates the bonding position to A or B;
$Z_1$ and $Z_2$ are independently atoms that form an aromatic hydrocarbon ring, an aromatic heterocyclic ring or an aliphatic ring, and are selected from the group consisting of carbon atoms, nitrogen atoms, oxygen atoms and sulfur atoms;
$Z_3$ is a single bond or a divalent linking group;
X is a nitrogen atom in the formula (2) and is a nitrogen atom, an oxygen atom or a sulfur atom in the formula (3);
the ring comprising X comprises atoms that form the ring and are selected from the group consisting of carbon atoms, nitrogen atoms, oxygen atoms and sulfur atoms in addition to X,
the ring formed of $Z_1$ is an aromatic hydrocarbon ring, an aromatic heterocyclic ring or an aliphatic ring; the aromatic hydrocarbon ring, the aromatic heterocyclic ring or the aliphatic ring, and the ring comprising X share two carbon atoms which form each ring; and the ring formed of $Z_2$ is an aromatic hydrocarbon ring, an aromatic heterocyclic ring or an aliphatic ring; the aromatic hydrocarbon ring, the aromatic heterocyclic ring or the aliphatic ring, and the ring comprising X share two carbon atoms which form each ring;

$Y_1$, $Y_3$ and $Y_4$ are independently selected from the group consisting of a hydrogen atom, a deuterium atom, a halogen atom, a cyano group, a substituted or unsubstituted linear, branched or cyclic alkyl group including 1 to 20 carbon atoms, a substituted or unsubstituted linear, branched or cyclic alkoxy group including 1 to 20 carbon atoms, a substituted or unsubstituted linear, branched or cyclic haloalkyl group including 1 to 20 carbon atoms, a substituted or unsubstituted linear, branched or cyclic haloalkoxy group including 1 to 20 carbon atoms, a substituted or unsubstituted linear, branched or cyclic alkylsilyl group including 1 to 10 carbon atoms, a substituted or unsubstituted arylsilyl group including 6 to 30 ring carbon atoms, a substituted or unsubstituted aromatic hydrocarbon group including 6 to 30 ring carbon atoms and a substituted or unsubstituted aromatic heterocyclic group including 2 to 30 ring carbon atoms;

$Y_2$ is selected from the group consisting of a deuterium atom, a substituted or unsubstituted linear, branched or cyclic haloalkoxy group including 1 to 20 carbon atoms, a substituted or unsubstituted linear, branched or cyclic alkylsilyl group including 1 to 10 carbon atoms, a substituted or unsubstituted arylsilyl group including 6 to 30 ring carbon atoms, a substituted or unsubstituted pyrrolyl group, a substituted or unsubstituted pyrazinyl group, a substituted or unsubstituted indolyl group, a substituted or unsubstituted isoindolyl group, a substituted or unsubstituted furyl group, a substituted or unsubstituted benzofuranyl group, a substituted or unsubstituted isobenzofuranyl group, a substituted or unsubstituted dibenzofuranyl group, a substituted or unsubstituted dibenzothiophenyl group, a substituted or unsubstituted quinolyl group, a substituted or unsubstituted isoquinolyl group, a substituted or unsubstituted quinoxalinyl group, a substituted or unsubstituted N-phenylcarbazolyl group, a substituted or unsubstituted phenanthrydinyl group, a substituted or unsubstituted acridinyl group, a substituted or unsubstituted phenanthrolinyl group, a substituted or unsubstituted group formed by a pyrazine ring, a substituted or unsubstituted group formed by a pyrimidine ring, a substituted or unsubstituted group formed by a pyridazine ring, a substituted or unsubstituted group formed by a triazine ring, a substituted or unsubstituted group formed by a quinoline ring, a substituted or unsubstituted group formed by a acrydine ring, a substituted or unsubstituted group formed by a pyrrolidine ring, a substituted or unsubstituted group formed by a dioxane ring, a substituted or unsubstituted group formed by a piperidine ring, a substituted or unsubstituted group formed by a morpholine ring, a substituted or unsubstituted group formed by a piperazine ring, a substituted or unsubstituted group formed by a furan ring, a substituted or unsubstituted group formed by a thiophene ring, a substituted or unsubstituted group formed by a oxazole ring, a substituted or unsubstituted group formed by a oxadiazole ring, a substituted or unsubstituted group formed by a benzoxazole ring, a substituted or unsubstituted group formed by a thiazole ring, a substituted or unsubstituted group formed by a benzothiazole ring, a substituted or unsubstituted group formed by a triazole ring, a substituted or unsubstituted group formed by a imidazole ring, a substituted or unsubstituted group formed by a benzimidazole ring, a substituted or unsubstituted group formed by a pyrane ring, and a substituted or unsubstituted group formed by a dibenzofuran ring;

provided that in the formula (3), when X is an oxygen atom or a sulfur atom, $Y_1$ is not present;

a is an integer of 1 or more;

b and c are independently an integer of 0, or 1 or more; and when $Y_2$, $Y_3$ and $Y_4$ are 2 or more, adjacent groups of $Y_e$s, Ys and Ys may be bonded to each other to form a substituted or unsubstituted, saturated or unsaturated ring structure.

2. The aromatic heterocyclic derivative according to claim 1, wherein the aromatic heterocyclic group represented by the formula (2) or (3) is selected from the group consisting of a substituted or unsubstituted carbazolyl group, a substituted or unsubstituted azacarbazolyl group, a substituted or unsubstituted benzcarbazolyl group, a substituted or unsubstituted hydrocarbazolyl group, a substituted or unsubstituted acrydinyl group, a substituted or unsubstituted indolyl group and a substituted or unsubstituted xanthenyl group.

3. The aromatic heterocyclic derivative according to claim 1, wherein $Y_2$ in the aromatic heterocyclic group represented by the formula (2) or (3) is selected from the group consisting of a substituted or unsubstituted N-phenylcarbazolyl group and a substituted or unsubstituted dibenzofuranyl group.

4. The aromatic heterocyclic derivative according to claim 1, wherein n is 2 or 3.

5. The aromatic heterocyclic derivative according to claim 1, wherein A is selected from the group consisting of n-valent groups derived from a substituted or unsubstituted pyridine group, a substituted or unsubstituted pyrimidine group, a substituted or unsubstituted triazine group, a substituted or unsubstituted quinoline group, a substituted or unsubstituted isoquinoline group, a substituted or unsubstituted quinoxaline group and a substituted or unsubstituted quinazoline group.

6. A material for an organic electroluminescence device comprising the aromatic heterocyclic derivative according to claim 1.

7. A material solution for an organic electroluminescence device obtained by dissolving the aromatic heterocyclic derivative according to claim 1 in a solvent.

8. An organic electroluminescence device comprising:
an anode, a cathode, and
a plurality of organic thin film layers including an emitting layer between the anode and the cathode,
wherein at least one of the organic thin film layers comprises the aromatic heterocyclic derivative according to claim 1.

9. The organic electroluminescence device according to claim 8, wherein the emitting layer comprises the aromatic heterocyclic derivative as a host material.

10. The organic electroluminescence device according to claim 8, wherein the emitting layer comprises a phosphorescent material.

11. The organic electroluminescence device according to claim 10, wherein the phosphorescent material is an ortho-metalized complex of a metal atom selected from the group consisting of iridium (Ir), osmium (Os) and platinum (Pt).

12. The organic electroluminescence device according to claim 8, comprising an electron-injecting layer between the cathode and the emitting layer, the electron-injecting layer comprising a nitrogen-containing ring derivative.

13. The organic electroluminescence device according to claim 8, comprising an electron-transporting layer between the cathode and the emitting layer, the electron-transporting layer comprising the aromatic heterocyclic derivative.

14. The organic electroluminescence device according to claim 8, comprising a hole-transporting layer between the anode and the emitting layer, the hole-transporting layer comprising the aromatic heterocyclic derivative.

15. The organic electroluminescence device according to claim 8, wherein a reducing dopant is added in the interface region between the cathode and the organic thin film layers.

16. An aromatic heterocyclic derivative represented by the following formula (1)-1 or (1)-2:

(1)-1

(1)-2 wherein
in the formula (1)-1 or (1)-2,
A is a n-valent group derived from
a substituted or unsubstituted pyridine ring,
a substituted or unsubstituted pyrimidine ring,
a substituted or unsubstituted triazine ring,
a substituted or unsubstituted quinoline ring,
an substituted or unsubstituted isoquinoline ring,
a substituted or unsubstituted phthalazine ring,
a substituted or unsubstituted cinnoline ring,
a substituted or unsubstituted quinoxaline ring, or
a substituted or unsubstituted quinazoline ring;
B is a substituted or unsubstituted aromatic hydrocarbon group including 6 to 30 ring carbon atoms;
n is an integer of 2 or more; and
Czs are independently an aromatic heterocyclic group represented by the following formula (2) or (3); in the formula (1)-1, n of Czs may be independently bonded to any position of A, and when A includes a substituent, n of Czs may be bonded to any position of the substituent; and in the formula (1)-2, n of Czs may be independently bonded to any position of A or B, and when A or B includes a substituent, n of Czs may be bonded to any position of the substituent:

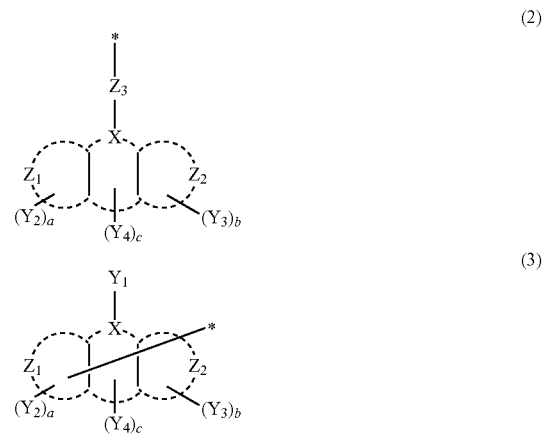

wherein
in the formula (2) or (3),
* indicates the bonding position to A or B;
$Z_1$ and $Z_2$ are independently atoms that form an aromatic hydrocarbon ring, an aromatic heterocyclic ring or an aliphatic ring, and are selected from the group consisting of carbon atoms, nitrogen atoms, oxygen atoms and sulfur atoms;
$Z_3$ is a single bond or a divalent linking group;
X is a nitrogen atom in the formula (2) and is a nitrogen atom, an oxygen atom or a sulfur atom in the formula (3);
the ring comprising X comprises atoms that form the ring and are selected from the group consisting of carbon atoms, nitrogen atoms, oxygen atoms and sulfur atoms in addition to X,
the ring formed of $Z_1$ is an aromatic hydrocarbon ring, an aromatic heterocyclic ring or an aliphatic ring; the aromatic hydrocarbon ring, the aromatic heterocyclic ring or the aliphatic ring, and the ring comprising X share two carbon atoms which form each ring; and the ring formed of $Z_2$ is an aromatic hydrocarbon ring, an aromatic heterocyclic ring or an aliphatic ring; the aromatic hydrocarbon ring, the aromatic heterocyclic ring or the aliphatic ring, and the ring comprising X share two carbon atoms which form each ring;
$Y_1$, $Y_3$ and $Y_4$ are independently selected from the group consisting of
a substituted or unsubstituted linear, branched or cyclic alkyl group including 1 to 20 carbon atoms,
a substituted or unsubstituted aromatic hydrocarbon group including 6 to 30 ring carbon atoms and
a substituted or unsubstituted aromatic heterocyclic group including 2 to 30 ring carbon atoms;
$Y_2$ is selected from the group consisting of
a substituted or unsubstituted dibenzofuranyl group,
a substituted or unsubstituted dibenzothiophenyl group,
a substituted or unsubstituted N-phenylcarbazolyl group
a substituted or unsubstituted group formed by a piperazine ring, and a substituted or unsubstituted group formed by a pyrane ring,
provided that in the formula (3), when X is an oxygen atom or a sulfur atom, $Y_1$ is not present;
a is an integer of 1 or more;
b and c are independently an integer of 0, or 1 or more; and
when $Y_2$, $Y_3$ and $Y_4$ are 2 or more, adjacent groups of $Y_e$s, Ys and Ys may be bonded to each other to form a substituted or unsubstituted, saturated or unsaturated ring structure.

17. The aromatic heterocyclic derivative according to claim 16, wherein
A is a n-valent group derived from
a substituted or unsubstituted pyridine ring,
a substituted or unsubstituted pyrimidine ring,
a substituted or unsubstituted triazine ring,
a substituted or unsubstituted quinoline ring,
an substituted or unsubstituted isoquinoline ring,
a substituted or unsubstituted phthalazine ring,
a substituted or unsubstituted quinoxaline ring, or
a substituted or unsubstituted quinazoline ring;
$Y_2$ is selected from the group consisting of
a substituted or unsubstituted dibenzofuranyl group,
a substituted or unsubstituted N-phenylcarbazolyl group
a substituted or unsubstituted group formed by a piperizine ring, and
a substituted or unsubstituted group formed by a pyrane ring;
$Y_3$ is a substituted or unsubstituted aromatic hydrocarbon group including 6 to 30 ring carbon atoms or a substituted or unsubstituted aromatic heterocyclic group including 2 to 30 ring carbon atoms, and
$Y_4$ is a substituted or unsubstituted linear, branched or cyclic alkyl group including 1 to 20 carbon atoms.

18. The aromatic heterocyclic derivative according to claim 16, wherein
A is a n-valent group derived from
a substituted or unsubstituted pyrimidine ring,
a substituted or unsubstituted triazine ring,
a substituted or unsubstituted quinoline ring,
an substituted or unsubstituted isoquinoline ring,
a substituted or unsubstituted phthalazine ring, or
a substituted or unsubstituted quinazoline ring;
Czs are independently a substituted or unsubstituted carbazolyl group represented by the following formula (4);

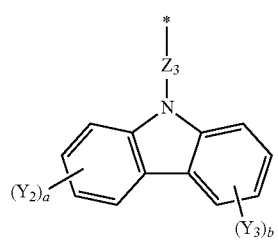

(4)

wherein *, $Z_3$, a and b are the same as those in formula (2),
$Y_2$ is a substituted or unsubstituted N-phenylcarbazolyl group, and
$Y_3$ is a substituted or unsubstituted aromatic hydrocarbon group including 6 to 30 ring carbon atoms or a substituted or unsubstituted aromatic heterocyclic group including 2 to 30 ring carbon atoms.

19. The aromatic heterocyclic derivative according to claim 16, wherein
A is a n-valent group derived from a substituted or unsubstituted pyrimidine ring, or a substituted or unsubstituted triazine ring,
Czs are independently a substituted or unsubstituted carbazolyl group represented by the following formula (4);

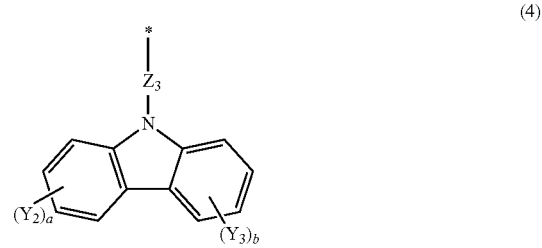

(4)

wherein *, $Z_3$ and a are the same as those in formula (2),
$Y_2$ is a substituted or unsubstituted N-phenylcarbazolyl group or a substituted or unsubstituted dibenzofuranyl group and
b is 0.

20. The aromatic heterocyclic derivative according to claim 1, wherein the substituent of A is
a linear, branched or cyclic alkyl group having 1 to 20 carbon atoms,
a linear, branched or cyclic alkoxy group having 1 to 20 carbon atoms,
a linear, branched or cyclic haloalkyl group having 1 to 20 carbon atoms,
a linear, branched or cyclic haloalkoxy group having 1 to 20 carbon atoms
a linear, branched or cyclic alkylsilyl group having 1 to 10 carbon atoms,
an arylsilyl group having 6 to 30 ring carbon atoms,
an aromatic hydrocarbon group having 6 to 30 ring carbon atoms or
a substituted or unsubstituted aromatic heterocyclic group including 2 to 30 ring carbon atoms.

21. The aromatic heterocyclic derivative according to claim 1, wherein Czs are independently represented by the following formula (4) or (5);

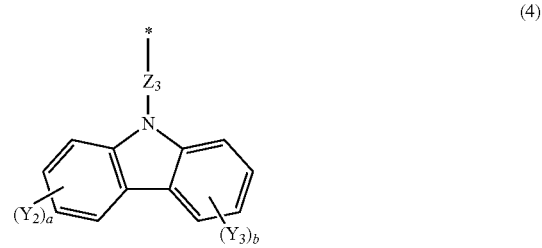

(4)

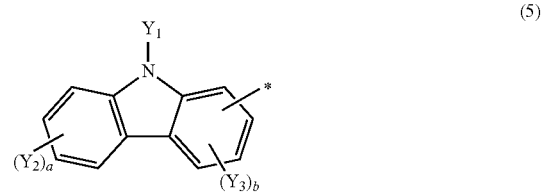

(5)

wherein *, $Y_1$ to $Y_3$, $Z_3$, a and b are the same as those in formula (2) or (3).

22. The aromatic heterocyclic derivative according to claim 21, wherein Czs are independently represented by the following formula (4):

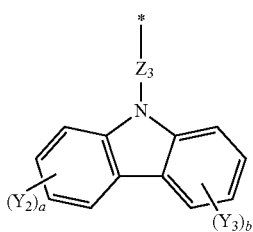

(4)

wherein *, $Y_2$, $Y_3$, $Z_3$, a and b are the same as those in formula (2).

23. The aromatic heterocyclic derivative according to claim 22, wherein $Y_2$ and $Y_3$ are independently a substituted or unsubstituted N-phenylcarbazolyl group.

24. The aromatic heterocyclic derivative according to claim 22, wherein Czs are independently represented by any of the following formulas;

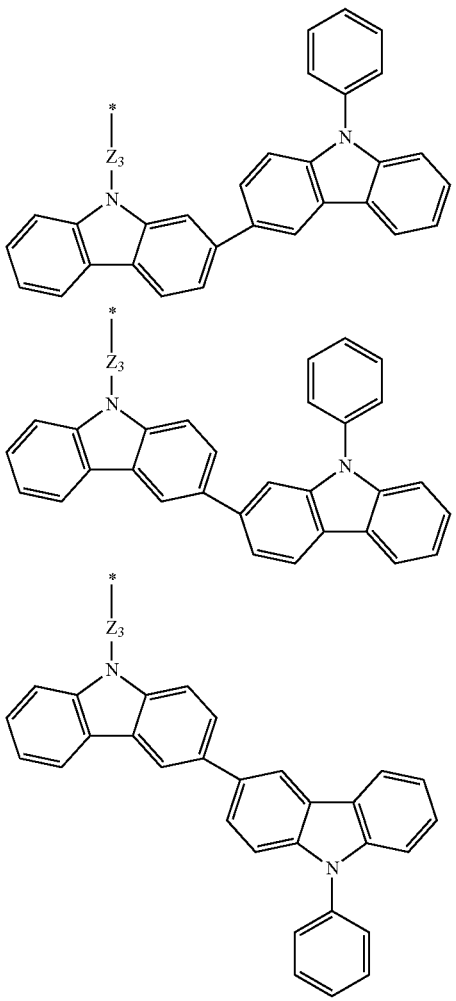

wherein * and $Z_3$ are the same as those in formula (4).

25. The aromatic heterocyclic derivative according to claim 22, wherein $Z_3$ is a single bond, a substituted or unsubstituted phenylene group or a substituted or unsubstituted biphenylene group.

26. The aromatic heterocyclic derivative according to claim 1, wherein in the formula (2) or (3),
$Z_1$ and $Z_2$ are independently atoms that form an aromatic hydrocarbon ring and are carbon atoms;
one or both of the aromatic hydrocarbon ring formed of $Z_1$ and the aromatic hydrocarbon ring formed of $Z_2$ are a fused aromatic hydrocarbon ring;
the aromatic hydrocarbon ring formed of $Z_1$ and the ring comprising X share two carbon atoms which form each ring; and the aromatic hydrocarbon ring formed of $Z_2$ and the ring comprising X share two carbon atoms which form each ring.

27. The aromatic heterocyclic derivative according to claim 22, which is represented by the following formula:

Cz-A-Cz

28. The aromatic heterocyclic derivative according to claim 22, which is represented by the following formula:

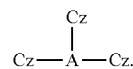

29. The aromatic heterocyclic derivative according to claim 22, wherein A is represented by any of the following formulas:

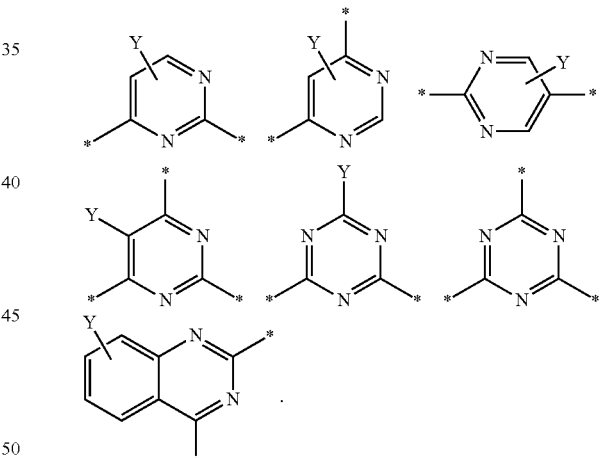

30. An aromatic heterocyclic derivative represented by the following formula (1)-1 or (1)-2:

  (1)-1

A—[Cz]$_n$

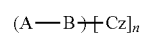  (1)-2

(A—B)—[Cz]$_n$ wherein, in the formula (1)-1 or (1)-2,
A is a n-valent group derived from a substituted or unsubstituted pyrimidine ring, a n-valent group derived from a substituted or unsubstituted triazine ring, or a n-valent group derived from a substituted or unsubstituted quinazoline ring;

B is a group derived from a substituted or unsubstituted benzene, a group derived from a substituted or unsubstituted naphthalene, a group derived from a substituted or unsubstituted biphenyl, a group derived from a substituted or unsubstituted terphenyl, a group derived from a substituted or unsubstituted fluorene, a group formed from a pyridine ring, a group formed from a pyrazine ring, a group formed from a pyridazine ring, or a group formed from a triazine ring;

when A or B includes a substituent the substituent is a methoxy group, an ethoxy group, a propoxy group, a pentyloxy group, a hexyloxy group, a group derived from benzene, naphthalene, biphenyl, terphenyl, fluorene, phenanthrene, triphenylene, perylene, chrysene, fluoranthene, benzofluorene, benzotriphenylene, benzochrysene or anthracene, A carbazolyl group, a dibenzofuranyl group, a dibenzothiophenyl group, a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, a 3-methylpentyl group, a cyclopentyl group, a cyclohexyl group, a cyclooctyl group, or a 3,5-tetramethylcyclohexyl group;

n is an integer of 2 or more; and

Czs are independently a substituted or unsubstituted carbazolyl group represented by the following formula (4);

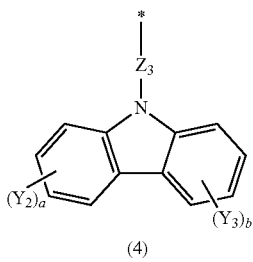

(4)

wherein * indicates the bonding position to A or B;

$Y_2$ is a substituted or unsubstituted N-phenylcarbazolyl group:

$Y_3$ is a substituted or unsubstituted N-phenylcarbazolyl group or a substituted or unsubstituted dibenzofuranyl group;

$Z_3$ is a single bond, a phenylene group, a biphenylene group, a terphenylene group, a naphthylene group, or a fluorenylene group;

a is an integer of 1 or more;

b is an integer of 0, or 1 or more:

in the formula (1)-1, n of Czs may be independently bonded to any position of A, and when A includes a substituent, n of Czs may be bonded to any position of the substituent;

and in the formula (1)-2, n of Czs may be independently bonded to any position of A or B, and when A or B includes a substituent, n of Czs may be bonded to any position of the substituent;

when $Y_2$ or $Y_3$ includes a substituent, the substituent is a methyl group, an ethyl group, a propyl group, an isopropyl group, an n-butyl group, an s-butyl group, an isobutyl group, a t-butyl group, an n-pentyl group, a phenyl group, a naphthyl group, a biphenyl group, a terphenyl group, a fluorenyl group, N-phenylcarbazolyl group, a dibenzofuranyl group, or a dibenzothiophenyl group;

when $Y_2$ and $Y_3$ are 2 or more, adjacent groups of $Y_e$s and $Y_3$s may be bonded to each other to form a substituted or unsubstituted, saturated or unsaturated ring structure.

32. The aromatic heterocyclic derivative according to claim 1, wherein, when A, B or $Y_1$ to $Y_4$ includes a substituent, the substituent is a linear, branched or cyclic alkyl group having 1 to 20 carbon atoms, a linear, branched or cyclic alkoxy group having 1 to 20 carbon atoms, a linear, branched or cyclic haloalkyl group having 1 to 20 carbon atoms, a linear, branched or cyclic haloalkoxy group having 1 to 20 carbon atoms a linear, branched or cyclic alkylsilyl group having 1 to 10 carbon atoms, an arylsilyl group having 6 to 30 ring carbon atoms, an aromatic hydrocarbon group having 6 to 30 ring carbon atoms, or an aromatic heterocyclic group including 2 to 30 ring carbon atoms.

32. The aromatic heterocyclic derivative according to claim 16, wherein, when A, B or $Y_1$ to $Y_4$ includes a substituent, the substituent is a linear, branched or cyclic alkyl group having 1 to 20 carbon atoms, a linear, branched or cyclic alkoxy group having 1 to 20 carbon atoms, a linear, branched or cyclic haloalkyl group having 1 to 20 carbon atoms, a linear, branched or cyclic haloalkoxy group having 1 to 20 carbon atoms, a linear, branched or cyclic alkylsilyl group having 1 to 10 carbon atoms, an arylsilyl group having 6 to 30 ring carbon atoms, an aromatic hydrocarbon group having 6 to 30 ring carbon atoms, or an aromatic heterocyclic group including 2 to 30 ring carbon atoms.

* * * * *

UNITED STATES PATENT AND TRADEMARK OFFICE
CERTIFICATE OF CORRECTION

PATENT NO. : 9,705,091 B2
APPLICATION NO. : 13/994249
DATED : July 11, 2017
INVENTOR(S) : Kiyoshi Ikeda and Mitsunori Ito It is certified that error appears in the above-identified patent and that said Letters Patent is hereby corrected as shown below:

In the Claims

On the 39th Line of Column 196, "Ys, Ys and Ys may be" should read "$Y_2s$, $Y_3s$ and $Y_4s$ may be".

On the 9th Line of Column 199, "Ys, Ys and Ys may be" should read "$Y_2s$, $Y_3s$ and $Y_4s$ may be".

On the 19th Line of Column 204, "adjacent groups of Ys and" should read "adjacent groups of $Y_2s$ and".

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*